United States Patent
Ashman et al.

(10) Patent No.: US 8,680,245 B2
(45) Date of Patent: Mar. 25, 2014

(54) IL-13 BINDING PROTEIN

(75) Inventors: Claire Ashman, Stevenage (GB); Jonathan Henry Ellis, Stevenage (GB); Paul Andrew Hamblin, Stevenage (GB); Alan Peter Lewis, Stevenage (GB); Martin Anibal Orecchia, Stevenage (GB)

(73) Assignee: Glaxo Group Limited (GB)

( * ) Notice: Subject to any disclaimer, the term of this patent is extended or adjusted under 35 U.S.C. 154(b) by 0 days.

(21) Appl. No.: 13/321,982

(22) PCT Filed: May 26, 2010

(86) PCT No.: PCT/EP2010/057228
§ 371 (c)(1), (2), (4) Date: Nov. 22, 2011

(87) PCT Pub. No.: WO2010/136481
PCT Pub. Date: Dec. 2, 2010

(65) Prior Publication Data
US 2012/0082682 A1    Apr. 5, 2012

Related U.S. Application Data

(60) Provisional application No. 61/288,930, filed on Dec. 22, 2009, provisional application No. 61/181,833, filed on May 28, 2009.

(51) Int. Cl.
*C07K 16/24* (2006.01)

(52) U.S. Cl.
USPC .................................................. 530/388.23

(58) Field of Classification Search
None
See application file for complete search history.

(56) References Cited

U.S. PATENT DOCUMENTS 5,859,205 A * 1/1999 Adair et al. ................. 530/387.3
6,811,780 B2   11/2004 Furfine et al.
7,553,487 B2    6/2009 Collins et al.

FOREIGN PATENT DOCUMENTS

| WO | WO 2006/003407 A2 | 1/2006 |
| WO | WO 2007/080174 A2 | 7/2007 |
| WO | WO 2007/085814 A1 | 8/2007 |
| WO | WO 2009/068649 | 6/2009 |
| WO | WO 2009/124090 | 10/2009 |
| WO | WO 2010/136481 | 12/2010 |

OTHER PUBLICATIONS

Eduardo Padlan, Mol Immunol. Feb. 1994;31(3):169-217.*
Portolano et al., J Immunol. Feb. 1, 1993;150(3):880-7.*
Vajdos et al., J Mol Biol. Jul. 5, 2002;320(2):415-28.*
Bratko, Dusan, et al., J. of the Am. Chem. Soc., vol. 128, No. 5, Feb. 8, 2006, pp. 1683-1691.
Hoogenboom, H. R., et al., Nature Biotech., vol. 23, No. 9, Sep. 1, 2005, pp. 1105-1116.
Jung, S., et al., Protein Engineering, vol. 10, No. 8, Jan. 1, 1997, pp. 959-966.
Punnonen, et al., J, Allergy Clin. Immunol., vol. 100, No. 6, Dec. 1, 1997, pp. 792-801.
Salvatore, G., et al., Clin. Can. Res., vol. 8, Apr. 1, 2002, pp. 995-1002.
Souriau, Christelle, et al., Ex. Opin. Biol. Ther., vol. 3, No. 2, Apr. 1, 2003, pp. 305-318.

* cited by examiner

*Primary Examiner* — Zachary Skelding
(74) *Attorney, Agent, or Firm* — William Peter Long; William T. Han

(57) ABSTRACT

The present invention relates to antigen binding proteins to human IL-13, including anti-IL-13 antibodies and anti-IL-3/anti-IL-4 mAbdAbs, pharmaceutical formulations containing them and to the use of such antigen binding proteins in the treatment and/or prophylaxis of inflammatory diseases such as asthma or IPF.

79 Claims, 9 Drawing Sheets

IL-13 BINDING PROTEIN

This application is a 371 of International Application No. PCT/EP2010/057228, filed 26 May 2010, which claims the benefit of U.S. Provisional Application Nos. 61/181,833, filed 28 May 2009 and 61/288,930, filed 22 Dec. 2009, which are incorporated by reference in their entireties.

FIELD OF THE INVENTION

The present invention relates to antigen binding proteins, particularly antibodies that bind to interleukin 13 (IL-13) and neutralise the activity thereof, polynucleotides encoding such antigen binding proteins, pharmaceutical formulations containing said antigen binding proteins and to the use of such antigen binding proteins in the treatment and/or prophylaxis of diseases associated with inflammation, such as asthma. Other aspects, objects and advantages of the present invention will become apparent from the description below.

BACKGROUND OF THE INVENTION

Interleukin-13 (IL-13)

IL-13 is a 12 kDa secreted cytokine originally described as a T cell-derived cytokine that inhibits inflammatory cytokine production. Structural studies indicate that it has a four-helical bundle arrangement held by two disulphide bonds. Although IL-13 has four potential glycosylation sites, analysis of native IL-13 from rat lung has indicated that it is produced as an unglycosylated molecule. Expression of human IL-13 from NSO and COS-7 cells confirms this observation (Eisenmesser et al, J. Mol. Biol. 2001 310(1):231-241; Moy et al, J. Mol. Biol. 2001 310(1):219-230; Cannon-Carlson et al, Protein Expression and Purification 1998 12(2):239-248).

IL-13 has been implicated in asthma, Chronic Obstructive Pulmonary Disease (COPD), Allergic disease including atopic dermatitis and allergic rhinitis, Esophagal eosinophilia, Oncology Indications, e.g. B-cell chronic lymphocytic leukemia (B-CLL) and Hodgkin's disease, Inflammatory Bowel Diseases e.g. ulcerative colitis, Crohn's disease and indeterminate colitis, Psoriasis and Psoriatic Arthritis, Acute graft-versus-host disease, Diabetic nephropathy, Fibrotic Conditions such as Pulmonary fibrosis e.g. Idiopathic Pulmonary Fibrosis (IPF).

SUMMARY OF INVENTION

The invention provides antigen binding proteins which bind to IL-13, for example IL-13 antibodies, and to the combination of such IL-13 antibodies with an IL-4 antagonist and/or an IL-5 antagonist. The IL-13 antibodies of the present invention are related to, or derived from, a murine mAb 6A1, wherein the CDRH3 is mutated. The 6A1 murine heavy chain variable region amino acid sequence is provided as SEQ ID NO: 58. The 6A1 murine light chain variable region amino acid sequence is provided as SEQ ID NO 59.

The heavy chain variable regions (VH) of the present invention comprise the following CDRs (as defined by Kabat (Kabat et al; *Sequences of proteins of Immunological Interest* NIH, 1987)):

The CDRs of the heavy chain variable regions of the present invention may comprise the following CDRs:

| CDR | According to Kabat |
|---|---|
| H1 | DTYMH (SEQ ID NO: 1) |
| H2 | TIDPANGNTKYVPKFQG (SEQ ID NO: 2) |
| H3 | WIYDDYHYDDYYAMDY (SEQ ID NO: 4); or |
|    | SVYDDYHYDDYYAMDY (SEQ ID NO: 5); or |
|    | SIFDDYHYDDYYAMDY (SEQ ID NO: 6); or |
|    | SIYEDYHYDDYYAMDY (SEQ ID NO: 7); or |
|    | SIYDDYAYDDYYAMDY (SEQ ID NO: 8); or |
|    | SIYDDYEYDDYYAMDY (SEQ ID NO: 9); or |
|    | SIYDDYQYDDYYAMDY (SEQ ID NO: 10); or |
|    | SIYDDYRYDDYYAMDY (SEQ ID NO: 11); or |
|    | SIYDDYSYDDYYAMDY (SEQ ID NO: 12); or |
|    | SIYDDYTYDDYYAMDY (SEQ ID NO: 13) or |
|    | SIYDDYVYDDYYAMDY (SEQ ID NO: 14); or |
|    | SIYDDYHADDYYAMDY (SEQ ID NO: 15); or |
|    | SIYDDYHIDDYYAMDY (SEQ ID NO: 16); or |
|    | SIYDDYHWDDYYAMDY (SEQ ID NO: 17); or |
|    | SIYDDYHVDDYYAMDY (SEQ ID NO: 18) |

The light chain variable regions of the present invention comprise the following CDRs (as defined by Kabat):

| CDR | According to Kabat |
|---|---|
| L1 | RSSQNIVHINGNTYLE (SEQ ID NO: 19) |
| L2 | KISDRFS (SEQ ID NO: 20) |
| L3 | FQGSHVPWT (SEQ ID NO: 21) |

The CDR sequences of antibodies can be determined by the Kabat numbering system (Kabat et al; *Sequences of proteins of Immunological Interest* NIH, 1987), as set out in the tables above, alternatively they can be determined using the Chothia numbering system (Al-Lazikani et al., (1997) JMB 273, 927-948), the contact definition method (MacCallum R. M., and Martin A. C. R. and Thornton J. M, (1996), Journal of Molecular Biology, 262 (5), 732-745) or any other established method for numbering the residues in an antibody and determining CDRs known to the skilled man in the art.

The CDRs of the invention described herein may be defined by any of these methods, or by using a combination of Chothia and Kabat numbering, for example CDRH1 may be defined as comprising FYIKDTYMH (SEQ ID NO 60) or GFYIKDTYMH (SEQ ID NO 61).

The present invention also provides an antigen-binding protein comprising the IL-13 antibody of the present invention which is linked to one or more epitope-binding domains, for example an antigen-binding protein comprising the IL-13 antibody of the present invention linked to an epitope-binding domain which is capable of binding to IL-4, or an antigen-binding protein comprising the IL-13 antibody of the present invention linked to an epitope-binding domain which is capable of binding to IL-5, or an antigen-binding protein comprising the IL-13 antibody of the present invention linked to a first epitope-binding domain which is capable of binding to IL-4 and a second epitope-binding domain which is capable of binding to IL-5.

The present invention also provides a method of decreasing the aggregation propensity of an immunoglobulin single variable domain, for example a human dAb™, for example human VK domain antibody, by mutation of residue 89 (Kabat numbering) to a residue selected from 'Q' (glutamine), 'G' (glycine), 'S' (serine), 'M' (methionine), 'A' (alanine), 'T' (threonine) and 'E' (glutamic acid). In one embodiment, the method involves mutation of residue 89 (Kabat numbering) to a residue selected from 'Q' (glutamine), 'G' (glycine), 'S' (serine), 'M' (methionine) and 'E' (glutamic acid). In a further embodiment the method involves mutation of residue 89 (Kabat numbering) to 'Q' (glutamine).

In one embodiment this method can be applied to the anti-IL-4 domain antibody of SEQ ID NO: 80, resulting in a mutated dAb™ sequence, for example SEQ ID NO:94. Such mutated dAb™s may be alone or as part of a larger sequence, for example part of a mAb-domain antibody sequence, resulting in for example, a dAb™ comprising a sequence selected from SEQ ID NO: 117-134.

The invention also provides human VK dAb™s which have improved aggregation profiles, for example a human VK dAb™ derived from a germline framework selected from IGKV1-17, IGKV1D-17, IGKV1/OR2-108, IGKV1-6, IGKV5-2, IGKV1D-42, IGKV2-24, IGKV2-28, IGKV2-30, IGKV2-40, IGKV2D-29, IGKV2D-30, IGKV2D-24 and IGKV6-21 wherein residue 89 (Kabat numbering) of the VK dAb™ is 'Q' (glutamine). In one such embodiment the VK dAb™ comprises germline framework regions selected from the germline frameworks of IGKV1-17, IGKV1D-17, IGKV1/OR2-108, IGKV1-6, IGKV5-2, IGKV1D-42, IGKV2-24, IGKV2-28, IGKV2-30, IGKV2-40, IGKV2D-29, IGKV2D-30, IGKV2D-24 and IGKV6-21 wherein residue 89 (Kabat numbering) of the VK dAb™ is 'Q' (glutamine).

In one embodiment, the invention provides a human dAb™ comprising the sequence of SEQ ID NO: 80 which comprises a mutation at position 89 (Kabat numbering) wherein the mutated position 89 is selected from 'Q' (glutamine), 'G' (glycine), 'S' (serine), 'M' (methionine), 'A' (alanine), 'T' (threonine) and 'E' (glutamic acid). For example the invention provides a human dAb comprising the sequence of SEQ ID NO:80 wherein position 89 (Kabat numbering) is mutated to a residue selected from 'Q' (glutamine), 'G' (glycine), 'S' (serine), 'M' (methionine) and 'E' (glutamic acid).

In one embodiment the invention provides a human dAb™ comprising the sequence of SEQ ID NO: 94

The invention also provides a polynucleotide sequence encoding a heavy chain of any of the antigen-binding proteins described herein, and a polynucleotide encoding a light chain of any of the antigen-binding proteins described herein. Such polynucleotides represent the coding sequence which corresponds to the equivalent polypeptide sequences, however it will be understood that such polynucleotide sequences could be cloned into an expression vector along with a start codon, an appropriate signal sequence and a stop codon.

The invention also provides a recombinant transformed or transfected host cell comprising one or more polynucleotides encoding a heavy chain and a light chain of any of the antigen-binding proteins described herein.

The invention further provides a method for the production of any of the antigen-binding proteins described herein which method comprises the step of culturing a host cell comprising a first and second vector, said first vector comprising a polynucleotide encoding a heavy chain of any of the antigen-binding proteins described herein and said second vector comprising a polynucleotide encoding a light chain of any of the antigen-binding proteins described herein, in a suitable culture media, for example serum-free culture media.

The invention further provides a pharmaceutical composition comprising an antigen-binding protein as described herein a pharmaceutically acceptable carrier.

In a further aspect, the present invention provides a method of treatment or prophylaxis of diseases or disorders associated with atopic diseases/disorders and chronic inflammatory diseases/disorders by administration of the antigen binding protein of the present invention. Of particular interest is their use in the treatment of asthma, such as allergic asthma, particularly severe asthma (that is asthma that is unresponsive to current treatment, including systemically administered corticosteroids; see Busse W W et al, J. Allergy Clin. Immunol 2000, 106: 1033-1042), "difficult" asthma (defined as the asthmatic phenotype characterised by failure to achieve control despite maximally recommended doses of prescribed inhaled steroids, see Barnes P J (1998), Eur Respir J 12:1208-1218), "brittle" asthma (defines a subgroup of patients with severe, unstable asthma who maintain a wide peak expiratory flow (PEF) variability despite high doses of inhaled steroids, see Ayres J G et al (1998) Thorax 58:315-321), nocturnal asthma, premenstrual asthma, steroid resistant asthma (see Woodcock A J (1993) Eur Respir J 6:743-747), steroid dependent asthma (defined as asthma that can be controlled only with high doses of oral steroids), aspirin induced asthma, adult-onset asthma, paediatric asthma. Antibodies of the invention maybe used to prevent, reduce the frequency of, or mitigate the effects of acute, asthmatic episodes (status asthmaticus). Antibodies of the invention may also be used to reduce the dosing required (either in terms of amount administered or frequency of dosing) of other medicaments used in the treatment of asthma. For example, antibodies of the invention may be used to reduce the dosing required for steroid treatment of asthma such as corticosteroid treatment ("steroid sparing"). Other diseases or disorders that may be treated with antibodies of the invention include atopic dermatitis, allergic rhinitis, Crohn's disease, chronic obstructive pulmonary disease (COPD), eosinophilic esophagitis, fibrotic diseases or disorders such as idiopathic pulmonary fibrosis, progressive systemic sclerosis (scleroderma), hepatic fibrosis, hepatic granulomas, schistosomiasis, leishmaniasis, and diseases of cell cycle regulation, e.g. Hodgkins disease, B cell chronic lymphocytic leukaemia.

In another aspect, the invention provides the use of an antigen binding protein of the invention in the preparation of a medicament for treatment or prophylaxis of atopic diseases/disorders and chronic inflammatory diseases/disorders. Of particular interest is their use in the treatment of asthma, such as allergic asthma, particularly severe asthma (that is asthma that is unresponsive to current treatment, including systemically administered corticosteroids; see Busse W W et al, J. Allergy Clin. Immunol 2000, 106: 1033-1042), "difficult" asthma (defined as the asthmatic phenotype characterised by failure to achieve control despite maximally recommended doses of prescribed inhaled steroids, see Barnes P J (1998), Eur Respir J 12:1208-1218), "brittle" asthma (defines a subgroup of patients with severe, unstable asthma who maintain a wide peak expiratory flow (PEF) variability despite high doses of inhaled steroids, see Ayres J G et al (1998) Thorax 58:315-321), nocturnal asthma, premenstrual asthma, steroid resistant asthma (see Woodcock A J (1993) Eur Respir J 6:743-747), steroid dependent asthma (defined as asthma that can be controlled only with high doses of oral steroids), aspirin induced asthma, adult-onset asthma, paediatric asthma. Antibodies of the invention maybe used to prevent, reduce the frequency of, or mitigate the effects of acute, asthmatic episodes (status asthmaticus). Antibodies of the invention may also be used to reduce the dosing required (either in terms of amount administered or frequency of dosing) of other medicaments used in the treatment of asthma.

For example, antibodies of the invention may be used to reduce the dosing required for steroid treatment of asthma such as corticosteroid treatment ("steroid sparing"). Other diseases or disorders that may be treated with antibodies of the invention include atopic dermatitis, allergic rhinitis, Crohn's disease, chronic obstructive pulmonary disease (COPD), eosinophilic esophagitis, fibrotic diseases or disorders such as idiopathic pulmonary fibrosis, progressive systemic sclerosis (scleroderma), hepatic fibrosis, hepatic granulomas, schistosomiasis, leishmaniasis, and diseases of cell cycle regulation, e.g. Hodgkins disease, B cell chronic lymphocytic leukaemia.

Other aspects and advantages of the present invention are described further in the detailed description and the embodiments thereof.

DEFINITIONS

The term "binds to human IL-13" as used throughout the present specification in relation to antigen binding proteins thereof of the invention means that the antigen binding protein binds human IL-13 (hereinafter referred to as hIL-13) with no or insignificant binding to other human proteins such as IL-4. In particular the antigen binding proteins of the present invention bind to human IL-13 in that they can be seen to bind to human IL-13 in a BIAcore™ assay (for example the BIAcore™ assay described in example 3). The term however does not exclude the fact that certain antigen binding proteins of the invention may also be cross-reactive with IL-13 from other species, for example cynomolgus IL-13.

The term "antigen binding protein" as used herein refers to antibodies, antibody fragments and other protein constructs which are capable of binding to and neutralising human IL-13.

The terms Fv, Fc, Fd, Fab, or F(ab)$_2$ are used with their standard meanings (see, e.g., Harlow et al., Antibodies A Laboratory Manual, Cold Spring Harbor Laboratory, (1988)).

A "chimeric antibody" refers to a type of engineered antibody which contains a naturally-occurring variable region (light chain and heavy chains) derived from a donor antibody in association with light and heavy chain constant regions derived from an acceptor antibody.

A "humanised antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p877-883.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. An "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain ($V_H$, $V_{HH}$, $V_L$) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb™" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid $V_{HH}$ dAb™s (nanobodies). Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are still considered to be "domain antibodies" according to the invention. As used herein "$V_H$ includes camelid $V_{HH}$ domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "Epitope-binding domain" refers to a domain that specifically binds an antigen or epitope independently of a different V region or domain, this may be a domain antibody (dAb™), for example a human, camelid or shark immunoglobulin single variable domain or it may be a domain which is a derivative of a non-Immunoglobulin scaffold, for example a non-immunoglobulin scaffold selected from the group consisting of CTLA-4 (EVIBODY™); lipocalin; Protein A derived molecules such as Z-domain of Protein A (AFFIBODY™, SpA), A-domain (Avimer/MAXIBODY™); Heat shock proteins such as GroEI and GroES; transferrin (TRANS-BODY™); ankyrin repeat protein (DARPin); peptide aptamer; C-type lectin domain (Tetranectin); human γ-crystallin and human ubiquitin (AFFILINS™); PDZ domains; scorpion toxinkunitz type domains of human protease inhibitors; and fibronectin (adnectin); which has been subjected to protein engineering in order to obtain binding to a ligand other than the natural ligand.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001)

Lipocalins are a family of extracellular proteins which transport small hydrophobic molecules such as steroids, bilins, retinoids and lipids. They have a rigid β-sheet secondary structure with a numer of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633

An AFFIBODY™ is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1

Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007)

A transferrin is a monomeric serum transport glycoprotein. Transferrins can be engineered to bind different target antigens by insertion of peptide sequences in a permissive surface loop. Examples of engineered transferrin scaffolds include the TRANS-BODY™. For further details see J. Biol. Chem. 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomising residues in the first α-helix and a β-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the β-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

MICROBODIES™ are derived from naturally occurring microproteins of 25-50 amino acids in length which contain 3-4 cysteine bridges—examples of microproteins include KalataB1 and conotoxin and knottins. The microproteins have a loop which can be engineered to include up to 25 amino acids without affecting the overall fold of the microprotein. For further details of engineered knottin domains, see WO2008098796.

Other epitope binding domains include proteins which have been used as a scaffold to engineer different target antigen binding properties include human γ-crystallin and human ubiquitin (AFFILINS™), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Epitope binding domains of the present invention could be derived from any of these alternative protein domains.

As used herein, the term "antigen-binding site" refers to a site on a protein which is capable of specifically binding to antigen, this may be a single domain, for example an epitope-binding domain, or it may be paired VH/VL domains as can be found on a standard antibody. In some aspects of the invention single-chain Fv (ScFv) domains can provide antigen-binding sites.

The terms mAb-domain antibody" and "domain antibody-mAb" are used herein to refer to antigen-binding proteins of the present invention. The two terms can be used interchangeably, and are intended to have the same meaning as used herein.

The term "antigen binding protein" as used herein refers to antibodies, antibody fragments, for example a domain antibody (dAb™), ScFv, FAb, FAb$_2$, and other protein constructs which are capable of binding to IL-13. Antigen binding molecules may comprise at least one Ig variable domain, for example antibodies, domain antibodies, Fab, Fab', F(ab')2, Fv, ScFv, diabodies, mAb-domain antibodies, affibodies, heteroconjugate antibodies or bispecifics. In one embodiment the antigen binding molecule is an antibody. In another embodiment the antigen binding molecule is a dAb™, i.e. an immunoglobulin single variable domain such as a VH, VHH or VL that specifically binds an antigen or epitope independently of a different V region or domain. Antigen binding molecules may be capable of binding to two targets, i.e. they may be dual targeting proteins. Antigen binding molecules may be a combination of antibodies and antigen binding fragments such as for example, one or more domain antibodies and/or one or more ScFvs linked to a monoclonal antibody. Antigen binding molecules may also comprise a non-Ig domain for example a domain which is a derivative of a scaffold selected from the group consisting of CTLA-4 (EVIBODY™); lipocalin; Protein A derived molecules such as Z-domain of Protein A (AFFIBODY™, SpA), A-domain (Avimer/MAXIBODY™); Heat shock proteins such as GroEI and GroES; transferrin (TRANS-BODY™); ankyrin repeat protein (DARPin); peptide aptamer; C-type lectin domain (Tetranectin); human γ-crystallin and human ubiquitin (AFFILINS™); PDZ domains; scorpion toxinkunitz type domains of human protease inhibitors; and fibronectin (adnectin); which has been subjected to protein engineering in order to obtain binding to IL-13. As used herein "antigen binding protein" will be capable of antagonising and/or neutralising human IL-13. In addition, an antigen binding protein may block IL-13 activity by binding to IL-13 and preventing a natural ligand from binding and/or activating the receptor.

As used herein "IL-13 antagonist" includes any compound capable of reducing and or eliminating at least one activity of IL-13. By way of example, an IL-13 antagonist may bind to IL-13 and that binding may directly reduce or eliminate IL-13 activity or it may work indirectly by blocking at least one ligand from binding the receptor.

As used herein "IL-4 antagonist" includes any compound capable of reducing and or eliminating at least one activity of IL-4. By way of example, an IL-4 antagonist may bind to IL-4 and that binding may directly reduce or eliminate IL-4 activity or it may work indirectly by blocking at least one ligand from binding the receptor.

As used herein "IL-5 antagonist" includes any compound capable of reducing and or eliminating at least one activity of IL-5. By way of example, an IL-5 antagonist may bind to IL-5 and that binding may directly reduce or eliminate IL-5 activity or it may work indirectly by blocking at least one ligand from binding the receptor.

DETAILED DESCRIPTION OF THE INVENTION

In one embodiment the antigen binding proteins of the present invention comprise a heavy chain variable region containing a CDRH3 selected from the list consisting of SEQ ID NO: 4, SEQ ID NO: 5, SEQ ID NO: 6, SEQ ID NO: 7, SEQ ID NO:8 and SEQ ID NO: 9, SEQ ID NO: 10, SEQ ID NO: 11, SEQ ID NO: 12, SEQ ID NO: 13, SEQ ID NO:14 and SEQ ID NO: 15, SEQ ID NO: 16, SEQ ID NO: 17 and SEQ ID NO: 18 and a suitable CDRH1 and CDRH2, paired with a light chain variable region containing a suitable CDRL1, CDRL2 and CDRL3 to form an antigen binding Fv unit which binds to human IL-13. In one embodiment the antigen binding proteins of the present invention neutralise the activity of human IL-13

In one aspect of this embodiment the CDRH1 as set out in SEQ ID NO: 1 or SEQ ID NO: 60, or SEQ ID NO:61 and CDRH2 as set out in SEQ ID NO: 2 are also present in the heavy chain variable region. In a further aspect of this embodiment the CDRHL1 as set out in SEQ ID NO: 19, CDRL2 as set out in SEQ ID NO:20 and CDRL3 as set out in SEQ ID NO: 21 are also present in the light chain variable region.

In another aspect the antigen binding protein binds to human IL-13 with high affinity as measured by BIAcore™ of 10 nM or less, and more particularly 2 nM or less, for example between about 0.8 nM and 2 nM, 1 nM or less, or 100 µM or less, for example between about 20 µM and about 100 µM or between about 20 µM and about 80 µM, or between about 20 µM and about 60 µM. In one such embodiment, this is measured by BIAcore™ with the antigen binding protein being captured on the biosensor chip, for example as set out in Example 3.

The heavy chain variable regions of the present invention may be formatted together with light chain variable regions to allow binding to human IL-13, in the conventional immunoglobulin manner (for example, human IgG, IgA, IgM etc.) or in any other "antibody-like" format that binds to human IL-13 (for example, single chain Fv, diabodies, TANDABS™ etc (for a summary of alternative "antibody" formats see Holliger and Hudson, Nature Biotechnology, 2005, Vol 23, No. 9, 1126-1136)).

The antigen binding proteins of the present invention are derived from the murine antibody having the variable regions as described in SEQ ID NO:58 and SEQ ID NO:59 or non-murine equivalents thereof, such as rat, human, chimeric or humanised variants thereof, for example they are derived from the humanised antibody having the heavy and light chains as described in SEQ ID NO:22 and SEQ ID NO:24.

In one aspect of the invention there is provided an antigen binding protein, for example an antibody which binds human IL-13 and which comprises variants of the CDRH3 SIYDDYHYDDYYAMDY (SEQ ID NO: 3), wherein CDRH3 is substituted by the alternative amino acids set out below at one or more of the following positions (using Kabat numbering):
a) S95 in position 1 is substituted for tryptophan (W)
b) I96 in position 2 is substituted for valine (V)
c) Y97 in position 3 is substituted for phenylalanine (F)
d) D98 in position 4 is substituted for glutamine (E)
e) H100A in position 7 is substituted for alanine (A), glutamic acid (E), glutamine (Q), Arginine (R), Serine (S), threonine (T) or valine (V), and
f) Y100B in position 8 is substituted for alanine (A), isoleucine, (1), tryptophan (W) or valine (V).

In another aspect of the invention there is provided an antigen binding protein, for example an antibody which binds human IL-13 and which comprises the CDRH3 set out in SEQ ID NO: 3, wherein CDRH3 comprises one or more of the following substitutions: S95W, I96V, Y97F, D98E, H100A_A, H100A_E, H100A_Q, H100A_R, H100A_S, H100A_T, H100A_V, Y100B_A, Y100B_I, Y100B_W, and Y100B_V.

In one aspect the antigen binding protein of the present invention, for example the antibody of the present invention, comprises a CDRH3 sequence selected from those set out in SEQ ID NO: 4, SEQ ID NO: 5, SEQ ID NO: 6, SEQ ID NO: 7, SEQ ID NO:8 and SEQ ID NO: 9, SEQ ID NO: 10, SEQ ID NO: 11, SEQ ID NO: 12, SEQ ID NO: 13,
SEQ ID NO:14 and SEQ ID NO: 15, SEQ ID NO: 16, SEQ ID NO: 17 and SEQ ID NO: 18. Such antigen binding proteins may further comprise the following CDR sequences:
CDRH1: selected from SEQ ID NO:1, 60 and 61,
CDRH2: SEQ ID NO: 2;
CDRL1: SEQ ID NO:19;
CDRL2: SEQ ID NO:20; and
CDRL3: SEQ ID NO:21.

In one embodiment the antigen binding protein comprises the following CDRs:
CDRH1: SEQ ID NO:1,
CDRH2: SEQ ID NO:2;
CDRH3: SEQ ID NO:18
CDRL1: SEQ ID NO:19;
CDRL2: SEQ ID NO:20; and
CDRL3: SEQ ID NO:21.

In another embodiment the antigen binding protein comprises the following CDRs:
CDRH1: SEQ ID NO:1,
CDRH2: SEQ ID NO:2;
CDRH3: SEQ ID NO:17
CDRL1: SEQ ID NO:19;
CDRL2: SEQ ID NO:20; and
CDRL3: SEQ ID NO:21.

In another embodiment the antigen binding protein comprises the following CDRs:
CDRH1: SEQ ID NO:1,
CDRH2: SEQ ID NO:2;
CDRH3: SEQ ID NO:16
CDRL1: SEQ ID NO:19;
CDRL2: SEQ ID NO:20; and
CDRL3: SEQ ID NO:21.

In another embodiment the antigen binding protein comprises the following CDRs:
CDRH1: SEQ ID NO:1,
CDRH2: SEQ ID NO:2;
CDRH3: SEQ ID NO:15
CDRL1: SEQ ID NO:19;
CDRL2: SEQ ID NO:20; and
CDRL3: SEQ ID NO:21.

Throughout this specification, amino acid residues in antibody sequences are numbered according to the Kabat scheme. Similarly, the terms "CDR", "CDRL1", "CDRL2", "CDRL3", "CDRH1", "CDRH2", "CDRH3", unless otherwise indicated (e.g. CDRH3 as set out in SEQ ID NO:60 and 61), follow the Kabat numbering system as set forth in Kabat et al; "Sequences of proteins of Immunological Interest" NIH, 1987.

In another aspect of the invention there is provided an antigen binding protein, such as a humanised antibody or antigen binding fragment thereof, comprising a heavy chain having the sequence selected from SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 88, SEQ ID NO: 89, SEQ ID NO: 90 and SEQ ID NO: 91; and the light chain of SEQ ID NO:24.

The invention provides an antigen binding protein, such as a humanised antibody or antigen binding fragment thereof, comprising a heavy chain selected from SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 88, SEQ ID NO: 89, SEQ ID NO: 90.

The invention also provides an antigen binding protein, such as a humanised antibody or antigen binding fragment thereof, comprising a light chain selected from SEQ ID NO: 108, SEQ ID NO: 110, SEQ ID NO: 112 and SEQ ID NO: 114.

The invention further provides an antigen binding protein, such as a humanised antibody or antigen binding fragment thereof, comprising a heavy chain having the sequence selected from SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 88, SEQ ID NO: 89, SEQ ID NO: 90 and SEQ ID NO: 91; and the light chain of SEQ ID NO: 108, SEQ ID NO: 110, SEQ ID NO: 112 and SEQ ID NO: 114.

In one embodiment the antigen binding protein of the present invention comprises an antibody comprising a heavy chain selected from SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 88, SEQ ID NO: 89, SEQ ID NO: 90 and SEQ ID NO: 91 and a light chain selected from SEQ ID NO:24, SEQ ID NO: 108, SEQ ID NO: 110, SEQ ID NO: 112 and SEQ ID NO: 114.

In one embodiment the antigen binding protein of the present invention comprises a heavy chain selected from SEQ ID NO: 48, SEQ ID NO: 50, SEQ ID NO: 52 and SEQ ID NO: 54; and a light chain selected from SEQ ID NO: 24, SEQ ID NO: 108, SEQ ID NO:110, SEQ ID NO:112 and SEQ ID NO:114, for example the antigen binding protein comprises the heavy chain of SEQ ID NO: 48 and the light chain of SEQ ID NO:24, or the heavy chain of SEQ ID NO: 50 and the light chain of SEQ ID NO:24, or the heavy chain of SEQ ID NO: 52 and the light chain of SEQ ID NO:24, or the heavy chain of SEQ ID NO: 54 and the light chain of SEQ ID NO:24, or the heavy chain of SEQ ID NO: 88 and the light chain of SEQ ID NO:24 or the heavy chain of SEQ ID NO: 89 and the light chain of SEQ ID NO:24, or the heavy chain of SEQ ID NO: 90 and the light chain of SEQ ID NO:24, or the heavy chain of SEQ ID NO: 91 and the light chain of SEQ ID NO:24, or the heavy chain of SEQ ID NO: 48 and the light chain of SEQ ID NO:108, or the heavy chain of SEQ ID NO: 50 and the light chain of SEQ ID NO:108, or the heavy chain of SEQ ID NO: 52 and the light chain of SEQ ID NO:108, or the heavy chain of SEQ ID NO: 54 and the light chain of SEQ ID NO:108, or the heavy chain of SEQ ID NO: 88 and the light chain of SEQ ID NO:108 or the heavy chain of SEQ ID NO: 89 and the light chain of SEQ ID NO:108, or the heavy chain of SEQ ID NO: 90 and the light chain of SEQ ID NO:108, or the heavy chain of SEQ ID NO: 91 and the light chain of SEQ ID NO:108, or the heavy chain of SEQ ID NO: 48 and the light chain of SEQ ID NO:110, or the heavy chain of SEQ ID NO: 50 and the light chain of SEQ ID NO:110, or the heavy chain of SEQ ID NO: 52 and the light chain of SEQ ID NO:110, or the heavy chain of SEQ ID NO: 54 and the light chain of SEQ ID NO:110, or the heavy chain of SEQ ID NO: 88 and the light chain of SEQ ID NO:110 or the heavy chain of SEQ ID NO: 89 and the light chain of SEQ ID NO:110, or the heavy chain of SEQ ID NO: 90 and the light chain of SEQ ID NO:110, or the heavy chain of SEQ ID NO: 91 and the light chain of SEQ ID NO:110.

In one such embodiment the antigen binding protein of the present invention comprises a heavy chain selected from SEQ ID NO: 48, SEQ ID NO: 50, SEQ ID NO: 52 and SEQ ID NO: 54; and a light chain selected from SEQ ID NO:108 and SEQ ID NO:110, for example the antigen binding protein comprises the heavy chain of SEQ ID NO: 48 and the light chain of SEQ ID NO:108, or the antigen binding protein comprises the heavy chain of SEQ ID NO: 48 and the light chain of SEQ ID NO:110, or the antigen binding protein comprises the heavy chain of SEQ ID NO: 50 and the light chain of SEQ ID NO:108, or the antigen binding protein comprises the heavy chain of SEQ ID NO: 50 and the light chain of SEQ ID NO:110, or the antigen binding protein comprises the heavy chain of SEQ ID NO: 52 and the light chain of SEQ ID NO:108, or the antigen binding protein comprises the heavy chain of SEQ ID NO: 52 and the light chain of SEQ ID NO:110, or the antigen binding protein comprises the heavy chain of SEQ ID NO: 54 and the light chain of SEQ ID NO:108, or the antigen binding protein comprises the heavy chain of SEQ ID NO: 54 and the light chain of SEQ ID NO:110.

The IL-13 antibodies of the present invention may be combined with an IL-4 and/or an IL-5 antagonist, for example an IL-4 antibody or epitope binding domain, and/or an IL-5 antibody or epitope binding domain. These may be administered as a mixture of separate molecules which are administered at the same time i.e. co-administered, or are administered within 24 hours of each other, for example within 20 hours, or within 15 hours or within 12 hours, or within 10 hours, or within 8 hours, or within 6 hours, or within 4 hours, or within 2 hours, or within 1 hour, or within 30 minutes of each other.

In a further embodiment the antagonists are present as one molecule capable of binding to two or more antigens, for example the invention provides an antigen binding protein comprising the IL-13 antibody of the present invention which is capable of binding to IL-13 and which is also capable of binding to IL-4 or which is also capable of binding to IL-5, or which is also capable of binding to IL-4 and IL-5.

In one embodiment the antigen binding protein of the present invention may be a multi-specific antibody which comprises at least CDRH3, and optionally one or more of CDRH1, CDRH2, CDRL1, CDRL2, and CDRL3 of the present invention, which is capable of binding to IL-13 and which is also capable of binding to one or more of IL-4 or IL-5. In one such embodiment, a multi-specific antibody is provided which comprises a CDRH3, or an antigen binding protein as defined herein, and which comprises a further antigen binding site which is capable of binding to IL-4, or IL-5.

One example of an antigen binding protein of the present invention is an antibody specific for IL-13 comprising CDRH1, CDRH2, CDRH3, CDRL1, CDRL2, and CDRL3 as defined herein, linked to one or more epitope-binding domains which have specificity for IL-4 or IL-5, for example a bispecific antigen binding protein which is capable of binding to IL-13 and IL-4, or IL-13 and IL-5, or a trispecific antigen binding protein which is capable of binding to IL-13, IL-4 and IL-5.

It will be understood that any of the antigen-binding proteins described herein may be capable of binding two or more antigens simultaneously, for example, as determined by stochiometry analysis by using a suitable assay such as that described in Example 8.

The present invention provides an antigen-binding protein comprising the IL-13 antibody of the present invention which is linked to one or more epitope-binding domains, for example an antigen-binding protein comprising the IL-13 antibody of the present invention linked to an epitope-binding domain which is capable of binding to IL-4, or an antigen-binding protein comprising the IL-13 antibody of the present invention linked to an epitope-binding domain which is capable of binding to IL-5, or an antigen-binding protein comprising the IL-13 antibody of the present invention linked to a first epitope-binding domain which is capable of binding to IL-4 and a second epitope-binding domain which is capable of binding to IL-5.

The epitope-binding domain may be attached to the c-terminus or the n-terminus of the heavy chain of the IL-13 antibody or the c-terminus or n-terminus of the light chain of the IL-13 antibody.

Antibodies of the present invention may be linked to epitope binding domains by the use of linkers. Examples of suitable linkers include amino acid sequences which may be from 1 amino acid to 150 amino acids in length, or from 1 amino acid to 140 amino acids, for example, from 1 amino acid to 130 amino acids, or from 1 to 120 amino acids, or from 1 to 80 amino acids, or from 1 to 50 amino acids, or from 1 to 20 amino acids, or from 1 to 10 amino acids, or from 5 to 18 amino acids. Such sequences may have their own tertiary structure, for example, a linker of the present invention may comprise a single variable domain. The size of a linker in one embodiment is equivalent to a single variable domain. Suitable linkers may be of a size from 1 to 20 angstroms, for example less than 15 angstroms, or less than 10 angstroms, or less than 5 angstroms.

In one embodiment of the present invention at least one of the epitope binding domains is directly attached to the IL-13 antibody with a linker comprising from 1 to 150 amino acids, for example 1 to 20 amino acids, for example 1 to 10 amino acids.

Such linkers may be selected from any one of those set out in SEQ ID NO:82-87, 92 to 93. or multiples of such linkers.

Linkers of use in the antigen-binding proteins of the present invention may comprise alone or in addition to other linkers, one or more sets of GS residues, for example 'GSTVAAPS' (SEQ ID NO: 92) or TVAAPSGS' (SEQ ID NO: 87) or 'GSTVAAPSGS' (SEQ ID NO: 93). In one embodiment the linker comprises SEQ ID NO: 83.

In one embodiment the epitope binding domain is linked to the IL-13 antibody by a linker having the amino acid sequence $(PAS)_n$ connected via its carboxy terminus to the amino terminus of the amino acid sequence $(GS)_m$ (e.g., '$(PAS)_n(GS)_m$'). In another embodiment the epitope binding domain is linked to the IL-13 antibody by a linker having the amino acid sequence (GGGGS (SEQ ID NO: 82)), connected via its carboxy terminus to the amino terminus of the amino acid sequence $(GS)_m$ (e.g., '$(GGGGS$ (SEQ ID NO: 82)$)_n$ $(GS)_m$'). In another embodiment the epitope binding domain is linked to the IL-13 antibody by a linker having the amino acid sequence (TVAAPS (SEQ ID NO: 83))$_n$ connected via its carboxy terminus to the amino terminus of the amino acid sequence $(GS)_m$ (e.g., '(TVAAPS (SEQ ID NO: 83))$_n$ $(GS)_m$'). In another embodiment the epitope binding domain is linked to the IL-13 antibody by a linker having the amino acid sequence $(GS)_m$, connected via its carboxy terminus to the amino terminus of the amino acid sequence (TVAAPSGS (SEQ ID NO: 87))$_n$ (e.g., '$(GS)_m$(TVAAPSGS (SEQ ID NO: 87))$_n$'). In another embodiment the epitope binding domain is linked to the IL-13 antibody by a linker having the amino acid sequence (PAVPPP (SEQ ID NO: 148))$_n$ connected via its carboxy terminus to the amino terminus of the amino acid sequence $(GS)_m$ (e.g., '(PAVPPP (SEQ ID NO: 148)$_n$(GS)$_m$'). In another embodiment the epitope binding domain is linked to the IL-13 antibody by a linker having the amino acid sequence (TVSDVP (SEQ ID NO: 149))$_n$ connected via its carboxy terminus to the amino terminus of the amino acid sequence $(GS)_m$ (e.g., '(TVSDVP (SEQ ID NO: 149)$_n$ $(GS)_m$'). In another embodiment the epitope binding domain is linked to the IL-13 antibody by a linker having the amino acid sequence (TGLDSP (SEQ ID NO: 150))$_n$ connected via its carboxy terminus to the amino terminus of the amino acid sequence $(GS)_m$ (e.g., '(TGLDSP (SEQ ID NO: 150))$_n$ $(GS)_m$'). In all such embodiments, n=1-10, and m 0-4.

Examples of such linkers include (PAS)$_n$(GS)$_m$ wherein n=1 and m=1 (i.e., PASGS (SEQ ID NO: 151)), (PAS)$_n$(GS)$_m$, wherein n=2 and m=1 (i.e., PASPASGS (SEQ ID NO: 152)), (PAS)$_n$(GS)$_m$ wherein n=3 and m=1 (i.e., PASPASPASGS (SEQ ID NO: 153)), (PAS)$_n$(GS)$_m$ wherein n=4 and m=1 (i.e., PASPASPASPASGS (SEQ ID NO: 154)), (PAS)$_n$(GS)$_m$ wherein n=2 and m=0 PASPAS (SEQ ID NO: 155)), (PAS)$_n$(GS)$_m$ wherein n=3 and m=0 (i.e., PASPASPAS (SEQ ID NO: 156)), (PAS)$_n$(GS)$_m$ wherein n=4 and m=0 (i.e., PASPASPASPAS (SEQ ID NO: 157)).

Examples of such linkers include (GGGGS (SEQ ID NO: 82))$_n$(GS)$_m$ wherein n=1 and m=1 (i.e., GGGGSGS (SEQ ID NO: 158)), (GGGGS (SEQ ID NO: 82))$_n$(GS)$_m$ wherein n=2 and m=1 (i.e., GGGGSGGGGSGS (SEQ ID NO: 159)), (GGGGS (SEQ ID NO: 82))$_n$(GS)$_m$ wherein n=3 and m=1 (i.e., GGGGSGGGGSGGGGSGS (SEQ ID NO: 160)), (GGGGS (SEQ ID NO: 82))$_n$(GS)$_m$ wherein n=4 and m=1 (i.e., GGGGSGGGGSGGGGSGGGGSGS (SEQ ID NO: 161)), (GGGGS (SEQ ID NO: 82))$_n$(GS)$_m$ wherein n=2 and m=0 (i.e., GGGGSGGGGS (SEQ ID NO: 162)), (GGGGS (SEQ ID NO: 82))$_n$(GS)$_m$ wherein n=3 and m=0 (i.e., GGGGSGGGGSGGGGS (SEQ ID NO: 163)), (GGGGS (SEQ ID NO: 82))$_n$(GS)$_m$ wherein n=4 and m=0 (i.e., GGGGSGGGGSGGGGSGGGGS (SEQ ID NO: 164)).

Examples of such linkers include (TVAAPS (SEQ ID NO: 83))$_n$(GS)$_m$ wherein n=1 and m=1 (TVAAPSGS (SEQ ID NO:87)), (TVAAPS (SEQ ID NO: 83))$_n$(GS)$_m$ wherein n=2 and m=1 TVAAPSTVAAPSGS (SEQ ID NO:145)), (TVAAPS (SEQ ID NO: 83))$_n$(GS)$_m$ wherein n=3 and m=1 (i.e., TVAAPSTVAAPSTVAAPSGS (SEQ ID NO:146)), (TVAAPS (SEQ ID NO: 83))$_n$(GS)$_m$ wherein n=4 and m=1 (i.e., TVAAPSTVAAPSTVAAPSTVAAPSGS (SEQ ID NO: 165)), (TVAAPS (SEQ ID NO: 83))$_n$(GS)$_m$ wherein n=2 and m=0 (i.e., TVAAPSTVAAPS (SEQ ID NO: 166)), (TVAAPS (SEQ ID NO: 83))$_n$(GS)$_m$ wherein n=3 and m=0 (i.e., TVAAPSTVAAPSTVAAPS (SEQ ID NO: 167)), (TVAAPS (SEQ ID NO: 83))$_n$(GS)$_m$ wherein n=4 and m=0 (i.e., TVAAPSTVAAPSTVAAPSTVAAPS (SEQ ID NO: 168)).

Examples of such linkers include (GS)$_m$(TVAAPSGS (SEQ ID NO: 87))$_n$ wherein n=1 and m=1 (i.e., GSTVAAPSGS (SEQ ID NO:139)), (GS)$_m$(TVAAPSGS (SEQ ID NO: 87))$_n$ wherein n=2 and m=1 (i.e., GSTVAAPSGSTVAAPSGS (SEQ ID NO:140)), (GS)$_m$(TVAAPSGS (SEQ ID NO: 87))$_n$ wherein n=3 and m=1 (i.e., GSTVAAPSGSTVAAPSGSTVAAPSGS (SEQ ID NO:141)), or (GS)$_m$(TVAAPSGS (SEQ ID NO: 87))$_n$ wherein n=4 and m=1 (i.e., GSTVAAPSGSTVAAPSGSTVAAPSGSTVAAPSGS (SEQ ID NO:142)), (GS)$_m$(TVAAPSGS (SEQ ID NO: 87))$_n$ wherein n=5 and m=1 (i.e., GSTVAAPSGSTVAAPSGSTVAAPSGSTVAAPSGSTVAAPSGS (SEQ ID NO:143)), (GS)$_m$(TVAAPSGS (SEQ ID NO: 87))$_n$ wherein n=6 and m=1 (i.e., GSTVAAPSGSTVAAPSGSTVAAPSGSTVAAPSGSTVAAPSGSTVAAPSGS (SEQ ID NO:144)), (GS)$_m$(TVAAPSGS (SEC) ID NO: 87))$_n$ wherein n=1 and m=0 (i.e., TVAAPSGS (SEQ ID NO:87)), (GS)$_m$(TVAAPSGS (SEQ ID NO: 87))$_n$ wherein n=2 and m=10 (i.e., GSGSGSGSGSGSGSGSGSGSTVAAPSGSTVAAPSGS (SEQ ID NO: 169)), (GS)$_m$(TVAAPSGS (SEQ ID NO: 87)), wherein n=3 and m=0 (i.e., TVAAPSGSTVAAPSGSTVAAPSGS (SEQ ID NO: 170)), or (GS)$_m$(TVAAPSGS (SEQ ID NO: 87))$_n$ wherein n=0.

Examples of such linkers include (PAVPPP (SEQ ID NO: 148))$_n$(GS)$_m$ wherein n=1 and m=1 (i.e., PAVPPPGS (SEQ ID NO: 171), (PAVPPP (SEQ ID NO: 148))$_n$(GS)$_m$ wherein n=2 and m=1 (i.e., PAVPPPPAVPPPGS (SEQ ID NO: 191)), (PAVPPP (SEQ ID NO: 148))$_n$(GS)$_m$ wherein n=3 and m=1 (i.e., PAVPPPPAVPPPPAVPPPGS (SEQ ID NO: 172)), (PAVPPP (SEQ ID NO: 148))$_n$(GS)$_m$ wherein n=4 and m=1 (i.e., PAVPPPPAVPPPPAVPPPPAVPPPGS (SEQ ID NO: 173)), (PAVPPP (SEQ ID NO: 148))$_n$(GS)$_m$ wherein n=2 and m=0 (i.e., PAVPPPPAVPPP (SEQ ID NO: 174)), (PAVPPP (SEQ ID NO: 148))$_n$(GS)$_m$ wherein n=3 and m=0 (i.e., PAVPPPPAVPPPPAVPPP (SEQ ID NO: 175)), (PAVPPP (SEQ ID NO: 148))$_n$(GS)$_m$ wherein n=4 and m=0 (i.e., PAVPPPPAVPPPPAVPPPPAVPPP (SEQ ID NO: 176)).

Examples of such linkers include (TVSDVP (SEQ ID NO: 149))$_n$(GS)$_m$ wherein n=1 and m=1 (i.e., TVSDVPGS (SEQ ID NO: 177)), (TVSDVP (SEQ ID NO: 149))$_n$(GS)$_m$ wherein n=2 and m=1 (i.e., TVSDVPTVSDVPGS (SEQ ID NO: 178)), (TVSDVP (SEQ ID NO: 149))$_n$(GS)$_m$ wherein n=3 and m=1 (i.e., TVSDVPTVSDVPTVSDVPGS (SEQ ID NO: 179)), (TVSDVP (SEQ ID NO: 149))$_n$(GS)$_m$ wherein n=4 and m=1 (i.e., TVSDVPTVSDVPTVSDVPTVSDVPGS (SEQ ID NO: 180)), (TVSDVP (SEQ ID NO: 149))$_n$(GS)$_m$ wherein n=2 and m=0 (i.e., TVSDVPTVSDVP (SEQ ID NO: 181)), (TVSDVP (SEQ 0 NO: 149))$_n$(GS)$_m$ wherein n=3 and m=0 (i.e., TVSDVPTVSDVPTVSDVP (SEQ ID NO: 182)), (TVSDVP (SEQ ID NO: 149))$_n$(GS)$_m$ wherein n=4 and m=0 (i.e., TVSDVPTVSDVPTVSDVPTVSDVP (SEQ ID NO: 183)).

Examples of such linkers include (TGLDSP (SEQ ID NO: 150))$_n$(GS)$_m$ wherein n=1 and m=1 (i.e., TGLDSPGS (SEQ ID NO: 184)), (TGLDSP (SEC) ID NO: 150))$_n$(GS)$_m$ wherein n=2 and m=1 (i.e., TGLDSPTGLDSPGS (SEQ ID NO: 185)), (TGLDSP (SEQ ID NO: 150))$_n$(GS)$_m$ wherein n=3 and m=1 (i.e., TGLDSPTGLDSPTGLDSPGS (SEQ ID NO: 186)), (TGLDSP (SEQ ID NO: 150))$_n$(GS)$_m$ wherein n=4 and m=1 (i.e., TGLDSPTGLDSPTGLDSPTGLDSPGS (SEQ ID NO: 187)), (TGLDSP (SEQ ID NO: 150))$_n$(GS)$_m$ wherein n=2 and m=0 (i.e., TGLDSPTGLDSP (SEQ ID NO: 188)), (TGLDSP (SEQ ID NO: 150))$_n$(GS)$_m$ wherein n=3 and m=0 (i.e., TGLDSPTGLDSPTGLDSP (SEQ ID NO: 189)), (TGLDSP (SEQ ID NO: 150))$_n$(GS)$_m$ wherein n=4 and m=0 TGLDSPTGLDSPTGLDSPTGLDSP (SEQ ID NO: 190)).

In another embodiment there is no linker between the epitope binding domain and the IL-13 antibody. In another embodiment the epitope binding domain is linked to the IL-13 antibody by the linker TVAAPS' (SEQ ID NO: 83). In another embodiment the epitope binding domain, is linked to the IL-13 antibody by the linker TVAAPSGS' (SEQ ID NO: 87). In another embodiment the epitope binding domain is linked to the IL-13 antibody by the linker 'GS'. In another embodiment the epitope binding domain is linked to the IL-13 antibody by the linker 'ASTKGPT' (SEQ ID NO: 84).

Epitope-binding domains of use in the present invention are domains that specifically bind an antigen or epitope independently of a different V region or domain, this may be a domain antibody or may be a non-Immunoglobulin domain, for example a domain which is a derivative of a scaffold selected from the group consisting of CTLA-4 (EVIBODY™); lipocalin; Protein A derived molecules such as Z-domain of Protein A (AFFIBODY™, SpA), A-domain (Avimer/MAXIBODY™); Heat shock proteins such as GroEI and GroES; transferrin (TRANS-BODY™); ankyrin repeat protein (DARPin); peptide aptamer; C-type lectin domain (Tetranectin); human γ-crystallin and human ubiquitin (AFFILINS™); PDZ domains; scorpion toxinkunitz type domains of human protease inhibitors; and fibronectin (adnectin); which has been subjected to protein engineering in order to obtain binding to a ligand other than the natural ligand. In one embodiment this may be an domain antibody or other suitable domains such as a domain selected from the group consisting of CTLA-4, lipocallin, SpA, an AFFI- BODY™, an avimer, GroEI, transferrin, GroES and fibronectin. In one embodiment this may be selected from an immunoglobulin single variable domain, an AFFIBODY™, an ankyrin repeat protein (DARPin) and an adnectin. In another embodiment this may be selected from an AFFIBODY™, an ankyrin repeat protein (DARPin) and an adnectin. In another embodiment this may be a domain antibody, for example a domain antibody selected from a human, camelid (NANOBODY™), or shark (NARV) domain antibody.

Examples of such antigen-binding proteins include the IL-13 antibodies of the present invention which have an epitope binding domain which is an IL-4 antagonist attached to the c-terminus or the n-terminus of the heavy chain or the c-terminus. Examples include an antigen binding protein comprising the heavy chain sequence set out in SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 98, SEQ ID NO: 100, SEQ ID NO:102, SEQ ID NO:104, SEQ ID NO:106 or SEQ ID NO: 117-138, and the light chain sequence set out in SEQ ID NO: 24, SEQ ID NO: 108, SEQ ID NO: 110, SEQ ID NO: 112 or SEQ ID NO: 114, wherein one or both of the Heavy and Light chain further comprise one or more epitope-binding domains which is capable of antagonising IL-4, for example single variable domains which are capable of binding to IL-4. Such epitope-binding domains can be selected from those set out in SEQ ID NO: 78-81 and 94.

In one embodiment the antigen binding constructs of the present invention comprise the heavy chain sequence of SEQ ID NO: 62 and the light chain sequence of SEQ ID NO: 24, or the heavy chain sequence of SEQ ID NO: 64 and the light chain sequence of SEQ ID NO: 24, or the heavy chain sequence of SEQ ID NO: 66 and the light chain sequence of SEQ ID NO: 24, or the heavy chain sequence of SEQ ID NO: 68 and the light chain sequence of SEQ ID NO: 24, or the heavy chain sequence of SEQ ID NO: 70 and the light chain sequence of SEQ ID NO: 24, or the heavy chain sequence of SEQ ID NO: 72 and the light chain sequence of SEQ ID NO: 24, or the heavy chain sequence of SEQ ID NO:74 and the light chain sequence of SEQ ID NO: 24, or the heavy chain sequence of SEQ ID NO: 76 and the light chain sequence of SEQ ID NO: 24.

In one embodiment the antigen binding constructs of the present invention comprise the heavy chain sequence of SEQ ID NO: 94 and the light chain sequence of SEQ ID NO: 24, or the heavy chain sequence of SEQ ID NO: 96 and the light chain sequence of SEQ ID NO: 24, or the heavy chain sequence of SEQ ID NO: 98 and the light chain sequence of SEQ ID NO: 24, or the heavy chain sequence of SEQ ID NO: 100 and the light chain sequence of SEQ ID NO: 24, or the heavy chain sequence of SEQ ID NO: 102 and the light chain sequence of SEQ ID NO: 24, or the heavy chain sequence of SEQ ID NO: 104 and the light chain sequence of SEQ ID NO: 24, or the heavy chain sequence of SEQ ID NO:106 and the light chain sequence of SEQ ID NO: 24.

In one embodiment the antigen binding constructs of the present invention comprise the heavy chain sequence of SEQ ID NO: 62 and the light chain sequence of SEQ ID NO: 108, or the heavy chain sequence of SEQ ID NO: 64 and the light chain sequence of SEQ ID NO: 108, or the heavy chain sequence of SEQ ID NO: 66 and the light chain sequence of SEQ ID NO: 108, or the heavy chain sequence of SEQ ID NO: 68 and the light chain sequence of SEQ ID NO: 108, or the heavy chain sequence of SEQ ID NO: 70 and the light chain sequence of SEQ ID NO: 108, or the heavy chain sequence of SEQ ID NO: 72 and the light chain sequence of SEQ ID NO: 108, or the heavy chain sequence of SEQ ID NO:74 and the light chain sequence of SEQ ID NO: 108, or the heavy chain sequence of SEQ ID NO: 76 and the light chain sequence of SEQ ID NO: 108, or the heavy chain sequence of SEQ ID NO: 62 and the light chain sequence of SEQ ID NO: 110, or the heavy chain sequence of SEQ ID NO: 64 and the light chain sequence of SEQ ID NO: 110, or the heavy chain sequence of SEQ ID NO: 66 and the light chain sequence of SEQ ID NO: 110, or the heavy chain sequence of SEQ ID NO: 68 and the light chain sequence of SEQ ID NO: 110, or the heavy chain sequence of SEQ ID NO: 70 and the light chain sequence of SEQ ID NO: 110, or the heavy chain sequence of SEQ ID NO: 72 and the light chain sequence of SEQ ID NO: 110, or the heavy chain sequence of SEQ ID NO:74 and the light chain sequence of SEQ ID NO: 110, or the heavy chain sequence of SEQ ID NO: 76 and the light chain sequence of SEQ ID NO: 110.

In one embodiment the antigen binding constructs of the present invention comprise the heavy chain sequence of SEQ ID NO: 96 and the light chain sequence of SEQ ID NO: 108, or the heavy chain sequence of SEQ ID NO: 98 and the light chain sequence of SEQ ID NO: 108, or the heavy chain sequence of SEQ ID NO: 100 and the light chain sequence of SEQ ID NO: 108, or the heavy chain sequence of SEQ ID NO: 102 and the light chain sequence of SEQ ID NO: 108, or the heavy chain sequence of SEQ ID NO: 104 and the light chain sequence of SEQ ID NO: 108, or the heavy chain sequence of SEQ ID NO: 106 and the light chain sequence of SEQ ID NO: 108, or the heavy chain sequence of SEQ ID NO: 96 and the light chain sequence of SEQ ID NO: 110, or the heavy chain sequence of SEQ ID NO: 98 and the light chain sequence of SEQ ID NO: 110, or the heavy chain sequence of SEQ ID NO: 100 and the light chain sequence of SEQ ID NO: 110, or the heavy chain sequence of SEQ ID NO: 102 and the light chain sequence of SEQ ID NO: 110, or the heavy chain sequence of SEQ ID NO: 104 and the light chain sequence of SEQ ID NO: 110, or the heavy chain sequence of SEQ ID NO: 106 and the light chain sequence of SEQ ID NO: 110.

In one embodiment the IL-13 antibody heavy chain is selected from those set out in SEQ ID NO: 48, SEQ ID NO: 50, SEQ ID NO: 52 and SEQ ID NO: 54. In another embodiment the heavy chain is selected from those set out in SEQ ID NO:88-91, SEQ ID NO:96-106, and SEQ ID NO:117-138. In one such embodiment the heavy chain is selected from SEQ ID NO:96, SEQ ID NO: 98, SEQ ID NO:100, SEQ ID NO:102, SEQ ID NO:104 and SEQ ID NO:106.

In one embodiment the antigen-binding protein will comprise an anti-IL-13 antibody linked to an epitope binding domain which is a IL-5 antagonist, wherein the anti-IL-13 antibody comprises the CDRH3 selected from those set out in SEQ ID NO: 3-18, for example SEQ ID NO: 15-18 and the light chain sequence of SEQ ID NO: 24.

Examples include an antigen binding protein comprising the heavy chain sequence set out in SEQ ID NO: 26, 28, 30, 32, 34, 36, 38, 40, 42, 44, 46, 48, 50, 52 or 54 and the light chain sequence set out in SEQ ID NO: 24 wherein one or both of the Heavy and Light chain further comprise one or more epitope-binding domains which is capable of antagonising IL-5, for example immunoglobulin single variable domains which are capable of binding to IL-5.

In a further embodiment, the antigen binding protein will comprise the heavy chain sequence set out in SEQ ID NO: 26, 28, 30, 32, 34, 36, 38, 40, 42, 44, 46, 48, 50, 52 or 54 and the light chain sequence set out in SEQ ID NO: 24 wherein one or both of the Heavy and Light chain further comprise one or more epitope-binding domains which are capable of antagonising IL-4 for example immunoglobulin single variable domains which are capable of binding to IL-4, and one or more epitope-binding domains which are capable of antagonising IL-5, for example immunoglobulin single variable domains which are capable of binding to IL-5.

In one embodiment, the antigen-binding protein of the present invention comprises at least one epitope binding domain, which is capable of binding human serum albumin.

In one embodiment, there are at least 3 antigen-binding sites, for example there are 4, or 5 or 6 or 8 or 10 antigen-binding sites and the antigen-binding protein is capable of binding at least 3 or 4 or 5 or 6 or 8 or 10 antigens, for example it is capable of binding 3 or 4 or 5 or 6 or 8 or 10 antigens simultaneously.

In one embodiment, a first epitope binding domain is linked to the protein scaffold and a second epitope binding domain is linked to the first epitope binding domain, for example where the protein scaffold is an IgG scaffold, a first epitope binding domain may be linked to the c-terminus of the heavy chain of the IgG scaffold, and that epitope binding domain can be linked at its c-terminus to a second epitope binding domain, or for example a first epitope binding domain may be linked to the c-terminus of the light chain of the IgG scaffold, and that first epitope binding domain may be further linked at its c-terminus to a second epitope binding domain, or for example a first epitope binding domain may be linked to the n-terminus of the light chain of the IgG scaffold, and that first epitope binding domain may be further linked at its n-terminus to a second epitope binding domain, or for example a first epitope binding domain may be linked to the n-terminus of the heavy chain of the IgG scaffold, and that first epitope binding domain may be further linked at its n-terminus to a second epitope binding domain.

When the epitope-binding domain is a domain antibody, some domain antibodies may be suited to particular positions within the scaffold.

Immunoglobulin single variable domains of use in the present invention can be linked at the C-terminal end of the heavy chain and/or the light chain of the IL-13 mAb. In addition some immunoglobulin single variable domains can be linked to the C-terminal ends of both the heavy chain and the light chain of conventional antibodies.

In constructs where the N-terminus of immunoglobulin single variable domains are fused to an antibody constant domain (either $C_H3$ or CL), a peptide linker may help the immunoglobulin single variable domain to bind to antigen. Indeed, the N-terminal end of a dAb™ is located closely to the CDRs involved in antigen-binding activity. Thus a short peptide linker acts as a spacer between the epitope-binding domain, and the constant domain of the antibody, which may allow the dAb™ CDRs to more easily reach the antigen, which may therefore bind with high affinity.

The surroundings in which immunoglobulin single variable domains are linked to the IgG will differ depending on which antibody chain they are fused to:

When fused at the C-terminal end of the antibody light chain, each immunoglobulin single variable domain is expected to be located in the vicinity of the antibody hinge and the Fc portion. It is likely that such immunoglobulin single variable domains will be located far apart from each other. In conventional antibodies, the angle between Fab fragments and the angle between each Fab fragment and the Fc portion can vary quite significantly. It is likely that—with mAb-domain antibodies—the angle between the Fab fragments will not be widely different, whilst some angular restrictions may be observed with the angle between each Fab fragment and the Fc portion.

When fused at the C-terminal end of the antibody heavy chain, each immunoglobulin single variable domain is expected to be located in the vicinity of the $C_H3$ domains of the Fc portion. This is not expected to impact on the Fc binding properties to Fc receptors (e.g. FcγRI, II, III an FcRn) as these receptors engage with the $C_H2$ domains (for the FcγRI, II and III class of receptors) or with the hinge between the $C_H2$ and $C_H3$ domains (e.g. FcRn receptor). Another feature of such antigen-binding proteins is that both immunoglobulin single variable domains are expected to be spatially close to each other and provided that flexibility is provided by provision of appropriate linkers, these immunoglobulin single variable domains may even form homodimeric species, hence propagating the 'zipped' quaternary structure of the Fc portion, which may enhance stability of the construct.

Such structural considerations can aid in the choice of the most suitable position to link an epitope-binding domain, for example an immunoglobulin single variable domain, on to an antibody.

The size of the antigen, its localization (in blood or on cell surface), its quaternary structure (monomeric or multimeric) can vary. Conventional antibodies are naturally designed to function as adaptor constructs due to the presence of the hinge region, wherein the orientation of the two antigen-binding sites at the tip of the Fab fragments can vary widely and hence adapt to the molecular feature of the antigen and its surroundings. In contrast immunoglobulin single variable domains linked to an antibody with no hinge region, may have less structural flexibility either directly or indirectly.

Understanding the solution state and mode of binding at the immunoglobulin single variable domain is also helpful. Evidence has accumulated that in vitro human dAb™s can predominantly exist in monomeric, homo-dimeric or multimeric forms in solution (Reiter et al. (1999) J Mol Biol 290 p685-698; Ewert et al (2003) J Mol Biol 325, p531-553, Jespers et al (2004) J Mol Biol 337 p893-903; Jespers et al (2004) Nat Biotechnol 22 p1161-1165; Martin et al (1997) Protein Eng. 10 p607-614; Sepulvada et al (2003) J Mol Biol 333 p355-365). This is fairly reminiscent to multimerisation events observed in vivo with Ig domains such as Bence-Jones proteins (which are dimers of immunoglobulin light chains (Epp et al (1975) Biochemistry 14 p4943-4952; Huan et al (1994) Biochemistry 33 p14848-14857; Huang et al (1997) Mol immunol 34 p1291-1301) and amyloid fibers (James et al. (2007) *J Mol. Biol.* 367:603-8).

For example, it may be desirable to link dAb™s that tend to dimerise in solution to the C-terminal end of the Fc portion in preference to the C-terminal end of the light chain as linking to the C-terminal end of the Fc will allow those dAb™s to dimerise in the context of the antigen-binding protein of the invention.

The antigen-binding proteins of the present invention may comprise antigen-binding sites specific for a single antigen, or may have antigen-binding sites specific for two or more antigens, or for two or more epitopes on a single antigen, or there may be antigen-binding sites each of which is specific for a different epitope on the same or different antigens.

The antigen binding proteins of the invention may comprise heavy chain variable regions and light chain variable regions of the invention which may be formatted into the structure of a natural antibody or functional fragment or equivalent thereof. An antigen binding protein of the invention may therefore comprise the VH regions of the invention formatted into a full length antibody, a (Fab')₂ fragment, a Fab fragment, or equivalent thereof (such as scFV, bi- tri- or tetra-bodies, TANDABS™ etc.), when paired with an appropriate light chain. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antigen binding protein may comprise modifications of all classes e.g. IgG dimers, Fc mutants that no longer bind Fc receptors or mediate C1q binding. The antigen binding protein may also be a chimeric antibody of the type described in WO86/01533 which comprises an antigen binding region and a non-immunoglobulin region.

The constant region is selected according to any functionality required. An IgG1 may demonstrate lytic ability through binding to complement and/or will mediate ADCC (antibody dependent cell cytotoxicity). An IgG4 can be used if a non-cytotoxic blocking antibody is required. However, IgG4 antibodies can demonstrate instability in production and therefore an alternative is to modify the generally more stable IgG1. Suggested modifications are described in EP0307434, for example mutations at positions 235 and 237. The invention therefore provides a lytic or a non-lytic form of an antigen binding protein, for example an antibody according to the invention.

In certain forms the antibody of the invention is a full length (e.g. H2L2 tetramer) lytic or non-lytic IgG1 antibody having any of the heavy chain variable regions described herein. In a further aspect, the invention provides polynucleotides encoding the light and heavy chain variable regions as described herein.

In one embodiment of the invention the antigen-binding site binds to antigen with a Kd of at least about 1 mM, for example a Kd of at least about 10 nM, at least about 1 nM, at least about 500 µM, at least about 200 µM, at least about 100 µM, or at least about 50 µM to each antigen as measured by BIAcore™.

In one embodiment of the invention the antigen-binding site binds to antigen with a Kd of at least about 1 mM, for example a Kd of at least about 10 nM, at least about 1 nM, at least about 500 µM, at least about 200 µM, at least about 100 µM, or at least about 50 µM to each antigen as measured by BIAcore™.

In one embodiment the invention provides antigen binding proteins which have at least a 2 fold higher affinity, or at least 4 fold higher affinity, or at least 6 fold higher affinity, or at least 8 fold higher affinity, or at least 10 fold higher affinity for human IL-13 as measured by BIAcore™ than the anti-IL-13 antibody comprising the heavy chain sequence set out in SEQ ID NO:22 and the light chain sequence set out in SEQ ID NO:24.

The term "neutralises" and grammatical variations thereof as used throughout the present specification in relation to antigen binding proteins of the invention means that a biological activity of IL-13 is reduced, either totally or partially, in the presence of the antigen binding proteins of the present invention in comparison to the activity of IL-13 in the absence of such antigen binding proteins. Neutralisation may be due to but not limited to one or more of blocking ligand binding, preventing the ligand activating the receptor, down regulating the IL-13 receptor or affecting effector functionality. Levels of neutralisation can be measured in several ways, for example by use of the assays as set out in the examples below, for example in a TF1 assay which may be carried out for example as described in Example 4. The neutralisation of IL-13, IL-4 or both of these cytokines in this assay is measured by assessing the inhibition of TF1 cell proliferation in the presence of neutralising antigen binding protein.

Other methods of assessing neutralisation, for example, by assessing the decreased binding between the IL-13 and its receptor in the presence of neutralising antigen binding protein are known in the art, and include, for example, BIAcore™ assays.

In an alternative aspect of the present invention there is provided antigen binding proteins which have at least substantially equivalent neutralising activity to the antibodies exemplified herein, for example antigen binding proteins which retain the neutralising activity of A1Y100BAlaL1, A1Y100BIleL1, A1 Y100BTrpL1 or A1Y100BValL1 in a TF1 cell proliferation assay which can be carried out as set out in Example 4.

The antigen binding proteins, for example antibodies of the present invention may be produced by transfection of a host cell with an expression vector comprising the coding sequence for the antigen binding protein of the invention. An expression vector or recombinant plasmid is produced by placing these coding sequences for the antigen binding protein in operative association with conventional regulatory control sequences capable of controlling the replication and expression in, and/or secretion from, a host cell. Regulatory sequences include promoter sequences, e.g., CMV promoter, and signal sequences which can be derived from other known antibodies. Similarly, a second expression vector can be produced having a DNA sequence which encodes a complementary antigen binding protein light or heavy chain. In certain embodiments this second expression vector is identical to the first except insofar as the coding sequences and selectable markers are concerned, so to ensure as far as possible that each polypeptide chain is functionally expressed. Alternatively, the heavy and light chain coding sequences for the antigen binding protein may reside on a single vector. A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antigen binding protein of the invention. The antigen binding protein which includes the association of both the recombinant heavy chain and/or light chain is screened from culture by appropriate assay, such as ELISA or RIA. Similar conventional techniques may be employed to construct other antigen binding proteins.

Suitable vectors for the cloning and subcloning steps employed in the methods and construction of the compositions of this invention may be selected by one of skill in the art. For example, the conventional pUC series of cloning vectors may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

The expression vectors may also be characterized by genes suitable for amplifying expression of the heterologous DNA sequences, e.g., the mammalian dihydrofolate reductase gene (DHFR). Other vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antigen binding proteins of the present invention. Host cells useful for the cloning and other manipulations of these cloning vectors are also conventional. However, cells from various strains of E. coli may be used for replication of the cloning vectors and other steps in the construction of antigen binding proteins of this invention.

Suitable host cells or cell lines for the expression of the antigen binding proteins of the invention include mammalian cells such as NS0, Sp2/0, CHO (e.g. DG44), COS, HEK, a fibroblast cell (e.g., 3T3), and myeloma cells, for example it may be expressed in a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs or other embodiments of the present invention (see, e.g., Plückthun, A., Immunol. Rev., 130:151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host, or in alternative embodiments the molecule may express in the bacterial host and then be subsequently re-folded. For example, various strains of E. coli used for expression are well-known as host cells in the field of biotechnology. Various strains of B. subtilis, Streptomyces, other bacilli and the like may also be employed in this method.

Where desired, strains of yeast cells known to those skilled in the art are also available as host cells, as well as insect cells, e.g. Drosophila and Lepidoptera and viral expression systems. See, e.g. Miller et al., Genetic Engineering, 8:277-298, Plenum Press (1986) and references cited therein.

The general methods by which the vectors may be constructed, the transfection methods required to produce the host cells of the invention, and culture methods necessary to produce the antigen binding protein of the invention from such host cell may all be conventional techniques. Typically, the culture method of the present invention is a serum-free culture method, usually by culturing cells serum-free in suspension. Likewise, once produced, the antigen binding proteins of the invention may be purified from the cell culture contents according to standard procedures of the art, including ammonium sulfate precipitation, affinity columns, column chromatography, gel electrophoresis and the like. Such techniques are within the skill of the art and do not limit this invention. For example, preparation of altered antibodies are described in WO 99/58679 and WO 96/16990.

Yet another method of expression of the antigen binding proteins may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

In a further aspect of the invention there is provided a method of producing an antibody of the invention which method comprises the step of culturing a host cell transformed or transfected with a vector encoding the light and/or heavy chain of the antibody of the invention and recovering the antibody thereby produced.

In accordance with the present invention there is provided a method of producing an anti-IL-13 antibody of the present invention which binds to and neutralises the activity of human IL-13 which method comprises the steps of;

(a) providing a first vector encoding a heavy chain of the antibody;
(b) providing a second vector encoding a light chain of the antibody;
(c) transforming a mammalian host cell (e.g. CHO) with said first and second vectors;
(d) culturing the host cell of step (c) under conditions conducive to the secretion of the antibody from said host cell into said culture media;
(e) recovering the secreted antibody of step (d).

Once expressed by the desired method, the antibody is then examined for in vitro activity by use of an appropriate assay. Presently conventional ELISA assay formats are employed to assess qualitative and quantitative binding of the antibody to IL-13. Additionally, other in vitro assays may also be used to verify neutralizing efficacy prior to subsequent human clinical studies performed to evaluate the persistence of the antibody in the body despite the usual clearance mechanisms.

The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks) over an extended time period (e.g. four to six months) maybe required to achieve maximal therapeutic efficacy.

The mode of administration of the therapeutic agent of the invention may be any suitable route which delivers the agent to the host. The antigen binding proteins, and pharmaceutical compositions of the invention are particularly useful for parenteral administration, i.e., subcutaneously (s.c.), intrathecally, intraperitoneally, intramuscularly (i.m.), intravenously (i.v.), or intranasally.

Therapeutic agents of the invention may be prepared as pharmaceutical compositions containing an effective amount of the antigen binding protein of the invention as an active ingredient in a pharmaceutically acceptable carrier. In one embodiment the prophylactic agent of the invention is an aqueous suspension or solution containing the antigen binding protein in a form ready for injection. In one embodiment the suspension or solution is buffered at physiological pH, In one embodiment the compositions for parenteral administration will comprise a solution of the antigen binding protein of the invention or a cocktail thereof dissolved in a pharmaceutically acceptable carrier. In one embodiment the carrier is an aqueous carrier. A variety of aqueous carriers may be employed, e.g., 0.9% saline, 0.3% glycine, and the like. These solutions may be made sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc.

The concentration of the antigen binding protein of the invention in such pharmaceutical formulation can vary widely, i.e., from less than about 0.5%, usually at or at least about 1% to as much as about 15 or 20% by weight and will be selected primarily based on fluid volumes, viscosities, etc., according to the particular mode of administration selected.

Thus, a pharmaceutical composition of the invention for intramuscular injection could be prepared to contain about 1 mL sterile buffered water, and between about 1 ng to about 100 mg, e.g. about 50 ng to about 30 mg or about 5 mg to about 25 mg, of an antigen binding protein, for example an antibody of the invention. Similarly, a pharmaceutical composition of the invention for intravenous infusion could be made up to contain about 250 ml of sterile Ringer's solution, and about 1 to about 30 or 5 mg to about 25 mg of an antigen binding protein of the invention per ml of Ringer's solution. Actual methods for preparing parenterally administrable compositions are well known or will be apparent to those skilled in the art and are described in more detail in, for example, Remington's Pharmaceutical Science, 15th ed., Mack Publishing Company, Easton, Pa. For the preparation of intravenously administrable antigen binding protein formulations of the invention see Lasmar U and Parkins D "The formulation of Biopharmaceutical products", Pharma. Sci. Tech. today, page 129-137, Vol. 3 ($3^{rd}$ April 2000); Wang, W "Instability, stabilisation and formulation of liquid protein pharmaceuticals", Int. J. Pharm 185 (1999) 129-188; Stability of Protein Pharmaceuticals Part A and B ed Ahern T. J., Manning M. C., New York, N.Y.: Plenum Press (1992); Akers, M. J. "Excipient-Drug interactions in Parenteral Formulations", J. Pharm Sci 91 (2002) 2283-2300; Imamura, K et al "Effects of types of sugar on stabilization of Protein in the dried state", J Pharm Sci 92 (2003) 266-274; Izutsu, Kkojima, S. "Excipient crystallinity and its protein-structure-stabilizing effect during freeze-drying", J. Pharm. Pharmacol, 54 (2002) 1033-1039; Johnson, R, "Mannitol-sucrose mixtures-versatile formulations for protein lyophilization", J. Pharm. Sci, 91 (2002) 914-922; and Ha, E Wang W, Wang Y. j. "Peroxide formation in polysorbate 80 and protein stability", J. Pharm Sci, 91, 2252-2264, (2002) the entire contents of which are incorporated herein by reference and to which the reader is specifically referred.

In one embodiment the therapeutic agent of the invention, when in a pharmaceutical preparation, is present in unit dose forms. The appropriate therapeutically effective dose will be determined readily by those of skill in the art. Suitable doses may be calculated for patients according to their weight, for example suitable doses may be in the range of about 0.1 to about 20 mg/kg, for example about 1 to about 20 mg/kg, for example about 10 to about 20 mg/kg or for example about 1 to about 15 mg/kg, for example about 10 to about 15 mg/kg. To effectively treat conditions such as asthma or IPF in a human, suitable doses may be within the range of about 0.1 to about 1000 mg, for example about 0.1 to about 500 mg, for example about 500 mg, for example about 0.1 to about 100 mg, or about 0.1 to about 80 mg, or about 0.1 to about 60 mg, or about 0.1 to about 40 mg, or for example about 1 to about 100 mg, or about 1 to about 50 mg, of an antigen binding protein of this invention, which may be administered parenterally, for example subcutaneously, intravenously or intramuscularly. Such dose may, if necessary, be repeated at appropriate time intervals selected as appropriate by a physician.

The antigen binding proteins described herein can be lyophilized for storage and reconstituted in a suitable carrier prior to use. This technique has been shown to be effective with conventional immunoglobulins and art-known lyophilization and reconstitution techniques can be employed.

In another aspect, the invention provides a pharmaceutical composition comprising an antigen binding protein of the present invention or a functional fragment thereof and a pharmaceutically acceptable carrier for treatment or prophylaxis of atopic diseases/disorders and chronic inflammatory diseases/disorders, for example, asthma, such as allergic asthma, particularly severe asthma (that is asthma that is unresponsive to current treatment, including systemically administered corticosteroids; see Busse W W et al, J. Allergy Clin. Immunol 2000, 106: 1033-1042), "difficult" asthma (defined as the asthmatic phenotype characterised by failure to achieve control despite maximally recommended doses of prescribed inhaled steroids, see Barnes P J (1998), Eur Respir J 12:1208-1218), "brittle" asthma (defines a subgroup of patients with severe, unstable asthma who maintain a wide peak expiratory flow (PEF) variability despite high doses of inhaled steroids, see Ayres J G et al (1998) Thorax 58:315-321), nocturnal asthma, premenstrual asthma, steroid resistant asthma (see Woodcock A J (1993) Eur Respir J 6:743-747), steroid dependent asthma (defined as asthma that can be controlled only with high doses of oral steroids), aspirin induced asthma, adult-onset asthma, paediatric asthma. Antibodies of the invention maybe used to prevent, reduce the frequency of, or mitigate the effects of acute, asthmatic episodes (status asthmaticus). Antibodies of the invention may also be used to reduce the dosing required (either in terms of amount administered or frequency of dosing) of other medicaments used in the treatment of asthma. For example, antibodies of the invention may be used to reduce the dosing required for steroid treatment of asthma such as corticosteroid treatment ("steroid sparing"). Other diseases or disorders that may be treated with antibodies of the invention include atopic dermatitis, allergic rhinitis, Crohn's disease, chronic obstructive pulmonary disease (COPD), eosinophilic esophagitis, fibrotic diseases or disorders such as idiopathic pulmonary fibrosis, progressive systemic sclerosis (scleroderma), hepatic fibrosis, hepatic granulomas, schistosomiasis, leishmaniasis, and diseases of cell cycle regulation, e.g. Hodgkins disease, B cell chronic lymphocytic leukaemia. In one embodiment the disorder is severe asthma. In a further embodiment the disorder is a fibrotic disorder such as IPF.

In a yet further aspect, the invention provides a pharmaceutical composition comprising an antigen binding protein of the present invention and a pharmaceutically acceptable carrier for treating atopic diseases/disorders and chronic inflammatory diseases/disorders, for example, asthma, such as allergic asthma, particularly severe asthma (that is asthma that is unresponsive to current treatment, including systemically administered corticosteroids; see Busse W W et al, J. Allergy Clin. Immunol 2000, 106: 1033-1042), "difficult" asthma (defined as the asthmatic phenotype characterised by failure to achieve control despite maximally recommended doses of prescribed inhaled steroids, see Barnes P J (1998), Eur Respir J 12:1208-1218), "brittle" asthma (defines a subgroup of patients with severe, unstable asthma who maintain a wide peak expiratory flow (PEF) variability despite high doses of inhaled steroids, see Ayres J G et al (1998) Thorax 58:315-321), nocturnal asthma, premenstrual asthma, steroid resistant asthma (see Woodcock A J (1993) Eur Respir J 6:743-747), steroid dependent asthma (defined as asthma that can be controlled only with high doses of oral steroids), aspirin induced asthma, adult-onset asthma, paediatric asthma. Antibodies of the invention maybe used to prevent, reduce the frequency of, or mitigate the effects of acute, asthmatic episodes (status asthmaticus). Antibodies of the invention may also be used to reduce the dosing required (either in terms of amount administered or frequency of dosing) of other medicaments used in the treatment of asthma.

For example, antibodies of the invention may be used to reduce the dosing required for steroid treatment of asthma such as corticosteroid treatment ("steroid sparing"). Other diseases or disorders that may be treated with antibodies of the invention include atopic dermatitis, allergic rhinitis, Crohn's disease, chronic obstructive pulmonary disease (COPD), eosinophilic esophagitis, fibrotic diseases or disorders such as idiopathic pulmonary fibrosis, progressive systemic sclerosis (scleroderma), hepatic fibrosis, hepatic granulomas, schistosomiasis, leishmaniasis, and diseases of cell cycle regulation, e.g. Hodgkins disease, B cell chronic lymphocytic leukaemia. In one embodiment the disorder is severe asthma. In a further embodiment the disorder is a fibrotic disorder such as IPF.

It will be understood that the sequences described herein (SEQ ID NO: 26 to SEQ ID NO: 55 and SEQ NO:62 to SEQ ID NO: 146) include sequences which are substantially identical, for example sequences which are at least 90% identical, for example which are at least 91%, or at least 92%, or at least 93%, or at least 94% or at least 95%, or at least 96%, or at least 97% or at least 98%, or at least 99% identical to the sequences described herein.

For nucleic acids, the term "substantial identity" indicates that two nucleic acids, or designated sequences thereof, when optimally aligned and compared, are identical, with appropriate nucleotide insertions or deletions, in at least about 80% of the nucleotides, at least about 90% to about 95%, or at least about 98% to about 99.5% of the nucleotides. Alternatively, substantial identity exists when the segments will hybridize under selective hybridization conditions, to the complement of the strand.

For nucleotide and amino acid sequences, the term "identical" indicates the degree of identity between two nucleic acid or amino acid sequences when optimally aligned and compared with appropriate insertions or deletions. Alternatively, substantial identity exists when the DNA segments will hybridize under selective hybridization conditions, to the complement of the strand.

The percent identity between two sequences is a function of the number of identical positions shared by the sequences (i.e., % identity=# of identical positions/total # of positions times 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

By way of example, a polynucleotide sequence of the present invention may be identical to the reference sequence of SEQ ID NO: 25, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO: 25 by the numerical percent of the respective percent identity(divided by 100) and subtracting that product from said total number of nucleotides in SEQ ID NO: 23, or:

$$nn \leq xn - (xn \cdot y),$$

wherein nn is the number of nucleotide alterations, xn is the total number of nucleotides in SEQ ID NO: 25, and y is 0.5 μl for 50%, 0.6 μl for 60%, 0.7 μl for 70%, 0.8 μl for 80%, 0.85 for 85%, 0.9 μl for 90%, 0.95 for 95%, 0.97 for 97% or 1.0 μl for 100%, and wherein any non-integer product of xn and y is rounded down to the nearest integer prior to subtracting it from xn. Alterations of the polynucleotide sequence of SEQ ID NO: 25 may create nonsense, missense or frameshift mutations in this coding sequence and thereby alter the polypeptide encoded by the polynucleotide following such alterations.

Similarly, in another example, a polypeptide sequence of the present invention may be identical to the reference sequence encoded by SEQ ID NO: 24, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by SEQ ID NO: 24 by the numerical percent of the respective percent identity (divided by 100) and then subtracting that product from said total number of amino acids in the polypeptide sequence encoded by SEQ ID NO: 24, or:

$$na \leq xa - (xa \cdot y),$$

wherein na is the number of amino acid alterations, xa is the total number of amino acids in the polypeptide sequence encoded by SEQ ID NO: 24, and y is, for instance 0.7 μl for 70%, 0.8 μl for 80%, 0.85 for 85% etc., and wherein any non-integer product of xa and y is rounded down to the nearest integer prior to subtracting it from xa.

The following examples illustrate but do not limit the invention.

EXAMPLES

Example 1

Construction of Recombinant Anti-IL-13 Antibodies

Original murine mAbs were produced by immunisation of mice with recombinant human IL-13. Spleens from responder animals were harvested and fused to myeloma cells to generate hybridomas. The hybridoma supernatant material was screened for binding. Hybridomas of interest were monocloned using standard techniques. The resulting murine antibody (6A1) comprises the variable regions shown in SEQ ID NO:58 and SEQ ID NO:59. Further details of this murine antibody and a humanised version of this antibody A1L1 (SEQ ID NO: 22 and 24) are described in WO2006/003407 which is herein incorporated by reference. The anti-IL-13 mAb antibody A1L1 was used in several of the following examples as a comparator antibody.

A number of variants of the humanised antibody comprising the heavy chain set out in SEQ ID NO: 22 were produced. These all differed in the CDRH3 region of the antibody (SEQ ID NO: 3).

The base DNA expression constructs for the antibodies of the present invention, SEQ ID NO: 23 (heavy chain) and SEQ ID NO:25 (light chain) were prepared de novo by build-up of overlapping oligonucleotides including restriction sites for cloning into RId and RIn mammalian expression vectors as well as a human signal sequence. Hind III and Spe I restriction sites were introduced to frame the $V_H$ domain containing the signal sequence (SEQ ID NO:56) for cloning into RId containing the human γ1 constant region. Hind III and BsiWI restriction sites were introduced to frame the $V_L$ domain containing the signal sequence (SEQ ID NO: 56) for cloning into RIn containing the human kappa constant region. Alternative constructs were produced using pTT vectors which also included human constant regions. Where appropriate, site-directed mutagenesis (SDM) was used to generate different humanised constructs.

Example 2

Antibody Expression in HEK 293 6E Cells pTT plasmids encoding the heavy and light chains respectively were transiently co-transfected into HEK 293 6E cells and expressed at small scale to produce antibody. Antibodies were assessed directly from the tissue culture supernatant. Other antibodies were purified using immobilised Protein A columns and quantified by reading absorbance at 280 nm and where indicated, the purified antibody material was assessed in the assays described in the examples set out below.

Where we refer to the antibodies by code (i.e. A1Y100BTrpL1) we are referring to the mAb generated by co-transfection and expression of the noted first and second plasmid, for example 'A1Y100BTrpL1' relates to a mAb generated by co-transfection of a plasmid containing the A1Y100BTrp sequence and a plasmid containing the L1 sequence in a suitable cell line.

Example 3

BIAcore™ Analysis of Anti IL-13 Humanised mAbs

Kinetic Analysis

The initial screen of CDRH3 mutants was carried out on the ProteOn™ XPR36 (Biorad). The method was as follows, antihuman IgG (Biacore BR-1008-39) was immobilised on a GLM chip by primary amine coupling, CDRH3 mutant antibodies were then captured on this surface and IL13 passed over at 256, 64, 16, 4, 1 nM with a 0 nM injection (i.e. buffer alone) used to double reference. 3M MgCl$_2$ was used to regenerate the capture surface, removing the bound CDRH3 mutant antibodies ready for another cycle of capture and analyte injection. The data was fitted to the 1:1 model using the software inherent to the machine. All work was carried out using antibodies directly from tissue culture supernatants except for the parental antibody which was purified material.

The screen identified several antibodies that appeared to have better kinetic profile than the parental molecule, these same samples were then analysed on the BIAcore™ T100 to confirm the results, using a similar method, in that the same antihuman IgG capture antibody was immobilised on a CM5 chip by primary amine coupling, IL13 was passed over the surface at 256, 64, 16, 4, 1 and 0.25 nM with a 0 nM used for double referencing, regeneration was with 3M MgCl$_2$ and the data was fitted to the 1:1 model inherent to the T100. Table 1 details the overall affinities (equilibrium dissociation constant $K_D$) for the selected constructs from the ProteOn™ screen and the T100 run

TABLE 1

| Molecule | ProteOn™ KD (pM) | BIAcore™ KD (pM) |
|---|---|---|
| A1S95TrpL1 | Not Analysable | 216 |
| A1I96ValL1 | 395 | 696 |
| A1Y97PheL1 | 683 | 618 |
| A1D98GluL1 | 873 | 779 |
| A1H100A AlaL1 | Not Analysable | 172 |
| A1H100A GluL1 | 110 | 195 |
| A1H100A GlnL1 | 195 | 278 |
| A1H100A ArgL1 | 256 | 307 |
| A1H100A SerL1 | 131 | 174 |
| A1H100A ThrL1 | 158 | 211 |
| A1H100A ValL1 | 112 | 152 |
| A1Y100B AlaL1 | 75 | 83 |
| A1Y100B IleL1 | 75 | 73 |
| A1Y100B TrpL1 | 68 | 95 |
| A1L1 | ~450-600* | 366 |

*A1L1 ran several times during the ProteOn™ screen so range of values obtained

The data highlighted that several mutations at the Y100B residue appeared to improve the overall affinity. In light of this, mutations at this residue that were not present in the initial screen were tested using the ProteOn™ using the same method as described earlier and again using antibodies direct from tissue culture supernatants. Of the mutations tested A1Y100B ValL1, appeared to improve the overall affinity (equilibrium dissociation constant $K_D$) with a value of 0.166 nM obtained compared to a parental value of 0.390-0.460 nM. When Y100B Val was tested on the BIAcore™ T100 using the same methodology as described earlier, the equilibrium dissociation constant $K_D$ was measured at 0.025 nM compared to a parental value of 0.346 nM.

In light of the work so far being carried out using antibody mutants direct from tissue culture supernatants, purified antibody was produced for A1Y100BL1 mutants Ala, Ile and Trp. These were run on the BIAcore™ T100, using the same method as before and including the A1Y100B ValL1 mutant which was not purified at this stage. Table 2 shows the data obtained from this experiment.

TABLE 2

| Molecule | ka (M$^{-1}$s$^{-1}$) | kd (s$^{-1}$) | KD (nM) |
|---|---|---|---|
| A1Y100B ValL1 (supernatant) | 1.018E+6 | 3.455E-5 | 0.034 |
| A1Y100B AlaL1 | 9.599E+5 | 3.004E-5 | 0.031 |
| A1Y100B IleL1 | 1.149E+6 | 5.584E-5 | 0.049 |
| A1Y100B TrpL1 | 2.572E+6 | 1.627E-4 | 0.063 |
| A1L1 | 1.267E+6 | 4.560E-4 | 0.360 |

The experiment confirmed that the mutants did improve the binding affinity to IL13 compared to the parental molecule.

Given that the purified A1Y100BL1 mutants gave better binding affinities than those obtained from tissue culture supernatants, A1Y100B ValL1 was purified and run alongside the other purified A1Y100BL1 mutants that also improved affinity using the BIAcore™ T100 machine using the method described earlier. Table 3, shows the data obtained from this experiment. This experiment was in good agreement with the data in Table 2 and confirmed the improvement of affinity for the Y100B mutations.

TABLE 3

| Molecule | ka (M$^{-1}$s$^{-1}$) | kd (s$^{-1}$) | KD (nM) |
|---|---|---|---|
| A1Y100B IleL1 (pur) | 9.886E+5 | 4.214E−5 | 0.043 |
| A1Y100B ValL1 (pur) | 7.757E+5 | 2.123E−5 | 0.027 |
| A1Y100B AlaL1 (pur) | 8.096E+5 | 2.583E−5 | 0.032 |
| A1Y100B TrpL1 (pur) | 2.385E+6 | 1.253E−4 | 0.053 |
| A1L1(pur) | 1.128E+6 | 3.677E−4 | 0.326 |

Example 4

Neutralisation of *E. Coli*-Expressed Recombinant Human IL-13 in a TF-1 Cell Proliferation Bioassay TF-1 cells proliferate in response to a number of different cytokines including human IL-13. The proliferative response of these cells for IL-13 can therefore be used to measure the bioactivity of IL-13 and subsequently an assay has been developed to determine the IL-13 neutralisation potency (inhibition of IL-13 bioactivity) of mAbs.

The assay was performed in sterile 96-well tissue culture plates under sterile conditions and all test wells were performed in triplicate. 14 ng/ml recombinant *E. Coli*-expressed human IL-13 was pre-incubated with various dilutions of mAbs (usually from 93.4 nM titrated in 3-fold dilutions to 0.014 nM) for 1 hour at 37 C. An antibody of irrelevant specificity was similarly titrated as a negative control. These samples were then added to 50 μl of TF-1 cells (at a concentration of 2×10$^5$ cells per ml) in a sterile 96-well tissue culture plate. Thus the final 100 μl assay volume contained various dilutions of mAbs (at a final concentration of 46.7 nM titrated in 3-fold dilutions to 0.007 nM), recombinant *E. Coli*-expressed human IL-13 (at a final concentration of 7 ng/ml) and TF-1 cells (at a final concentration of 1×10$^5$ cells per ml). The assay plate was incubated at 37 C for approximately 3 days in a humidified CO$_2$ incubator. The amount of cell proliferation was then determined using the 'CellTitre 96® Non-Radioactive Cell Proliferation Assay' from Promega (catalogue number G4100), as described in the manufacturers instructions. The absorbance of the samples in the 96-well plate was read in a plate reader at 570 nm.

The capacity of the mAbs to neutralise recombinant *E. Coli*-expressed human IL-13 bioactivity was expressed as that concentration of the mAb required to neutralise the bioactivity of the defined amount of human IL-13 (7 ng/ml) by 50% (=ND$_{50}$). The lower the concentration of the mAb required, the more potent the neutralisation capacity. The ND$_{50}$ data provided herein (Table 4) were calculated using ROBOSAGE™ in Microsoft Excel™. Graphical representation of the data can be seen in FIG. 1.

TABLE 4

| Molecule | ND$_{50}$ (nM) | Standard Error (nM) |
|---|---|---|
| A1L1 | 9.77 | 34.82 |
| A1Y100BAla L1 | 0.92 | 0.08 |
| A1Y100BIle L1 | 1.10 | 0.21 |
| A1Y100BTrpL1 | 1.25 | 0.34 |

Example 5

Construction and Expression of mAb-Domain Antibodies Comprising the CDRH3 Variant Anti-IL-13 mAb Using standard molecular biology techniques, genes encoding each of the sequences for the variable heavy regions of the CDRH3 variants of the A1 antibodies were transferred from existing constructs to an expression vector containing the hIgG1 constant region fused to an anti-human IL-4 domain antibody (DOM9-112-210) via a TVAAPS (SEQ ID NO: 83) or ASTKGPS (SEQ ID NO: 84) linker at the c-terminus of the hIgG1 constant region. Details of the heavy chains constructed are listed in Table 5.

TABLE 5

| Molecule number | Name | Description | Protein Seq ID | DNA Seq ID |
|---|---|---|---|---|
| BPC1624 | A1Y100BAla H-TVAAPS-210 L1 | H Chain = A1Y100B Ala H chain-TVAAPS linker-DOM9-112-210 dAb ™ | 62 | 63 |
| | | L chain = L1 | 24 | 25 |
| BPC1625 | A1Y100BIle H-TVAAPS-210 L1 | H chain = A1Y100BIle H chain-TVAAPS linker-DOM9-112-210 dAb ™ | 64 | 65 |
| | | L chain = L1 | 24 | 25 |
| BPC1626 | A1Y100BTrp H-TVAAPS-210 L1 | H chain = A1Y100BTrp H chain-TVAAPS linker-DOM9-112-210 dAb ™ | 66 | 67 |
| | | L chain = L1 | 24 | 25 |
| BPC1627 | A1Y100BVal H-TVAAPS-210 L1 | H chain = A1Y100BVal H chain-TVAAPS linker-DOM9-112-210 dAb ™ | 68 | 69 |
| | | L chain = L1 | 24 | 25 |

TABLE 5-continued

| Molecule number | Name | Description | Protein Seq ID | DNA Seq ID |
|---|---|---|---|---|
| BPC1628 | A1Y100BAla H-ASTKGPS-210 L1 | H Chain = A1Y100B Ala H chain-ASTKGPS linker-DOM9-112-210 dAb ™ | 70 | 71 |
|  |  | L chain = L1 | 24 | 25 |
| BPC1629 | A1 Y100BIle H-ASTKGPS-210 L1 | H chain = A1Y100BIle H chain-ASTKGPS linker-DOM9-112-210 dAb ™ | 72 | 73 |
|  |  | L chain = L1 | 24 | 25 |
| BPC1630 | A1Y100BTrp H-ASTKGPS-210 L1 | H chain = A1Y100BTrp H chain-ASTKGPS linker-DOM9-112-210 dAb ™ | 74 | 75 |
|  |  | L chain = L1 | 24 | 25 |
| BPC1631 | A1Y100BVal H-ASTKGPS-210 L1 | H chain = A1Y100BVal H chain-ASTKGPS linker-DOM9-112-210 dAb ™ | 76 | 77 |
|  |  | L chain = L1 | 24 | 25 |

(In this table the TVAAPS linker amino acid sequence is shown in SEQ ID NO: 83 and the ASTKGPS linker amino acid sequence is shown in SEQ ID NO: 84.)

BPC1624, BPC1625, BPC1626 and BPC1627 were expressed in HEK293 cells. Briefly, 250 ml of HEK293 cells at $1.5 \times 10^6$ cells/ml were co-transfected with heavy and light chain expression plasmids previously incubated with 293FECTIN™ reagent (Invitrogen #51-0031). These were placed in a shaking incubator at 37° C., 5% $CO_2$, and 95% relative humidity. After 24 hours tryptone feeding media was added and the cells grown for a further 5 days. Supernatant was harvested by centrifugation and filter sterilised. The expressed molecules were purified by affinity chromatography using immobilised Protein A columns and the concentration was determined by measuring the absorbance at 280 nm. The level of aggregated protein in the purified samples was determined by size exclusion chromatography. The yield of purified protein and levels of aggregation are shown in Table 5b.

TABLE 5b

| BPC | Name | Yield | % aggregate |
|---|---|---|---|
| BPC1624 | 586Y100BA H-TVAAPS-210 | 0.81 mg | 3.6% |
| BPC1625 | 586Y100BI H-TVAAPS-210 | 0.944 mg | 6.7% |
| BPC1626 | 586Y100BW H-TVAAPS-210 | 1.14 mg | 5.5% |
| BPC1627 | 586Y100BV H-TVAAPS-210 | 1.26 mg | 8.4% |

(In this table the TVAAPS linker amino acid sequences is shown in SEQ ID NO: 83.)

Example 6

Neutralisation Activity Data for mAb-Domain Antibodies Comprising the CDRH3 variant anti-IL-13 mAb mAb-domain antibodies comprising the CDRH3 variant anti-IL-13 mAb were tested for neutralisation of *E. Coli*-expressed recombinant human IL-13 in a TF-1 cell proliferation bioassay The assay was performed in sterile 96-well tissue culture plates under sterile conditions and all test wells were performed in triplicate. Approximately 20 ng/ml recombinant *E. Coli*-expressed human IL-13 was pre-incubated with various dilutions of mAb-domain antibodies (usually from 50 nM titrated in 3-fold dilutions to 0.02 nM) (those mAb-domain antibodies made in HEK cells and purified as described in example 5) in a total volume of 50 µl for 1 hour at 37° C. An antibody of irrelevant specificity was similarly titrated as a negative control (data not shown). These samples were then added to 50 µl of TF-1 cells (at a concentration of $2 \times 10^5$ cells per ml) in a sterile 96-well tissue culture plate. Thus the final 100 µl assay volume contained various dilutions of mAb-domain antibodies (at a final concentration of 25 nM titrated in 3-fold dilutions to 0.01 nM), recombinant *E. Coli*-expressed human IL-13 (at a final concentration of 10 ng/ml) and TF-1 cells (at a final concentration of $1 \times 10^5$ cells per ml). The assay plate was incubated at 37° C. for approximately 3 days in a humidified $CO_2$ incubator. The amount of cell proliferation was then determined using the 'CellTitre 96® Non-Radioactive Cell Proliferation Assay' from Promega (catalogue number G4100), as described in the manufacturer's instructions. The absorbance of the samples in the 96-well plate was read in a plate reader at 570 nm.

The capacity of the mAb-domain antibodies to neutralise human IL-13 bioactivity was expressed as that concentration of the mAb-domain antibody required to neutralise the bioactivity of the defined amount of human IL-13 (10 ng/ml) by 50% (=$ND_{50}$). The lower the concentration of the mAb-domain antibody required, the more potent the neutralisation capacity. The $ND_{50}$ data provided herein (Table 6) were calculated using GraphPad Prism. These data are represented graphically in FIG. 2.

TABLE 6

| Antibody ID | Description | $ND_{50}$ human IL-13 |
|---|---|---|
| BPC1624 | A1Y100BAla H-TVAAPS-210L1 | 0.553 nM |
| BPC1625 | A1Y100BIle H-TVAAPS-210L1 | 0.542 nM |
| BPC1626 | A1Y100BTrp H-TVAAPS-210L1 | 0.681 nM |
| BPC1627 | A1Y100BVal H-TVAAPS-210L1 | 0.615 nM |
| A1L1 | Anti IL-13 antibody | 2.524 nM |

(In this table the TVAAPS linker amino acid sequences is shown in SEQ ID NO: 83.)

Example 7

Expression of mAb-Domain Antibodies Comprising the CDRH3 Variant Anti-IL-13 mAb in the CHOE1a Expression System Molecules BPC 1624 to 1631 as shown in Table 5 were also expressed in CHOE1a cells. DNA vectors encoding the heavy and light chains were co-electroporated into suspension CHO cells. Cells were passaged in shake flasks in MR1 basal selective medium at 37° C., 5% $CO_2$, 130 rpm until cell viability and cell counts improved. CHO cells were then inoculated into MR1 basal×2 selective medium and incubated for 8 to 12 days at 34° C., 5% $CO_2$, 130 rpm. The cells were pelleted by centrifugation and the supernatant sterile filtered.

Expressed material was purified by affinity chromatography using immobilised protein A columns and the yield determined by measurement of absorbance at 280 nm. The level of aggregates was determined by size exclusion chromatography. Aggregates were removed by preparative size exclusion chromatography and the yield re-assessed. Table 7 lists the yields and levels of aggregate obtained from this expression system.

TABLE 7

| Molecule | Expression Volume (ml) | Yield (mgs) (post protein A pre clean-up) | Aggregates (%) (post protein A pre clean-up) | Final Yield (mgs) | Final Aggregates (%) |
|---|---|---|---|---|---|
| BPC1628 | 850 | 80.70 | 17.1% | 39.50 | 2.6% |
| BPC1629 | 850 | 77.90 | 20.3% | 35.25 | 2.8% |
| BPC1630 | 850 | 69.30 | 15.7% | 38.00 | 3.3% |
| BPC1631 | 850 | 61.47 | 20.3% | 30.00 | 2.3% |
| BPC1624 | 850 | 88.65 | 15.2% | 45.00 | 2.6% |
| BPC1625 | 850 | 77.49 | 16.2% | 37.49 | 2.3% |
| BPC1626 | 850 | 65.16 | 12.6% | 30.80 | 3.1% |
| BPC1627 | 850 | 73.26 | 15.2% | 34.44 | 1.9% |

Example 8

Stoichiometry Assessment of Antigen Binding Proteins (Using BIAcore™)

This example is prophetic. It provides guidance for carrying out an additional assay in which the antigen binding proteins of the invention can be tested, Anti-human IgG will be immobilised onto a CM5 biosensor chip by primary amine coupling. Antigen binding proteins will be captured onto this surface after which a single concentration of IL-13 or IL-4 or IL-5 will be passed over, this concentration is will be enough to saturate the binding surface and the binding signal observed will reach full R-max. Stoichiometries will then be calculated using the given formula:

Stoich=$R$max*$Mw$ (ligand)/$Mw$ (analyte)*$R$ (ligand immobilised or captured)

Where the stoichiometries will be calculated for more than one analyte binding at the same time, the different antigens will be passed over sequentially at the saturating antigen concentration and the stoichiometries will be calculated as above. The work can be carried out on the BIAcore™ 3000, at 25° C. using HBS-EP running buffer.

Example 9

Dose Prediction of Improved Humanised Variant mAbs

An antibody-ligand binding PK-PD model was developed in order to rank the different monoclonal antibody (mAb) candidates based on binding affinity and predicted potential therapeutic dose in human.

The predicted potential therapeutic dose in human was defined for this purpose as the dose providing 90% inhibition of the target IL-13 in the lung (site of action) at steady-state following monthly intravenous administration of the mAbs for 1 h. The molecular weight of each molecule was assumed to be the same and equal to the standard molecular weight of a mAb i.e. 150 kDa. In addition, in the absence of animal or human pharmacokinetics data for the different candidates, the human pharmacokinetics of the A1L1 antibody was inferred to all the candidates.

The same antibody-ligand binding PK-PD model is used for each mAb as well as the same assumptions regarding the target concentration, the target turnover, the target tissue: plasma ratio and the mAb tissue penetration. The ranking provided by the model is therefore solely based on the binding affinity of the molecules, the only parameter differing. In such conditions, the potential therapeutic dose in human for the 4 candidates A1Y100BIleL1, A1Y100BValL1, A1Y100BAlaL1 and A1Y100BTrpL1 is predicted to provide a substantial improvement above the predicted potential therapeutic dose in human for A1L1.

Example 10

Anti-IL13/1L4 mAb-Domain Antibodies with Variant IL-4 dAb™s 10.1 Construction and Expression The anti IL-4 dAb™ (DOM9-155-154, SEQ ID NO: 80), was investigated for aggregation-prone residues using an aggregation prediction algorithm. The leucine residue, at Kabat position 89 was identified as a key residue for promotion of aggregation.

In order to reduce the aggregation potential of mAb-domain antibodies containing this dAb™, this amino acid residue was substituted for other amino acids to generate a number of mAb-domain antibody variants. Expression constructs were generated by site directed mutagenesis using the DNA expression vector coding for the heavy chain of an existing mAb-domain antibody construct. The protein sequences for the resulting new mAb-domain antibody heavy chains comprising the mutated dAb™ sequences are given in SEQ ID NOs 117-134.

Other heavy chain sequences incorporating another mutation at position 89 are SEQ ID NOs: 96-106. These are described in detail in Example 11.

Table 8 provide a list of the molecules expressed.

TABLE 8

| Identifier | Alternative names | Linker | Molecule description | Protein SEQ ID NO: |
|---|---|---|---|---|
| BPC1090 | 829H-(TVAAPS)$_2$GS-154 (89G) | (TVAAPS)$_2$GS | H chain: Anti-human IL-13 mAb heavy chain Y100B_V-(TVAAPS)$_2$GS-DOM9-155-154 (89G) | 117 |
| | | | L chain: Anti-human IL-13 mAb light chain | 24 |

TABLE 8-continued

| Identifier | Alternative names | Linker | Molecule description | Protein SEQ ID NO: |
|---|---|---|---|---|
| BPC1091 | 829H-(TVAAPS)$_2$GS-154 (89S) | (TVAAPS)$_2$GS | H chain: Anti-human IL-13 mAb heavy chain Y100B_V-(TVAAPS)$_2$GS-DOM9-155-154 (89S) | 118 |
| | | | L chain: Anti-human IL-13 mAb light chain | 24 |
| BPC1092 | 829H-(TVAAPS)$_2$GS-154 (89H) | (TVAAPS)$_2$GS | H chain: Anti-human IL-13 mAb heavy chain Y100B_V-(TVAAPS)$_2$GS-DOM9-155-154 (89H) | 119 |
| | | | L chain: Anti-human IL-13 mAb light chain | 24 |
| BPC1093 | 829H-(TVAAPS)$_2$GS-154 (89M) | (TVAAPS)$_2$GS | H chain: Anti-human IL-13 mAb heavy chain Y100B_V-(TVAAPS)$_2$GS-DOM9-155-154 (89M) | 147 |
| | | | L chain: Anti-human IL-13 mAb light chain | 24 |
| BPC1094 | 829H-(TVAAPS)$_2$GS-154 (89A) | (TVAAPS)$_2$GS | H chain: Anti-human IL-13 mAb heavy chain Y100B_V-(TVAAPS)$_2$GS-DOM9-155-154 (89A) | 121 |
| | | | L chain: Anti-human IL-13 mAb light chain | 24 |
| BPC1095 | 829H-(TVAAPS)$_2$GS-154 (89T) | (TVAAPS)$_2$GS | H chain: Anti-human IL-13 mAb heavy chain Y100B_V-(TVAAPS)$_2$GS-DOM9-155-154 (89T) | 122 |
| | | | L chain: Anti-human IL-13 mAb light chain | 24 |
| BPC1108 | 829H-(TVAAPS)$_2$GS-154 (89C) | (TVAAPS)$_2$GS | H chain: Anti-human IL-13 mAb heavy chain Y100B_V-(TVAAPS)$_2$GS-DOM9-155-154 (89C) | 123 |
| | | | L chain: Anti-human IL-13 mAb light chain | 24 |
| BPC1109 | 829H-(TVAAPS)$_2$GS-154 (89R) | (TVAAPS)$_2$GS | H chain: Anti-human IL-13 mAb heavy chain Y100B_V-(TVAAPS)$_2$GS-DOM9-155-154 (89R) | 124 |
| | | | L chain: Anti-human IL-13 mAb light chain | 24 |
| BPC1110 | 829H-(TVAAPS)$_2$GS-154 (89W) | (TVAAPS)$_2$GS | H chain: Anti-human IL-13 mAb heavy chain Y100B_V-(TVAAPS)$_2$GS-DOM9-155-154 (89W) | 125 |
| | | | L chain: Anti-human IL-13 mAb light chain | 24 |
| BPC1111 | 829H-(TVAAPS)$_2$GS-154 (89E) | (TVAAPS)$_2$GS | H chain: Anti-human IL-13 mAb heavy chain Y100B_V-(TVAAPS)$_2$GS-DOM9-155-154 (89E) | 126 |
| | | | L chain: Anti-human IL-13 mAb light chain | 24 |
| BPC1112 | 829H-(TVAAPS)$_2$GS-154 (89K) | (TVAAPS)$_2$GS | H chain: Anti-human IL-13 mAb heavy chain Y100B_V-(TVAAPS)$_2$GS-DOM9-155-154 (89K) | 127 |
| | | | L chain: Anti-human IL-13 mAb light chain | 24 |
| BPC1113 | 829H-(TVAAPS)$_2$GS-154 (89D) | (TVAAPS)$_2$GS | H chain: Anti-human IL-13 mAb heavy chain Y100B_V-(TVAAPS)$_2$GS-DOM9-155-154 (89D) | 128 |
| | | | L chain: Anti-human IL-13 mAb light chain | 24 |
| BPC1114 | 829H-(TVAAPS)$_2$GS-154 (89N) | (TVAAPS)$_2$GS | H chain: Anti-human IL-13 mAb heavy chain Y100B_V-(TVAAPS)$_2$GS-DOM9-155-154 (89N) | 129 |
| | | | L chain: Anti-human IL-13 mAb light chain | 24 |
| BPC1115 | 829H-(TVAAPS)$_2$GS-154 (89Y) | (TVAAPS)$_2$GS | H chain: Anti-human IL-13 mAb heavy chain Y100B_V-(TVAAPS)$_2$GS-DOM9-155-154 (89Y) | 130 |

TABLE 8-continued

| Identifier | Alternative names | Linker | Molecule description | Protein SEQ ID NO: |
|---|---|---|---|---|
| | | | L chain: Anti-human IL-13 mAb light chain | 24 |
| BPC1116 | 829H-(TVAAPS)₂GS-154 (89V) | (TVAAPS)₂GS | H chain: Anti-human IL-13 mAb heavy chain Y100B_V-(TVAAPS)₂GS-DOM9-155-154 (89V) | 131 |
| | | | L chain: Anti-human IL-13 mAb light chain | 24 |
| BPC1117 | 829H-(TVAAPS)₂GS-154 (89I) | (TVAAPS)₂GS | H chain: Anti-human IL-13 mAb heavy chain Y100B_V-(TVAAPS)₂GS-DOM9-155-154 (89I) | 132 |
| | | | L chain: Anti-human IL-13 mAb light chain | 24 |
| BPC1118 | 829H-(TVAAPS)₂GS-154 (89F) | (TVAAPS)₂GS | H chain: Anti-human IL-13 mAb heavy chain Y100B_V-(TVAAPS)₂GS-DOM9-155-154 (89F) | 133 |
| | | | L chain: Anti-human IL-13 mAb light chain | 24 |
| BPC1119 | 829H-(TVAAPS)₂GS-154 (89P) | (TVAAPS)₂GS | H chain: Anti-human IL-13 mAb heavy chain Y100B_V-(TVAAPS)₂GS-DOM9-155-154 (89P) | 134 |
| | | | L chain: Anti-human IL-13 mAb light chain | 24 |

(In this table the TVAAPS linker amino acid sequence is shown in SEQ ID NO: 83, and the (TVAAPS)₂GS linker amino acid sequence (TVAAPSTVAAPSGS) is shown in SEQ ID NO: 145.)

10.2 Molecule Expression in HEK 293 6E Cells

Plasmids encoding the heavy and light chains respectively were transiently co-transfected into HEK 293 6E cells and expressed at small scale to produce antibody molecules. A tryptone feed was added to each cell culture up to 24 hours after transfection and the cells were harvested after 3 days.

Antibody molecules were assessed directly from the tissue culture supernatant and quantified using the GYROLAB™ workstation.

GYROLAB™ workstation method for quantification of antibody molecules in cell supernatant Antibodies produced from small scale transient HEK 2936E transfections (0.75-2.0 ml) were quantified from tissue culture supernatants by a quantitative immunoassay using a GYROLAB™ BIOAFFY™ Workstation (Gyros). Antibody was captured via the Fc region using a biotinylated anti-IgG AFFIBODY™ molecule (Abcam) immobilised onto streptavidin-coated particles on a compact disc (CD) microlaboratory (Gyros). The AFFIBODY™ reagent was vortexed briefly and diluted with PBS-TWEEN™ 20 (0.01% v/v) to a final working concentration of 0.1 mg/ml. Antibody was then detected by an ALEXA FLUOR™ 647 labelled Fab₂ anti-human IgG kappa light chain molecule using laser-induced fluorescence. The ALEXA FLUOR™ 647 labelled detection reagent was prepared by vortexing briefly and by centrifugation at 13000 rpm for 4 minutes. The labelled Fab₂ detection reagent was added to unlabelled Fab₂ which were diluted to final concentrations of 75 nM and 1.5 µM respectively using REXCIP™ F Detection reagent diluant (Gyros). The antibody quantification range was between 0.244-250 µg/ml relative to an anti-CD23 monoclonal antibody standard curve. The anti-CD23 (1 mg/ml) standard curve was generated by serial dilution of the antibody with tissue culture media (FREESTYLE 293™ Expression Media, PLURONIC F68™ and Geneticin, Invitrogen).

In some instances, the antibody molecules were purified using immobilised Protein A columns and quantified by reading absorbance at 280 nm and where indicated, the purified antibody molecule was assessed in the assays described in the examples set out below.

10.3 IL-4 Binding ELISA

These mAb-domain antibodies were tested for binding to IL-4 in a direct binding ELISA using the following method.

96-well high binding plates were coated with 5 µg/ml human IL-4 (made at GSK) in NaHCO₃ and stored overnight at 4° C. The plates were washed twice with Tris-Buffered Saline with 0.05% of TWEEN™-20 (TBST). 100 µL of blocking solution (1% BSA in TBST buffer) was added in each well and the plates were incubated for at least one hour at room temperature. The mAb-domain antibodies were successively diluted across the plates in blocking solution. After one hour incubation, the plates were washed three times. Goat anti-human kappa light chain specific peroxidase conjugated antibody (Sigma A7164) was diluted in blocking solution to 1 µg/mL and 50 µL was added to each well. The plates were incubated for one hour. After another three washing steps, 50 µl of OPD (o-phenylenediamine dihydrochloride) SIGMA-FAST™ substrate solution was added to each well and the reaction was stopped after about 5 minutes by addition of 25 µL of 3M sulphuric acid. Absorbance was read at 490 nm using the VERSAMAX™ Tunable Microplate Reader (Molecular Devices) using a basic endpoint protocol.

The experiment was carried out using mAb-domain antibodies directly from tissue culture supernatants which had been quantified using the GYROLAB™ platform except for the positive control (anti-IL-4 mAb) and the anti-IL13 negative control mAb, which were purified material. These data are shown in FIG. 17.

The result of the ELISA shows that most of these transiently expressed anti-IL13 mAb-anti-IL4 dAb™s bound IL-4, but some variation in IL-4 binding activity was observed. The purified positive control anti-IL-4 mAb, also showed binding to IL-4, whereas the purified negative control mAb showed no binding to human IL-4.

10.4 Analysis of Levels of Aggregate in mAb-Domain Antibody Expressions pTT plasmids encoding the heavy and light chains of BPC1090, BPC1091, BPC1092, BPC1093, BPC1094 and BPC1095 were transiently co-transfected into HEK 293 6E cells and expressed using 293FECTIN™ (Invitrogen, 12347019) at slightly larger scale (between 200 and 600 ml) than the mAb-domain antibodies described above in Example 10.2. The BPC1111 and BPC1085 were independently transiently expressed in HEK293 6E cells using the same methodology. The plasmids used for the above transfections were generated using the ENDOFREE™ Plasmid Maxi Kit (Qiagen, 12362). A tryptone feed was added to each of the cell cultures after 24 hours and the cells were harvested after 72 hours. The antibodies were purified using a Protein A column, quantified by reading absorbance at 280 nm and analyzed by size exclusion chromatography (SEC).

These mAb-domain antibodies were compared with BPC2223, anti-IL13 mAb (829) and anti-11-13 mAb (586) which had been independently expressed.

Both antibodies (586 with the original CDRH3 and 829 with the mutated CDRH3) showed low levels of aggregation, as did the mAb-domain antibodies comprising the mutated dAb™ (BPC1090, BPC 1091, BPC 1093, BPC1094 and BPC1095). BPC2223 which comprised the original dAb™ i.e. where position 89 was not mutated had higher levels of aggregation, as did BPC1092 which had an L89H mutation. Representative aggregation data is shown in Table 8b.

TABLE 8b

| Molecule number | Molecule description | % aggregates (SEC) |
|---|---|---|
| BPC1085 | 829H-GS(TVAAPSGS)$_2$-154 (89Q) | ~1.6 |
| BPC 1090 | 829H-(TVAAPS)$_2$GS-154 (89G) | ~0.7 |
| BPC 1091 | 829H-(TVAAPS)$_2$GS-154 (89S) | ~1.5 |
| BPC 1092 | 829H-(TVAAPS)$_2$GS-154 (89H) | ~20 |
| BPC 1093 | 829H-(TVAAPS)$_2$GS-154 (89M) | ~4.3 |
| BPC 1094 | 829H-(TVAAPS)$_2$GS-154 (89A) | ~0.8 |
| BPC 1095 | 829H-(TVAAPS)$_2$GS-154 (89T) | ~2 |
| BPC 1111 | 829H-(TVAAPS)$_2$GS-154 (89E) | <5% |
| BPC 2223 | 586H-GS(TVAAPSGS)$_2$-154 | ~25% |
| — | 829 (mAb) | ~2.1 |
| — | 586 (mAb) | <1 |

(In this table the TVAAPSGS linker amino acid sequence is shown in SEQ ID NO: 87, the GS(TVAAPSGS)$_2$ linker amino acid sequence (i.e., GSTVAAPSGSTVAAPSGS) is shown in SEQ ID NO: 140, the TVAAPS linker amino acid sequence is shown in SEQ ID NO: 83, the (TVAAPS)$_2$GS linker amino acid sequence (i.e., TVAAPSTVAAPSGS) is shown in SEQ ID NO: 145).

10.5 BIAcore™ Analysis

Purified mAbs and mAb-domain antibody constructs were tested in a BIAcore™ assay to determine whether the mutation of position 89 had any effect on the binding of the dAb™ to IL-4.

Protein A was immobilised on a CM5 chip by primary amine coupling; this surface was used as a capture surface for the antibody molecules to be tested. Recombinant *E. coli*-expressed Human IL4 was used as analyte at 256, 64, 16, 4 and 1, 0.25 and 0.0625 with 0 nM (i.e. buffer alone) used to double reference the binding curves. Regeneration of the anti-Protein A surface was achieved using 50 mM NaOH. The assay was run at 25° C. using HBS-EP as running buffer. The data was fitted to 1:1 model inherent to the BIAcore™ T100 analysis software.

TABLE 8c

| Molecule Number | Molecule Description | ka (1/Ms) | kd (1/s) | KD (nM) |
|---|---|---|---|---|
| BPC1085 | 829H-GS(TVAAPSGS)$_2$-256 | 2.38E+07 | 1.23E-03 | 0.052 |
| BPC2223 | 586H-GS(TVAAPSGS)$_2$-154 | 9.71E+06 | 9.34E-05 | 0.010 |
| BPC1090 | 829H-(TVAAPS)$_2$GS-154 (89G) | 3.00E+06 | 4.55E-04 | 0.152 |
| BPC1091 | 829H-(TVAAPS)$_2$GS-154 (89S) | 3.96E+06 | 9.66E-04 | 0.244 |
| BPC1092 | 829H-(TVAAPS)$_2$GS-154 (89H) | 2.98E+06 | 5.34E-03 | 1.794 |
| BPC1093 | 829H-(TVAAPS)$_2$GS-154 (89M) | 4.19E+06 | 2.16E-04 | 0.051 |
| BPC1094 | 829H-(TVAAPS)$_2$GS-154 (89A) | 1.91E+06 | 3.73E-03 | 1.948 |
| BPC1095 | 829H-(TVAAPS)$_2$GS-154 (89T) | 2.50E+06 | 1.44E-02 | 5.760 |
| BPC1111 | 829H-(TVAAPS)$_2$GS-154 (89E) | 3.37E+06 | 1.04E-04 | 0.031 |

(In this table the TVAAPSGS linker amino acid sequence is shown in SEQ ID NO: 87, the GS(TVAAPSGS)$_2$ linker amino acid sequence (i.e., GSTVAAPSGSTVAAPSGS) is shown in SEQ ID NO: 140, the TVAAPS linker amino acid sequence is shown in SEQ ID NO: 83, the (TVAAPS)$_2$GS linker amino acid sequence (i.e., TVAAPSTVAAPSGS) is shown in SEQ ID NO: 145).

Example 11

Construction and Testing of Antigen Binding Proteins Comprising the CDRH3 Variant Anti-IL-13 mAb and a Mutated dAb™ (BPC1085, BPC1086 & BPC1087)

11.1 Construction and Expression

Plasmids encoding heavy chains consisting of an anti-IL-13 mAb and an anti-IL-4 dAb™ were used as base constructs to generate alternative plasmid constructs. A two step cloning strategy was required. In step 1, the DNA sequence encoding the VH of the anti-IL13 mAb component of the H chain was replaced with the DNA sequence encoding the VH of another humanized anti-IL13 antibody (SEQ ID NO:54) by restriction cloning using HindIII and SpeI. In step 2, the codon encoding the leucine at Kabat position 89 in the anti-IL4 dAb™ (DOM9-155-154, SEQ ID NO: 80) component of the mAb-domain antibody was mutated by site directed mutagenesis to glutamine. All of the resulting heavy chain DNA sequences generated are given in SEQ ID NOs: 96, 98 and 100. Table 9 provides a list of the molecules constructed and expressed.

TABLE 9

Summary of the antibodies constructed and expressed

| Identifier | Alternative names | Linker | Molecule description | Protein SEQ ID NO: |
|---|---|---|---|---|
| BPC1085 | 829H-GS(TVAAPSGS)$_2$-154 (89Q) or 829H-GS(TVAAPSGS)$_2$- | GS(TVAAPSGS)$_2$ | H chain: Anti-human IL-13 mAb heavy chain Y100B_V-GS(TVAAPSGS)$_2$-DOM9-155-256 | 96 |

TABLE 9-continued

Summary of the antibodies constructed and expressed

| Identifier | Alternative names | Linker | Molecule description | Protein SEQ ID NO: |
|---|---|---|---|---|
| | 256 | | L chain: Anti-human IL-13 mAb light chain | 24 |
| BPC1086 | 829H-GS(TVAAPSGS)₃-154 (89Q) or 829H-GS(TVAAPSGS)₃-256 | GS(TVAAPSGS)₃ | H chain: Anti-human IL-13 mAb heavy chain Y100B_V-GS(TVAAPSGS)₃-DOM9-155-256 | 98 |
| | | | L chain: Anti-human IL-13 mAb light chain | 24 |
| BPC1087 | 829H-GS(TVAAPSGS)₄-154 (89Q) or 829H-GS(TVAAPSGS)₄-256 | GS(TVAAPSGS)₄ | H chain: Anti-human IL-13 mAb heavy chain Y100B_V-GS(TVAAPSGS)₄-DOM9-155-256 | 100 |
| | | | L chain: Anti-human IL-13 mAb light chain | 24 |

(In this table the TVAAPSGS linker amino acid sequence is shown in SEQ ID NO: 87, the GS(TVAAPSGS)₂ linker amino acid sequence (i.e., GSTVAAPSGSTVAAPSGS) is shown in SEQ ID NO: 140, the GS(TVAAPSGS)₃ linker amino acid sequence (i.e., GSTVAAPSGSTVAAPSGSTVAAPSGS) is shown in SEQ ID NO: 141 and the GS(TVAAPSGS)₄ linker amino acid sequence (i.e., GSTVAAPSGSTVAAPSGSTVAAPSGSTVAAPSGS)
# is shown in SEQ ID NO: 142.)

Heavy and light chain expression plasmids encoding BPC1085, BPC1086 and BPC1087 mAb-domain antibodies were co-transfected into HEK 2936E cells using 293FECTIN™ (Invitrogen, 12347019). A tryptone feed was added to each of the cell cultures after 24 hours and the cells were harvested after 72 hours. The antibodies were purified using a Protein A column before being tested in binding assays.

BPC1085, BPC1086 and BPC1087 mAb-domain antibodies were purified using Protein A affinity. 1 ml Protein A columns were used (GE Healthcare) on the AKTA XPRESS™ system, columns were equilibrated in PBS (Gibco/Invitrogen) and the antibodies eluted using Pierce IgG elute. Eluted fractions were neutralised using 1M Tris (Hydroxymethyl) Aminomethane buffer (in general 5-10% v/v). Eluted antibody fractions were pooled and analysed for aggregation by size exclusion chromatography and quantified by reading at OD$_{280}$ nm using a spectrophotometer.

These were compared to equivalent mAb-domain antibodies (2222, 2223, 2230 and 2231) which are described in Table 10. These comprise:
i) a dAb™ which is identical to that used in BPC1085, BPC1086 and BPC1087 except for position 89 which is 'L' in BPC2222, BPC2223, BPC2230 & BPC2231 and 'Q' in BPC1085, BPC1086 & BPC1087).
ii) same linkers
iii) an IL-13 mAb sequence which is identical to that used BPC1085, BPC1086 and BPC1087 except for position 100B which is 'Y' in BPC2222, BPC2223, BPC2230 & BPC2231 and 'V' in BPC1085, BPC1086 and BPC1087).

TABLE 10

| Identifier | mAb | Linker | dAb™ | Heavy chain | Light chain |
|---|---|---|---|---|---|
| BPC2222 | A1L1 | GS(TVAAPSGS)₁ | DOM9-155-154 | 135 | 24 |
| BPC2223 | A1L1 | GS(TVAAPSGS)₂ | DOM9-155-154 | 136 | 24 |
| BPC2230 | A1L1 | GS(TVAAPSGS)₃ | DOM9-155-154 | 137 | 24 |
| BPC2231 | A1L1 | GS(TVAAPSGS)₄ | DOM9-155-154 | 138 | 24 |

(In this table the TVAAPSGS linker amino acid sequence is shown in SEQ ID NO: 87, the GS(TVAAPSGS)₁ linker amino acid sequence (i.e., GSTVAAPSGS) is shown in SEQ ID NO: 139, the GS(TVAAPSGS)₂ linker amino acid sequence (i.e., GSTVAAPSGSTVAAPSGS) is shown in SEQ ID NO: 140, the GS(TVAAPSGS)₃ linker amino acid sequence (i.e., GSTVAAPSGSTVAAPSGSTVAAPSGS) is
shown in SEQ ID NO: 141 and the GS(TVAAPSGS)₄ linker amino acid sequence (i.e., GSTVAAPSGSTVAAPSGSTVAAPSGSTVAAPSGS) is shown in SEQ ID NO: 142.)

BPC2222, 2223, 2230 and 2231 mAb-domain antibodies were purified using Protein A affinity. 1 ml Protein A columns were used (GE Healthcare) on the AKTA XPRESS™ system, columns were equilibrated in PBS (Gibco/Invitrogen) and the antibodies eluted using Pierce IgG elute. Eluted fractions were neutralised using 1M Tris (Hydroxymethyl) Aminomethane buffer (in general 5-10% v/v). Eluted antibody fractions were pooled and analysed for aggregation by size exclusion chromatography and quantified by reading at OD$_{280}$ nm using a spectrophotometer.

BPC2222, 2223, 2230 and 2231 showed aggregation of between 30-40%, with the aggregated material eluting before 10 minutes.

Compared to BPC2222, 2223, 2230 and 2231 the constructs BPC1085, 1086 and 1087 showed lower levels of aggregation as assessed by size exclusion chromatography. The SEC profiles for these molecules are shown in FIGS. 3-9 11.2 IL-4 Binding ELISA Purified BPC1085, BPC1086 and BPC1087 mAb-domain antibodies were tested for binding to IL-4 in a direct binding ELISA according to the method described in Example 10.3.

These data are shown in FIG. 10. The results of the ELISA confirmed that these purified mAb-domain antibodies bound to IL-4. The positive controls anti-IL-4 mAb and BPC2231 also showed binding to IL-4 whereas the negative control mAb (anti IL-13 mAb) showed no binding to IL-4. This indicated in this ELISA the dAb™ potency increased when the linker length was increased from GS(TVAAPSGS (SEQ ID NO: 87)) (i.e., GSTVAAPSGS (SEQ ID NO: 93)) to GS(TVAAPSGS (SEQ ID NO: 87))$_{2-4}$ (i.e., GSTVAPSG-STVAPSGS (SEQ ID NO: 140), GSTVAPSGSTVAPSG-STVAPSGS (SEQ ID NO: 141) and GSTVAPSGSTVAPSG-STVAPSGSTVAPSGS (SEQ ID NO: 142).

11.3 Neutralization of IL-4 in a TF-1 Cell Proliferation Bioassay

Purified BPC1085, BPC1086 and BPC1087 mAb-domain antibodies were tested for neutralization of human IL-4 in a TF-1 cell bioassay.

TF-1 cells proliferate in response to a number of different cytokines including human IL-4. The proliferative response of these cells for IL-4 can therefore be used to measure the bioactivity of IL-4 and subsequently an assay has been developed to determine the IL-4 neutralisation potency (inhibition of IL-4 bioactivity) of mAb-domain antibodies. The assay was performed in sterile 96-well tissue culture plates under sterile conditions and all test wells were performed in duplicate. Approximately 2.2 ng/ml recombinant *E. Coli*-expressed human IL-4 was pre-incubated with various dilutions of mAb-domain antibodies (usually from 560 nM titrated in 3-fold dilutions to 0.009 nM) in a total volume of 120 μl for 1 hour at 37° C. An antibody of irrelevant specificity was similarly titrated as a negative control (anti-IL13 mAb). 50 μl of these samples were then added to 50 μl of TF-1 cells (at a concentration of 2×10$^5$ cells per ml) in a sterile 96-well tissue culture plate. Thus the final 100 μl assay volume contained various dilutions of mAb-domain antibodies (at a final concentration of 270 nM titrated in 3-fold dilutions to 0.005 nM), recombinant *E. Coli*-expressed human IL-4 (at a final concentration of 1.1 ng/ml) and TF-1 cells (at a final concentration of 1×10$^5$ cells per ml). The assay plate was incubated at 37° C. for approximately 4 days in a humidified CO$_2$ incubator. The amount of cell proliferation was then determined using the 'CellTitre 96® Non-Radioactive Cell Proliferation Assay' from Promega (catalogue number G4100), as described in the manufacturers instructions. The absorbance of the samples in the 96-well plate was read in a plate reader at 570 nm. These data were entered on an Excel™ spreadsheet, values for duplicate test wells were averaged and the average background value (no mAb-domain antibody and no IL-4 test wells) was subtracted.

The capacity of the mAb-domain antibodies to neutralise recombinant *E. Coli*-expressed human IL-4 bioactivity was expressed as that concentration of the mAb-domain antibody required to neutralise the bioactivity of the defined amount of human IL-4 (1.1 ng/ml) by 50% (=ND$_{50}$). The lower the concentration of the mAb-domain antibody required, the more potent the neutralisation capacity. The ND$_{50}$ data provided herein (Table 11) were calculated using the ROBOS-AGE™ function in Excel™. These data are represented graphically in FIG. 11.

An anti-IL-4 mAb and DOM9-155-154 (SEQ ID NO: 80) were included as positive controls for neutralization of human and cynomolgus IL-4 in the TF-1 cell bioassays. Additionally, a dAb™ with specificity for an irrelevant antigen (dummy dAb™) was also included as a negative control for neutralization of human or cynomolgus IL-4 in the TF-1 cell bioassays.

These were repeated several times and FIG. 11 shows the results for one of these experiments. ND$_{50}$ values were calculated from the dataset. The ND$_{50}$ value is the concentration of the mAb-domain antibody or mAb or dAb™, which is able to neutralise the bioactivity of IL-4 by 50%. The mean ND$_{50}$ value and the number of times tested (n) are shown in Table 11.

TABLE 11

| Molecule | Mean ND$_{50}$ value & standard deviation (nM) | Number of repeats |
|---|---|---|
| BPC1085 | 9.21 | 3 |
| BPC1086 | 4.32 | 3 |
| BPC1087 | 3.59 | 3 |
| anti-IL-4 mAb | 1.95 | 2 |
| DOM9-155-154 | 0.98 | 2 |
| Negative control dAb ™ | did not neutralise | 2 |

These data confirm that purified BPC1085, BPC1086 and BPC1087 mAb-domain antibodies, neutralized the bioactivity of human and cyno IL-4. Anti-IL-4 mAb and DOM9-155-154 also neutralised the bioactivity of human and cynomolgus IL-4, whereas the negative dAb™ (dummy dAb™) showed no neutralization in the same bioassay. All three mAb-domain antibodies show good potency, and there is a clear trend of increasing dAb™ potency with increasing linker length was apparent from the neutralisation assays, despite the more crude ELISA not picking up this difference in potency. A negative control anti-IL-4 mAb) showed no neutralization in the same bioassay.

11.4 Neutralization of Human IL-13 in a TF-1 Cell Proliferation Bioassay

Purified BPC1085, BPC1086 and BPC1087 mAb-domain antibodies were tested for neutralization of human IL-13 in a TF-1 cell bioassay as described below.

TF-1 cells proliferate in response to a number of different cytokines including human IL-13. The proliferative response of these cells for IL-13 can therefore be used to measure the bioactivity of IL-13 and subsequently an assay has been developed to determine the IL-13 neutralisation potency (inhibition of IL-13 bioactivity) of mAb-domain antibodies. The assay was performed in sterile 96-well tissue culture plates under sterile conditions and all test wells were performed in duplicate. Approximately 14 ng/ml recombinant *E. Coli*-expressed human IL-13 was pre-incubated with various dilutions of mAb-domain antibodies (usually from 560 nM titrated in 3-fold dilutions to 0.009 nM) in a total volume of 120 μl for 1 hour at 37° C. An antibody and dAb™ of irrelevant specificity was similarly titrated as negative controls (anti-IL-4 mAb and DOM9-155-154 respectively). 50 μl of these samples were then added to 50 μl of TF-1 cells (at a concentration of 2×10$^5$ cells per ml) in a sterile 96-well tissue culture plate. Thus the final 1000 assay volume contained various dilutions of mAb-domain antibodies (at a final concentration of 270 nM titrated in 3-fold dilutions to 0.005 nM), recombinant *E. Coli*-expressed human IL-13 (at a final concentration of 7 ng/ml) and TF-1 cells (at a final concentration of 1×10$^5$ cells per ml). The assay plate was incubated at 37° C. for approximately 4 days in a humidified CO$_2$ incubator. The amount of cell proliferation was then determined using the 'CellTitre 96® Non-Radioactive Cell Proliferation Assay' from Promega (catalogue number G4100), as described in the manufacturer's instructions. The absorbance of the samples in the 96-well plate was read in a plate reader at 570 nm. These data were entered on an Excel™ spreadsheet, values for duplicate test wells were averaged and the average background value (no mAb-domain antibody and no IL-13 test wells) was subtracted. The capacity of the mAb-domain antibodies to neutralise recombinant *E. Coli*-expressed human IL-13 bioactivity was expressed as that concentration of the mAb-dAb™ required to neutralise the bioactivity of the defined amount of human IL-13 (7 ng/ml) by 50% (=$ND_{50}$).

tors containing the human kappa C region. Table 13 summarises the re-humanised light chains that have been constructed.

TABLE 13

| Light chain name | Description | Backbone | Back Mutations | SEQ ID NO: Nucleotide sequence | SEQ ID NO: Amino acid sequence |
|---|---|---|---|---|---|
| P0 | Anti-IL-13 808VL kappa light chain | IGKV1 39 + JK2 | N/A | 108 | 109 |
| P1 | Anti-IL-13 809VL kappa light chain | IGKV1 39 + JK2 | I2V + Q3L | 110 | 111 |
| Q0 | | IGKV3 20 + JK2 | N/A | 112 | 113 |
| Q1 | | IGKV3 20 + JK2 | I2V, V3L, L4M, E1D, R45K, I58V | 114 | 115 |

The lower the concentration of the mAb-domain antibody required, the more potent the neutralisation capacity. The $ND_{50}$ data provided herein (Table 12) were calculated using the ROBOSAGE™ function in Excel™. These data are represented graphically in FIG. 12.

An anti IL-13 mAb (SEQ ID NO:22 & 24) was included as a positive control for neutralization of human IL-13 in the TF-1 cell bioassays. Additionally, an anti-IL-4 mAb was also included as a negative control.

FIG. 12 shows the result of the TF-1 cell neutralization assay. $ND_{50}$ values were calculated from the dataset. The $ND_{50}$ value is the concentration of the mAb-domain antibody or mAb or dAb™, which is able to neutralise the bioactivity of IL-13 by 50%. The mean $ND_{50}$ value and the number of times tested are shown in Table 12.

TABLE 12

| Molecule | Mean $ND_{50}$ value & standard deviation (nM) | Number of repeats |
|---|---|---|
| BPC1085 | 0.88 | 1 |
| BPC1086 | 1.01 | 1 |
| BPC1087 | 1.14 | 1 |
| Anti-IL-13 mAb | 5.01 | 1 |
| anti-IL-4 mAb | did not neutralise | 1 |

These data confirm that purified BPC1085, BPC1086 and BPC1087 mAb-domain antibodies, neutralized the bioactivity of recombinant human and cyno IL-13. A negative control anti-IL-4 mAb showed no neutralization in the same bioassay.

Example 12

Re-Humanisation of Anti-IL-13 mAb Light Chain 12.1 Re-Humanisation

The light chain CDRs of the murine antibody 6A1 (The light chain of which is set out in SEQ ID NO:59) were re-grafted onto new frameworks in order to improve the expression of some anti-IL-13 mAb-anti-IL-4 dAb™ molecules (BPC1085). Codon optimised light chain variable region sequences (summarised in Table 13) were constructed de novo using a PCR-based strategy and overlapping oligonucleotides. PCR primers were designed to incorporate the signal sequence (SEQ ID NO: 56) and to include HindIII and BsiWI restriction sites designed to frame the $V_L$ domain and allow cloning into pTT and RIn mammalian expression vec- 12.2 Molecule Expression in HEK 293 6E Cells Expression properties of the re-humanised light chains were initially examined in mAb format. Plasmids encoding the A1Y100BVAL1 (SEQ ID NO: 54) heavy chain, the existing light chain (SEQ ID NO: 24) and the re-humanised light chains were transiently co-transfected into HEK 293 6E cells using 293FECTIN™ (Invitrogen, 12347019). Plasmids were expressed at small scale (2×0.75 ml culture volumes) to produce antibody. A tryptone feed was added to the cell culture after 24 hours and the cells were harvested after a further 72 hours. Table 14 summarises all of the mAbs which were constructed and expressed.

TABLE 14

| Antibody ID | Molecule description | Protein SEQ ID NO: |
|---|---|---|
| A1Y100BVAL1 | H chain: Anti human IL-13 Y100b V mAb | 54 |
| | L chain: 586 anti-human IL-13 mAb | 24 |
| BPC3208 | H chain: Anti human IL-13 Y100b V mAb | 54 |
| | L chain: P0 re-humanised anti-human IL-13 mAb | 108 |
| BPC3211 | H chain: Anti human IL-13 Y100b V mAb | 54 |
| | L chain: P1 re-humanised anti-human IL-13 mAb | 110 |
| BPC3219 | H chain: Anti human IL-13 Y100b V mAb | 54 |
| | L chain: Q0 re-humanised anti-human IL-13 mAb | 112 |
| BPC3220 | H chain: Anti human IL-13 Y100b V mAb | 54 |
| | L chain: Q1 re-humanised anti-human IL-13 mAb | 114 |

Antibody expression was assessed directly from the tissue culture supernatant, by a quantitative immunoassay using a GYROLAB™ workstation. Antibodies BPC3208 and BPC3211 containing re-humanised light chains (denoted P0 and P1 respectively), exhibited improved expression yields in comparison to the A1Y100BVAL1 mAb. Q0 and Q1 light chains (BPC3219 and BPC3220) did not improve expression of the anti-IL-13 mAb. Expression data is presented in Table 15.

TABLE 15

| Antibody ID | Total yield in cell supernatant (µg) |
|---|---|
| A1Y100BVAL1 | 19.9 |
| BPC3208 | 111.0 |
| BPC3211 | 115.0 |

TABLE 15-continued

| Antibody ID | Total yield in cell supernatant (µg) |
|---|---|
| BPC3219 | 16.0 |
| BPC3220 | 18.3 |

12.3 mAb-Domain Antibody Expression in HEK 293 6E Cells

As the re-humanised light chains of BPC3208 and BPC3211 exhibited improved expression of the anti-IL-13 mAb, they were examined in the context of an anti-IL-13 mAb-anti IL-4-dAb™. Re-humanised light chains P0 and P1 and the 586 (L1) light chain were co-transfected with the 829H-GS(TVAAPSGS)$_2$-256 heavy chain (SEQ ID NO: 96, details summarised in Table 16) into HEK 293 6E cells using 293FECTIN™ (Invitrogen, 12347019). Plasmids were expressed at the 50 to 500 ml scale to produce antibody molecules. A tryptone feed was added to the cell culture after 24 hours and the cells were harvested after a further 48 hours. Antibodies were purified using immobilised Protein A columns and quantified by reading absorbance at 280 nm and where indicated, the purified antibody molecule was assessed in the assays described in the examples set out below. BPC3214 and BPC3215 were analysed by size exclusion chromatography (SEC) as illustrated in FIGS. 13 and 14.

12.4 Human IL-13 Binding ELISA

Purified BPC3214 and BPC3215 were tested for binding to human IL-13 in comparison to BPC1085 (described in Example 10) via a direct binding ELISA. Anti-IL-13 mAb A1Y100BVAL1 and anti-IL-4 mAb were also examined as positive and negative controls respectively. 96-well high binding plates were coated with 500/well of recombinant E. coli-expressed human IL-13 (Batch number: GRITS31061) at 5 µg/ml and incubated at +4° C. overnight. All subsequent steps were carried out at room temperature. The plates were washed 3 times with phosphate-buffered saline with 0.05% of TWEEN™-20. 100 µL of blocking solution (1% BSA in phosphate-buffered saline with 0.05% of TWEEN™-20) was added to each well and the plates were incubated for at least 1 hour at room temperature. Another wash step was then performed. The purified antibodies were successively diluted across the plates in blocking solution. After 1 hour incubation, the plate was washed. Goat anti-human kappa light chain specific peroxidase conjugated antibody was diluted in blocking solution to 0.75 µg/ml and 50 µl was added to each well. The plates were incubated for one hour. After another two wash steps, 50 µl of OPD (o-phenylenediamine dihydrochloride) SIGMAFAST™ substrate solution was added to each well and the reaction was stopped by addition of 50 µL of 3M sulphuric acid. Absorbance was read at 490 nm using the VERSAMAX™ Microplate Reader (Molecular Devices) using a basic endpoint protocol. These data are shown in FIG. 15. Direct binding ELISA confirmed that BPC3214 and BPC3215 bind to human IL-13. BPC3214 and BPC3215 exhibit similar IL-13 binding potency to BPC1085. Positive control anti-IL-13 mAb A1Y100BVAL1 also showed binding to recombinant IL-13 whereas negative control anti-IL-4 mAb demonstrated no binding to human IL-13.

TABLE 16

| Antibody ID | Alternative names | Linker | Molecule description | Protein SEQ ID NO: | DNA SEQ ID NO: |
|---|---|---|---|---|---|
| BPC1085 | 829H-GS(TVAAPSGS)$_2$-256 | GS(TVAAPSGS)$_2$ | H chain: Anti-human IL-13 mAb heavy chain Y100B V-GS(TVAAPSGS)$_2$-DOM9-155-256 | 96 | 97 |
| | | | L chain: 586 anti-human IL-13 mAb light chain | 24 | 25 |
| BPC3214 | 808H-GS(TVAAPSGS)$_2$-256 | GS(TVAAPSGS)$_2$ | H chain: Anti-human IL-13 mAb heavy chain Y100B V-GS(TVAAPSGS)$_2$-DOM9-155-256 | 96 | 97 |
| | | | L chain: P0 re-humanised anti-human IL-13 mAb | 108 | 109 |
| BPC3215 | 809H-GS(TVAAPSGS)$_2$-256 | GS(TVAAPSGS)$_2$ | H chain: Anti-human IL-13 mAb heavy chain Y100B V-GS(TVAAPSGS)$_2$-DOM9-155-256 | 96 | 97 |
| | | | L chain: P1 re-humanised anti-human IL-13 mAb | 110 | 111 |

(In this table the TVAAPSGS linker amino acid sequence is shown in SEQ ID NO: 87 and the GS(TVAAPSGS)$_2$ linker amino acid sequence (i.e., GSTVAAPSGSTVAAPSGS) is shown in SEQ ID NO: 140.)

Consistent with observations in the mAb format, the mAb-domain antibodies containing the re-humanised light chains (BPC3214 and BPC3215) exhibited improved expression in comparison to BPC1085. Representative expression data is summarised in table 17 5.

TABLE 17

| Antibody ID | Yield of purified mAb-domain antibody (µg/ml) |
|---|---|
| BPC1085 | 5.6 |
| BPC3214 | 9.8 |
| BPC3215 | 7.2 |

12.5 Human IL-4 Binding ELISA

Purified BPC3214 and BPC3215 were also tested for binding to recombinant E. coli-expressed human IL-4 in a direct binding ELISA. An ELISA was performed as described in example 4, coating 96-well high binding plates with 500/well of recombinant E. coli-expressed human IL-4 at 5 µg/ml and incubated at +4° C. overnight. These data are shown in FIG. 16. Direct binding ELISA confirms that BPC3214 and BPC3215 bind to human IL-4. BPC1085 was also examined. BPC3214 exhibits similar IL-4 binding potency to BPC1085.

Positive control anti-IL-4 mAb also showed binding to recombinant IL-4 whereas negative control anti-IL-13 mAb A1Y100BVAL1 demonstrated no binding to human IL-4.

Example 13

Binding Affinity of mAb-Domain Antibodies Comprising the Original IL-13 mAb CDRH3 (BPC2222, BPC2223 & BPC2230-2231) for IL-13 and IL-4 as Assessed by BIAcore™ Analysis Method Protein A was immobilised on a C1 chip by primary amine coupling; this surface was used as a capture surface for the antibody molecules to be tested. Recombinant E. coli-expressed human IL13 was used at 256, 64, 16, 4, and 1 nM, recombinant E. coli-expressed human IL4 was used at 64, 16, 4, 1 and 0.25 nM, with 0 nM (i.e. buffer alone) used to double reference the binding curves of both IL4 and IL13 binding. Regeneration of the Protein A surface was with 100 mM Phosphoric acid. The assay was run at 25° C. using HBS-EP as running buffer. The data was fitted to 1:1 model inherent to the BIAcore™ T100 analysis software.

The results of binding to human IL13 are shown in Table 18 and the result of binding to human IL4 are shown in Table 19.

TABLE 18

| Molecule name | ka(M/s)  | kd(1/s)  | KD (nM) |
|---------------|----------|----------|---------|
| BPC2222       | 1.31E+06 | 4.93E−04 | 0.376   |
| BPC2223       | 1.32E+06 | 4.90E−04 | 0.372   |
| BPC2230       | 1.31E+06 | 4.88E−04 | 0.373   |
| BPC2231       | 1.30E+06 | 5.13E−04 | 0.394   |

TABLE 19

| Molecule name | ka(M/s)  | kd(1/s)  | KD (nM) |
|---------------|----------|----------|---------|
| BPC2222       | 1.06E+05 | 1.09E−04 | 1.027   |
| BPC2223       | 8.59E+06 | 1.56E−04 | 0.018   |
| BPC2230*      | 2.48E+07 | 2.48E−04 | 0.010   |
| BPC2231*      | 4.03E+07 | 2.31E−04 | 0.006   |

*The on-rate for BPC2230 and 2231 are beyond the sensitivity of BIAcore ™, but the fact that we cannot accurately analyse this data does indicate that the interaction with IL4 is likely to be of high affinity with a fast on-rate.

Example 14

Binding Affinity of mAb-Domain Antibodies Comprising the Original IL-13 mAb CDRH3 (BPC2222, BPC2231) & Variant Anti-IL-13 mAb CDRH3 (BPC1085-1087) for IL-13 and IL-4 as Assessed by BIAcore™ Analysis Method Protein A was immobilised on a CM5 chip by primary amine coupling; this surface was used as a capture surface for the antibody molecules to be tested. Recombinant E. coli-expressed human IL13 was used at 256 nM only, Recombinant E. coli-expressed human IL4 was used at 64, 16, 4 and 1 nM, with 0 nM (i.e. buffer alone) used to double reference the binding curves for both IL4 and IL13 binding. Regeneration of the Protein A surface was with 50 mM NaOH. The assay was run at 25° C. using HBS-EP as running buffer. The data was fitted to 1:1 model inherent to the BIAcore™ T100 analysis software.

The results of binding to human IL13 are shown in Table 20, and the results of binding to human IL4 are shown in Table 21.

TABLE 20

| Molecule name | ka(M/s)  | kd(1/s)  | KD (nM) |
|---------------|----------|----------|---------|
| BPC2222       | 1.64E+05 | 5.15E−05 | 0.314   |
| BPC2231       | 5.36E+08 | 1.16E−03 | 0.002   |
| BPC1085       | 1.87E+07 | 8.97E−04 | 0.048   |
| BPC1086       | 7.99E+07 | 1.64E−03 | 0.021   |
| BPC1087       | 9.86E+07 | 1.79E−03 | 0.018   |

On-rate for BPC1086 and BPC1087 are beyond the sensitivity of BIAcore ™, but the fact that we cannot accurately analyse this data does indicate that the interaction with IL4 is likely to be of high affinity with a fast on-rate.

TABLE 21

| Molecule name | ka(M/s)  | kd(1/s)  | KD (nM) |
|---------------|----------|----------|---------|
| BPC2222       | 1.44E+06 | 4.44E−04 | 0.308   |
| BPC2231       | 1.56E+06 | 4.95E−04 | 0.316   |
| BPC1085       | 1.20E+06 | 6.39E−05 | 0.053   |
| BPC1086       | 1.28E+06 | 6.57E−05 | 0.051   |
| BPC1087       | 1.13E+06 | 6.42E−05 | 0.057   |

Example 15

Binding Affinity of mAb-Domain Antibodies Comprising a Number of Variant Anti-IL-13 mAb CDRH3 (BPC1085, BPC1090-BPC1095, & BPC1108-BPC1119) for IL-4 as Assessed by BIAcore™ Analysis Method (Human IL-4 Binding Affinity)

Protein A was immobilised on a CM5 chip by primary amine coupling; this surface was used as a capture surface for the antibody molecules to be tested.

Recombinant E. coli-expressed human IL4 was used at 64, 16, 4, 1 and 0.25 nM. All binding curves were double referenced with a 0 nM injection (i.e. buffer alone).

Regeneration of the Protein A surface was with 50 mM NaOH. The assay was run at 25° C. using HBS-EP as running buffer. The data was fitted to 1:1 model inherent to the BIAcore™ T100 analysis software.

The results of binding to human IL4 are shown in Table 22.

TABLE 22

| Molecule name | ka(M/s)  | kd(1/s)  | KD (nM)    |
|---------------|----------|----------|------------|
| BPC1085       | 1.07E+07 | 8.34E−04 | 0.078      |
| BPC1090       | 4.34E+06 | 4.16E−04 | 0.096      |
| BPC1091       | 6.05E+06 | 1.02E−03 | 0.168      |
| BPC1092       | 2.27E+06 | 3.89E−03 | 1.713      |
| BPC1093       | 3.84E+06 | 2.11E−04 | 0.055      |
| BPC1094       | 1.46E+06 | 3.04E−03 | 2.078      |
| BPC1095       | 6.78E+06 | 3.18E−02 | 4.687      |
| BPC1108       | 4.38E+06 | 1.23E−03 | 0.281      |
| BPC1109       | 1.20E+06 | 1.77E−01 | 147.300    |
| BPC1110       | 1.07E+06 | 1.73E−03 | 1.626      |
| BPC1111       | 2.98E+06 | 1.11E−04 | 0.037      |
| BPC1112*      | 1.14E+08 | 3.31E+00 | 28.980     |
| BPC1113       | no       | binding  | seen       |
| BPC1114       | 3.89E+06 | 2.55E−03 | 0.656      |
| BPC1115**     | 1.44E+08 | 3.29E−01 | 2.292      |
| BPC1116       | 6.82E+06 | 2.74E−03 | 0.402      |

TABLE 22-continued

| Molecule name | ka(M/s) | kd(1/s) | KD (nM) |
|---|---|---|---|
| BPC1117 | 3.95E+06 | 9.13E−04 | 0.231 |
| BPC1118 | 6.39E+06 | 2.58E−03 | 0.405 |
| BPC1119 | no binding seen | | |

*BPC1112 data has a positive off-rate as a result of the machine being unable to calculate real off-rate, possibly due to the fact it is so rapid, in addition the on-rate for this construct is beyond what is measurable by BIAcore ™, but construct is a very poor binder to IL4.
*BPC1115 also has an impossible on-rate, it is outside scope of BIAcore ™ to calculate affinity.

Example 16

IL-13 Binding Affinity of mAb-Domain Antibodies Comprising the Re-Humanised Light Chain (BPC3214 & BPC3215) Compared to the Original Light Chain (BPC1085) as Assessed by BIAcore™ Analysis Method (Human and Cyno IL-13 Binding Affinity)

Protein A was immobilised on a CM5 chip by primary amine coupling; this surface was used as a capture surface for the antibody molecules to be tested.

Recombinant *E. coli-expressed* human IL13 and cyno IL13 were used 64, 16, 4, 1 and 0.25 nM. All binding curves were double referenced with a 0 nM injection (i.e. buffer alone).

Regeneration of the Protein A surface was with 50 mM NaOH. The assay was run at 25° C. using HBS-EP as running buffer. The data was fitted to 1:1 model inherent to the BIAcore™ T100 analysis software.

The results of binding to human and cyno IL13 are shown in Table 23.

TABLE 23

| Molecule name | ka(M/s) | kd(1/s) | KD (nM) | Comment |
|---|---|---|---|---|
| Binding to human IL13 | | | | |
| BPC3214 | 7.749E+05 | 7.18E−05 | 0.093 | |
| BPC3215 | 8.220E+05 | 5.23E−05 | 0.064 | |
| BPC1085 | 8.652E+05 | 6.34E−05 | 0.073 | |
| Binding to cyno IL13 | | | | |
| BPC3214* | 3.214E+05 | 5.07E−06 | 0.015770 | Impossible off-rates |
| BPC3215* | 3.283E+05 | 3.13E−06 | 0.009546 | Impossible off-rates |
| BPC1085* | 3.552E+05 | 5.19E−10 | 0.000001 | Impossible off-rates |

*The off-rates (ka) for cyno IL13 binding to BPC3214, BPC3215 and BPC1085 are beyond the sensitivity of the BIAcore ™ T100, this indicates the dissociation rate is very slow and that the interaction is likely to be of very high affinity.

Example 17

Stressor Studies of mAb-Domain Antibodies with and without the Mutated dAb™

A number of mAb-domain antibodies were placed in PBS or 50 mM acetate buffer and incubated at 37° C. for up to 14 days. They were then analysed for presence of a visual precipitate, soluble aggregate and adherence to concentration stability.

The results indicate that the mAb-domain antibodies comprising the mutated dAb™ (BPC2222, 2223, 2230, 2231) behaved similarly to the non-mutated dAb™ (BPC1085, 1086, 1087) both categories of mAb-domain antibody appeared to be stable in both PBS and acetate buffers over the two week incubation period at 37° C., as indicated by no change in the protein concentration in the solutions. In addition no or very little change was noted for the levels of aggregates in the solutions and no precipitation was observed.

Example 18

PK Assessment

The pharmacokinetics of BPC1085, BPC1086, and BPC1087 were investigated in separate studies following IV administration to rats. The PK of BPC1085 was also investigated in cynomolgus monkeys following IV administration.

The PK of all three molecules in rat and BPC1085 in monkey were found to be consistent with that of a standard mAb.

Figure 1:
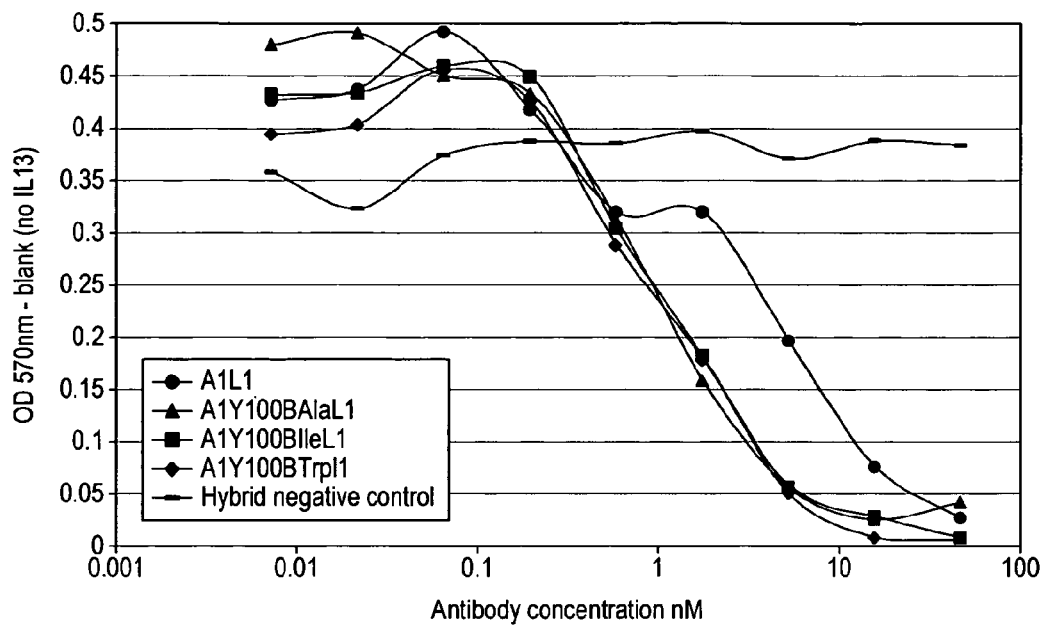
FIG. 1: A graph showing the capacity of the mAb-domain antibodies comprising the Y100B variants to neutralise human IL-13 in a TF-1 cell proliferation assay
Figure 2:
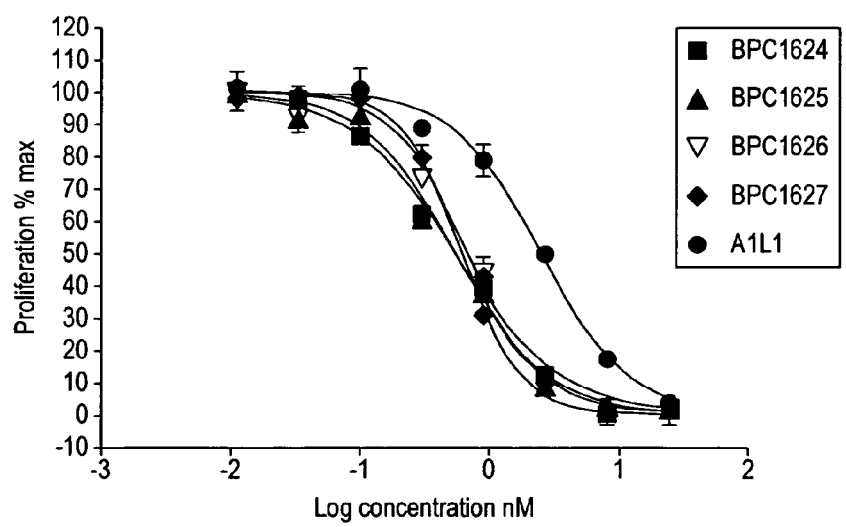
FIG. 2: A graph showing the capacity of the mAb-domain antibodies comprising the Y100B variants to neutralise human IL-13 in a TF-1 cell proliferation assay
Figure 3:
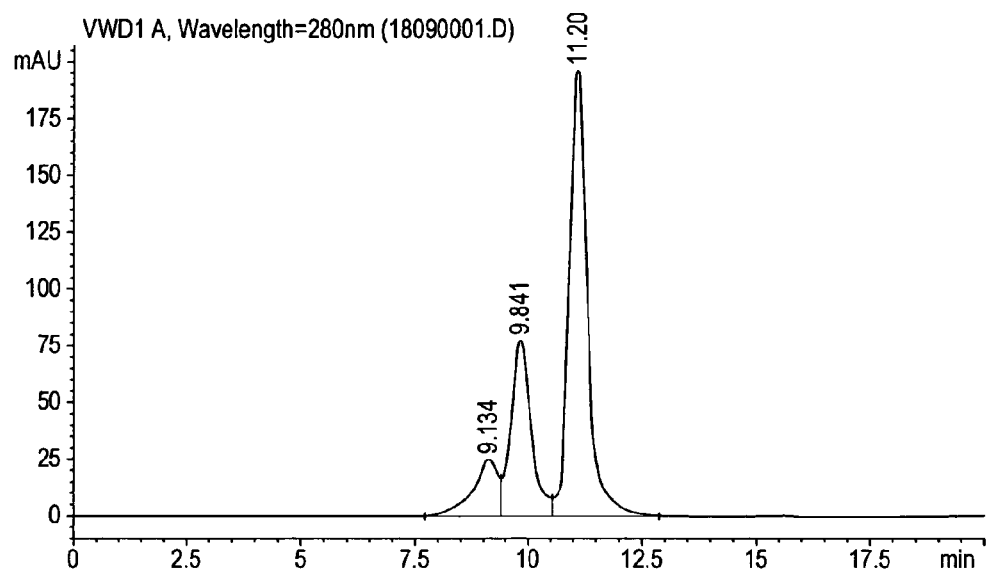
FIG. 3: SEC trace of BPC2222
Figure 4:
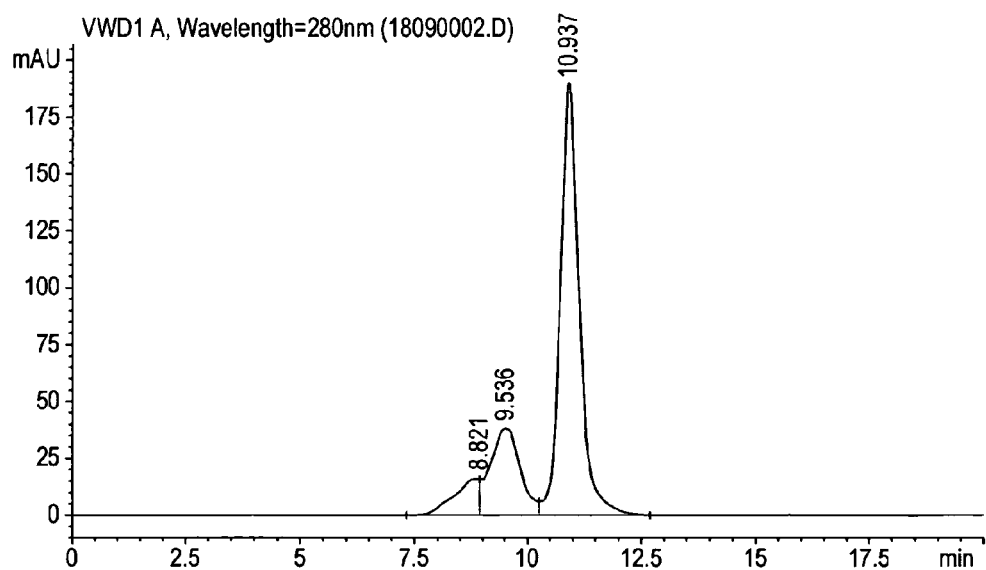
FIG. 4: SEC trace of BPC2223
Figure 5:
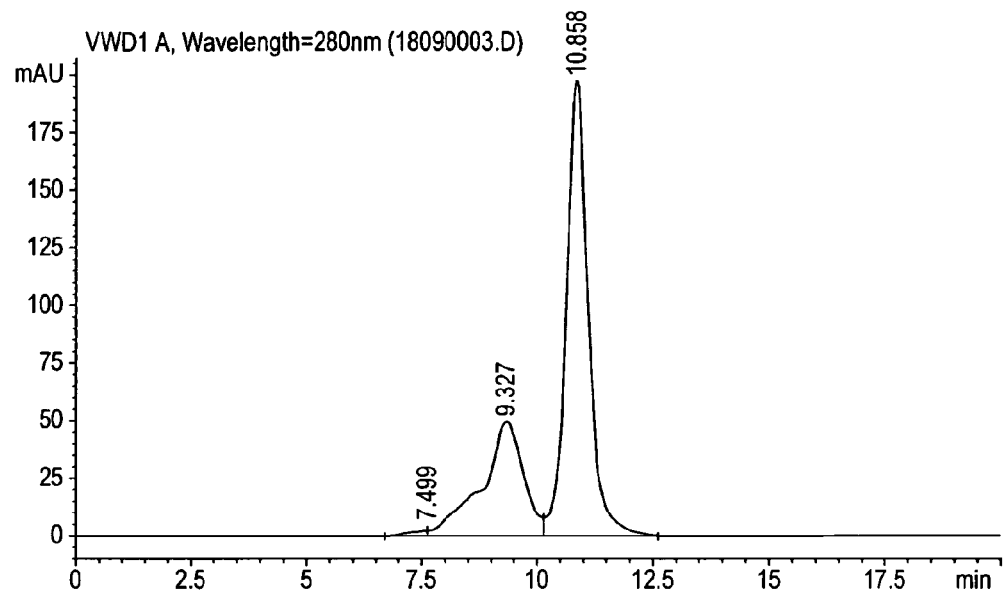
FIG. 5: SEC trace of BPC2230
Figure 6:
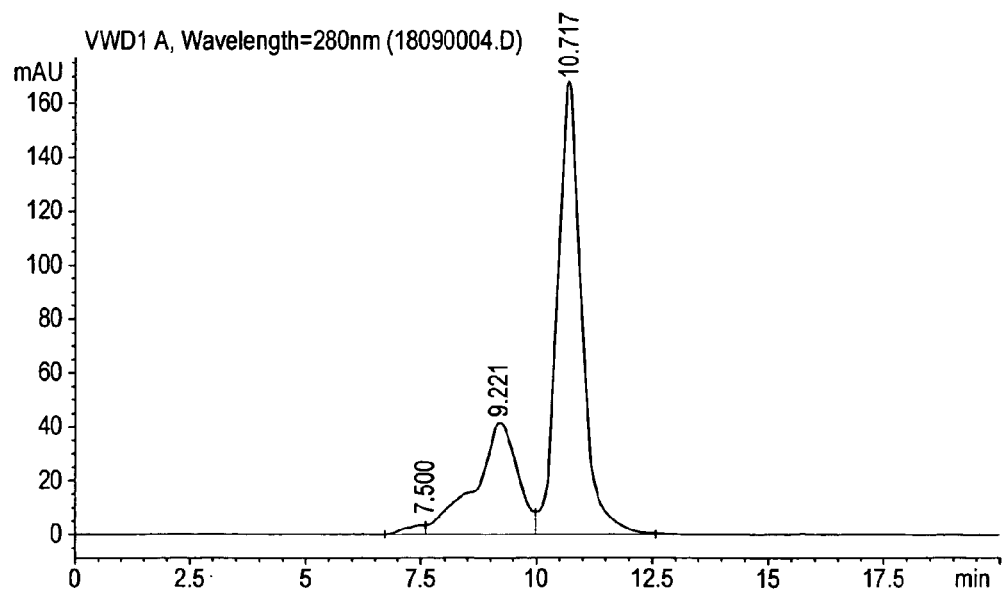
FIG. 6: SEC trace of BPC2231
Figure 7:
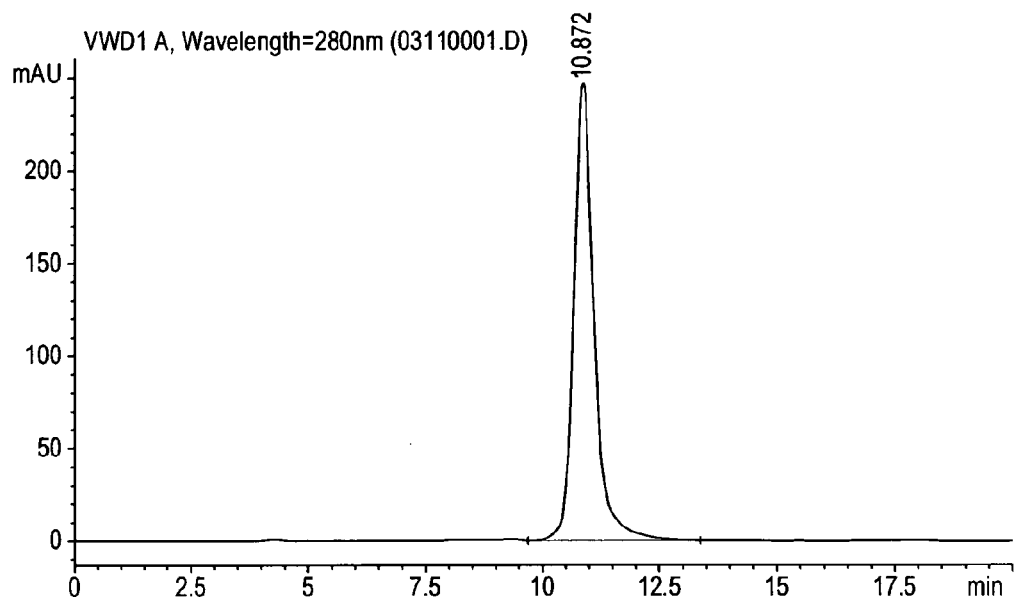
FIG. 7: SEC trace of BPC1085
Figure 8:
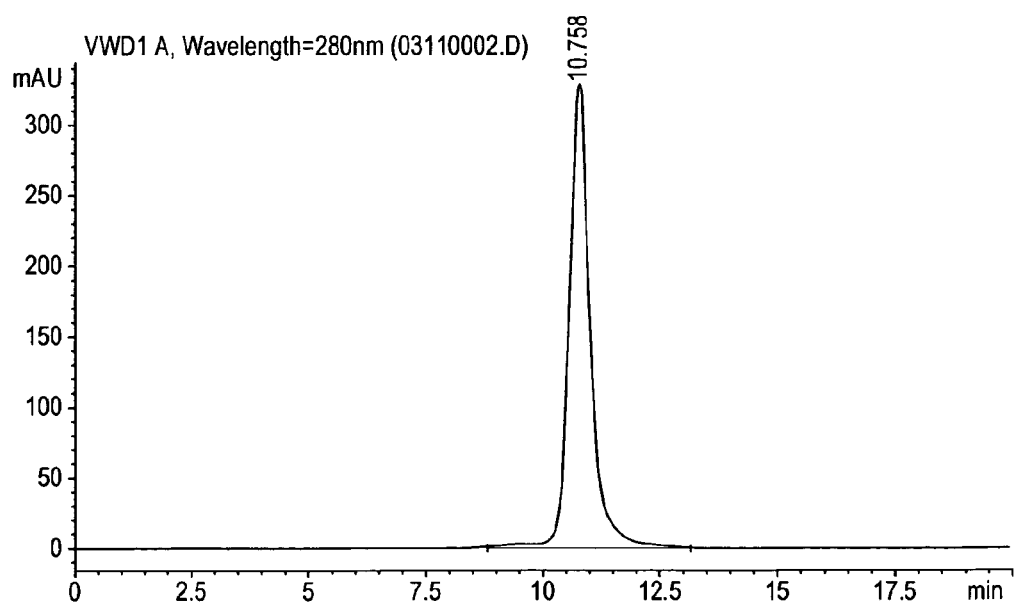
FIG. 8: SEC trace of BPC1086
Figure 9:
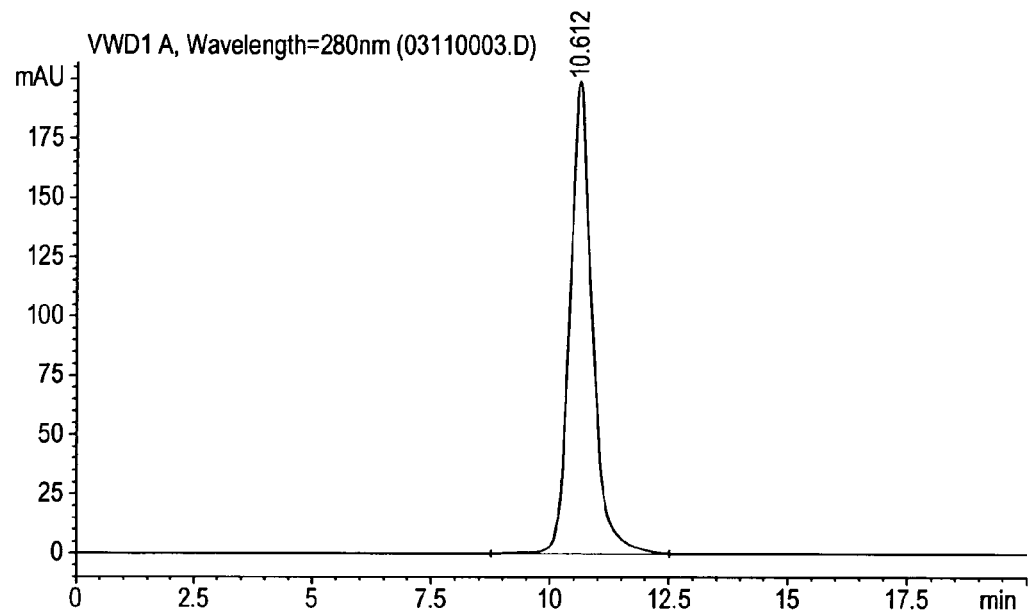
FIG. 9: SEC trace of BPC1087
Figure 10:
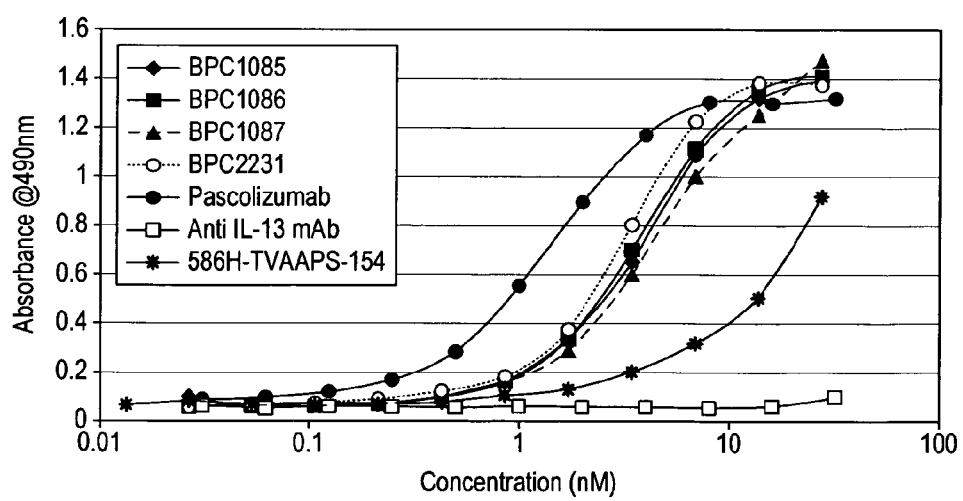
FIG. 10: A graph showing binding of purified mAb-domain antibodies (BPC1085, BPC1086 and BPC1087) to human IL-4 as determined by ELISA. The IL-4 control mAb is labelled as 'pascolizumab'.
Figure 11:
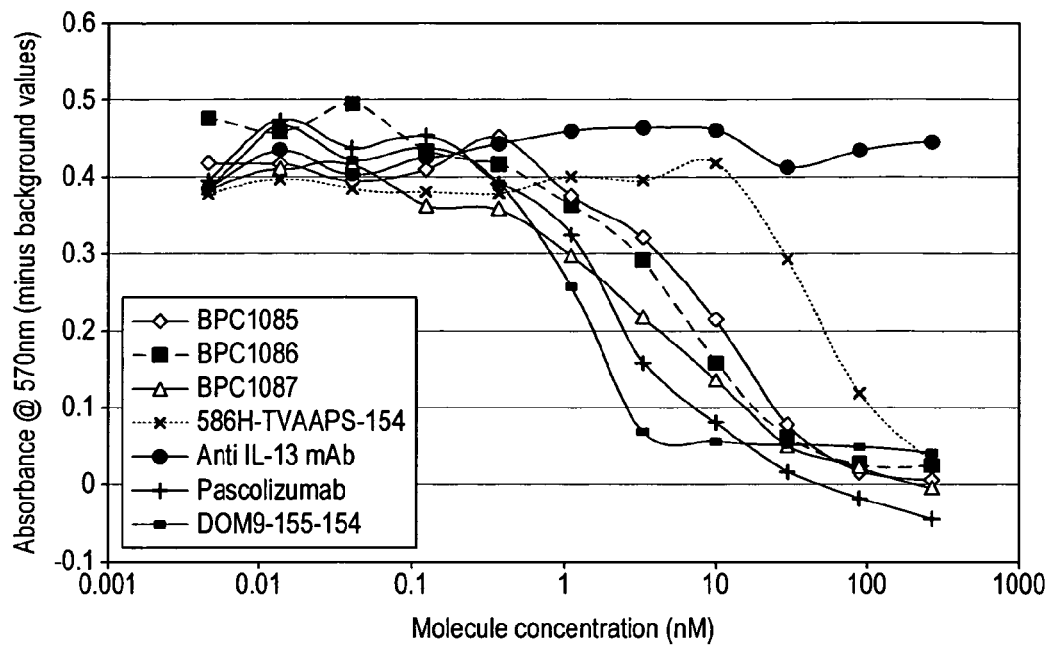
FIG. 11: A graph showing neutralization of human IL-4 by purified mAb-domain antibodies (BPC1085, BPC1086 and BPC1087) to human IL-4 in the TF-1 cell bioassay. The IL-4 control mAb is labelled as 'pascolizumab'.
Figure 12:
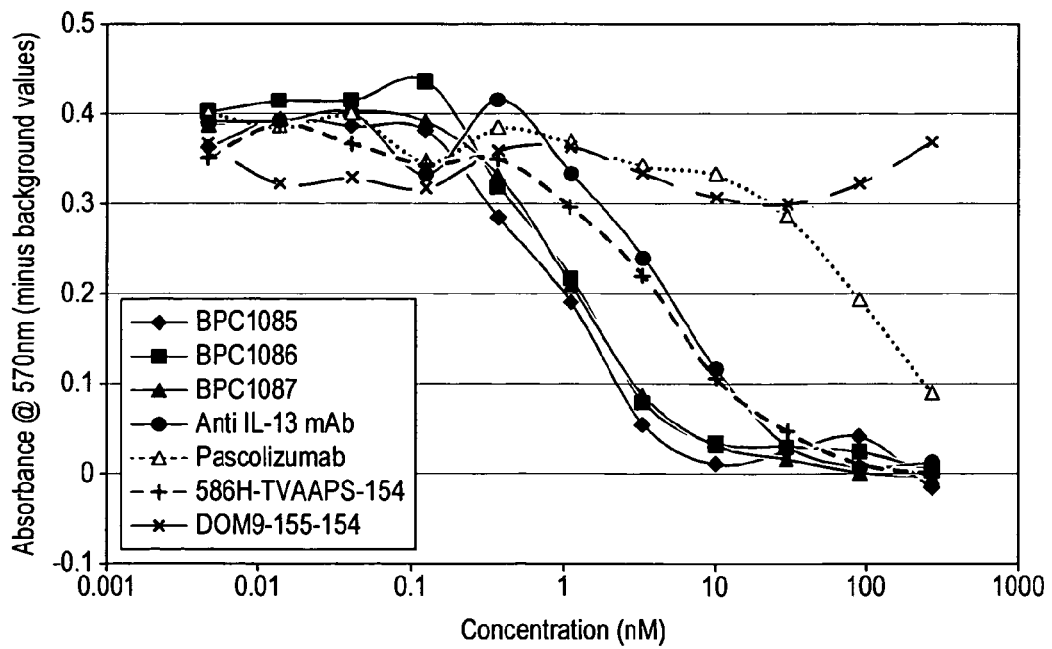
FIG. 12: A graph showing neutralization of human IL-13 by purified mAb-domain antibodies (BPC1085, BPC1086 and BPC1087) to human IL-13 in the TF-1 cell bioassay. The IL-4 control mAb is labelled as 'pascolizumab'.
Figure 13:
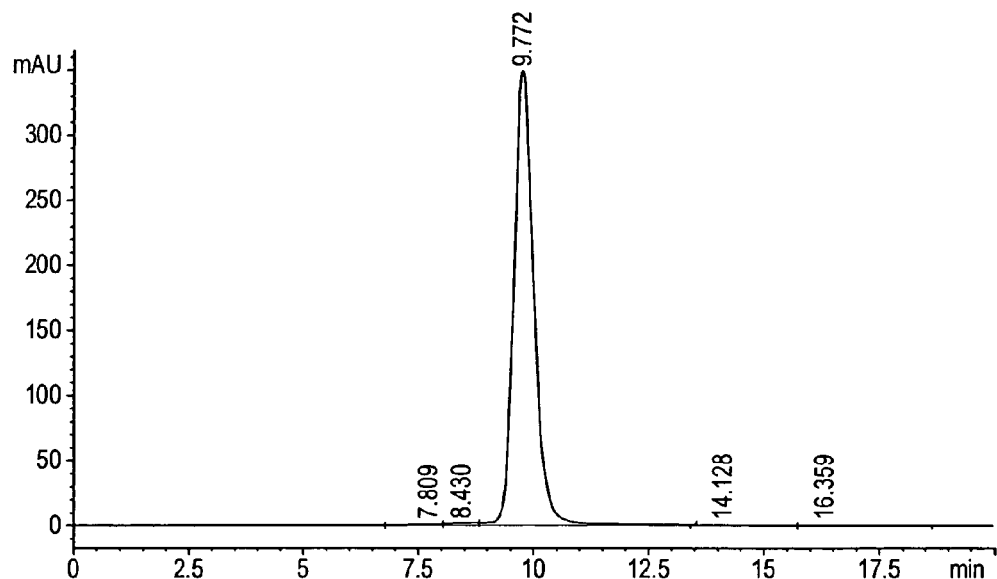
FIG. 13: SEC profile for BPC3214.
Figure 14:
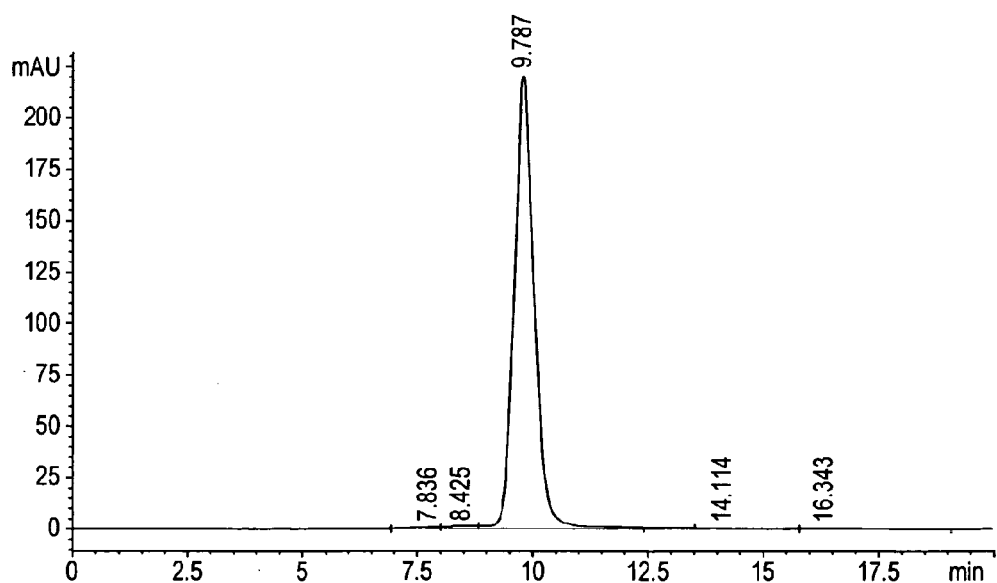
FIG. 14: SEC profile for BPC3215.
Figure 15:
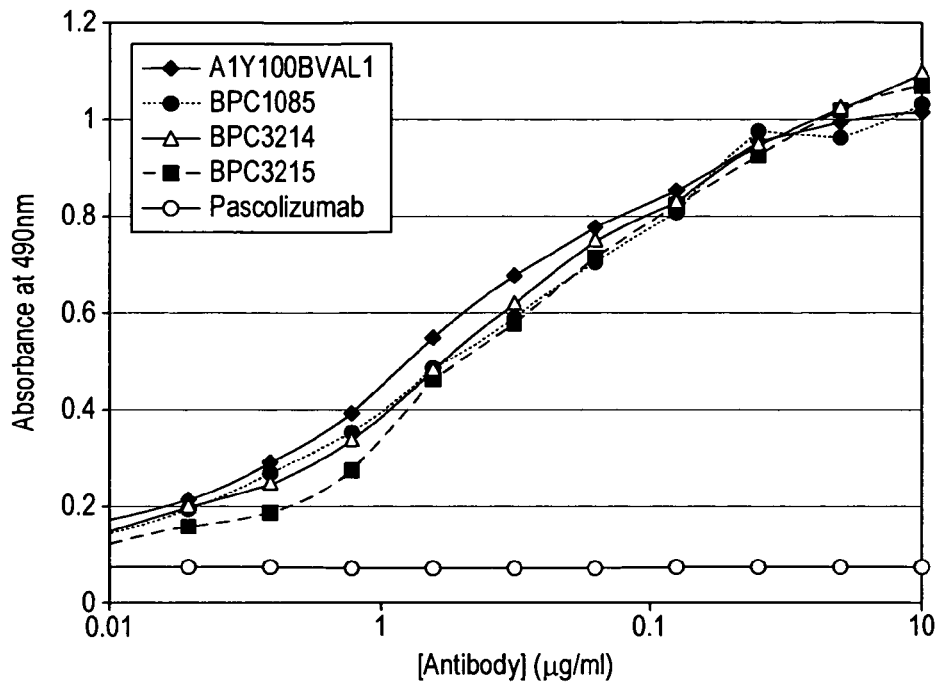
FIG. 15: A graph showing binding of purified mAb-domain antibodies BPC3214, BPC3215, BPC1085 and control mAbs A1Y100BVAL1 and anti-IL-4 mAb to human IL-13 as determined by ELISA. The IL-4 control mAb is labelled as 'pascolizumab'.
Figure 16:
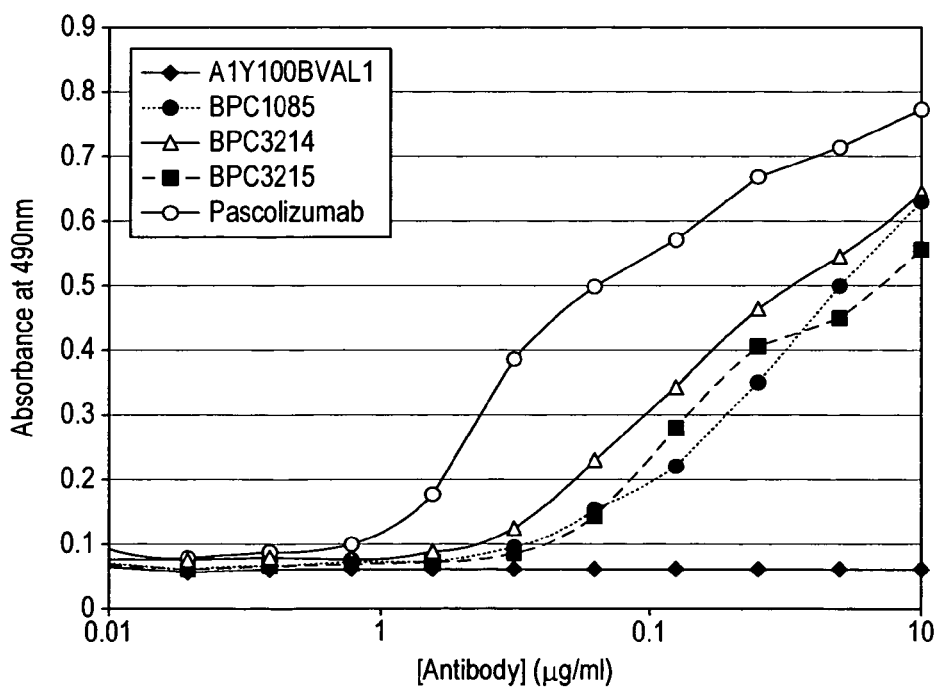
FIG. 16: A graph showing binding of purified mAb-domain antibodies BPC3214, BPC3215, BPC1085 and control mAbs A1Y100BVAL1 and anti-IL-4 mAb to human IL-4 as determined by ELISA. The IL-4 control mAb is labelled as 'pascolizumab'.
Figure 17:
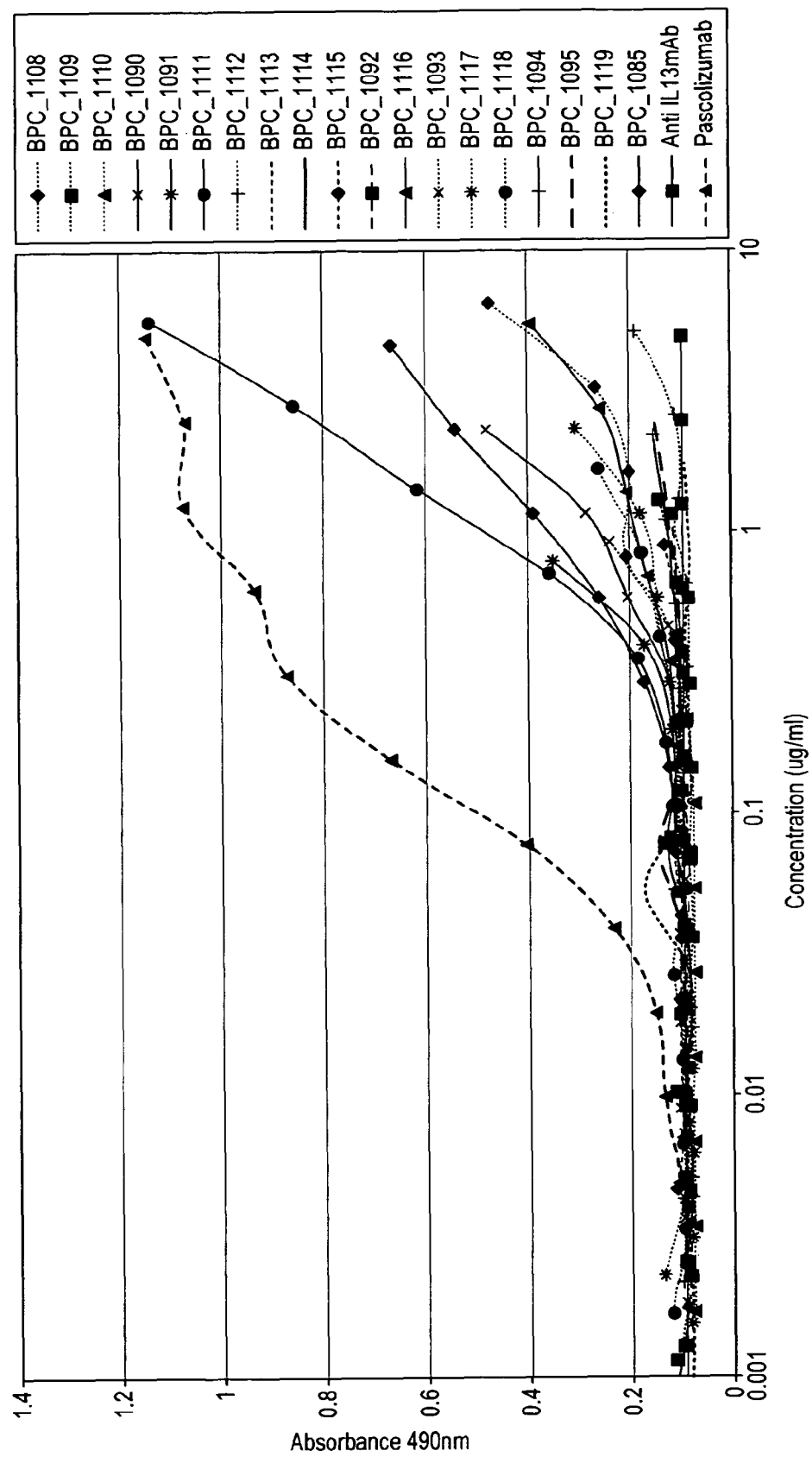
FIG. 17: A graph showing binding of transiently expressed mAb-domain antibodies to recombinant *E. coli-expressed* human IL-4 as determined by ELISA. The IL-4 control mAb is labelled as 'pascolizumab'.

Sequence Summary (Table 24). (In this table the TVAAPS linker amino acid sequence is shown in SEQ ID NO: 83, the ASTKGPS linker amino acid sequence is shown in SEQ ID NO: 84 and the TVAAPSGS linker amino acid sequence is shown in SEQ ID NO: 87.)

| Description | Sequence identifier (SEQ ID NO) | |
|---|---|---|
| | amino acid sequence | Polynucleotide sequence |
| Anti IL13 A1, CDRH1 | 1 | — |
| Anti IL13 A1, CDRH2 | 2 | — |
| Anti IL13 A1, CDRH3 | 3 | — |
| CDRH3 alternative | 4 | — |
| CDRH3 alternative | 5 | — |
| CDRH3 alternative | 6 | — |
| CDRH3 alternative | 7 | — |
| CDRH3 alternative | 8 | — |
| CDRH3 alternative | 9 | — |
| CDRH3 alternative | 10 | — |
| CDRH3 alternative | 11 | — |
| CDRH3 alternative | 12 | — |
| CDRH3 alternative | 13 | — |
| CDRH3 alternative | 14 | — |
| CDRH3 alternative | 15 | — |
| CDRH3 alternative | 16 | — |
| CDRH3 alternative | 17 | — |
| CDRH3 alternative | 18 | — |
| Anti IL13 L1, CDRL1 | 19 | — |
| Anti IL13 L1, CDRL2 | 20 | — |
| Anti IL13 L1, CDRL3 | 21 | — |
| Anti IL13 A1 (Heavy Chain) | 22 | 23 |
| Anti IL13 L1 (Light Chain) | 24 | 25 |
| Anti IL13 humanised variant A1 S95 Trp (Heavy Chain) | 26 | 27 |
| Anti IL13 humanised variant A1 I96 Val (Heavy Chain) | 28 | 29 |
| Anti IL13 humanised variant A1 Y97 Phe (Heavy Chain) | 30 | 31 |
| Anti IL13 humanised variant A1 D98 Glu (Heavy Chain) | 32 | 33 |
| Anti IL13 humanised variant A1 H100A Ala (Heavy Chain) | 34 | 35 |
| Anti IL13 humanised variant A1 H100A Glu (Heavy Chain) | 36 | 37 |
| Anti IL13 humanised variant A1 H100A Gln (Heavy Chain) | 38 | 39 |
| Anti IL13 humanised variant A1 H100A Arg (Heavy Chain) | 40 | 41 |
| Anti IL13 humanised variant A1 H100A Ser (Heavy Chain) | 42 | 43 |
| Anti IL13 humanised variant A1 H100A Thr (Heavy Chain) | 44 | 45 |
| Anti IL13 humanised variant A1 H100A Val (Heavy Chain) | 46 | 47 |
| Anti IL13 humanised variant A1 Y100B Ala (Heavy Chain) | 48 | 49 |
| Anti IL13 humanised variant A1 Y100B Ile (Heavy Chain) | 50 | 51 |
| Anti IL13 humanised variant A1 Y100B Trp (Heavy Chain) | 52 | 53 |
| Anti IL13 humanised variant A1 Y100B Val (Heavy Chain) | 54 | 55 |
| Signal sequence | 56 | — |
| Human IL13 | 57 | — |
| Murine 6A1 VH | 58 | — |
| Murine 6A1 VL | 59 | — |
| Alternative CDRH1 (Chothia and Kabat numbering) | 60 | — |
| Alternative CDRH1 (Chothia and Kabat numbering) | 61 | — |
| A1Y100BAla H-TVAAPS-210 (Heavy chain) | 62 | 63 |
| A1 Y100BIle H-TVAAPS-210 (Heavy chain) | 64 | 65 |
| A1Y100BTrp H-TVAAPS-210 (Heavy chain) | 66 | 67 |
| A1Y100BVal H-TVAAPS-210 (Heavy chain) | 68 | 69 |
| A1Y100BAla H-ASTKGPS-210 (Heavy chain) | 70 | 71 |
| A1 Y100BIle H-ASTKGPS-210 (Heavy chain) | 72 | 73 |
| A1Y100BTrp H-ASTKGPS-210 (Heavy chain) | 74 | 75 |
| A1Y100BVal H-ASTKGPS-210 (Heavy chain) | 76 | 77 |
| DOM9-155-25 | 78 | |
| DOM9-155-147 | 79 | |
| DOM9-155-154 | 80 | |
| DOM9-112-210 | 81 | |
| Linker | 82 | |
| Linker | 83 | |
| Linker | 84 | |

-continued

| Description | Sequence identifier (SEQ ID NO) | |
|---|---|---|
| | amino acid sequence | Polynucleotide sequence |
| Linker | 85 | |
| Linker | 86 | |
| Linker | 87 | |
| 147-TVAAPS-586 Y100B V Heavy chain | 88 | |
| 147-ASTKG-586 Y100B V Heavy chain | 89 | |
| 154-TVAAPS-586 Y100B V Heavy chain | 90 | |
| 154-ASTKG-586 Y100B V Heavy chain | 91 | |
| Linker | 92 | |
| Linker | 93 | |
| DOM9-155-154 L89Q (aka DOM9-155-256) | 94 | 95 |
| 829H-GS(TVAAPSGS)$_2$-154 L89Q | 96 | 97 |
| 829H-GS(TVAAPSGS)$_3$-154 L89Q | 98 | 99 |
| 829H-GS(TVAAPSGS)$_4$-154 L89Q | 100 | 101 |
| 829H-(TVAAPS)$_2$GS-154 L89Q | 102 | 103 |
| 829H-(TVAAPS)$_3$GS-154 L89Q | 104 | 105 |
| 829H-(TVAAPS)$_4$GS-154 L89Q | 106 | 107 |
| P0 | 108 | 109 |
| P1 | 110 | 111 |
| Q0 | 112 | 113 |
| Q1 | 114 | 115 |
| 586H-TVAAPS-154 (H chain) | 116 | |
| Anti-human IL-13 mAb heavy chain Y100B_V-(TVAAPS)$_2$GS-DOM9-155-154 (89G) | 117 | |
| Anti-human IL-13 mAb heavy chain Y100B_V-(TVAAPS)$_2$GS-DOM9-155-154 (89S) | 118 | |
| Anti-human IL-13 mAb heavy chain Y100B_V-(TVAAPS)$_2$GS-DOM9-155-154 (89H) | 119 | |
| Anti-human IL-13 mAb heavy chain Y100B_V-(TVAAPS)$_2$GS-DOM9-155-154 (89M) | 120 | |
| Anti-human IL-13 mAb heavy chain Y100B_V-(TVAAPS)$_2$GS-DOM9-155-154 (89A) | 121 | |
| Anti-human IL-13 mAb heavy chain Y100B_V-(TVAAPS)$_2$GS-DOM9-155-154 (89T) | 122 | |
| Anti-human IL-13 mAb heavy chain Y100B_V-(TVAAPS)$_2$GS-DOM9-155-154 (89C) | 123 | |
| Anti-human IL-13 mAb heavy chain Y100B_V-(TVAAPS)$_2$GS-DOM9-155-154 (89R) | 124 | |
| Anti-human IL-13 mAb heavy chain Y100B_V-(TVAAPS)$_2$GS-DOM9-155-154 (89W) | 125 | |
| Anti-human IL-13 mAb heavy chain Y100B_V-(TVAAPS)$_2$GS-DOM9-155-154 (89E) | 126 | |
| Anti-human IL-13 mAb heavy chain Y100B_V-(TVAAPS)$_2$GS-DOM9-155-154 (89K) | 127 | |
| Anti-human IL-13 mAb heavy chain Y100B_V-(TVAAPS)$_2$GS-DOM9-155-154 (89D) | 128 | |
| Anti-human IL-13 mAb heavy chain Y100B_V-(TVAAPS)$_2$GS-DOM9-155-154 (89N) | 129 | |
| Anti-human IL-13 mAb heavy chain Y100B_V-(TVAAPS)$_2$GS-DOM9-155-154 (89Y) | 130 | |
| Anti-human IL-13 mAb heavy chain Y100B_V-(TVAAPS)$_2$GS-DOM9-155-154 (89V) | 131 | |
| Anti-human IL-13 mAb heavy chain Y100B_V-(TVAAPS)$_2$GS-DOM9-155-154 (89I) | 132 | |
| Anti-human IL-13 mAb heavy chain Y100B_V-(TVAAPS)$_2$GS-DOM9-155-154 (89F) | 133 | |
| Anti-human IL-13 mAb heavy chain Y100B_V-(TVAAPS)$_2$GS-DOM9-155-154 (89P) | 134 | |
| Anti-IL-13 mAb heavy chain-GS(TVAAPSGS)$_1$-DOM9-155-154 | 135 | — |
| Anti-IL-13 mAb heavy chain-GS(TVAAPSGS)$_2$-DOM9-155-154 | 136 | — |
| Anti-IL-13 mAb heavy chain-GS(TVAAPSGS)$_3$-DOM9-155-154 | 137 | — |
| Anti-IL-13 mAb heavy chain-GS(TVAAPSGS)$_4$-DOM9-155-154 | 138 | |
| GS(TVAAPSGS)$_1$ | 139 | |
| GS(TVAAPSGS)$_2$ | 140 | |
| GS(TVAAPSGS)$_3$ | 141 | |
| GS(TVAAPSGS)$_4$ | 142 | |
| GS(TVAAPSGS)$_5$ | 143 | |
| GS(TVAAPSGS)$_6$ | 144 | |
| (TVAAPS)$_2$(GS)$_1$ | 145 | |
| (TVAAPS)$_3$(GS)$_1$ | 146 | |

| Description | Sequence identifier (SEQ ID NO) | |
|---|---|---|
| | amino acid sequence | Polynucleotide sequence |
| Anti-human IL-13 mAb heavy chain Y100B_V-(TVAAPS)$_2$GS-DOM9-155-154 (89M) | 147 | |

The invention claimed is:

1. An antigen binding protein which binds human IL-13 and comprises a heavy chain amino acid sequence having a CDRH1 amino acid sequence as shown in SEQ ID NO:1; a CDRH2 amino acid sequence as shown in SEQ ID NO: 2; a CDRH3 amino acid sequence as shown in SEQ ID NO: 3 comprising one or more substitute amino acid residues selected from the group consisting of:
   a) a substitute amino acid residue that is a tryptophan at S95 in position 1 of the amino acid sequence shown in SEQ ID NO: 3,
   b) a substitute amino acid residue that is a valine at I96 in position 2 of the amino acid sequence shown in SEQ ID NO: 3,
   c) a substitute amino acid residue that is a phenylalanine at Y97 in position 3 of the amino acid sequence shown in SEQ ID NO: 3,
   d) a substitute amino acid residue that is a glutamine at D98 in position 4 of the amino acid sequence shown in SEQ ID NO: 3,
   e) a substitute amino acid residue that is an alanine, a glutamic acid, a glutamine, an arginine, a serine, a threonine or a valine at H100A in position 7 of the amino acid sequence shown in SEQ ID NO: 3 and
   f) a substituted amino acid residue that is an alanine, an isoleucine, a tryptophan or valine at Y100B in position 8 of the amino acid sequence shown in SEQ ID NO: 3; and a light chain amino acid sequence having
   a CDRL1 amino acid sequence as shown in SEQ ID NO:19;
   a CDRL2 amino acid sequence as shown in SEQ ID NO:20; and
   a CDRL3 amino acid sequence as shown in SEQ ID NO:21.

2. An antigen binding protein which binds human IL-13 and comprises
   a CDRH1 amino acid sequence as shown in SEQ ID NO:1,
   a CDRH2 acid sequence as shown in SEQ ID NO: 2;
   a CDRH3 amino acid sequence as shown in SEQ ID NO: 18
   a CDRL1 amino acid sequence as shown in SEQ ID NO:19;
   a CDRL2 amino acid sequence as shown in SEQ ID NO:20; and a CDRL3 amino acid sequence as shown in SEQ ID NO:21.

3. The antigen binding protein of claim 1 wherein the antigen binding protein comprises a humanised antibody of the IgG isotype.

4. An antigen binding protein which binds human IL-13 and comprises a heavy chain comprising an amino acid sequence selected from the group consisting of the amino acid sequence shown in SEQ ID NO: 26, the amino acid sequence shown in SEQ ID NO: 28, the amino acid sequence shown in SEQ ID NO: 30, the amino acid sequence shown in SEQ ID NO: 32, the amino acid sequence shown in SEQ ID NO: 34, the amino acid sequence shown in SEQ ID NO: 36, the amino acid sequence shown in SEQ ID NO: 38, the amino acid sequence shown in SEQ ID NO: 40, the amino acid sequence shown in SEQ ID NO: 42, the amino acid sequence shown in SEQ ID NO: 44, the amino acid sequence shown in SEQ ID NO: 46, the amino acid sequence shown in SEQ ID NO: 48, the amino acid sequence shown in SEQ ID NO: 50, the amino acid sequence shown in SEQ ID NO: 52 and the amino acid sequence shown in SEQ ID NO: 54; and a light chain comprising an amino acid sequence selected from the group consisting of the amino acid sequence shown in SEQ ID NO: 24, the amino acid sequence shown in SEQ ID NO: 108, the amino acid sequence shown in SEQ ID NO: 110, the amino acid sequence shown in SEQ ID NO: 112 and the amino acid sequence shown in SEQ ID NO: 114.

5. The antigen binding protein according to claim 4 which comprises the heavy chain comprising the amino acid sequence shown in SEQ ID NO: 54 and the light chain comprising the amino acid sequence shown in SEQ ID NO:108.

6. The antigen binding protein of claim 1 comprising a polypeptide in which an amino acid linker is connected to the carboxy terminus of the heavy chain and a domain antibody is connected to the carboxy terminus of the amino acid linker; wherein said domain antibody is capable of binding to IL-4 and comprises an amino acid sequence selected from the group consisting of the amino acid sequence shown in SEQ ID NO: 78, the amino acid sequence shown in SEQ ID NO: 79, the amino acid sequence shown in SEQ ID NO: 80, the amino acid sequence shown in SEQ ID NO: 81 and the amino acid sequence shown in SEQ ID NO: 94.

7. The antigen binding protein of claim 6 wherein the amino acid linker comprises, from the amino terminus to the carboxyl terminus of the amino acid linker, a n-portion comprising 1 to 10 amino acid sequences wherein the carboxyl terminal amino acid residue of the n-portion is fused to the amino terminal amino acid residue of a m-portion comprising 0 to 4 amino acid sequences, and wherein the linker has a formula selected from the group consisting of $(PAS)_n(GS)_m$; $(GGGGS \text{ (SEQ ID NO: 82)})_n(GS)_m$; $(TVAAPS \text{ (SEQ ID NO: 83)})_n(GS)_m$; $(GS)_m(TVAAPSGS \text{ (SEQ ID NO: 87)})_n$; $(PAVPPP \text{ (SEQ ID NO: 148)})_n(GS)_m$; $(TVSDVP \text{ (SEQ ID NO: 149)})_n(GS)_m$; and $(TGLDSP \text{ (SEQ ID NO: 150)})_n(GS)_m$.

8. An antigen binding protein which binds human IL-13 and is capable of binding IL-4 comprising a first amino acid sequence selected from the group consisting of the amino acid sequence shown in SEQ ID NO: 62, the amino acid sequence shown in SEQ ID NO: 64, the amino acid sequence shown in SEQ ID NO: 66, the amino acid sequence shown in SEQ ID NO: 68, the amino acid sequence shown in SEQ ID NO: 70, the amino acid sequence shown in SEQ ID NO: 72, the amino acid sequence shown in SEQ ID NO: 74, the amino acid sequence shown in SEQ ID NO: 76, the amino acid sequence shown in SEQ ID NO: 96, the amino acid sequence shown in SEQ ID NO: 98, the amino acid sequence shown in SEQ ID NO: 100, the amino acid sequence shown in SEQ ID NO: 102, the amino acid sequence shown in SEQ ID NO: 104, the amino acid sequence shown in SEQ ID NO: 106, the amino acid sequence shown in SEQ ID NO: 117, the amino acid sequence shown in SEQ ID NO: 118, the amino acid sequence shown in SEQ ID NO: 119, the amino acid sequence shown in SEQ ID NO: 120, the amino acid sequence shown in SEQ ID NO: 121, the amino acid sequence shown in SEQ ID NO: 122, the amino acid sequence shown in SEQ ID NO: 123, the amino acid sequence shown in SEQ ID NO: 124, the amino acid sequence shown in SEQ ID NO: 125, the amino acid sequence shown in SEQ ID NO: 126, the amino acid sequence shown in SEQ ID NO: 127, the amino acid sequence shown in SEQ ID NO: 128, the amino acid sequence shown in SEQ ID NO: 129, the amino acid sequence shown in SEQ ID NO: 130, the amino acid sequence shown in SEQ ID NO: 131, the amino acid sequence shown in SEQ ID NO: 132, the amino acid sequence shown in SEQ ID NO: 133 and the amino acid sequence shown in SEQ ID NO: 134;

and a light chain amino acid sequence selected from the group consisting of the amino acid sequence shown in SEQ ID NO: 24, the amino acid sequence shown in SEQ ID NO: 108, the amino acid sequence shown in SEQ ID NO: 110, the amino acid sequence shown in SEQ ID NO: 112 and the amino acid sequence shown in SEQ ID NO: 114.

9. The antigen binding protein according to claim 8 comprising the first amino acid sequence selected from the group consisting of the amino acid sequence shown in SEQ ID NO: 96, the amino acid sequence shown in SEQ ID NO: 98, the amino acid sequence shown in SEQ ID NO: 100, the amino acid sequence shown in SEQ ID NO: 102, the amino acid sequence shown in SEQ ID NO: 104 and the amino acid sequence shown in SEQ ID NO: 106; and the light chain amino acid sequence selected from the group consisting of the amino acid sequence shown in SEQ ID NO: 24, the amino acid sequence shown in SEQ ID NO:108 and the amino acid sequence shown in SEQ ID NO: 110.

10. The antigen binding protein of claim 6 wherein the amino acid linker comprises an amino acid sequence selected from the group consisting of the amino sequence shown in SEQ ID NO: 92, the amino sequence shown in SEQ ID NO: 87, the amino sequence shown in SEQ ID NO: 93, the amino sequence shown in SEQ ID NO: 83, the amino sequence shown in SEQ ID NO: 84, the amino sequence shown in SEQ ID NO: 152, the amino sequence shown in SEQ ID NO: 153, the amino sequence shown in SEQ ID NO: 154, the amino sequence shown in SEQ ID NO: 155, the amino sequence shown in SEQ ID NO: 156, the amino sequence shown in SEQ ID NO: 157, the amino sequence shown in SEQ ID NO: 158, the amino sequence shown in SEQ ID NO: 159, the amino sequence shown in SEQ ID NO: 160, the amino sequence shown in SEQ ID NO: 161, the amino sequence shown in SEQ ID NO: 162, the amino sequence shown in SEQ ID NO: 163, the amino sequence shown in SEQ ID NO: 164, the amino sequence shown in SEQ ID NO: 145, the amino sequence shown in SEQ ID NO: 146, the amino sequence shown in SEQ ID NO: 165, the amino sequence shown in SEQ ID NO: 166, the amino sequence shown in SEQ ID NO: 167, the amino sequence shown in SEQ ID NO: 168, the amino sequence shown in SEQ ID NO: 139, the amino sequence shown in SEQ ID NO: 140, the amino sequence shown in SEQ ID NO: 141, the amino sequence shown in SEQ ID NO: 142, the amino sequence shown in SEQ ID NO: 143, the amino sequence shown in SEQ ID NO: 144, the amino sequence shown in SEQ ID NO: 169, the amino sequence shown in SEQ ID NO: 170, the amino acid sequence GS, the amino sequence shown in SEQ ID NO: 171, the amino sequence shown in SEQ ID NO: 191, the amino sequence shown in SEQ ID NO: 172, the amino sequence shown in SEQ ID NO: 173, the amino sequence shown in SEQ ID NO: 174, the amino sequence shown in SEQ ID NO: 175, the amino sequence shown in SEQ ID NO: 176, the amino sequence shown in SEQ ID NO: 177, the amino sequence shown in SEQ ID NO: 178, the amino sequence shown in SEQ ID NO: 179, the amino sequence shown in SEQ ID NO: 180, the amino sequence shown in SEQ ID NO: 181, the amino sequence shown in SEQ ID NO: 182, the amino sequence shown in SEQ ID NO: 183, the amino sequence shown in SEQ ID NO: 184, the amino sequence shown in SEQ ID NO: 185, the amino sequence shown in SEQ ID NO: 186, the amino sequence shown in SEQ ID NO: 187, the amino sequence shown in SEQ ID NO: 188, the amino sequence shown in SEQ ID NO: 189, and the amino sequence shown in SEQ ID NO: 190.

11. An antigen binding protein which binds human IL-13 and comprises a heavy chain amino acid sequence having a
- CDRH1 amino acid sequence as shown in SEQ ID NO:1;
- a CDRH2 amino acid sequence as shown in SEQ ID NO: 2;
- a CDRH3 amino acid sequence as shown in SEQ ID NO: 3 comprising a substituted amino acid residue that is an alanine, an isoleucine, a tryptophan or valine at Y100B in position 8 of the amino acid sequence shown in SEQ ID NO: 3; and a light chain amino acid sequence having
- a CDRL1 amino acid sequence as shown in SEQ ID NO:19;
- a CDRL2 amino acid sequence as shown in SEQ ID NO:20; and
- a CDRL3 amino acid sequence as shown in SEQ ID NO:21.

12. The antigen binding protein of claim 11 wherein the antigen binding protein comprises a humanised antibody of the IgG isotype.

13. The antigen binding protein according to claim 1 which binds human IL-13 and which comprises a CDRH3 sequence selected from the group consisting of the amino acid sequence shown in SEQ ID NO: 4, the amino acid sequence shown in SEQ ID NO: 5, the amino acid sequence shown in SEQ ID NO: 6, the amino acid sequence shown in SEQ ID NO: 7, the amino acid sequence shown in SEQ ID NO:8, the amino acid sequence shown in SEQ ID NO: 9, the amino acid sequence shown in SEQ ID NO: 10, the amino acid sequence shown in SEQ ID NO: 11, the amino acid sequence shown in SEQ ID NO: 12, the amino acid sequence shown in SEQ ID NO: 13, the amino acid sequence shown in SEQ ID NO:14, the amino acid sequence shown in SEQ ID NO: 15, the amino acid sequence shown in SEQ ID NO: 16, the amino acid sequence shown in SEQ ID NO: 17 and the amino acid sequence shown in SEQ ID NO: 18.

14. The antigen binding protein of claim 13 wherein the antigen binding protein comprises a humanised antibody of the IgG isotype.

15. The antigen binding protein of claim 2 comprising a heavy chain amino acid sequence as shown in SEQ ID NO: 54 and a light chain amino acid sequence as shown in SEQ ID NO: 24.

16. The antigen binding protein of claim 2 comprising a polypeptide in which an amino acid linker is connected to the carboxy terminus of the heavy chain and a domain antibody is connected to the carboxy terminus of the amino acid linker; wherein the amino acid linker comprises, from the amino terminus to the carboxyl terminus of the amino acid linker, a n-portion comprising 1 to 10 amino acid sequences wherein the carboxyl terminal amino acid residue of the n-portion is fused to the amino terminal amino acid residue of a m-portion comprising 0 to 4 amino acid sequences, and wherein the linker has a formula selected from the group consisting of $(PAS)_n(GS)_m$; $(GGGGS$ (SEQ ID NO: 82)$)_n(GS)_m$; $(TVAAPS$ (SEQ ID NO: 83)$)_n(GS)_m$; $(GS)_m(TVAAPSGS$ (SEQ ID NO: 87)$)_n$; $(PAVPPP$ (SEQ ID NO: 148)$)_n(GS)_m$; $(TVSDVP$ (SEQ ID NO: 149)$)_n(GS)_m$; and $(TGLDSP$ (SEQ ID NO: 150)$)_n(GS)_m$; and wherein the domain antibody is capable of binding IL-4 and the domain antibody comprises a CDR1 amino acid sequence as shown in amino acid residues 24 to 34 of SEQ ID NO: 94, a CDR2 amino acid sequence as shown in amino acid residues 50 to 56 of SEQ ID NO: 94 and a CDR3 amino acid sequence as shown in amino acid residues 89 to 97 of SEQ ID NO: 94.

17. The antigen binding protein of claim 16 wherein the amino acid linker comprises an amino acid sequence selected from the group consisting of the amino sequence shown in SEQ ID NO: 92, the amino sequence shown in SEQ ID NO: 87, the amino sequence shown in SEQ ID NO: 93, the amino sequence shown in SEQ ID NO: 83, the amino sequence shown in SEQ ID NO: 84, the amino sequence shown in SEQ ID NO: 152, the amino sequence shown in SEQ ID NO: 153, the amino sequence shown in SEQ ID NO: 154, the amino sequence shown in SEQ ID NO: 155, the amino sequence shown in SEQ ID NO: 156, the amino sequence shown in SEQ ID NO: 157, the amino sequence shown in SEQ ID NO: 158, the amino sequence shown in SEQ ID NO: 159, the amino sequence shown in SEQ ID NO: 160, the amino sequence shown in SEQ ID NO: 161, the amino sequence shown in SEQ ID NO: 162, the amino sequence shown in SEQ ID NO: 163, the amino sequence shown in SEQ ID NO: 164, the amino sequence shown in SEQ ID NO: 145, the amino sequence shown in SEQ ID NO: 146, the amino sequence shown in SEQ ID NO: 165, the amino sequence shown in SEQ ID NO: 166, the amino sequence shown in SEQ ID NO: 167, the amino sequence shown in SEQ ID NO: 168, the amino sequence shown in SEQ ID NO: 139, the amino sequence shown in SEQ ID NO: 140, the amino sequence shown in SEQ ID NO: 141, the amino sequence shown in SEQ ID NO: 142, the amino sequence shown in SEQ ID NO: 143, the amino sequence shown in SEQ ID NO: 144, the amino sequence shown in SEQ ID NO: 169, the amino sequence shown in SEQ ID NO: 170, the amino acid sequence GS, the amino sequence shown in SEQ ID NO: 171, the amino sequence shown in SEQ ID NO: 191, the amino sequence shown in SEQ ID NO: 172, the amino sequence shown in SEQ ID NO: 173, the amino sequence shown in SEQ ID NO: 174, the amino sequence shown in SEQ ID NO: 175, the amino sequence shown in SEQ ID NO: 176, the amino sequence shown in SEQ ID NO: 177, the amino sequence shown in SEQ ID NO: 178, the amino sequence shown in SEQ ID NO: 179, the amino sequence shown in SEQ ID NO: 180, the amino sequence shown in SEQ ID NO: 181, the amino sequence shown in SEQ ID NO: 182, the amino sequence shown in SEQ ID NO: 183, the amino sequence shown in SEQ ID NO: 184, the amino sequence shown in SEQ ID NO: 185, the amino sequence shown in SEQ ID NO: 186, the amino sequence shown in SEQ ID NO: 187, the amino sequence shown in SEQ ID NO: 188, the amino sequence shown in SEQ ID NO: 189, and the amino sequence shown in SEQ ID NO: 190.

18. The antigen binding protein of claim 16 wherein the domain antibody comprises the amino acid sequence shown in SEQ ID NO: 94.

19. The antigen binding protein of claim 17 wherein the domain antibody comprises the amino acid sequence shown in SEQ ID NO: 94.

20. The antigen binding protein of claim 2 comprising a heavy chain amino acid sequence as shown in SEQ ID NO: 54.

21. The antigen binding protein of claim 20 comprising a polypeptide in which an amino acid linker is connected to the carboxy terminus of the heavy chain and a domain antibody is connected to the carboxy terminus of the amino acid linker; wherein the amino acid linker comprises, from the amino terminus to the carboxyl terminus of the amino acid linker, a n-portion comprising 1 to 10 amino acid sequences wherein the carboxyl terminal amino acid residue of the n-portion is fused to the amino terminal amino acid residue of a m-portion comprising 0 to 4 amino acid sequences, and wherein the linker has a formula selected from the group consisting of $(PAS)_n(GS)_m$; $(GGGGS$ (SEQ ID NO: 82)$)_n(GS)_m$; $(TVAAPS$ (SEQ ID NO: 83)$)_n(GS)_m$; $(GS)_m(TVAAPSGS$ (SEQ ID NO: 87)$)_n$; $(PAVPPP$ (SEQ ID NO: 148)$)_n(GS)_m$; $(TVSDVP$ (SEQ ID NO: 149)$)_n(GS)_m$; and $(TGLDSP$ (SEQ ID NO: 150)$)_n(GS)_m$; and wherein the domain antibody is capable of binding IL-4 and the domain antibody comprises a CDR1 amino acid sequence as shown in amino acid residues 24 to 34 of SEQ ID NO: 94, a CDR2 amino acid sequence as shown in amino acid residues 50 to 56 of SEQ ID NO: 94 and a CDR3 amino acid sequence as shown in amino acid residues 89 to 97 of SEQ ID NO: 94.

22. The antigen binding protein of claim 21 wherein the amino acid linker comprises an amino acid sequence selected from the group consisting of the amino sequence shown in SEQ ID NO: 92, the amino sequence shown in SEQ ID NO: 87, the amino sequence shown in SEQ ID NO: 93, the amino sequence shown in SEQ ID NO: 83, the amino sequence shown in SEQ ID NO: 84, the amino sequence shown in SEQ ID NO: 152, the amino sequence shown in SEQ ID NO: 153, the amino sequence shown in SEQ ID NO: 154, the amino sequence shown in SEQ ID NO: 155, the amino sequence shown in SEQ ID NO: 156, the amino sequence shown in SEQ ID NO: 157, the amino sequence shown in SEQ ID NO: 158, the amino sequence shown in SEQ ID NO: 159, the amino sequence shown in SEQ ID NO: 160, the amino sequence shown in SEQ ID NO: 161, the amino sequence shown in SEQ ID NO: 162, the amino sequence shown in SEQ ID NO: 163, the amino sequence shown in SEQ ID NO: 164, the amino sequence shown in SEQ ID NO: 145, the amino sequence shown in SEQ ID NO: 146, the amino sequence shown in SEQ ID NO: 165, the amino sequence shown in SEQ ID NO: 166, the amino sequence shown in SEQ ID NO: 167, the amino sequence shown in SEQ ID NO: 168, the amino sequence shown in SEQ ID NO: 139, the amino sequence shown in SEQ ID NO: 140, the amino sequence shown in SEQ ID NO: 141, the amino sequence shown in SEQ ID NO: 142, the amino sequence shown in SEQ ID NO: 143, the amino sequence shown in SEQ ID NO: 144, the amino sequence shown in SEQ ID NO: 169, the amino sequence shown in SEQ ID NO: 170, the amino acid sequence GS, the amino sequence shown in SEQ ID NO: 171, the amino sequence shown in SEQ ID NO: 191, the amino sequence shown in SEQ ID NO: 172, the amino sequence shown in SEQ ID NO: 173, the amino sequence shown in SEQ ID NO: 174, the amino sequence shown in SEQ ID NO: 175, the amino sequence shown in SEQ ID NO: 176, the amino sequence shown in SEQ ID NO: 177, the amino sequence shown in SEQ ID NO: 178, the amino sequence shown in SEQ ID NO: 179, the amino sequence shown in SEQ ID NO: 180, the amino sequence shown in SEQ ID NO: 181, the amino sequence shown in SEQ ID NO: 182, the amino sequence shown in SEQ ID NO: 183, the amino sequence shown in SEQ ID NO: 184, the amino sequence shown in SEQ ID NO: 185, the amino sequence shown in SEQ ID NO: 186, the amino sequence shown in SEQ ID NO: 187, the amino sequence shown in SEQ ID NO: 188, the amino sequence shown in SEQ ID NO: 189, and the amino sequence shown in SEQ ID NO: 190.

23. The antigen binding protein of claim 21 wherein the domain antibody comprises the amino acid sequence shown in SEQ ID NO: 94.

24. The antigen binding protein of claim 22 wherein the domain antibody comprises the amino acid sequence shown in SEQ ID NO: 94.

25. The antigen binding protein of claim 16 comprising a light chain amino acid sequence as shown in SEQ ID NO: 24.

26. The antigen binding protein of claim 17 comprising a light chain amino acid sequence as shown in SEQ ID NO: 24.

27. The antigen binding protein of claim 18 comprising a light chain amino acid sequence as shown in SEQ ID NO: 24.

28. The antigen binding protein of claim 19 comprising a light chain amino acid sequence as shown in SEQ ID NO: 24.

29. The antigen binding protein of claim 20 comprising a light chain amino acid sequence as shown in SEQ ID NO: 24.

30. The antigen binding protein of claim 20 comprising a light chain amino acid sequence as shown in SEQ ID NO: 24.

31. The antigen binding protein of claim 22 comprising a light chain amino acid sequence as shown in SEQ ID NO: 24.

32. The antigen binding protein of claim 23 comprising a light chain amino acid sequence as shown in SEQ ID NO: 24.

33. The antigen binding protein of claim 24 comprising a light chain amino acid sequence as shown in SEQ ID NO: 24.

34. The antigen binding protein of claim 16 wherein the antigen binding protein comprises a humanised antibody of the IgG isotype.

35. The antigen binding protein of claim 17 wherein the antigen binding protein comprises a humanised antibody of the IgG isotype.

36. The antigen binding protein of claim 18 wherein the antigen binding protein comprises a humanised antibody of the IgG isotype.

37. The antigen binding protein of claim 19 wherein the antigen binding protein comprises a humanised antibody of the IgG isotype.

38. The antigen binding protein of claim 21 wherein the antigen binding protein comprises a humanised antibody of the IgG isotype.

39. The antigen binding protein of claim 22 wherein the antigen binding protein comprises a humanised antibody of the IgG isotype.

40. The antigen binding protein of claim 23 wherein the antigen binding protein comprises a humanised antibody of the IgG isotype.

41. The antigen binding protein of claim 24 wherein the antigen binding protein comprises a humanised antibody of the IgG isotype.

42. The antigen binding protein of claim 25 wherein the antigen binding protein comprises a humanised antibody of the IgG isotype.

43. The antigen binding protein of claim 26 wherein the antigen binding protein comprises a humanised antibody of the IgG isotype.

44. The antigen binding protein of claim 27 wherein the antigen binding protein comprises a humanised antibody of the IgG isotype.

45. The antigen binding protein of claim 28 wherein the antigen binding protein comprises a humanised antibody of the IgG isotype.

46. The antigen binding protein of claim 2 comprising a polypeptide in which an amino acid linker is connected to the carboxy terminus of the heavy chain and a domain antibody is connected to the carboxy terminus of the amino acid linker; wherein the amino acid linker comprises, from the amino terminus to the carboxyl terminus of the amino acid linker, a n-portion comprising 1 to 10 amino acid sequences wherein the carboxyl terminal amino acid residue of the n-portion is fused to the amino terminal amino acid residue of a m-portion comprising 0 to 4 amino acid sequences, and wherein the linker has a formula selected from the group consisting of $(PAS)_n(GS)_m$; (GGGGS (SEQ ID NO: 82))$_n(GS)_m$; (TVAAPS (SEQ ID NO: 83))$_n(GS)_m$; $(GS)_m$(TVAAPSGS (SEQ ID NO: 87))$_n$; (PAVPPP (SEQ ID NO: 148))$_n(GS)_m$; (TVSDVP (SEQ ID NO: 149)$_n(GS)_m$; and (TGLDSP (SEQ ID NO: 150))$_n(GS)_m$; and wherein the domain antibody is capable of binding IL-4 and the domain antibody comprises a CDR1 amino acid sequence as shown in amino acid residues 31 to 34 of SEQ ID NO: 81, a CDR2 amino acid sequence as shown in amino acid residues 50 to 66 of SEQ ID NO: 81 and a CDR3 amino acid sequence as shown in amino acid residues 99 to 105 of SEQ ID NO: 81.

47. The antigen binding protein of claim 46 wherein the amino acid linker comprises an amino acid sequence selected from the group consisting of the amino sequence shown in SEQ ID NO: 92, the amino sequence shown in SEQ ID NO: 87, the amino sequence shown in SEQ ID NO: 93, the amino sequence shown in SEQ ID NO: 83, the amino sequence shown in SEQ ID NO: 84, the amino sequence shown in SEQ ID NO: 152, the amino sequence shown in SEQ ID NO: 153, the amino sequence shown in SEQ ID NO: 154, the amino sequence shown in SEQ ID NO: 155, the amino sequence shown in SEQ ID NO: 156, the amino sequence shown in SEQ ID NO: 157, the amino sequence shown in SEQ ID NO: 158, the amino sequence shown in SEQ ID NO: 159, the amino sequence shown in SEQ ID NO: 160, the amino sequence shown in SEQ ID NO: 161, the amino sequence shown in SEQ ID NO: 162, the amino sequence shown in SEQ ID NO: 163, the amino sequence shown in SEQ ID NO: 164, the amino sequence shown in SEQ ID NO: 145, the amino sequence shown in SEQ ID NO: 146, the amino sequence shown in SEQ ID NO: 165, the amino sequence shown in SEQ ID NO: 166, the amino sequence shown in SEQ ID NO: 167, the amino sequence shown in SEQ ID NO: 168, the amino sequence shown in SEQ ID NO: 139, the amino sequence shown in SEQ ID NO: 140, the amino sequence shown in SEQ ID NO: 141, the amino sequence shown in SEQ ID NO: 142, the amino sequence shown in SEQ ID NO: 143, the amino sequence shown in SEQ ID NO: 144, the amino sequence shown in SEQ ID NO: 169, the amino sequence shown in SEQ ID NO: 170, the amino acid sequence GS, the amino sequence shown in SEQ ID NO: 171, the amino sequence shown in SEQ ID NO: 191, the amino sequence shown in SEQ ID NO: 172, the amino sequence shown in SEQ ID NO: 173, the amino sequence shown in SEQ ID NO: 174, the amino sequence shown in SEQ ID NO: 175, the amino sequence shown in SEQ ID NO: 176, the amino sequence shown in SEQ ID NO: 177, the amino sequence shown in SEQ ID NO: 178, the amino sequence shown in SEQ ID NO: 179, the amino sequence shown in SEQ ID NO: 180, the amino sequence shown in SEQ ID NO: 181, the amino sequence shown in SEQ ID NO: 182, the amino sequence shown in SEQ ID NO: 183, the amino sequence shown in SEQ ID NO: 184, the amino sequence shown in SEQ ID NO: 185, the amino sequence shown in SEQ ID NO: 186, the amino sequence shown in SEQ ID NO: 187, the amino sequence shown in SEQ ID NO: 188, the amino sequence shown in SEQ ID NO: 189, and the amino sequence shown in SEQ ID NO: 190.

48. The antigen binding protein of claim 46 wherein the domain antibody comprises the amino acid sequence shown in SEQ ID NO: 81.

49. The antigen binding protein of claim 47 wherein the domain antibody comprises the amino acid sequence shown in SEQ ID NO: 81.

50. The antigen binding protein of claim 20 comprising a polypeptide in which an amino acid linker is connected to the carboxy terminus of the heavy chain and a domain antibody is connected to the carboxy terminus of the amino acid linker; wherein the amino acid linker comprises, from the amino terminus to the carboxyl terminus of the amino acid linker, a n-portion comprising 1 to 10 amino acid sequences wherein the carboxyl terminal amino acid residue of the n-portion is fused to the amino terminal amino acid residue of a m-portion comprising 0 to 4 amino acid sequences, and wherein the linker has a formula selected from the group consisting of $(PAS)_n(GS)_m$; (GGGGS (SEQ ID NO: 82))$_n(GS)_m$; (TVAAPS (SEQ ID NO: 83))$_n(GS)_m$; $(GS)_m$(TVAAPSGS (SEQ ID NO: 87))$_n$; (PAVPPP (SEQ ID NO: 148))$_n(GS)_m$; (TVSDVP (SEQ ID NO: 149))$_n(GS)_m$; and (TGLDSP (SEQ ID NO: 150))$_n(GS)_m$; and wherein the domain antibody is capable of binding IL-4 and the domain antibody comprises a CDR1 amino acid sequence as shown in amino acid residues 31 to 34 of SEQ ID NO: 81, a CDR2 amino acid sequence as shown in amino acid residues 50 to 66 of SEQ ID NO: 81 and a CDR3 amino acid sequence as shown in amino acid residues 99 to 105 of SEQ ID NO: 81.

51. The antigen binding protein of claim 50 wherein the amino acid linker comprises an amino acid sequence selected from the group consisting of the amino sequence shown in SEQ ID NO: 92, the amino sequence shown in SEQ ID NO: 87, the amino sequence shown in SEQ ID NO: 93, the amino sequence shown in SEQ ID NO: 83, the amino sequence shown in SEQ ID NO: 84, the amino sequence shown in SEQ ID NO: 152, the amino sequence shown in SEQ ID NO: 153, the amino sequence shown in SEQ ID NO: 154, the amino sequence shown in SEQ ID NO: 155, the amino sequence shown in SEQ ID NO: 156, the amino sequence shown in SEQ ID NO: 157, the amino sequence shown in SEQ ID NO: 158, the amino sequence shown in SEQ ID NO: 159, the amino sequence shown in SEQ ID NO: 160, the amino sequence shown in SEQ ID NO: 161, the amino sequence shown in SEQ ID NO: 162, the amino sequence shown in SEQ ID NO: 163, the amino sequence shown in SEQ ID NO: 164, the amino sequence shown in SEQ ID NO: 145, the amino sequence shown in SEQ ID NO: 146, the amino sequence shown in SEQ ID NO: 165, the amino sequence shown in SEQ ID NO: 166, the amino sequence shown in SEQ ID NO: 167, the amino sequence shown in SEQ ID NO: 168, the amino sequence shown in SEQ ID NO: 139, the amino sequence shown in SEQ ID NO: 140, the amino sequence shown in SEQ ID NO: 141, the amino sequence shown in SEQ ID NO: 142, the amino sequence shown in SEQ ID NO: 143, the amino sequence shown in SEQ ID NO: 144, the amino sequence shown in SEQ ID NO: 169, the amino sequence shown in SEQ ID NO: 170, the amino acid sequence GS, the amino sequence shown in SEQ ID NO: 171, the amino sequence shown in SEQ ID NO: 191, the amino sequence shown in SEQ ID NO: 172, the amino sequence shown in SEQ ID NO: 173, the amino sequence shown in SEQ ID NO: 174, the amino sequence shown in SEQ ID NO: 175, the amino sequence shown in SEQ ID NO: 176, the amino sequence shown in SEQ ID NO: 177, the amino sequence shown in SEQ ID NO: 178, the amino sequence shown in SEQ ID NO: 179, the amino sequence shown in SEQ ID NO: 180, the amino sequence shown in SEQ ID NO:

181, the amino sequence shown in SEQ ID NO: 182, the amino sequence shown in SEQ ID NO: 183, the amino sequence shown in SEQ ID NO: 184, the amino sequence shown in SEQ ID NO: 185, the amino sequence shown in SEQ ID NO: 186, the amino sequence shown in SEQ ID NO: 187, the amino sequence shown in SEQ ID NO: 188, the amino sequence shown in SEQ ID NO: 189, and the amino sequence shown in SEQ ID NO: 190.

52. The antigen binding protein of claim 50 wherein the domain antibody comprises the amino acid sequence shown in SEQ ID NO: 81.

53. The antigen binding protein of claim 51 wherein the domain antibody comprises the amino acid sequence shown in SEQ ID NO: 81.

54. The antigen binding protein of claim 46 comprising a light chain amino acid sequence as shown in SEQ ID NO: 24.

55. The antigen binding protein of claim 47 comprising a light chain amino acid sequence as shown in SEQ ID NO: 24.

56. The antigen binding protein of claim 48 comprising a light chain amino acid sequence as shown in SEQ ID NO: 24.

57. The antigen binding protein of claim 49 comprising a light chain amino acid sequence as shown in SEQ ID NO: 24.

58. The antigen binding protein of claim 50 comprising a light chain amino acid sequence as shown in SEQ ID NO: 24.

59. The antigen binding protein of claim 51 comprising a light chain amino acid sequence as shown in SEQ ID NO: 24.

60. The antigen binding protein of claim 52 comprising a light chain amino acid sequence as shown in SEQ ID NO: 24.

61. The antigen binding protein of claim 53 comprising a light chain amino acid sequence as shown in SEQ ID NO: 24.

62. The antigen binding protein of claim 46 wherein the antigen binding protein comprises a humanised antibody of the IgG isotype.

63. The antigen binding protein of claim 47 wherein the antigen binding protein comprises a humanised antibody of the IgG isotype.

64. The antigen binding protein of claim 48 wherein the antigen binding protein comprises a humanised antibody of the IgG isotype.

65. The antigen binding protein of claim 49 wherein the antigen binding protein comprises a humanised antibody of the IgG isotype.

66. The antigen binding protein of claim 50 wherein the antigen binding protein comprises a humanised antibody of the IgG isotype.

67. The antigen binding protein of claim 51 wherein the antigen binding protein comprises a humanised antibody of the IgG isotype.

68. The antigen binding protein of claim 52 wherein the antigen binding protein comprises a humanised antibody of the IgG isotype.

69. The antigen binding protein of claim 53 wherein the antigen binding protein comprises a humanised antibody of the IgG isotype.

70. The antigen binding protein of claim 54 wherein the antigen binding protein comprises a humanised antibody of the IgG isotype.

71. The antigen binding protein of claim 55 wherein the antigen binding protein comprises a humanised antibody of the IgG isotype.

72. The antigen binding protein of claim 56 wherein the antigen binding protein comprises a humanised antibody of the IgG isotype.

73. The antigen binding protein of claim 57 wherein the antigen binding protein comprises a humanised antibody of the IgG isotype.

74. An antigen binding protein which binds human IL-13 and is capable of binding IL-4 comprising a first amino acid sequence having the amino acid sequence shown in SEQ ID NO: 96 and a light chain amino acid sequence having the amino acid sequence shown in SEQ ID NO: 24.

75. An antigen binding protein comprising a first amino acid sequence having the amino acid sequence shown in SEQ ID NO: 96 and a light chain amino acid sequence having the amino acid sequence shown in SEQ ID NO: 24.

76. A protein comprising a first amino acid sequence having the amino acid sequence shown in SEQ ID NO: 96 and a light chain amino acid sequence having the amino acid sequence shown in SEQ ID NO: 24.

77. An antigen binding protein which binds human IL-13 and is capable of binding IL-4 comprising a first amino acid sequence having the amino acid sequence shown in SEQ ID NO: 68 and a light chain amino acid sequence having the amino acid sequence shown in SEQ ID NO: 24.

78. An antigen binding protein comprising a first amino acid sequence having the amino acid sequence shown in SEQ ID NO: 68 and a light chain amino acid sequence having the amino acid sequence shown in SEQ ID NO: 24.

79. A protein comprising a first amino acid sequence having the amino acid sequence shown in SEQ ID NO: 68 and a light chain amino acid sequence having the amino acid sequence shown in SEQ ID NO: 24.

* * * * *

SEQUENCE LISTING

<160> NUMBER OF SEQ ID NOS: 191

<210> SEQ ID NO 1
<211> LENGTH: 5
<212> TYPE: PRT
<213> ORGANISM: Mus sp.
<220> FEATURE:

<400> SEQUENCE: 1

Asp Thr Tyr Met His
1               5

<210> SEQ ID NO 2
<211> LENGTH: 17
<212> TYPE: PRT
<213> ORGANISM: Mus sp.

<400> SEQUENCE: 2

Thr Ile Asp Pro Ala Asn Gly Asn Thr Lys Tyr Val Pro Lys Phe Gln
1               5                   10                  15

Gly

<210> SEQ ID NO 3
<211> LENGTH: 16
<212> TYPE: PRT
<213> ORGANISM: Mus sp.

<400> SEQUENCE: 3

Ser Ile Tyr Asp Asp Tyr His Tyr Asp Tyr Tyr Ala Met Asp Tyr
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Mutated CDR

<400> SEQUENCE: 4

Trp Ile Tyr Asp Asp Tyr His Tyr Asp Tyr Tyr Ala Met Asp Tyr
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Mutated CDR

<400> SEQUENCE: 5

Ser Val Tyr Asp Asp Tyr His Tyr Asp Tyr Tyr Ala Met Asp Tyr
1               5                   10                  15

```
<210> SEQ ID NO 6
<211> LENGTH: 16
<212> TYPE: PRT
<213> ORGANISM: Artificial Sequence
<220> FEATURE:
<223> OTHER INFORMATION: Mutated CDR

<400> SEQUENCE: 6

Ser Ile Phe Asp Asp Tyr His Tyr Asp Asp Tyr Tyr Ala Met Asp Tyr
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: Mutated CDR

<400> SEQUENCE: 7

Ser Ile Tyr Glu Asp Tyr His Tyr Asp Asp Tyr Tyr Ala Met Asp Tyr
 1               5                  10                  15

<210> SEQ ID NO 8
<211> LENGTH: 16
<212> TYPE: PRT
<213> ORGANISM: Artificial Sequence
<220> FEATURE:
<223> OTHER INFORMATION: Mutated CDR

<400> SEQUENCE: 8

Ser Ile Tyr Asp Asp Tyr Ala Tyr Asp Asp Tyr Tyr Ala Met Asp Tyr
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: Mutated CDR

<400> SEQUENCE: 9

Ser Ile Tyr Asp Asp Tyr Glu Tyr Asp Asp Tyr Tyr Ala Met Asp Tyr
 1               5                  10                  15

<210> SEQ ID NO 10
<211> LENGTH: 16
<212> TYPE: PRT
<213> ORGANISM: Artificial Sequence
<220> FEATURE:
<223> OTHER INFORMATION: Mutated CDR

<400> SEQUENCE: 10

Ser Ile Tyr Asp Asp Tyr Gln Tyr Asp Asp Tyr Tyr Ala Met Asp Tyr
 1               5                  10                  15

<210> SEQ ID NO 11
<211> LENGTH: 16
<212> TYPE: PRT
<213> ORGANISM: Artificial Sequence
<220> FEATURE:
<223> OTHER INFORMATION: Mutated CDR

<400> SEQUENCE: 11

Ser Ile Tyr Asp Asp Tyr Arg Tyr Asp Asp Tyr Tyr Ala Met Asp Tyr
 1               5                  10                  15

<210> SEQ ID NO 12
```

```
<211> LENGTH: 16
<212> TYPE: PRT
<213> ORGANISM: Artificial Sequence
<220> FEATURE:
<223> OTHER INFORMATION: Mutated CDR

<400> SEQUENCE: 12

Ser Ile Tyr Asp Asp Tyr Ser Tyr Asp Asp Tyr Tyr Ala Met Asp Tyr
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Mutated CDR

<400> SEQUENCE: 13

Ser Ile Tyr Asp Asp Tyr Thr Tyr Asp Asp Tyr Tyr Ala Met Asp Tyr
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Mutated CDR

<400> SEQUENCE: 14

Ser Ile Tyr Asp Asp Tyr Val Tyr Asp Asp Tyr Tyr Ala Met Asp Tyr
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Mutated CDR

<400> SEQUENCE: 15

Ser Ile Tyr Asp Asp Tyr His Ala Asp Asp Tyr Tyr Ala Met Asp Tyr
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Mutated CDR

<400> SEQUENCE: 16

Ser Ile Tyr Asp Asp Tyr His Ile Asp Asp Tyr Tyr Ala Met Asp Tyr
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Mutated CDR

<400> SEQUENCE: 17

Ser Ile Tyr Asp Asp Tyr His Trp Asp Asp Tyr Tyr Ala Met Asp Tyr
1               5                   10                  15

<210> SEQ ID NO 18
<211> LENGTH: 16
<212> TYPE: PRT
```

<213> ORGANISM: Artificial Sequence
<220> FEATURE:
<223> OTHER INFORMATION: Mutated CDR

<400> SEQUENCE: 18

Ser Ile Tyr Asp Asp Tyr His Val Asp Tyr Tyr Ala Met Asp Tyr
1               5                   10                  15

<210> SEQ ID NO 19
<211> LENGTH: 16
<212> TYPE: PRT
<213> ORGANISM: Mus sp.

<400> SEQUENCE: 19

Arg Ser Ser Gln Asn Ile Val His Ile Asn Gly Asn Thr Tyr Leu Glu
1               5                   10                  15

<210> SEQ ID NO 20
<211> LENGTH: 7
<212> TYPE: PRT
<213> ORGANISM: Mus sp.

<400> SEQUENCE: 20

Lys Ile Ser Asp Arg Phe Ser
1               5

<210> SEQ ID NO 21
<211> LENGTH: 9
<212> TYPE: PRT
<213> ORGANISM: Mus sp.

<400> SEQUENCE: 21

Phe Gln Gly Ser His Val Pro Trp Thr
1               5

<210> SEQ ID NO 22
<211> LENGTH: 455
<212> TYPE: PRT
<213> ORGANISM: Artificial Sequence
<220> FEATURE:
<223> OTHER INFORMATION: Humanised

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu

```
              145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 23
<211> LENGTH: 1365
<212> TYPE: DNA
<213> ORGANISM: Artificial Sequence
<220> FEATURE:
<223> OTHER INFORMATION: Humanised

<400> SEQUENCE: 23
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accactacga cgactactac gccatggact actggggaca gggcacacta     360
```

```
gtgaccgtgt ccagcgccag caccaagggc cccagcgtgt tccccctggc cccagcagc      420 aagagcacca gcggcggcac agccgccctg gctgcctgg tgaaggacta cttccccgaa      480
ccggtgaccg tgtcctggaa cagcggagcc ctgaccagcg gcgtgcacac cttccccgcc    540
gtgctgcaga gcagcggcct gtacagcctg agcagcgtgg tgaccgtgcc cagcagcagc    600
ctgggcaccc agacctacat ctgtaacgtg aaccacaagc ccagcaacac caaggtggac    660
aagaaggtgg agcccaagag ctgtgacaag acccacacct gccccccctg ccctgccccc    720
gagctgctgg gaggcccag cgtgttcctg ttccccccca gcctaagga caccctgatg      780 atcagcagaa ccccgaggt gacctgtgtg gtggtggatg tgagccacga ggaccctgag     840
gtgaagttca actggtacgt ggacggcgtg gaggtgcaca atgccaagac caagcccagg    900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc   1020
gagaaaacca tcagcaaggc caggccag cccagagag cccaggtgta caccctgccc      1080
cctagcagag atgagctgac caagaaccag gtgtccctga cctgcctggt gaagggcttc   1140 tacccagcg acatcgccgt ggagtgggag agcaacggcc agcccgagaa caactacaag    1200
accacccccc ctgtgctgga cagcgatggc agcttcttcc tgtacagcaa gctgaccgtg   1260
gacaagagca gatggcagca gggcaacgtg ttcagctgct ccgtgatgca cgaggccctg   1320
cacaatcact acacccagaa gagcctgagc ctgtcccctg gcaag                    1365

<210> SEQ ID NO 24
<211> LENGTH: 219
<212> TYPE: PRT
<213> ORGANISM: Artificial Sequence
<220> FEATURE:
<223> OTHER INFORMATION: Humanised

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Ile
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Ile Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Phe Gln Gly
                85                  90                  95

Ser His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 25
<211> LENGTH: 657
<212> TYPE: DNA
<213> ORGANISM: Artificial Sequence
<220> FEATURE:
<223> OTHER INFORMATION: Humanised

<400> SEQUENCE: 25
gacatcgtga tgacccagtc tcctctgagc ctccccgtga cccccggcga accagccagc      60
atctcctgca gaagcagcca gaacatcgtg cacatcaacg gcaacaccta cctggagtgg     120
tacctgcaaa agcccggcca gagccccagg ctgctgatct acaagatcag cgacaggttc     180
agcggcgtgc ccgataggtt cagcggcagc ggcagcggca ccgacttcac cctgaagatc     240
agcagggtgg aggccgacga cgtgggcatc tactactgct tccagggcag ccacgtcccc     300
tggactttcg gacagggcac caagctggag attaagcgta cggtggccgc ccccagcgtg     360
ttcatcttcc cccccagcga tgagcagctg aagagcggca ccgccagcgt ggtgtgtctg     420
ctgaacaact tctaccccccg ggaggccaag gtgcagtgga aggtggacaa tgccctgcag     480
agcggcaaca gccaggagag cgtgaccgag caggacagca aggactccac ctacagcctg     540
agcagcaccc tgaccctgag caaggccgac tacgagaagc acaaggtgta cgcctgtgag     600
gtgacccacc agggcctgtc cagccccgtg accaagagct tcaaccgggg cgagtgc        657

<210> SEQ ID NO 26
<211> LENGTH: 455
<212> TYPE: PRT
<213> ORGANISM: Artificial Sequence
<220> FEATURE:
<223> OTHER INFORMATION: Humanised

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His

```
                        165                 170                 175
Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 27
<211> LENGTH: 1365
<212> TYPE: DNA
<213> ORGANISM: Artificial Sequence
<220> FEATURE:
<223> OTHER INFORMATION: Humanised

<400> SEQUENCE: 27
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagccacag caccgcctac     240
atggaactga gcagcctgag gtctgaggac accgccgtgt actattgcgc aggtggatc      300 tacgacgact accactacga cgactactac gccatggact actggggaca gggcacacta     360
gtgaccgtgt ccagcgccag caccaagggc ccagcgtgt ccccctggc cccagcagc       420
```

```
aagagcacca gcggcggcac agccgccctg ggctgcctgg tgaaggacta cttccccgaa      480
ccggtgaccg tgtcctggaa cagcggagcc ctgaccagcg gcgtgcacac cttccccgcc      540
gtgctgcaga gcagcggcct gtacagcctg agcagcgtgg tgaccgtgcc cagcagcagc      600
ctgggcaccc agacctacat ctgtaacgtg aaccacaagc ccagcaacac caaggtggac      660
aagaaggtgg agcccaagag ctgtgacaag acccacacct gcccccctg ccctgccccc       720 gagctgctgg gaggccccag cgtgttcctg ttccccccca gcctaagga cacctgatg        780 atcagcagaa ccccgaggt gacctgtgtg gtggtggatg tgagccacga ggaccctgag       840
gtgaagttca actggtacgt ggacggcgtg gaggtgcaca tgccaagac caagcccagg       900 gaggagcagt acaacagcac ctaccgggtg gtgtccgtgc tgaccgtgct gcaccaggat     960
tggctgaacg gcaaggagta caagtgtaag gtgtccaaca aggccctgcc tgcccctatc     1020
gagaaaacca tcagcaaggc caagggccag cccagagagc ccaggtgta caccctgccc      1080 cctagcagag atgagctgac caagaaccag gtgtccctga cctgcctggt gaagggcttc     1140
taccccagcg acatcgccgt ggagtgggag agcaacggcc agcccgagaa caactacaag     1200
accacccccc ctgtgctgga cagcgatggc agcttcttcc tgtacagcaa gctgaccgtg     1260
gacaagagca gatggcagca gggcaacgtg ttcagctgct ccgtgatgca cgaggccctg    1320
cacaatcact acacccagaa gagcctgagc ctgtcccctg gcaag                     1365

<210> SEQ ID NO 28
<211> LENGTH: 455
<212> TYPE: PRT
<213> ORGANISM: Artificial Sequence
<220> FEATURE:
<223> OTHER INFORMATION: Humanised

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205
```

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 29
<211> LENGTH: 1365
<212> TYPE: DNA
<213> ORGANISM: Artificial Sequence
<220> FEATURE:
<223> OTHER INFORMATION: Humanised

<400> SEQUENCE: 29
caggtgcagc tcgtgcagag cggcgccgaa gtgaaaaagc ccggcagcag cgtgaaggtg     60
agctgcaagg cctccggctt ctacatcaag gacacctaca tgcactgggt caggcaggct    120
cctggccagg gctggagtg atgggcact atcgaccccg ccaacggcaa caccaagtac    180
gtgcccaagt tccagggcag ggtgaccatc accgccgatg agagcaccag caccgcctac    240
atggaactga gcagcctgag gtctgaggac accgccgtgt actattgcgc caggagcgtc    300
tacgacgact accactacga cgactactac gccatggact actggggaca gggcacacta    360
gtgaccgtgt ccagcgccag caccaagggc ccagcgtgt tcccctggc ccccagcagc    420 aagagcacca gcggcggcac agccgccctg ggctgcctgg tgaaggacta cttccccgaa    480
ccggtgaccg tgtcctggaa cagcggagcc ctgaccagcg gcgtgcacac cttcccgcc    540 gtgctgcaga gcagcggcct gtacagcctg agcagcgtgg tgaccgtgcc cagcagcagc    600
ctgggcaccc agacctacat ctgtaacgtg aaccacaagc ccagcaacac caaggtggac    660

```
aagaaggtgg agcccaagag ctgtgacaag acccacacct gccccccctg ccctgccccc      720
gagctgctgg gaggccccag cgtgttcctg ttcccccca agcctaagga caccctgatg      780
atcagcagaa cccccgaggt gacctgtgtg gtggtggatg tgagccacga ggaccctgag      840
gtgaagttca actggtacgt ggacggcgtg gaggtgcaca atgccaagac caagcccagg      900
gaggagcagt acaacagcac ctaccgggtg gtgtccgtgc tgaccgtgct gcaccaggat      960
tggctgaacg gcaaggagta caagtgtaag gtgtccaaca aggccctgcc tgcccctatc     1020
gagaaaacca tcagcaaggc caagggccag cccagagagc ccaggtgta caccctgccc      1080 cctagcagag atgagctgac caagaaccag gtgtccctga cctgcctggt gaagggcttc     1140
taccccagcg acatcgccgt ggagtgggag agcaacggcc agcccgagaa caactacaag     1200
accacccccc ctgtgctgga cagcgatggc agcttcttcc tgtacagcaa gctgaccgtg     1260
gacaagagca gatggcagca gggcaacgtg ttcagctgct ccgtgatgca cgaggccctg     1320
cacaatcact acacccagaa gagcctgagc ctgtcccctg gcaag                     1365
```

<210> SEQ ID NO 30
<211> LENGTH: 455
<212> TYPE: PRT
<213> ORGANISM: Artificial Sequence
<220> FEATURE:
<223> OTHER INFORMATION: Humanised

<400> SEQUENCE: 30

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Phe Asp Asp Tyr His Tyr Asp Asp Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240
```

-continued

```
Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
        260                 265                 270

Asp Val Ser His Glu Asp Pro Glu Val Lys Phe Asn Trp Tyr Val Asp
    275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Asp Glu Leu Thr Lys
    355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro Gly Lys
450                 455
```

<210> SEQ ID NO 31
<211> LENGTH: 1365
<212> TYPE: DNA
<213> ORGANISM: Artificial Sequence
<220> FEATURE:
<223> OTHER INFORMATION: Humanised

<400> SEQUENCE: 31

```
caggtgcagc tcgtgcagag cggcgccgaa gtgaaaaagc ccggcagcag cgtgaaggtg     60
agctgcaagg cctccggctt ctacatcaag gacaccctac atgcactggg tcaggcaggct    120 cctggccagg gcctggagtg gatgggcact atcgaccccg ccaacggcaa caccaagtac    180
gtgcccaagt tccagggcag ggtgaccatc accgccgatg agagcaccag caccgcctac    240
atggaactga gcagcctgag gtctgaggac accgccgtgt actattgcgc caggagcatc    300
tttgacgact accactacga cgactactac gccatggact actggggaca gggcacacta    360
gtgaccgtgt ccagcgccag caccaagggc ccagcgtgt tccccctggc cccagcagc    420 aagagcacca gcggcggcac agccgccctg ggctgcctgg tgaaggacta cttccccgaa    480
ccggtgaccg tgtcctggaa cagcggagcc ctgaccagcg gcgtgcacac cttccccgcc    540
gtgctgcaga gcagcggcct gtacagcctg agcagcgtgg tgaccgtgcc cagcagcagc    600
ctgggcaccc agacctacat ctgtaacgtg aaccacaagc ccagcaacac caaggtggac    660
aagaaggtgg agcccaagag ctgtgacaag acccacacct gccccccctg ccctgccccc    720
gagctgctgg gaggcccag cgtgttcctg ttccccccca gcctaagga cccctgatg    780 atcagcagaa ccccgaggt gacctgtgtg gtggtggatg tgagccacga ggaccctgag    840
```

-continued

```
gtgaagttca actggtacgt ggacggcgtg gaggtgcaca atgccaagac caagcccagg    900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc   1020
gagaaaacca tcagcaaggc caagggccag cccagagagc ccaggtgta cacccctgccc   1080 cctagcagag atgagctgac caagaaccag gtgtccctga cctgcctggt gaagggcttc   1140
taccccagcg acatcgccgt ggagtgggag agcaacggcc agcccgagaa caactacaag   1200
accacccccc ctgtgctgga cagcgatggc agcttcttcc tgtacagcaa gctgaccgtg   1260
gacaagagca gatggcagca gggcaacgtg ttcagctgct ccgtgatgca cgaggccctg   1320
cacaatcact acacccagaa gagcctgagc ctgtcccctg gcaag              1365
```

<210> SEQ ID NO 32
<211> LENGTH: 455
<212> TYPE: PRT
<213> ORGANISM: Artificial Sequence
<220> FEATURE:
<223> OTHER INFORMATION: Humanised

<400> SEQUENCE: 32

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Glu Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
```

```
          275                 280                 285
Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 33
<211> LENGTH: 1365
<212> TYPE: DNA
<213> ORGANISM: Artificial Sequence
<220> FEATURE:
<223> OTHER INFORMATION: Humanised

<400> SEQUENCE: 33
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagccagag caccgcctac     240
atggaactga gcagcctgag gtctgaggac accgccgtgt actattgcgc caggagcatc     300
tacgaggact accactacga cgactactac gccatggact actggggaca gggcacacta     360
gtgaccgtgt ccagcgccag caccaagggc ccagcgtgt tccccctggc cccagcagc      420 aagagcacca gcggcggcac agccgccctg ggctgcctgg tgaaggacta cttccccgaa     480
ccggtgaccg tgtcctggaa cagcggagcc ctgaccagcg gcgtgcacac cttcccgcc      540 gtgctgcaga gcagcggcct gtacagcctg agcagcgtgg tgaccgtgcc agcagcagc     600 ctgggcaccc agacctacat ctgtaacgtg aaccacaagc ccagcaacac caaggtggac     660
aagaaggtgg agcccaagag ctgtgacaag acccacacct gccccccctg ccctgccccc     720
gagctgctgg gaggccccag cgtgttcctg ttcccccca agcctaagga cacccctgatg     780 atcagcagaa ccccccgaggt gacctgtgtg gtggtggatg tgagccacga ggaccctgag     840
gtgaagttca actggtacgt ggacggcgtg gaggtgcaca tgccaagac caagccagg      900 gaggagcagt acaacagcac ctaccgggtg gtgtccgtgc tgaccgtgct gcaccaggat     960
tggctgaacg gcaaggagta caagtgtaag gtgtccaaca aggccctgcc tgccctatc    1020 gagaaaacca tcagcaaggc caagggccag cccagagagc ccaggtgta caccctgccc    1080
```

-continued

```
cctagcagag atgagctgac caagaaccag gtgtccctga cctgcctggt gaagggcttc    1140
taccccagcg acatcgccgt ggagtgggag agcaacggcc agcccgagaa caactacaag    1200 accaccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg gcaag                    1365
```

<210> SEQ ID NO 34
<211> LENGTH: 455
<212> TYPE: PRT
<213> ORGANISM: Artificial Sequence
<220> FEATURE:
<223> OTHER INFORMATION: Humanised

<400> SEQUENCE: 34

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr Ala Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320
```

```
Trp Leu Asn Gly Lys Glu Tyr Lys Cys Lys Val Ser Asn Lys Ala Leu
            325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
            355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
            405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
            435                 440                 445
Leu Ser Leu Ser Pro Gly Lys
450                 455
```

<210> SEQ ID NO 35
<211> LENGTH: 1365
<212> TYPE: DNA
<213> ORGANISM: Artificial Sequence
<220> FEATURE:
<223> OTHER INFORMATION: Humanised

<400> SEQUENCE: 35

```
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact acgcgtacga cgactactac gccatggact actggggaca gggcacacta     360
gtgaccgtgt ccagcgccag caccaagggc ccagcgtgt tcccctggc ccccagcagc      420
aagagcacca gcggcggcac agccgccctg ggctgcctgg tgaaggacta cttccccgaa     480
ccggtgaccg tgtcctggaa cagcggagcc ctgaccagcg gcgtgcacac cttccccgcc     540
gtgctgcaga gcagcggcct gtacagcctg agcagcgtgg tgaccgtgcc cagcagcagc     600
ctgggcaccc agacctacat ctgtaacgtg aaccacaagc ccagcaacac caaggtggac     660
aagaaggtgg agcccaagag ctgtgacaag ccacacct gccccccctg ccctgccccc      720
gagctgctgg gaggcccag cgtgttcctg ttccccccca gcctaagga caccctgatg      780
atcagcagaa cccccgaggt gacctgtgtg gtggtggatg tgagccacga ggaccctgag     840
gtgaagttca actggtacgt ggacggcgtg gaggtgcaca tgccaagac caagcccagg     900
gaggagcagt acaacagcac ctaccgggtg gtgtccgtgc tgaccgtgct gcaccaggat     960
tggctgaacg gcaaggagta caagtgtaag gtgtccaaca aggccctgcc tgcccctatc    1020
gagaaaacca tcagcaaggc caagggccag cccagagagc ccaggtgta caccctgccc    1080
cctagcagag atgagctgac caagaaccag gtgtccctga cctgcctggt gaagggcttc    1140
taccccagcg acatcgccgt ggagtgggag agcaacggcc agcccgagaa caactacaag    1200
accaccccc ctgtgctgga cagcgatggc agcttcttcc tgtacagcaa gctgaccgtg    1260
```

```
gacaagagca gatggcagca gggcaacgtg ttcagctgct ccgtgatgca cgaggccctg      1320
cacaatcact acacccagaa gagcctgagc ctgtcccctg gcaag                     1365
```

<210> SEQ ID NO 36
<211> LENGTH: 455
<212> TYPE: PRT
<213> ORGANISM: Artificial Sequence
<220> FEATURE:
<223> OTHER INFORMATION: Humanised

<400> SEQUENCE: 36

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr Glu Tyr Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350
```

-continued

```
Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 37
<211> LENGTH: 1365
<212> TYPE: DNA
<213> ORGANISM: Artificial Sequence
<220> FEATURE:
<223> OTHER INFORMATION: Humanised

<400> SEQUENCE: 37

```
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gctggagtg atgggcact atcgaccccg ccaacggcaa caccaagtac       180
gtgcccaagt ccagggcag ggtgaccatc accgccgatg agagcaccag caccgcctac      240
atggaactga gcagcctgag gtctgaggac accgccgtgt actattgcgc caggagcatc    300
tacgacgact acgagtacga cgactactac gccatggact actggggaca gggcacacta    360
gtgaccgtgt ccagcgccag caccaagggc cccagcgtgt tccccctggc cccagcagc     420
aagagcacca gcggcggcac agccgccctg ggctgcctgg tgaaggacta cttccccgaa    480
ccggtgaccg tgtcctggaa cagcggagcc ctgaccagcg gcgtgcacac cttccccgcc    540
gtgctgcaga gcagcggcct gtacagcctg agcagcgtgg tgaccgtgcc cagcagcagc    600
ctgggcaccc agacctacat ctgtaacgtg aaccacaagc ccagcaacac caaggtggac    660
aagaaggtgg agcccaagag ctgtgacaag acccacacct gcccccctg ccctgccccc     720
gagctgctgg gaggcccag cgtgttcctg ttcccccca gcctaagga cccctgatg       780
atcagcagaa ccccgaggt gacctgtgtg gtggtggatg tgagccacga ggaccctgag    840
gtgaagttca actggtacgt ggacggcgtg gaggtgcaca tgccaagac caagcccagg    900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc   1020
gagaaaacca tcagcaaggc caagggccag cccagagagc cccaggtgta caccctgccc   1080
cctagcagag atgagctgac caagaaccag gtgtccctga cctgcctggt gaagggcttc   1140
taccccagcg acatcgccgt ggagtggag agcaacggcc agcccgagaa caactacaag    1200
accacccccc ctgtgctgga cagcgatggc agcttcttcc tgtacagcaa gctgaccgtg   1260
gacaagagca gatggcagca gggcaacgtg ttcagctgct ccgtgatgca cgaggccctg   1320
cacaatcact acacccagaa gagcctgagc ctgtcccctg gcaag                   1365
```

<210> SEQ ID NO 38
<211> LENGTH: 455

```
<212> TYPE: PRT
<213> ORGANISM: Artificial Sequence
<220> FEATURE:
<223> OTHER INFORMATION: Humanised

<400> SEQUENCE: 38
```

| | | | | | | | | | | | | | | | |
|---|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Ser|
|1| | | |5| | | | |10| | | | |15| |
|Ser|Val|Lys|Val|Ser|Cys|Lys|Ala|Ser|Gly|Phe|Tyr|Ile|Lys|Asp|Thr|
| | | |20| | | | |25| | | | |30| | |
|Tyr|Met|His|Trp|Val|Arg|Gln|Ala|Pro|Gly|Gln|Gly|Leu|Glu|Trp|Met|
| | |35| | | | |40| | | | |45| | | |
|Gly|Thr|Ile|Asp|Pro|Ala|Asn|Gly|Asn|Thr|Lys|Tyr|Val|Pro|Lys|Phe|
| |50| | | | |55| | | | |60| | | | |
|Gln|Gly|Arg|Val|Thr|Ile|Thr|Ala|Asp|Glu|Ser|Thr|Ser|Thr|Ala|Tyr|
|65| | | | |70| | | | |75| | | | |80|
|Met|Glu|Leu|Ser|Ser|Leu|Arg|Ser|Glu|Asp|Thr|Ala|Val|Tyr|Tyr|Cys|
| | | | |85| | | | |90| | | | |95| |
|Ala|Arg|Ser|Ile|Tyr|Asp|Asp|Tyr|Gln|Tyr|Asp|Asp|Tyr|Tyr|Ala|Met|
| | | |100| | | | |105| | | | |110| | |
|Asp|Tyr|Trp|Gly|Gln|Gly|Thr|Leu|Val|Thr|Val|Ser|Ser|Ala|Ser|Thr|
| | |115| | | | |120| | | | |125| | | |
|Lys|Gly|Pro|Ser|Val|Phe|Pro|Leu|Ala|Pro|Ser|Ser|Lys|Ser|Thr|Ser|
| |130| | | | |135| | | | |140| | | | |
|Gly|Gly|Thr|Ala|Ala|Leu|Gly|Cys|Leu|Val|Lys|Asp|Tyr|Phe|Pro|Glu|
|145| | | | |150| | | | |155| | | | |160|
|Pro|Val|Thr|Val|Ser|Trp|Asn|Ser|Gly|Ala|Leu|Thr|Ser|Gly|Val|His|
| | | | |165| | | | |170| | | | |175| |
|Thr|Phe|Pro|Ala|Val|Leu|Gln|Ser|Ser|Gly|Leu|Tyr|Ser|Leu|Ser|Ser|
| | | |180| | | | |185| | | | |190| | |
|Val|Val|Thr|Val|Pro|Ser|Ser|Ser|Leu|Gly|Thr|Gln|Thr|Tyr|Ile|Cys|
| | |195| | | | |200| | | | |205| | | |
|Asn|Val|Asn|His|Lys|Pro|Ser|Asn|Thr|Lys|Val|Asp|Lys|Lys|Val|Glu|
| |210| | | | |215| | | | |220| | | | |
|Pro|Lys|Ser|Cys|Asp|Lys|Thr|His|Thr|Cys|Pro|Pro|Cys|Pro|Ala|Pro|
|225| | | | |230| | | | |235| | | | |240|
|Glu|Leu|Leu|Gly|Gly|Pro|Ser|Val|Phe|Leu|Phe|Pro|Pro|Lys|Pro|Lys|
| | | | |245| | | | |250| | | | |255| |
|Asp|Thr|Leu|Met|Ile|Ser|Arg|Thr|Pro|Glu|Val|Thr|Cys|Val|Val|Val|
| | | |260| | | | |265| | | | |270| | |
|Asp|Val|Ser|His|Glu|Asp|Pro|Glu|Val|Lys|Phe|Asn|Trp|Tyr|Val|Asp|
| | |275| | | | |280| | | | |285| | | |
|Gly|Val|Glu|Val|His|Asn|Ala|Lys|Thr|Lys|Pro|Arg|Glu|Glu|Gln|Tyr|
| |290| | | | |295| | | | |300| | | | |
|Asn|Ser|Thr|Tyr|Arg|Val|Val|Ser|Val|Leu|Thr|Val|Leu|His|Gln|Asp|
|305| | | | |310| | | | |315| | | | |320|
|Trp|Leu|Asn|Gly|Lys|Glu|Tyr|Lys|Cys|Lys|Val|Ser|Asn|Lys|Ala|Leu|
| | | | |325| | | | |330| | | | |335| |
|Pro|Ala|Pro|Ile|Glu|Lys|Thr|Ile|Ser|Lys|Ala|Lys|Gly|Gln|Pro|Arg|
| | | |340| | | | |345| | | | |350| | |
|Glu|Pro|Gln|Val|Tyr|Thr|Leu|Pro|Pro|Ser|Arg|Asp|Glu|Leu|Thr|Lys|
| | |355| | | | |360| | | | |365| | | |
|Asn|Gln|Val|Ser|Leu|Thr|Cys|Leu|Val|Lys|Gly|Phe|Tyr|Pro|Ser|Asp|
| |370| | | | |375| | | | |380| | | | |
|Ile|Ala|Val|Glu|Trp|Glu|Ser|Asn|Gly|Gln|Pro|Glu|Asn|Asn|Tyr|Lys|

```
                385                 390                 395                 400
Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 39
<211> LENGTH: 1365
<212> TYPE: DNA
<213> ORGANISM: Artificial Sequence
<220> FEATURE:
<223> OTHER INFORMATION: Humanised

<400> SEQUENCE: 39
caggtgcagc tcgtgcagag cggcgccgaa gtgaaaaagc ccggcagcag cgtgaaggtg        60
agctgcaagg cctccggctt ctacatcaag gacacctaca tgcactgggt caggcaggct       120
cctggccagg gcctggagtg gatgggcact atcgaccccg ccaacggcaa caccaagtac       180
gtgcccaagt tccagggcag ggtgaccatc accgccgatg agagcaccag caccgcctac       240
atggaactga gcagcctgag gtctgaggac accgccgtgt actattgcgc caggagcatc       300
tacgacgact accagtacga cgactactac gccatggact actggggaca gggcacacta       360
gtgaccgtgt ccagcgccag caccaagggc ccagcgtgt tccccctggc ccccagcagc       420
aagagcacca gcggcggcac agccgccctg ggctgcctgg tgaaggacta cttccccgaa       480
ccggtgaccg tgtcctggaa cagcggagcc ctgaccagcg gcgtgcacac cttccccgcc       540
gtgctgcaga gcagcggcct gtacagcctg agcagcgtgg tgaccgtgcc cagcagcagc       600
ctgggcaccc agacctacat ctgtaacgtg aaccacaagc ccagcaacac caaggtggac       660
aagaaggtgg agcccaagag ctgtgacaag acccacacct gccccccctg ccctgccccc       720
gagctgctgg gaggccccag cgtgttcctg ttccccccca gcctaagga caccctgatg       780 atcagcagaa cccccgaggt gacctgtgtg gtggtggatg tgagccacga ggaccctgag       840
gtgaagttca actggtacgt ggacggcgtg gaggtgcaca tgccaagac caagcccagg       900 gaggagcagt acaacagcac ctaccgggtg gtgtccgtgc tgaccgtgct gcaccaggat       960
tggctgaacg gcaaggagta caagtgtaag gtgtccaaca aggccctgcc tgcccctatc      1020
gagaaaacca tcagcaaggc caagggccag cccagagagc ccaggtgta cacctgccc       1080 cctagcagag atgagctgac caagaaccag gtgtccctga cctgcctggt gaagggcttc      1140
taccccagcg acatcgccgt ggagtgggag agcaacggcc agcccgagaa caactacaag      1200
accacccccc ctgtgctgga cagcgatggc agcttcttcc tgtacagcaa gctgaccgtg      1260
gacaagagca gatggcagca gggcaacgtg ttcagctgct ccgtgatgca cgaggccctg      1320
cacaatcact acacccagaa gagcctgagc ctgtcccctg gcaag                     1365

<210> SEQ ID NO 40
<211> LENGTH: 455
<212> TYPE: PRT
<213> ORGANISM: Artificial Sequence
<220> FEATURE:
<223> OTHER INFORMATION: Humanised

<400> SEQUENCE: 40
```

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
                 20                  25                  30

Tyr Met His Trp Val Arg Gln Ala Pro Gly Gln Gly Leu Glu Trp Met
             35                  40                  45

Gly Thr Ile Asp Pro Ala Asn Gly Asn Thr Lys Tyr Val Pro Lys Phe
         50                  55                  60

Gln Gly Arg Val Thr Ile Thr Ala Asp Glu Ser Ser Thr Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr Arg Tyr Asp Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
                195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
                310                 315                 320
305

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430
```

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 41
<211> LENGTH: 1365
<212> TYPE: DNA
<213> ORGANISM: Artificial Sequence
<220> FEATURE:
<223> OTHER INFORMATION: Humanised

<400> SEQUENCE: 41
caggtgcagc tcgtgcagag cggcgccgaa gtgaaaaagc ccggcagcag cgtgaaggtg    60
agctgcaagg cctccggctt ctacatcaag gacacctaca tgcactgggt caggcaggct   120
cctggccagg gcctggagtg gatgggcact atcgaccccg ccaacggcaa caccaagtac   180
gtgcccaagt tccagggcag ggtgaccatc accgccgatg agagccacag caccgcctac   240
atggaactga gcagcctgag gtctgaggac accgccgtgt actattgcgc caggagcatc   300
tacgacgact acaggtacga cgactactac gccatggact actggggaca gggcacacta   360
gtgaccgtgt ccagcgccag caccaagggc ccagcgtgt tccccctggc cccagcagc    420 aagagcacca gccgcggcac agccgccctg ggctgcctgg tgaaggacta cttccccgaa   480
ccggtgaccg tgtcctggaa cagcggagcc ctgaccagcg gcgtgcacac cttccccgcc   540
gtgctgcaga gcagcggcct gtacagcctg agcagcgtgg tgaccgtgcc cagcagcagc   600
ctgggcaccc agacctacat ctgtaacgtg aaccacaagc ccagcaacac caaggtggac   660
aagaaggtgg agcccaagag ctgtgacaag acccacacct gcccccctg ccctgccccc    720 gagctgctgg gaggcccag cgtgttcctg ttccccccca gcctaagga caccctgatg    780 atcagcagaa cccccgaggt gacctgtgtg gtggtggatg tgagccacga ggaccctgag   840
gtgaagttca actggtacgt ggacggcgtg gaggtgcaca atgccaagac caagcccagg   900
gaggagcagt acaacagcac ctaccgggtg gtgtccgtgc tgaccgtgct gcaccaggat   960
tggctgaacg gcaaggagta caagtgtaag gtgtccaaca aggccctgcc tgcccctatc   1020
gagaaaacca tcagcaaggc caagggccag cccagagagc ccaggtgta caccctgccc   1080 cctagcagag atgagctgac caagaaccag gtgtccctga cctgcctggt gaagggcttc   1140
taccccagcg acatcgccgt ggagtgggag agcaacggcc agcccgagaa caactacaag   1200
accacccccc ctgtgctgga cagcgatggc agcttcttcc tgtacagcaa gctgaccgtg   1260
gacaagagca gatggcagca gggcaacgtg ttcagctgct ccgtgatgca cgaggccctg   1320
cacaatcact acacccagaa gagcctgagc ctgtcccctg gcaag              1365

<210> SEQ ID NO 42
<211> LENGTH: 455
<212> TYPE: PRT
<213> ORGANISM: Artificial Sequence
<220> FEATURE:
<223> OTHER INFORMATION: Humanised

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met

```
            35                  40                  45
Gly Thr Ile Asp Pro Ala Asn Gly Asn Thr Lys Tyr Val Pro Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr Ser Tyr Asp Tyr Tyr Ala Met
               100                 105                 110

Asp Tyr Trp Gly Gln Gly Thr Leu Val Thr Val Ser Ser Ala Ser Thr
           115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 43
<211> LENGTH: 1365
<212> TYPE: DNA
<213> ORGANISM: Artificial Sequence
<220> FEATURE:
<223> OTHER INFORMATION: Humanised

<400> SEQUENCE: 43

```
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact actcctacga cgactactac gccatggact actggggaca gggcacacta     360
gtgaccgtgt ccagcgccag caccaagggc ccagcgtgt tcccctggc cccagcagc        420
aagagcacca gcggcggcac agccgccctg ggctgcctgg tgaaggacta cttccccgaa     480
ccggtgaccg tgtcctggaa cagcggagcc ctgaccagcg gcgtgcacac cttcccgcc      540
gtgctgcaga gcagcggcct gtacagcctg agcagcgtgg tgaccgtgcc agcagcagc      600
ctgggcaccc agacctacat ctgtaacgtg aaccacaagc ccagcaacac caaggtggac     660
aagaaggtgg agcccaagag ctgtgacaag acccacacct gcccccctg ccctgcccc       720
gagctgctgg gaggcccag cgtgttcctg ttcccccca gcctaagga cccctgatg         780
atcagcagaa ccccgaggt gacctgtgtg gtggtggatg tgagccacga ggaccctgag     840
gtgaagttca actggtacgt ggacggcgtg gaggtgcaca atgccaagac caagcccagg     900
gaggagcagt acaacagcac ctaccgggtg gtgtccgtgc tgaccgtgct gcaccaggat     960
tggctgaacg gcaaggagta caagtgtaag gtgtccaaca aggccctgcc tgcccctatc    1020
gagaaaacca tcagcaaggc caagggccag cccagagagc ccaggtgta caccctgccc     1080
cctagcagag atgagctgac caagaaccag gtgtccctga cctgcctggt gaagggcttc    1140
taccccagcg acatcgccgt ggagtgggag agcaacggcc agcccgagaa caactacaag    1200
accacccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg gcaag                    1365
```

<210> SEQ ID NO 44
<211> LENGTH: 455
<212> TYPE: PRT
<213> ORGANISM: Artificial Sequence
<220> FEATURE:
<223> OTHER INFORMATION: Humanised

<400> SEQUENCE: 44

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80
```

```
Met Glu Leu Ser Ser Leu Arg Ser Glu Asp Thr Ala Val Tyr Tyr Cys
                85                  90                  95

Ala Arg Ser Ile Tyr Asp Asp Tyr Thr Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
                295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 45
<211> LENGTH: 1365
<212> TYPE: DNA
<213> ORGANISM: Artificial Sequence
<220> FEATURE:
<223> OTHER INFORMATION: Humanised
```

<400> SEQUENCE: 45

```
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact acacgtacga cgactactac gccatggact actggggaca gggcacacta     360
gtgaccgtgt ccagcgccag caccaagggc cccagcgtgt tccccctggc cccagcagc     420
aagagcacca gcggcggcac agccgccctg ggctgcctgg tgaaggacta cttccccgaa     480
ccggtgaccg tgtcctggaa cagcggagcc ctgaccagcg gcgtgcacac cttccccgcc     540
gtgctgcaga gcagcggcct gtacagcctg agcagcgtgg tgaccgtgcc cagcagcagc     600
ctgggcaccc agacctacat ctgtaacgtg aaccacaagc ccagcaacac caaggtggac     660
aagaaggtgg agcccaagag ctgtgacaag acccacacct gccccccctg ccctgccccc     720
gagctgctgg gaggccccag cgtgttcctg ttccccccca gcctaaagga caccctgatg     780
atcagcagaa cccccgaggt gacctgtgtg gtggtggatg tgagccacga ggaccctgag     840
gtgaagttca actggtacgt ggacggcgtg gaggtgcaca tgccaagac caagcccagg     900
gaggagcagt acaacagcac ctaccgggtg gtgtccgtgc tgaccgtgct gcaccaggat     960
tggctgaacg gcaaggagta caagtgtaag gtgtccaaca aggccctgcc tgcccctatc    1020
gagaaaacca tcagcaaggc caagggccag cccagagagc ccaggtgta caccctgccc    1080
cctagcagag atgagctgac caagaaccag gtgtccctga cctgcctggt gaagggcttc    1140
taccccagcg acatcgccgt ggagtgggag agcaacggcc agcccgagaa caactacaag    1200
accaccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg gcaag                     1365
```

<210> SEQ ID NO 46
<211> LENGTH: 455
<212> TYPE: PRT
<213> ORGANISM: Artificial Sequence
<220> FEATURE:
<223> OTHER INFORMATION: Humanised

<400> SEQUENCE: 46

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr Val Tyr Asp Tyr Tyr Ala Met
            100                 105                 110
```

```
Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 47
<211> LENGTH: 1365
<212> TYPE: DNA
<213> ORGANISM: Artificial Sequence
<220> FEATURE:
<223> OTHER INFORMATION: Humanised

<400> SEQUENCE: 47
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
```

```
cctggccagg gcctggagtg gatgggcact atcgaccccg ccaacggcaa caccaagtac    180
gtgcccaagt tccagggcag ggtgaccatc accgccgatg agagccacag caccgcctac    240
atggaactga gcagcctgag gtctgaggac accgccgtgt actattgcgc caggagcatc    300
tacgacgact acgtgtacga cgactactac gccatggact actggggaca gggcacacta    360
gtgaccgtgt ccagcgccag caccaagggc ccagcgtgt tcccctggc cccagcagc      420 aagagcacca gcggcggcac agccgccctg ggctgcctgg tgaaggacta cttccccgaa    480
ccggtgaccg tgtcctggaa cagcggagcc ctgaccagcg gcgtgcacac cttccccgcc    540
gtgctgcaga gcagcggcct gtacagcctg agcagcgtgg tgaccgtgcc cagcagcagc    600
ctgggcaccc agacctacat ctgtaacgtg aaccacaagc ccagcaacac caaggtggac    660
aagaaggtgg agcccaagag ctgtgacaag acccacacct gccccccctg ccctgccccc    720
gagctgctgg gaggccccag cgtgttcctg ttcccccca agcctaagga caccctgatg     780
atcagcagaa cccccgaggt gacctgtgtg gtggtggatg tgagccacga ggaccctgag    840
gtgaagttca actggtacgt ggacggcgtg gaggtgcaca atgccaagac caagcccagg    900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc    1020 gagaaaaacca tcagcaaggc caagggccag cccagagagc cccaggtgta caccctgccc   1080
cctagcagag atgagctgac caagaaccag gtgtccctga cctgcctggt gaagggcttc    1140
taccccagcg acatcgccgt ggagtgggag agcaacggcc agcccgagaa caactacaag    1200 accaccccc ctgtgctgga cagcgatggc agcttcttcc tgtacagcaa gctgaccgtg     1260
gacaagagca gatggcagca gggcaacgtg ttcagctgct ccgtgatgca cgaggccctg    1320
cacaatcact acacccagaa gagcctgagc ctgtcccctg gcaag                    1365
```

<210> SEQ ID NO 48
<211> LENGTH: 455
<212> TYPE: PRT
<213> ORGANISM: Artificial Sequence
<220> FEATURE:
<223> OTHER INFORMATION: Humanised

<400> SEQUENCE: 48

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Ala Asp Tyr Tyr Ala Met
                100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
```

```
           145                 150                 155                 160
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 49
<211> LENGTH: 1365
<212> TYPE: DNA
<213> ORGANISM: Artificial Sequence
<220> FEATURE:
<223> OTHER INFORMATION: Humanised

<400> SEQUENCE: 49
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accacgcgga cgactactac gccatggact actggggaca gggcacacta     360
```

```
gtgaccgtgt ccagcgccag caccaagggc cccagcgtgt tccccctggc cccagcagc      420 aagagcacca gcggcggcac agccgccctg ggctgcctgg tgaaggacta cttccccgaa      480
ccggtgaccg tgtcctggaa cagcggagcc ctgaccagcg gcgtgcacac cttccccgcc      540
gtgctgcaga gcagcggcct gtacagcctg agcagcgtgg tgaccgtgcc cagcagcagc      600
ctgggcaccc agacctacat ctgtaacgtg aaccacaagc ccagcaacac caaggtggac      660
aagaaggtgg agcccaagag ctgtgacaag acccacacct gccccccctg ccctgccccc      720
gagctgctgg gaggcccag cgtgttcctg ttccccccca gcctaagga cacctgatg       780 atcagcagaa cccccgaggt gacctgtgtg gtggtggatg tgagccacga ggaccctgag      840
gtgaagttca actggtacgt ggacggcgtg gaggtgcaca atgccaagac caagcccagg      900
gaggagcagt acaacagcac ctaccgggtg gtgtccgtgc tgaccgtgct gcaccaggat      960
tggctgaacg gcaaggagta caagtgtaag gtgtccaaca aggccctgcc tgcccctatc     1020
gagaaaacca tcagcaaggc caagggccag cccagagagc ccaggtgta caccctgccc     1080 cctagcagag atgagctgac caagaaccag gtgtccctga cctgcctggt gaagggcttc     1140
tacccccagc gcatcgccgt ggagtgggag agcaacggcc agcccgagaa caactacaag     1200
accacccccc ctgtgctgga cagcgatggc agcttcttcc tgtacagcaa gctgaccgtg     1260
gacaagagca gatggcagca gggcaacgtg ttcagctgct ccgtgatgca cgaggccctg     1320
cacaatcact acacccagaa gagcctgagc ctgtcccctg gcaag              1365
```

<210> SEQ ID NO 50
<211> LENGTH: 455
<212> TYPE: PRT
<213> ORGANISM: Artificial Sequence
<220> FEATURE:
<223> OTHER INFORMATION: Humanised

<400> SEQUENCE: 50

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Ile Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 51
<211> LENGTH: 1365
<212> TYPE: DNA
<213> ORGANISM: Artificial Sequence
<220> FEATURE:
<223> OTHER INFORMATION: Humanised

<400> SEQUENCE: 51
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac    180
gtgcccaagt tccagggcag ggtgaccatc accgccgatg agagcaccag caccgcctac    240
atggaactga gcagcctgag gtctgaggac accgccgtgt actattgcgc caggagcatc    300
tacgacgact accacattga cgactactac gccatggact actggggaca gggcacacta    360
gtgaccgtgt ccagcgccag caccaagggc cccagcgtgt tccccctggc ccccagcagc    420
aagagcacca gcggcggcac agccgccctg ggctgcctgg tgaaggacta cttccccgaa    480
ccggtgaccg tgtcctggaa cagcggagcc ctgaccagcg gcgtgcacac cttccccgcc    540

```
gtgctgcaga gcagcggcct gtacagcctg agcagcgtgg tgaccgtgcc cagcagcagc      600
ctgggcaccc agacctacat ctgtaacgtg aaccacaagc ccagcaacac caaggtggac      660
aagaaggtgg agcccaagag ctgtgacaag acccacacct gccccccctg ccctgccccc      720
gagctgctgg gaggccccag cgtgttcctg ttccccccca gcctaagga caccctgatg      780 atcagcagaa cccccgaggt gacctgtgtg gtggtggatg tgagccacga ggaccctgag      840
gtgaagttca actggtacgt ggacggcgtg gaggtgcaca tgccaagac caagcccagg      900 gaggagcagt acaacagcac ctaccgggtg gtgtccgtgc tgaccgtgct gcaccaggat      960
tggctgaacg gcaaggagta caagtgtaag gtgtccaaca aggccctgcc tgcccctatc     1020
gagaaaacca tcagcaaggc caagggccag cccagagagc ccaggtgta caccctgccc     1080 cctagcagag atgagctgac caagaaccag gtgtccctga cctgcctggt gaagggcttc     1140
taccccagcg acatcgccgt ggagtgggag agcaacggcc agcccgagaa caactacaag     1200
accacccccc ctgtgctgga cagcgatggc agcttcttcc tgtacagcaa gctgaccgtg     1260
gacaagagca gatggcagca gggcaacgtg ttcagctgct ccgtgatgca cgaggccctg     1320
cacaatcact acacccagaa gagcctgagc ctgtcccctg gcaag                     1365
```

<210> SEQ ID NO 52
<211> LENGTH: 455
<212> TYPE: PRT
<213> ORGANISM: Artificial Sequence
<220> FEATURE:
<223> OTHER INFORMATION: Humanised

<400> SEQUENCE: 52

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Trp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220
```

-continued

```
Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 53
<211> LENGTH: 1365
<212> TYPE: DNA
<213> ORGANISM: Artificial Sequence
<220> FEATURE:
<223> OTHER INFORMATION: Humanised

<400> SEQUENCE: 53

```
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accactggga cgactactac gccatggact actggggaca gggcacacta     360
gtgaccgtgt ccagcgccag caccaagggc ccagcgtgt tcccctggc cccagcagc      420 aagagcacca gcggcggcac agccgccctg ggctgcctgg tgaaggacta cttccccgaa     480
ccggtgaccg tgtcctggaa cagcggagcc ctgaccagcg gcgtgcacac cttccccgcc     540
gtgctgcaga gcagcggcct gtacagcctg agcagcgtgg tgaccgtgcc agcagcagc     600 ctgggcaccc agacctacat ctgtaacgtg aaccacaagc ccagcaacac caaggtggac     660
aagaaggtgg agcccaagag ctgtgacaag acccacacct gccccccctg ccctgccccc     720
gagctgctgg gaggccccag cgtgttcctg ttcccccca agcctaagga caccctgatg     780
```

-continued

```
atcagcagaa ccccccgaggt gacctgtgtg gtggtggatg tgagccacga ggaccctgag      840
gtgaagttca actggtacgt ggacggcgtg gaggtgcaca atgccaagac caagcccagg      900
gaggagcagt acaacagcac ctaccgggtg gtgtccgtgc tgaccgtgct gcaccaggat      960
tggctgaacg gcaaggagta caagtgtaag gtgtccaaca aggccctgcc tgcccctatc     1020
gagaaaacca tcagcaaggc caagggccag cccagagagc ccagggtgta caccctgccc     1080
cctagcagag atgagctgac caagaaccag gtgtccctga cctgcctggt gaagggcttc     1140
taccccagcg acatcgccgt ggagtgggag agcaacggcc agcccgagaa caactacaag     1200 accaccccc ctgtgctgga cagcgatggc agcttcttcc tgtacagcaa gctgaccgtg     1260
gacaagagca gatggcagca gggcaacgtg ttcagctgct ccgtgatgca cgaggccctg     1320
cacaatcact acacccagaa gagcctgagc ctgtcccctg gcaag                     1365
```

<210> SEQ ID NO 54
<211> LENGTH: 455
<212> TYPE: PRT
<213> ORGANISM: Artificial Sequence
<220> FEATURE:
<223> OTHER INFORMATION: Humanised

<400> SEQUENCE: 54

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
                 20                  25                  30

Tyr Met His Trp Val Arg Gln Ala Pro Gly Gln Gly Leu Glu Trp Met
             35                  40                  45

Gly Thr Ile Asp Pro Ala Asn Gly Asn Thr Lys Tyr Val Pro Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
```

```
                    260               265                 270
Asp Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln Tyr
        290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 55
<211> LENGTH: 1365
<212> TYPE: DNA
<213> ORGANISM: Artificial Sequence
<220> FEATURE:
<223> OTHER INFORMATION: Humanised

<400> SEQUENCE: 55
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accacgtcga cgactactac gccatggact actggggaca gggcacacta     360
gtgaccgtgt ccagcgccag caccaagggc ccagcgtgt tccccctggc cccagcagc      420 aagagcacca gcggcggcac agccgccctg ggctgcctgg tgaaggacta cttccccgaa     480
ccggtgaccg tgtcctggaa cagcggagcc ctgaccagcg gcgtgcacac cttccccgcc     540
gtgctgcaga gcagcggcct gtacagcctg agcagcgtgg tgaccgtgcc cagcagcagc     600
ctgggcaccc agacctacat ctgtaacgtg aaccacaagc ccagcaacac caaggtggac     660
aagaaggtgg agcccaagag ctgtgacaag acccacacct gcccccccctg ccctgccccc     720 gagctgctgg gaggcccag cgtgttcctg ttccccccca gcctaagga cccctgatg      780 atcagcagaa ccccgaggt gacctgtgtg gtggtggatg tgagccacga ggaccctgag     840
gtgaagttca actggtacgt ggacggcgtg gaggtgcaca atgccaagac caagcccagg     900
gaggagcagt acaacagcac ctaccgggtg gtgtccgtgc tgaccgtgct gcaccaggat     960
```

-continued

```
tggctgaacg gcaaggagta caagtgtaag gtgtccaaca aggccctgcc tgcccctatc    1020
gagaaaacca tcagcaaggc caagggccag cccagagagc cccaggtgta caccctgccc    1080
cctagcagag atgagctgac caagaaccag gtgtccctga cctgcctggt gaagggcttc    1140
taccccagcg acatcgccgt ggagtgggag agcaacggcc agcccgagaa caactacaag    1200
accacccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg gcaag                    1365
```

<210> SEQ ID NO 56
<211> LENGTH: 19
<212> TYPE: PRT
<213> ORGANISM: Artificial Sequence
<220> FEATURE:
<223> OTHER INFORMATION: signal sequecne

<400> SEQUENCE: 56

Met Gly Trp Ser Cys Ile Ile Leu Phe Leu Val Ala Thr Ala Thr Gly
 1               5                  10                  15

Val His Ser

<210> SEQ ID NO 57
<211> LENGTH: 112
<212> TYPE: PRT
<213> ORGANISM: Homo Sapiens

<400> SEQUENCE: 57

Gly Pro Val Pro Pro Ser Thr Ala Leu Arg Glu Leu Ile Glu Glu Leu
 1               5                  10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

<210> SEQ ID NO 58
<211> LENGTH: 125
<212> TYPE: PRT
<213> ORGANISM: Mus sp.

<400> SEQUENCE: 58

Glu Ile Gln Leu Gln Gln Ser Val Ala Glu Leu Val Arg Pro Gly Ala
 1               5                  10                  15

Ser Val Arg Leu Ser Cys Thr Ala Ser Gly Phe Tyr Ile Lys Asp Thr
            20                  25                  30

Tyr Met His Trp Val Ile Gln Arg Pro Glu Gln Gly Leu Glu Trp Ile
        35                  40                  45

Gly Thr Ile Asp Pro Ala Asn Gly Asn Thr Lys Tyr Val Pro Lys Phe
    50                  55                  60

Gln Gly Lys Ala Thr Ile Thr Ala Asp Thr Ser Ser Asn Thr Ala Tyr
65                  70                  75                  80

```
Leu Arg Leu Ser Ser Leu Thr Ser Glu Asp Thr Ala Ile Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Ser Val Thr Val Ser Ser
        115                 120                 125

<210> SEQ ID NO 59
<211> LENGTH: 112
<212> TYPE: PRT
<213> ORGANISM: Mus sp.

<400> SEQUENCE: 59

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ile
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Ile Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 60
<211> LENGTH: 9
<212> TYPE: PRT
<213> ORGANISM: Artificial Sequence
<220> FEATURE:
<223> OTHER INFORMATION: Mutated CDR

<400> SEQUENCE: 60

Phe Tyr Ile Lys Asp Thr Tyr Met His
1               5

<210> SEQ ID NO 61
<211> LENGTH: 10
<212> TYPE: PRT
<213> ORGANISM: Artificial Sequence
<220> FEATURE:
<223> OTHER INFORMATION: Mutated CDR

<400> SEQUENCE: 61

Gly Phe Tyr Ile Lys Asp Thr Tyr Met His
1               5                   10

<210> SEQ ID NO 62
<211> LENGTH: 577
<212> TYPE: PRT
<213> ORGANISM: Artificial Sequence
<220> FEATURE:
<223> OTHER INFORMATION: Humanised

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30
```

```
Tyr Met His Trp Val Arg Gln Ala Pro Gly Gln Gly Leu Glu Trp Met
        35                  40                  45
Gly Thr Ile Asp Pro Ala Asn Gly Asn Thr Lys Tyr Val Pro Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Ile Tyr Asp Asp Tyr His Ala Asp Tyr Tyr Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys Thr Val Ala Ala Pro Ser Glu Val Gln
```

```
                450            455            460
Leu Leu Glu Ser Gly Gly Gly Leu Val Gln Pro Gly Gly Ser Leu Arg
465                 470                 475                 480

Leu Ser Cys Ala Ala Ser Gly Phe Thr Phe Arg Asn Phe Gly Met Gly
                485                 490                 495

Trp Val Arg Gln Ala Pro Gly Lys Gly Leu Glu Trp Val Ser Trp Ile
                500                 505                 510

Ile Ser Ser Gly Thr Glu Thr Tyr Tyr Ala Asp Ser Val Lys Gly Arg
                515                 520                 525

Phe Thr Ile Ser Arg Asp Asn Ser Lys Asn Thr Leu Tyr Leu Gln Met
            530                 535                 540

Asn Ser Leu Arg Ala Glu Asp Thr Ala Val Tyr Tyr Cys Ala Lys Ser
545                 550                 555                 560

Leu Gly Arg Phe Asp Tyr Trp Gly Gln Gly Thr Leu Val Thr Val Ser
                565                 570                 575

Ser
```

<210> SEQ ID NO 63
<211> LENGTH: 1731
<212> TYPE: DNA
<213> ORGANISM: Artificial Sequence
<220> FEATURE:
<223> OTHER INFORMATION: Humanised

<400> SEQUENCE: 63

```
caggtgcagc tcgtgcagag cggcgccgaa gtgaaaaagc ccggcagcag cgtgaaggtg      60
agctgcaagg cctccggctt ctacatcaag gacaccctac atgcactggg tcaggcaggct    120
cctggccagg gcctggagtg gatgggcact atcgaccccg ccaacggcaa caccaagtac    180
gtgcccaagt tccagggcag ggtgaccatc accgccgatg agagcaccag caccgcctac    240
atggaactga gcagcctgag gtctgaggac accgccgtgt actattgcgc caggagcatc    300
tacgacgact accacgcgga cgactactac gccatggact actggggaca gggcacacta    360
gtgaccgtgt ctagcgccag caccaagggc ccagcgtgt tccccctggc cccagcagc      420
aagagcacca gcggcggcac agccgccctg ggctgcctgg tgaaggacta cttccccgaa    480
ccggtgaccg tgtcctggaa cagcggagcc ctgaccagcg gcgtgcacac cttcccgcc     540
gtgctgcaga gcagcggcct gtacagcctg agcagcgtgg tgaccgtgcc cagcagcagc    600
ctgggcaccc agacctacat ctgtaacgtg aaccacaagc ccagcaacac caaggtggac    660
aagaaggtgg agcccaagag ctgtgacaag acccacacct gcccccctg ccctgccccc    720
gagctgctgg gaggcccag cgtgttcctg ttcccccca gcctaagga cccctgatg       780
atcagcagaa ccccgaggt gacctgtgtg gtggtggatg tgagccacga ggaccctgag    840
gtgaagttca actggtacgt ggacggcgtg gaggtgcaca atgccaagac caagcccagg    900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc   1020
gagaaaacca tcagcaaggc caagggccag cccagagagc ccaggtgta caccctgcc    1080
cctagcagag atgagctgac caagaaccag gtgtccctga cctgcctggt gaagggcttc    1140
tacccagcg acatcgccgt ggagtgggag agcaacggcc agcccgagaa caactacaag    1200
accaccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg gcaagaccgt ggccgccccc    1380
```

-continued

```
tcggaagtgc agctcctgga gagcggcggc ggcctggtgc agcccggcgg cagcctgagg    1440
ctgagctgcg ccgctagcgg cttcaccttc aggaacttcg gcatgggctg ggtcaggcag    1500
gcccccggca agggcctgga gtgggtcagc tggatcatca gctccggcac cgagacctac    1560
tacgccgaca gcgtgaaggg caggttcacc atcagccgcg acaacagcaa gaacaccctg    1620
tacctgcaga tgaacagcct gagggccgag gacaccgccg tctactactg cgccaagagc    1680
ctgggcaggt tcgactactg gggacagggg accctggtga ctgtgagcag c              1731
```

<210> SEQ ID NO 64
<211> LENGTH: 577
<212> TYPE: PRT
<213> ORGANISM: Artificial Sequence
<220> FEATURE:
<223> OTHER INFORMATION: Humanised

<400> SEQUENCE: 64

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Ile Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300
```

```
Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Asp Glu Leu Thr Lys
    355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro Gly Lys Thr Val Ala Ala Pro Ser Glu Val Gln
450                 455                 460

Leu Leu Glu Ser Gly Gly Gly Leu Val Gln Pro Gly Gly Ser Leu Arg
465                 470                 475                 480

Leu Ser Cys Ala Ala Ser Gly Phe Thr Phe Arg Asn Phe Gly Met Gly
            485                 490                 495

Trp Val Arg Gln Ala Pro Gly Lys Gly Leu Glu Trp Val Ser Trp Ile
        500                 505                 510

Ile Ser Ser Gly Thr Glu Thr Tyr Tyr Ala Asp Ser Val Lys Gly Arg
    515                 520                 525

Phe Thr Ile Ser Arg Asp Asn Ser Lys Asn Thr Leu Tyr Leu Gln Met
530                 535                 540

Asn Ser Leu Arg Ala Glu Asp Thr Ala Val Tyr Tyr Cys Ala Lys Ser
545                 550                 555                 560

Leu Gly Arg Phe Asp Tyr Trp Gly Gln Gly Thr Leu Val Thr Val Ser
            565                 570                 575

Ser

<210> SEQ ID NO 65
<211> LENGTH: 1731
<212> TYPE: DNA
<213> ORGANISM: Artificial Sequence
<220> FEATURE:
<223> OTHER INFORMATION: Humanised

<400> SEQUENCE: 65
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accacattga cgactactac gccatggact actggggaca gggcacacta     360
gtgaccgtgt ctagcgccag caccaagggc ccagcgtgt tccccctggc cccagcagc      420 aagagcacca gcggcggcac agccgccctg ggctgcctgg tgaaggacta cttccccgaa     480
ccggtgaccg tgtcctggaa cagcggagcc ctgaccagcg gcgtgcacac cttccccgcc     540
```

```
gtgctgcaga gcagcggcct gtacagcctg agcagcgtgg tgaccgtgcc cagcagcagc    600
ctgggcaccc agacctacat ctgtaacgtg aaccacaagc ccagcaacac caaggtggac    660
aagaaggtgg agcccaagag ctgtgacaag acccacacct gcccccctg ccctgccccc     720 gagctgctgg gaggcccag cgtgttcctg ttccccccca agcctaagga caccctgatg     780
atcagcagaa cccccgaggt gacctgtgtg gtggtggatg tgagccacga ggaccctgag    840
gtgaagttca actggtacgt ggacggcgtg gaggtgcaca atgccaagac caagcccagg    900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc   1020
gagaaaacca tcagcaaggc caagggccag cccagagagc ccaggtgta caccctgccc    1080 cctagcagag atgagctgac caagaaccag gtgtccctga cctgcctggt gaagggcttc   1140
taccccagcg acatcgccgt ggagtgggag agcaacggcc agcccgagaa caactacaag   1200
accacccccc ctgtgctgga cagcgatggc agcttcttcc tgtacagcaa gctgaccgtg   1260
gacaagagca gatggcagca gggcaacgtg ttcagctgct ccgtgatgca cgaggccctg   1320
cacaatcact acacccagaa gagcctgagc ctgtcccctg caagaccgt ggccgccccc    1380 tcggaagtgc agctcctgga gagcggcggc ggcctggtgc agcccggcgg cagcctgagg   1440
ctgagctgcg ccgctagcgg cttcaccttc aggaacttcg gcatgggctg ggtcaggcag   1500
gcccccggca agggcctgga gtgggtcagc tggatcatca gctccggcac cgagacctac   1560
tacgccgaca gcgtgaaggg caggttcacc atcagccgcg acaacagcaa gaacaccctg   1620
tacctgcaga tgaacagcct gagggccgag gacaccgccg tctactactg cgccaagagc   1680
ctgggcaggt tcgactactg gggacagggg accctggtga ctgtgagcag c            1731
```

<210> SEQ ID NO 66
<211> LENGTH: 577
<212> TYPE: PRT
<213> ORGANISM: Artificial Sequence
<220> FEATURE:
<223> OTHER INFORMATION: Humanised

<400> SEQUENCE: 66

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Trp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys Thr Val Ala Ala Pro Ser Glu Val Gln
            450                 455                 460

Leu Leu Glu Ser Gly Gly Gly Leu Val Gln Pro Gly Gly Ser Leu Arg
465                 470                 475                 480

Leu Ser Cys Ala Ala Ser Gly Phe Thr Phe Arg Asn Phe Gly Met Gly
            485                 490                 495

Trp Val Arg Gln Ala Pro Gly Lys Gly Leu Glu Trp Val Ser Trp Ile
            500                 505                 510

Ile Ser Ser Gly Thr Glu Thr Tyr Tyr Ala Asp Ser Val Lys Gly Arg
            515                 520                 525

Phe Thr Ile Ser Arg Asp Asn Ser Lys Asn Thr Leu Tyr Leu Gln Met
            530                 535                 540

Asn Ser Leu Arg Ala Glu Asp Thr Ala Val Tyr Tyr Cys Ala Lys Ser
545                 550                 555                 560

Leu Gly Arg Phe Asp Tyr Trp Gly Gln Gly Thr Leu Val Thr Val Ser
            565                 570                 575

Ser
```

<210> SEQ ID NO 67
<211> LENGTH: 1731
<212> TYPE: DNA
<213> ORGANISM: Artificial Sequence
<220> FEATURE:
<223> OTHER INFORMATION: Humanised

<400> SEQUENCE: 67

```
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accactggga cgactactac gccatggact actggggaca gggcacacta     360
gtgaccgtgt ctagcgccag caccaagggc cccagcgtgt tccccctggc cccagcagc     420
aagagcacca gcggcggcac agccgccctg gctgcctgg tgaaggacta cttccccgaa     480
ccggtgaccg tgtcctggaa cagcggagcc ctgaccagcg gcgtgcacac cttccccgcc     540
gtgctgcaga gcagcggcct gtacagcctg agcagcgtgg tgaccgtgcc cagcagcagc     600
ctgggcaccc agacctacat ctgtaacgtg aaccacaagc ccagcaacac caaggtggac     660
aagaaggtgg agcccaagag ctgtgacaag acccacacct gccccccctg ccctgccccc     720
gagctgctgg gaggcccag cgtgttcctg ttccccccca gcctaagga cacctgatg     780
atcagcagaa cccccgaggt gacctgtgtg gtggtggatg tgagccacga ggaccctgag     840
gtgaagttca ctggtacgt ggacggcgtg gaggtgcaca atgccaagac caagcccagg     900
gaggagcagt acaacagcac ctaccgggtg gtgtccgtgc tgaccgtgct gcaccaggat     960
tggctgaacg gcaaggagta caagtgtaag gtgtccaaca aggccctgcc tgcccctatc    1020
gagaaaacca tcagcaaggc caagggccag cccagagagc ccaggtgta cacctgccc    1080
cctagcagag atgagctgac caagaaccag gtgtccctga cctgcctggt gaagggcttc    1140
taccccagcg acatcgccgt ggagtgggag agcaacggcc agcccgagaa caactacaag    1200
accacccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg caagaccgt ggccgccccc    1380
tcggaagtgc agctcctgga gagcggcggc ggcctggtgc agcccggcgg cagcctgagg    1440
ctgagctgcg ccgctagcgg cttcaccttc aggaacttcg gcatgggctg ggtcaggcag    1500
gcccccggca agggcctgga gtgggtcagc tggatcatca gctccggcac cgagacctac    1560
tacgccgaca gcgtgaaggg caggttcacc atcagccgcg acaacagcaa gaacaccctg    1620
tacctgcaga tgaacagcct gagggccgag gacaccgccg tctactactg cgccaagagc    1680
ctgggcaggt tcgactactg gggacagggg accctggtga ctgtgagcag c            1731
```

<210> SEQ ID NO 68
<211> LENGTH: 577
<212> TYPE: PRT
<213> ORGANISM: Artificial Sequence
<220> FEATURE:
<223> OTHER INFORMATION: Humanised

<400> SEQUENCE: 68

Gln Val Gln Leu Val Gln Ser Gly Ala Glu Val Lys Lys Pro Gly Ser

-continued

```
          1               5                   10                  15
Ser Val Lys Val Ser Cys Lys Ala Ser Gly Phe Tyr Ile Lys Asp Thr
                    20                  25                  30

Tyr Met His Trp Val Arg Gln Ala Pro Gly Gln Gly Leu Glu Trp Met
                35                  40                  45

Gly Thr Ile Asp Pro Ala Asn Gly Asn Thr Lys Tyr Val Pro Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
                210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
                370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430
```

```
Cys Ser Val Met His Glu Ala Leu His Asn His Tyr Thr Gln Lys Ser
            435                 440                 445
Leu Ser Leu Ser Pro Gly Lys Thr Val Ala Ala Pro Ser Glu Val Gln
450                 455                 460
Leu Leu Glu Ser Gly Gly Gly Leu Val Gln Pro Gly Gly Ser Leu Arg
465                 470                 475                 480
Leu Ser Cys Ala Ala Ser Gly Phe Thr Phe Arg Asn Phe Gly Met Gly
                485                 490                 495
Trp Val Arg Gln Ala Pro Gly Lys Gly Leu Glu Trp Val Ser Trp Ile
            500                 505                 510
Ile Ser Ser Gly Thr Glu Thr Tyr Tyr Ala Asp Ser Val Lys Gly Arg
        515                 520                 525
Phe Thr Ile Ser Arg Asp Asn Ser Lys Asn Thr Leu Tyr Leu Gln Met
    530                 535                 540
Asn Ser Leu Arg Ala Glu Asp Thr Ala Val Tyr Tyr Cys Ala Lys Ser
545                 550                 555                 560
Leu Gly Arg Phe Asp Tyr Trp Gly Gln Gly Thr Leu Val Thr Val Ser
                565                 570                 575
Ser
```

<210> SEQ ID NO 69
<211> LENGTH: 1731
<212> TYPE: DNA
<213> ORGANISM: Artificial Sequence
<220> FEATURE:
<223> OTHER INFORMATION: Humanised

<400> SEQUENCE: 69

```
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg cctggagtg atgggcact atcgacccg ccaacggcaa caccaagtac        180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accacgtcga cgactactac gccatggact actggggaca gggcacacta     360
gtgaccgtgt ccagcgccag caccaagggc ccagcgtgt tccccctggc cccagcagc       420
aagagcacca gcggcggcac agccgccctg ggctgcctgg tgaaggacta cttccccgaa     480
ccggtgaccg tgtcctggaa cagcggagcc ctgaccagcg gcgtgcacac cttccccgcc     540
gtgctgcaga gcagcggcct gtacagcctg agcagcgtgg tgaccgtgcc cagcagcagc     600
ctgggcaccc agacctacat ctgtaacgtg aaccacaagc ccagcaacac caaggtggac     660
aagaaggtgg agcccaagag ctgtgacaag acccacacct gccccccctg ccctgccccc     720
gagctgctgg gaggccccag cgtgttcctg ttccccccca gcctaagga cccctgatg      780
atcagcagaa ccccgaggt gacctgtgtg gtggtggatg tgagccacga ggaccctgag     840
gtgaagttca actggtacgt ggacggcgtg gaggtgcaca atgccaagac caagcccagg     900
gaggagcagt acaacagcac ctaccgggtg gtgtccgtgc tgaccgtgct gcaccaggat     960
tggctgaacg gcaaggagta caagtgtaag gtgtccaaca aggccctgcc tgcccctatc    1020
gagaaaacca tcagcaaggc caagggccag cccagagag cccaggtgta caccctgccc    1080
cctagcagag atgagctgac caagaaccag gtgtccctga cctgcctggt gaagggcttc    1140
taccccagcg acatcgccgt ggagtgggag agcaacggcc agcccgagaa caactacaag    1200
accaccccc ctgtgctgga cagcgatggc agcttcttcc tgtacagcaa gctgaccgtg    1260
```

-continued

```
gacaagagca gatggcagca gggcaacgtg ttcagctgct ccgtgatgca cgaggccctg    1320
cacaatcact acacccagaa gagcctgagc ctgtcccctg gcaagaccgt ggccgccccc    1380
tcggaagtgc agctcctgga gagcggcggc ggcctggtgc agcccggcgg cagcctgagg    1440
ctgagctgcg ccgctagcgg cttcaccttc aggaacttcg gcatgggctg ggtcaggcag    1500
gcccccggca agggcctgga gtgggtcagc tggatcatca gctccggcac cgagacctac    1560
tacgccgaca gcgtgaaggg caggttcacc atcagccgcg acaacagcaa gaacaccctg    1620
tacctgcaga tgaacagcct gagggccgag gacaccgccg tctactactg cgccaagagc    1680
ctgggcaggt tcgactactg gggacagggg accctggtga ctgtgagcag c             1731
```

<210> SEQ ID NO 70
<211> LENGTH: 578
<212> TYPE: PRT
<213> ORGANISM: Artificial Sequence
<220> FEATURE:
<223> OTHER INFORMATION: Humanised

<400> SEQUENCE: 70

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Ala Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285
```

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Ala Ser Thr Lys Gly Pro Ser Glu Val
450                 455                 460

Gln Leu Leu Glu Ser Gly Gly Leu Val Gln Pro Gly Gly Ser Leu
465                 470                 475                 480

Arg Leu Ser Cys Ala Ala Ser Gly Phe Thr Phe Arg Asn Phe Gly Met
                485                 490                 495

Gly Trp Val Arg Gln Ala Pro Gly Lys Gly Leu Glu Trp Val Ser Trp
            500                 505                 510

Ile Ile Ser Ser Gly Thr Glu Thr Tyr Tyr Ala Asp Ser Val Lys Gly
        515                 520                 525

Arg Phe Thr Ile Ser Arg Asp Asn Ser Lys Asn Thr Leu Tyr Leu Gln
530                 535                 540

Met Asn Ser Leu Arg Ala Glu Asp Thr Ala Val Tyr Tyr Cys Ala Lys
545                 550                 555                 560

Ser Leu Gly Arg Phe Asp Tyr Trp Gly Gln Gly Thr Leu Val Thr Val
                565                 570                 575

Ser Ser

<210> SEQ ID NO 71
<211> LENGTH: 1734
<212> TYPE: DNA
<213> ORGANISM: Artificial Sequence
<220> FEATURE:
<223> OTHER INFORMATION: Humanised

<400> SEQUENCE: 71
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagccacag caccgcctac     240
atggaactga gcagcctgag gtctgaggac accgccgtgt actattgcgc caggagcatc     300
tacgacgact accacgcgga cgactactac gccatggact actggggaca gggcacacta     360
gtgaccgtgt ccagcgccag caccaagggc cccagcgtgt tcccctggc ccccagcagc     420

```
aagagcacca gcggcggcac agccgccctg ggctgcctgg tgaaggacta cttccccgaa    480
ccggtgaccg tgtcctggaa cagcggagcc ctgaccagcg gcgtgcacac cttccccgcc    540
gtgctgcaga gcagcggcct gtacagcctg agcagcgtgg tgaccgtgcc agcagcagc    600 ctgggcaccc agacctacat ctgtaacgtg aaccacaagc ccagcaacac caaggtggac    660
aagaaggtgg agcccaagag ctgtgacaag acccacacct gcccccctg ccctgccccc    720 gagctgctgg gaggccccag cgtgttcctg ttccccccca gcctaagga cacctgatg    780 atcagcagaa ccccgaggt gacctgtgtg gtggtggatg tgagccacga ggaccctgag    840
gtgaagttca actggtacgt ggacggcgtg gaggtgcaca atgccaagac caagcccagg    900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc   1020
gagaaaacca tcagcaaggc caagggccag cccagagagc ccaggtgta caccctgccc   1080 cctagcagag atgagctgac caagaaccag gtgtccctga cctgcctggt gaagggcttc   1140
taccccagcg atatcgccgt ggagtgggag agcaacggcc agcccgagaa caactacaag   1200
accacccccc ctgtgctgga cagcgatggc agcttcttcc tgtacagcaa gctgaccgtg   1260
gacaagagca gatggcagca gggcaacgtg ttcagctgct ccgtgatgca cgaggccctg   1320
cacaatcact acacccagaa gagcctgagc ctgtcccctg caaggccag caccaagggc   1380 ccctcggaag tgcagctcct ggagagcggc ggcggcctgg tgcagccgg cggcagcctg   1440 aggctgagct cgccgctag cggcttcacc ttcaggaact tcggcatggg ctgggtcagg   1500
caggcccccg caagggcct ggagtgggtc agctggatca tcagctccgg caccgagacc   1560
tactacgccg acagcgtgaa gggcaggttc accatcagcc gcgacaacag caagaacacc   1620
ctgtacctgc agatgaacag cctgagggcc gaggacaccg ccgtctacta ctgcgccaag   1680
agcctgggca ggttcgacta ctggggacag gggaccctgg tgactgtgag cagc        1734
```

<210> SEQ ID NO 72
<211> LENGTH: 578
<212> TYPE: PRT
<213> ORGANISM: Artificial Sequence
<220> FEATURE:
<223> OTHER INFORMATION: Humanised

<400> SEQUENCE: 72

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Ile Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
```

-continued

```
            130                 135                 140
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                    245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys Ala Ser Thr Lys Gly Pro Ser Glu Val
450                 455                 460

Gln Leu Leu Glu Ser Gly Gly Gly Leu Val Gln Pro Gly Gly Ser Leu
465                 470                 475                 480

Arg Leu Ser Cys Ala Ala Ser Gly Phe Thr Phe Arg Asn Phe Gly Met
                485                 490                 495

Gly Trp Val Arg Gln Ala Pro Gly Lys Gly Leu Glu Trp Val Ser Trp
                500                 505                 510

Ile Ile Ser Ser Gly Thr Glu Thr Tyr Tyr Ala Asp Ser Val Lys Gly
                515                 520                 525

Arg Phe Thr Ile Ser Arg Asp Asn Ser Lys Asn Thr Leu Tyr Leu Gln
                530                 535                 540

Met Asn Ser Leu Arg Ala Glu Asp Thr Ala Val Tyr Tyr Cys Ala Lys
545                 550                 555                 560
```

Ser Leu Gly Arg Phe Asp Tyr Trp Gly Gln Gly Thr Leu Val Thr Val
           565                 570                 575

Ser Ser

<210> SEQ ID NO 73
<211> LENGTH: 1734
<212> TYPE: DNA
<213> ORGANISM: Artificial Sequence
<220> FEATURE:
<223> OTHER INFORMATION: Humanised

<400> SEQUENCE: 73

| | | | | | |
|---|---|---|---|---|---|
| caggtgcagc | tcgtgcagag | cggcgccgaa | gtgaaaaagc | ccggcagcag | cgtgaaggtg | 60 |
| agctgcaagg | cctccggctt | ctacatcaag | gacacctaca | tgcactgggt | caggcaggct | 120 |
| cctggccagg | gcctggagtg | gatgggcact | atcgaccccg | ccaacggcaa | caccaagtac | 180 |
| gtgcccaagt | tccagggcag | ggtgaccatc | accgccgatg | agagcaccag | caccgcctac | 240 |
| atggaactga | gcagcctgag | gtctgaggac | accgccgtgt | actattgcgc | caggagcatc | 300 |
| tacgacgact | accacattga | cgactactac | gccatggact | actggggaca | gggcacacta | 360 |
| gtgaccgtgt | ccagcgccag | caccaagggc | ccagcgtgt | tccccctggc | cccagcagc | 420 |
| aagagcacca | gcggcggcac | agccgccctg | ggctgcctgg | tgaaggacta | cttccccgaa | 480 |
| ccggtgaccg | tgtcctggaa | cagcggagcc | ctgaccagcg | gcgtgcacac | cttcccgcc | 540 |
| gtgctgcaga | gcagcggcct | gtacagcctg | agcagcgtgg | tgaccgtgcc | cagcagcagc | 600 |
| ctgggcaccc | agacctacat | ctgtaacgtg | aaccacaagc | ccagcaacac | caaggtggac | 660 |
| aagaaggtgg | agcccaagag | ctgtgacaag | acccacacct | gcccccctg | ccctgccccc | 720 |
| gagctgctgg | gaggccccag | cgtgttcctg | ttcccccca | agcctaagga | cacctgatg | 780 |
| atcagcagaa | ccccgaggt | gacctgtgtg | gtggtggatg | tgagccacga | ggaccctgag | 840 |
| gtgaagttca | actggtacgt | ggacggcgtg | gaggtgcaca | atgccaagac | caagcccagg | 900 |
| gaggagcagt | acaacagcac | ctaccgggtg | gtgtccgtgc | tgaccgtgct | gcaccaggat | 960 |
| tggctgaacg | gcaaggagta | caagtgtaag | gtgtccaaca | aggccctgcc | tgcccctatc | 1020 |
| gagaaaacca | tcagcaaggc | caagggccag | cccagagagc | cccaggtgta | caccctgccc | 1080 |
| cctagcagag | atgagctgac | caagaaccag | gtgtccctga | cctgcctggt | gaagggcttc | 1140 |
| taccccagcg | atatcgccgt | ggagtgggag | agcaacggcc | agcccgagaa | caactacaag | 1200 |
| accacccccc | ctgtgctgga | cagcgatggc | agcttcttcc | tgtacagcaa | gctgaccgtg | 1260 |
| gacaagagca | gatggcagca | gggcaacgtg | ttcagctgct | ccgtgatgca | cgaggccctg | 1320 |
| cacaatcact | acacccagaa | gagcctgagc | ctgtcccctg | gcaaggccag | caccaagggc | 1380 |
| ccctcggaag | tgcagctcct | ggagagcggc | ggcggcctgg | tgcagcccgg | cggcagcctg | 1440 |
| aggctgagct | gcgccgctag | cggcttcacc | ttcaggaact | cggcatggg | ctgggtcagg | 1500 |
| caggccccg | gcaagggcct | ggagtgggtc | agctggatca | tcagctccgg | caccgagacc | 1560 |
| tactacgccg | acagcgtgaa | gggcaggttc | accatcagcc | gcgacaacag | caagaacacc | 1620 |
| ctgtacctgc | agatgaacag | cctgagggcc | gaggacaccg | ccgtctacta | ctgcgccaag | 1680 |
| agcctgggca | ggttcgacta | ctggggacag | gggaccctgg | tgactgtgag | cagc | 1734 |

<210> SEQ ID NO 74
<211> LENGTH: 578
<212> TYPE: PRT
<213> ORGANISM: Artificial Sequence
<220> FEATURE:
<223> OTHER INFORMATION: Humanised

<400> SEQUENCE: 74

```
Gln Val Gln Leu Val Gln Ser Gly Ala Glu Val Lys Lys Pro Gly Ser
  1               5                  10                  15
Ser Val Lys Val Ser Cys Lys Ala Ser Gly Phe Tyr Ile Lys Asp Thr
             20                  25                  30
Tyr Met His Trp Val Arg Gln Ala Pro Gly Gln Gly Leu Glu Trp Met
         35                  40                  45
Gly Thr Ile Asp Pro Ala Asn Gly Asn Thr Lys Tyr Val Pro Lys Phe
     50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Ile Tyr Asp Asp Tyr His Trp Asp Asp Tyr Tyr Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
```

```
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
            435                 440                 445
Leu Ser Leu Ser Pro Gly Lys Ala Ser Thr Lys Gly Pro Ser Glu Val
450                 455                 460
Gln Leu Leu Glu Ser Gly Gly Gly Leu Val Gln Pro Gly Gly Ser Leu
465                 470                 475                 480
Arg Leu Ser Cys Ala Ala Ser Gly Phe Thr Phe Arg Asn Phe Gly Met
            485                 490                 495
Gly Trp Val Arg Gln Ala Pro Gly Lys Gly Leu Glu Trp Val Ser Trp
            500                 505                 510
Ile Ile Ser Ser Gly Thr Glu Thr Tyr Tyr Ala Asp Ser Val Lys Gly
            515                 520                 525
Arg Phe Thr Ile Ser Arg Asp Asn Ser Lys Asn Thr Leu Tyr Leu Gln
            530                 535                 540
Met Asn Ser Leu Arg Ala Glu Asp Thr Ala Val Tyr Tyr Cys Ala Lys
545                 550                 555                 560
Ser Leu Gly Arg Phe Asp Tyr Trp Gly Gln Gly Thr Leu Val Thr Val
            565                 570                 575
Ser Ser

<210> SEQ ID NO 75
<211> LENGTH: 1734
<212> TYPE: DNA
<213> ORGANISM: Artificial Sequence
<220> FEATURE:
<223> OTHER INFORMATION: Humanised

<400> SEQUENCE: 75
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accactggga cgactactac gccatggact actggggaca gggcacacta     360
gtgaccgtgt ccagcgccag caccaagggc ccagcgtgt tcccctggc cccagcagc        420
aagagcacca gcggcggcac agccgccctg ggctgcctgg tgaaggacta cttccccgaa     480
ccggtgaccg tgtcctggaa cagcggagcc ctgaccagcg gcgtgcacac cttcccgcc       540
gtgctgcaga gcagcggcct gtacagcctg agcagcgtgg tgaccgtgcc agcagcagc      600
ctgggcaccc agacctacat ctgtaacgtg aaccacaagc ccagcaacac caaggtggac     660
aagaaggtgg agcccaagag ctgtgacaag acccacacct gccccccctg ccctgccccc    720
gagctgctgg gaggcccag cgtgttcctg ttcccccca gcctaagga caccctgatg        780
atcagcagaa ccccgaggt gacctgtgtg gtggtggatg tgagccacga ggaccctgag     840
gtgaagttca actggtacgt ggacggcgtg gaggtgcaca atgccaagac caagcccagg     900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc   1020
gagaaaacca tcagcaaggc caagggccag cccagagagc ccagggtgta caccctgccc   1080
cctagcagag atgagctgac caagaaccag gtgtccctga cctgcctggt gaagggcttc   1140
```

```
taccccagcg atatcgccgt ggagtgggag agcaacggcc agcccgagaa caactacaag    1200
accacccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg gcaaggccag caccaagggc    1380
ccctcggaag tgcagctcct ggagagcggc ggcggcctgg tgcagcccgg cggcagcctg    1440
aggctgagct gcgccgctag cggcttcacc ttcaggaact tcggcatggg ctgggtcagg    1500
caggcccccg gcaagggcct ggagtgggtc agctggatca tcagctccgg caccgagacc    1560
tactacgccg acagcgtgaa gggcaggttc accatcagcc gcgacaacag caagaacacc    1620
ctgtacctgc agatgaacag cctgagggcc gaggacaccg ccgtctacta ctgcgccaag    1680
agcctgggca ggttcgacta ctggggacag gggaccctgg tgactgtgag cagc          1734
```

<210> SEQ ID NO 76
<211> LENGTH: 578
<212> TYPE: PRT
<213> ORGANISM: Artificial Sequence
<220> FEATURE:
<223> OTHER INFORMATION: Humanised

<400> SEQUENCE: 76

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
```

```
                    260              265              270
Asp Val Ser His Glu Asp Pro Glu Val Lys Phe Asn Trp Tyr Val Asp
        275              280              285
Gly Val Glu Val His Asn Ala Lys Thr Lys Pro Arg Glu Glu Gln Tyr
    290              295              300
Asn Ser Thr Tyr Arg Val Val Ser Val Leu Thr Val Leu His Gln Asp
305              310              315              320
Trp Leu Asn Gly Lys Glu Tyr Lys Cys Lys Val Ser Asn Lys Ala Leu
                325              330              335
Pro Ala Pro Ile Glu Lys Thr Ile Ser Lys Ala Lys Gly Gln Pro Arg
            340              345              350
Glu Pro Gln Val Tyr Thr Leu Pro Pro Ser Arg Asp Glu Leu Thr Lys
        355              360              365
Asn Gln Val Ser Leu Thr Cys Leu Val Lys Gly Phe Tyr Pro Ser Asp
    370              375              380
Ile Ala Val Glu Trp Glu Ser Asn Gly Gln Pro Glu Asn Asn Tyr Lys
385              390              395              400
Thr Thr Pro Pro Val Leu Asp Ser Asp Gly Ser Phe Phe Leu Tyr Ser
                405              410              415
Lys Leu Thr Val Asp Lys Ser Arg Trp Gln Gln Gly Asn Val Phe Ser
            420              425              430
Cys Ser Val Met His Glu Ala Leu His Asn His Tyr Thr Gln Lys Ser
        435              440              445
Leu Ser Leu Ser Pro Gly Lys Ala Ser Thr Lys Gly Pro Ser Glu Val
    450              455              460
Gln Leu Leu Glu Ser Gly Gly Gly Leu Val Gln Pro Gly Gly Ser Leu
465              470              475              480
Arg Leu Ser Cys Ala Ala Ser Gly Phe Thr Phe Arg Asn Phe Gly Met
                485              490              495
Gly Trp Val Arg Gln Ala Pro Gly Lys Gly Leu Glu Trp Val Ser Trp
            500              505              510
Ile Ile Ser Ser Gly Thr Glu Thr Tyr Tyr Ala Asp Ser Val Lys Gly
        515              520              525
Arg Phe Thr Ile Ser Arg Asp Asn Ser Lys Asn Thr Leu Tyr Leu Gln
    530              535              540
Met Asn Ser Leu Arg Ala Glu Asp Thr Ala Val Tyr Tyr Cys Ala Lys
545              550              555              560
Ser Leu Gly Arg Phe Asp Tyr Trp Gly Gln Gly Thr Leu Val Thr Val
                565              570              575
Ser Ser

<210> SEQ ID NO 77
<211> LENGTH: 1734
<212> TYPE: DNA
<213> ORGANISM: Artificial Sequence
<220> FEATURE:
<223> OTHER INFORMATION: Humanised

<400> SEQUENCE: 77
caggtgcagc tcgtgcagag cggcgccgaa gtgaaaaagc ccggcagcag cgtgaaggtg      60
agctgcaagg cctccggctt ctacatcaag acacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagccacag caccgcctac     240
atggaactga gcagcctgag gtctgaggac accgccgtgt actattgcgc caggagcatc     300
```

```
tacgacgact accacgtcga cgactactac gccatggact actggggaca gggcacacta      360
gtgaccgtgt ccagcgccag caccaagggc cccagcgtgt tcccctggc  cccagcagc      420 aagagcacca gcggcggcac agccgccctg ggctgcctgg tgaaggacta cttccccgaa     480
ccggtgaccg tgtcctggaa cagcggagcc ctgaccagcg gcgtgcacac cttccccgcc    540
gtgctgcaga gcagcggcct gtacagcctg agcagcgtgg tgaccgtgcc agcagcagc     600 ctgggcaccc agacctacat ctgtaacgtg aaccacaagc ccagcaacac caaggtggac    660
aagaaggtgg agcccaagag ctgtgacaag acccacacct gccccccctg ccctgccccc    720
gagctgctgg gaggccccag cgtgttcctg ttcccccca  agcctaagga cccctgatg     780 atcagcagaa cccccgaggt gacctgtgtg gtggtggatg tgagccacga ggaccctgag    840
gtgaagttca actggtacgt ggacggcgtg gaggtgcaca atgccaagac caagcccagg    900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc    1020
gagaaaacca tcagcaaggc caagggccag cccagagagc ccaggtgta  caccctgccc    1080 cctagcagag atgagctgac caagaaccag gtgtccctga cctgcctggt gaagggcttc    1140
taccccagcg atatcgccgt ggagtgggag agcaacggcc agcccgagaa caactacaag    1200
accacccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg gcaaggccag caccaagggc    1380
ccctcggaag tgcagctcct ggagagcggc ggcggcctgg tgcagcccgg cggcagcctg    1440
aggctgagct gcgccgctag cggcttcacc ttcaggaact tcggcatggg ctgggtcagg    1500
caggcccccg gcaagggcct ggagtgggtc agctggatca tcagctccgg caccgagacc    1560
tactacgccg acagcgtgaa gggcaggttc accatcagcc gcgacaacag caagaacacc    1620
ctgtacctgc agatgaacag cctgagggcc gaggacaccg ccgtctacta ctgcgccaag    1680
agcctgggca ggttcgacta ctggggacag gggaccctgg tgactgtgag cagc          1734
```

<210> SEQ ID NO 78
<211> LENGTH: 108
<212> TYPE: PRT
<213> ORGANISM: Homo Sapiens

<400> SEQUENCE: 78

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Pro Ile Ser Asp Trp
            20                  25                  30

Leu His Trp Tyr Gln Gln Lys Pro Gly Lys Ala Pro Lys Leu Leu Ile
        35                  40                  45

Ala Trp Ala Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Glu Gly Trp Gly Pro Pro
                85                  90                  95

Thr Phe Gly Gln Gly Thr Lys Val Glu Ile Lys Arg
            100                 105
```

<210> SEQ ID NO 79

```
<211> LENGTH: 108
<212> TYPE: PRT
<213> ORGANISM: Homo Sapiens

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Ser Asp Trp
            20                  25                  30

Leu His Trp Tyr Gln Gln Lys Pro Gly Lys Ala Pro Lys Leu Leu Ile
        35                  40                  45

Ala Trp Ala Ser Ser Leu Tyr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Glu Gly Trp Gly Pro Pro
                85                  90                  95

Thr Phe Gly Gln Gly Thr Lys Val Glu Ile Lys Arg
            100                 105

<210> SEQ ID NO 80
<211> LENGTH: 108
<212> TYPE: PRT
<213> ORGANISM: Homo Sapiens

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Ser Asp Trp
            20                  25                  30

Leu His Trp Tyr Gln Gln Lys Pro Gly Lys Ala Pro Lys Leu Leu Ile
        35                  40                  45

Ala Trp Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Glu Gly Trp Gly Pro Pro
                85                  90                  95

Thr Phe Gly Gln Gly Thr Lys Val Glu Ile Lys Arg
            100                 105

<210> SEQ ID NO 81
<211> LENGTH: 116
<212> TYPE: PRT
<213> ORGANISM: Homo Sapiens

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Phe
            20                  25                  30

Gly Met Gly Trp Val Arg Gln Ala Pro Gly Lys Gly Leu Glu Trp Val
        35                  40                  45

Ser Trp Ile Ile Ser Ser Gly Thr Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Lys Ser Leu Gly Arg Phe Asp Tyr Trp Gly Gln Gly Thr Leu Val
                100                 105                 110

Thr Val Ser Ser
        115

<210> SEQ ID NO 82
<211> LENGTH: 5
<212> TYPE: PRT
<213> ORGANISM: Artificial Sequence
<220> FEATURE:
<223> OTHER INFORMATION: Linker

<400> SEQUENCE: 82

Gly Gly Gly Gly Ser
1               5

<210> SEQ ID NO 83
<211> LENGTH: 6
<212> TYPE: PRT
<213> ORGANISM: Artificial Sequence
<220> FEATURE:
<223> OTHER INFORMATION: Linker

<400> SEQUENCE: 83

Thr Val Ala Ala Pro Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Linker

<400> SEQUENCE: 84

Ala Ser Thr Lys Gly Pro Thr
1               5

<210> SEQ ID NO 85
<211> LENGTH: 7
<212> TYPE: PRT
<213> ORGANISM: Artificial Sequence
<220> FEATURE:
<223> OTHER INFORMATION: Linker

<400> SEQUENCE: 85

Ala Ser Thr Lys Gly Pro Ser
1               5

<210> SEQ ID NO 86
<211> LENGTH: 2
<212> TYPE: PRT
<213> ORGANISM: Artificial Sequence
<220> FEATURE:
<223> OTHER INFORMATION: Linker

<400> SEQUENCE: 86

Gly Ser
1

<210> SEQ ID NO 87
<211> LENGTH: 8
<212> TYPE: PRT
<213> ORGANISM: Artificial Sequence
<220> FEATURE:
<223> OTHER INFORMATION: Linker
```

-continued

<400> SEQUENCE: 87

Thr Val Ala Ala Pro Ser Gly Ser
1               5

<210> SEQ ID NO 88
<211> LENGTH: 571
<212> TYPE: PRT
<213> ORGANISM: Artificial Sequence
<220> FEATURE:
<223> OTHER INFORMATION: Humanised

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Ser Asp Trp
            20                  25                  30

Leu His Trp Tyr Gln Gln Lys Pro Gly Lys Ala Pro Lys Leu Leu Ile
        35                  40                  45

Ala Trp Ala Ser Ser Leu Tyr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Glu Gly Trp Gly Pro Pro
                85                  90                  95

Thr Phe Gly Gln Gly Thr Lys Val Glu Ile Lys Arg Gly Ser Thr Val
            100                 105                 110

Ala Ala Pro Ser Gln Val Gln Leu Val Gln Ser Gly Ala Glu Val Lys
        115                 120                 125

Lys Pro Gly Ser Ser Val Lys Val Ser Cys Lys Ala Ser Gly Phe Tyr
    130                 135                 140

Ile Lys Asp Thr Tyr Met His Trp Val Arg Gln Ala Pro Gly Gln Gly
145                 150                 155                 160

Leu Glu Trp Met Gly Thr Ile Asp Pro Ala Asn Gly Asn Thr Lys Tyr
                165                 170                 175

Val Pro Lys Phe Gln Gly Arg Val Thr Ile Thr Ala Asp Glu Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Arg Ser Ile Tyr Asp Asp Tyr His Val Asp Asp
    210                 215                 220

Tyr Tyr Ala Met Asp Tyr Trp Gly Gln Gly Thr Leu Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro

```
                    340                 345                 350
Cys Pro Ala Pro Glu Leu Leu Gly Gly Pro Ser Val Phe Leu Phe Pro
            355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 89
<211> LENGTH: 572
<212> TYPE: PRT
<213> ORGANISM: Artificial Sequence
<220> FEATURE:
<223> OTHER INFORMATION: Humanised

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Ser Asp Trp
            20                  25                  30

Leu His Trp Tyr Gln Gln Lys Pro Gly Lys Ala Pro Lys Leu Leu Ile
        35                  40                  45

Ala Trp Ala Ser Ser Leu Tyr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Glu Gly Trp Gly Pro Pro
                85                  90                  95

Thr Phe Gly Gln Gly Thr Lys Val Glu Ile Lys Arg Gly Ser Ala Ser
            100                 105                 110

Thr Lys Gly Pro Ser Gln Val Gln Leu Val Gln Ser Gly Ala Glu Val
        115                 120                 125

Lys Lys Pro Gly Ser Ser Val Lys Val Ser Cys Lys Ala Ser Gly Phe
    130                 135                 140
```

```
Tyr Ile Lys Asp Thr Tyr Met His Trp Val Arg Gln Ala Pro Gly Gln
145                 150                 155                 160

Gly Leu Glu Trp Met Gly Thr Ile Asp Pro Ala Asn Gly Asn Thr Lys
            165                 170                 175

Tyr Val Pro Lys Phe Gln Gly Arg Val Thr Ile Thr Ala Asp Glu Ser
            180                 185                 190

Thr Ser Thr Ala Tyr Met Glu Leu Ser Ser Leu Arg Ser Glu Asp Thr
            195                 200                 205

Ala Val Tyr Tyr Cys Ala Arg Ser Ile Tyr Asp Asp Tyr His Val Asp
    210                 215                 220

Asp Tyr Tyr Ala Met Asp Tyr Trp Gly Gln Gly Thr Leu Val Thr Val
225                 230                 235                 240

Ser Ser Ala Ser Thr Lys Gly Pro Ser Val Phe Pro Leu Ala Pro Ser
            245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
    275                 280                 285

Thr Ser Gly Val His Thr Phe Pro Ala Val Leu Gln Ser Ser Gly Leu
290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
            325                 330                 335

Asp Lys Lys Val Glu Pro Lys Ser Cys Asp Lys Thr His Thr Cys Pro
            340                 345                 350

Pro Cys Pro Ala Pro Glu Leu Leu Gly Gly Pro Ser Val Phe Leu Phe
    355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
            405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
    435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Asp Glu Leu Thr Lys Asn Gln Val Ser Leu Thr Cys Leu Val Lys Gly
            485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
            515                 520                 525

Phe Phe Leu Tyr Ser Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
```

<210> SEQ ID NO 90
<211> LENGTH: 571
<212> TYPE: PRT
<213> ORGANISM: Artificial Sequence
<220> FEATURE:
<223> OTHER INFORMATION: Humanised

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Ser Asp Trp
            20                  25                  30

Leu His Trp Tyr Gln Gln Lys Pro Gly Lys Ala Pro Lys Leu Leu Ile
        35                  40                  45

Ala Trp Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Glu Gly Trp Gly Pro Pro
                85                  90                  95

Thr Phe Gly Gln Gly Thr Lys Val Glu Ile Lys Arg Gly Ser Thr Val
            100                 105                 110

Ala Ala Pro Ser Gln Val Gln Leu Val Gln Ser Gly Ala Glu Val Lys
        115                 120                 125

Lys Pro Gly Ser Ser Val Lys Val Ser Cys Lys Ala Ser Gly Phe Tyr
    130                 135                 140

Ile Lys Asp Thr Tyr Met His Trp Val Arg Gln Ala Pro Gly Gln Gly
145                 150                 155                 160

Leu Glu Trp Met Gly Thr Ile Asp Pro Ala Asn Gly Asn Thr Lys Tyr
                165                 170                 175

Val Pro Lys Phe Gln Gly Arg Val Thr Ile Thr Ala Asp Glu Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Arg Ser Ile Tyr Asp Asp Tyr His Val Asp Asp
    210                 215                 220

Tyr Tyr Ala Met Asp Tyr Trp Gly Gln Gly Thr Leu Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
        355                 360                 365
```

```
Pro Lys Pro Lys Asp Thr Leu Met Ile Ser Arg Thr Pro Glu Val Thr
            370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
                435                 440                 445

Asn Lys Ala Leu Pro Ala Pro Ile Glu Lys Thr Ile Ser Lys Ala Lys
            450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
                500                 505                 510

Asn Asn Tyr Lys Thr Thr Pro Pro Val Leu Asp Ser Asp Gly Ser Phe
                515                 520                 525

Phe Leu Tyr Ser Lys Leu Thr Val Asp Lys Ser Arg Trp Gln Gln Gly
            530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 91
<211> LENGTH: 572
<212> TYPE: PRT
<213> ORGANISM: Artificial Sequence
<220> FEATURE:
<223> OTHER INFORMATION: Humanised

<400> SEQUENCE: 91

Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Pro Ile Ser Asp Trp
                20                  25                  30

Leu His Trp Tyr Gln Gln Lys Pro Gly Lys Ala Pro Lys Leu Leu Ile
             35                  40                  45

Ala Trp Ala Ser Ser Leu Gln Gly Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Gly Trp Gly Pro Pro
                 85                  90                  95

Thr Phe Gly Gln Gly Thr Lys Val Glu Ile Lys Arg Gly Ser Ala Ser
                100                 105                 110

Thr Lys Gly Pro Ser Gln Val Gln Leu Val Gln Ser Gly Ala Glu Val
            115                 120                 125

Lys Lys Pro Gly Ser Ser Val Lys Val Ser Cys Lys Ala Ser Gly Phe
130                 135                 140

Tyr Ile Lys Asp Thr Tyr Met His Trp Val Arg Gln Ala Pro Gly Gln
145                 150                 155                 160
```

```
Gly Leu Glu Trp Met Gly Thr Ile Asp Pro Ala Asn Gly Asn Thr Lys
                165                 170                 175

Tyr Val Pro Lys Phe Gln Gly Arg Val Thr Ile Thr Ala Asp Glu Ser
            180                 185                 190

Thr Ser Thr Ala Tyr Met Glu Leu Ser Ser Leu Arg Ser Glu Asp Thr
        195                 200                 205

Ala Val Tyr Tyr Cys Ala Arg Ser Ile Tyr Asp Asp Tyr His Val Asp
    210                 215                 220

Asp Tyr Tyr Ala Met Asp Tyr Trp Gly Gln Gly Thr Leu Val Thr Val
225                 230                 235                 240

Ser Ser Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Lys Val Glu Pro Lys Ser Cys Asp Lys Thr His Thr Cys Pro
            340                 345                 350

Pro Cys Pro Ala Pro Glu Leu Leu Gly Gly Pro Ser Val Phe Leu Phe
        355                 360                 365

Pro Pro Lys Pro Lys Asp Thr Leu Met Ile Ser Arg Thr Pro Glu Val
    370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Asp Glu Leu Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 92
```

```
<211> LENGTH: 8
<212> TYPE: PRT
<213> ORGANISM: Artificial Sequence
<220> FEATURE:
<223> OTHER INFORMATION: Linker

<400> SEQUENCE: 92

Gly Ser Thr Val Ala Ala Pro Ser
 1               5

<210> SEQ ID NO 93
<211> LENGTH: 10
<212> TYPE: PRT
<213> ORGANISM: Artificial Sequence
<220> FEATURE:
<223> OTHER INFORMATION: Linker

<400> SEQUENCE: 93

Gly Ser Thr Val Ala Ala Pro Ser Gly Ser
 1               5                  10

<210> SEQ ID NO 94
<211> LENGTH: 108
<212> TYPE: PRT
<213> ORGANISM: Homo Sapiens
<220> FEATURE:
<223> OTHER INFORMATION: Mutated dAb

<400> SEQUENCE: 94

Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Pro Ile Ser Asp Trp
                20                  25                  30

Leu His Trp Tyr Gln Gln Lys Pro Gly Lys Ala Pro Lys Leu Leu Ile
            35                  40                  45

Ala Trp Ala Ser Ser Leu Gln Gly Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Gly Trp Gly Pro Pro
                85                  90                  95

Thr Phe Gly Gln Gly Thr Lys Val Glu Ile Lys Arg
            100                 105

<210> SEQ ID NO 95
<211> LENGTH: 324
<212> TYPE: DNA
<213> ORGANISM: Homo Sapiens

<400> SEQUENCE: 95
gacatccaga tgacccagag ccccagcagc ctgagcgcca gcgtgggcga cagggtgacc        60
attacctgca gggccagcag gcccatcagc gactggctgc actggtacca acagaagccc       120
ggcaaggctc ccaagctgct gatcgcctgg gccagcagcc tgcagggagg cgtgcccagc       180
aggtttagcg gcagcggcag cggcaccgac ttcaccctca ccatctcttc cctgcagccc       240
gaggacttcg ccacctacta ctgccagcag gagggctggg ggcccctac tttcggccag       300 ggcaccaagg tggagatcaa gagg                                              324

<210> SEQ ID NO 96
<211> LENGTH: 581
<212> TYPE: PRT
<213> ORGANISM: Artificial Sequence
```

```
<220> FEATURE:
<223> OTHER INFORMATION: Humanised

<400> SEQUENCE: 96

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Tyr Tyr Ala Met
             100                 105                 110

Asp Tyr Trp Gly Gln Gly Thr Leu Val Thr Val Ser Ser Ala Ser Thr
         115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400
```

```
Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
            435                 440                 445

Leu Ser Leu Ser Pro Gly Lys Gly Ser Thr Val Ala Ala Pro Ser Gly
    450                 455                 460

Ser Thr Val Ala Ala Pro Ser Gly Ser Asp Ile Gln Met Thr Gln Ser
465                 470                 475                 480

Pro Ser Ser Leu Ser Ala Ser Val Gly Asp Arg Val Thr Ile Thr Cys
            485                 490                 495

Arg Ala Ser Arg Pro Ile Ser Asp Trp Leu His Trp Tyr Gln Gln Lys
            500                 505                 510

Pro Gly Lys Ala Pro Lys Leu Leu Ile Ala Trp Ala Ser Ser Leu Gln
        515                 520                 525

Gly Gly Val Pro Ser Arg Phe Ser Gly Ser Gly Ser Gly Thr Asp Phe
    530                 535                 540

Thr Leu Thr Ile Ser Ser Leu Gln Pro Glu Asp Phe Ala Thr Tyr Tyr
545                 550                 555                 560

Cys Gln Gln Glu Gly Trp Gly Pro Pro Thr Phe Gly Gln Gly Thr Lys
            565                 570                 575

Val Glu Ile Lys Arg
            580

<210> SEQ ID NO 97
<211> LENGTH: 1743
<212> TYPE: DNA
<213> ORGANISM: Artificial Sequence
<220> FEATURE:
<223> OTHER INFORMATION: Humanised

<400> SEQUENCE: 97
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagccacag caccgcctac     240
atggaactga gcagcctgag gtctgaggac accgccgtgt actattgcgc caggagcatc     300
tacgacgact accacgtcga cgactactac gccatggact actggggaca gggcacacta     360
gtgaccgtgt ccagcgccag caccaagggc ccagcgtgt tcccctggc ccccagcagc      420
aagagcacca gcggcggcac agccgccctg ggctgcctgg tgaaggacta cttccccgaa     480
ccggtgaccg tgtcctggaa cagcggagcc ctgaccagcg gcgtgcacac cttccccgcc     540
gtgctgcaga gcagcggcct gtacagcctg agcagcgtgg tgaccgtgcc agcagcagc      600
ctgggcaccc agacctacat ctgtaacgtg aaccacaagc ccagcaacac caaggtggac     660
aagaaggtgg agcccaagag ctgtgacaag acccacacct gccccccctg ccctgccccc     720
gagctgctgg gaggccccag cgtgttcctg ttccccccca gcctaagga cacctgatg      780
atcagcagaa cccccgaggt gacctgtgtg tggtggatg tgagccacga ggaccctgag     840
gtgaagttca actggtacgt ggacggcgtg gaggtgcaca tgccaagac caagcccagg     900
gaggagcagt acaacagcac ctaccgggtg gtgtccgtgc tgaccgtgct gcaccaggat     960
tggctgaacg gcaaggagta caagtgtaag gtgtccaaca aggcctgcc tgcccctatc    1020
```

-continued

```
gagaaaacca tcagcaaggc caagggccag cccagagagc cccaggtgta caccctgccc    1080
cctagcagag atgagctgac caagaaccag gtgtccctga cctgcctggt gaagggcttc    1140
taccccagcg acatcgccgt ggagtgggag agcaacggcc agcccgagaa caactacaag    1200 accaccccc ctgtgctgga cagcgatggc agcttcttcc tgtacagcaa gctgaccgtg     1260
gacaagagca gatggcagca gggcaacgtg ttcagctgct ccgtgatgca cgaggccctg    1320
cacaatcact acacccagaa gagcctgagc ctgtccctg gcaagggatc taccgtggca     1380
gcaccatccg gatctaccgt agcagcacca tccggatccg acatccagat gacccagagc    1440
cccagcagcc tgagcgccag cgtgggcgac agggtgacca ttacctgcag ggccagcagg    1500
cccatcagcg actggctgca ctggtaccaa cagaagcccg gcaaggctcc caagctgctg    1560
atcgcctggg ccagcagcct gcagggaggc gtgcccagca ggtttagcgg cagcggcagc    1620
ggcaccgact tcaccctcac catctcttcc ctgcagcccg aggacttcgc cacctactac    1680
tgccagcagg agggctgggg gccccctact ttcggccagg gcaccaaggt ggagatcaag    1740
agg                                                                 1743
```

<210> SEQ ID NO 98
<211> LENGTH: 589
<212> TYPE: PRT
<213> ORGANISM: Artificial Sequence
<220> FEATURE:
<223> OTHER INFORMATION: Humanised

<400> SEQUENCE: 98

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240
```

```
Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly Ser Thr Val Ala Ala Pro Ser Gly
450                 455                 460

Ser Thr Val Ala Ala Pro Ser Gly Ser Thr Val Ala Ala Pro Ser Gly
465                 470                 475                 480

Ser Asp Ile Gln Met Thr Gln Ser Pro Ser Ser Leu Ser Ala Ser Val
                485                 490                 495

Gly Asp Arg Val Thr Ile Thr Cys Arg Ala Ser Arg Pro Ile Ser Asp
            500                 505                 510

Trp Leu His Trp Tyr Gln Gln Lys Pro Gly Lys Ala Pro Lys Leu Leu
        515                 520                 525

Ile Ala Trp Ala Ser Ser Leu Gln Gly Gly Val Pro Ser Arg Phe Ser
530                 535                 540

Gly Ser Gly Ser Gly Thr Asp Phe Thr Leu Thr Ile Ser Ser Leu Gln
545                 550                 555                 560

Pro Glu Asp Phe Ala Thr Tyr Tyr Cys Gln Gln Glu Gly Trp Gly Pro
                565                 570                 575

Pro Thr Phe Gly Gln Gly Thr Lys Val Glu Ile Lys Arg
            580                 585
```

<210> SEQ ID NO 99
<211> LENGTH: 1767
<212> TYPE: DNA
<213> ORGANISM: Artificial Sequence
<220> FEATURE:
<223> OTHER INFORMATION: Humanised

<400> SEQUENCE: 99

```
caggtgcagc tcgtgcagag cggcgccgaa gtgaaaaagc ccggcagcag cgtgaaggtg      60
agctgcaagg cctccggctt ctacatcaag gacaccctac tgcactgggt caggcaggct     120
```

```
cctggccagg gcctggagtg gatgggcact atcgacccg ccaacggcaa caccaagtac    180
gtgcccaagt tccagggcag ggtgaccatc accgccgatg agagcaccag caccgcctac    240
atggaactga gcagcctgag gtctgaggac accgccgtgt actattgcgc caggagcatc    300
tacgacgact accacgtcga cgactactac gccatggact actggggaca gggcacacta    360
gtgaccgtgt ccagcgccag caccaagggc ccagcgtgt tccccctggc cccagcagc    420
aagagcacca gcggcggcac agccgccctg ggctgcctgg tgaaggacta cttccccgaa    480
ccggtgaccg tgtcctggaa cagcggagcc ctgaccagcg gcgtgcacac cttccccgcc    540
gtgctgcaga gcagcggcct gtacagcctg agcagcgtgt gaccgtgcc cagcagcagc    600
ctgggcaccc agacctacat ctgtaacgtg aaccacaagc ccagcaacac caaggtggac    660
aagaaggtgg agcccaagag ctgtgacaag acccacacct gccccccctg ccctgccccc    720
gagctgctgg gaggcccag cgtgttcctg ttccccccca gcctaagga cccctgatg    780
atcagcagaa cccccgaggt gacctgtgtg gtggtggatg tgagccacga ggaccctgag    840
gtgaagttca actggtacgt ggacggcgtg gaggtgcaca atgccaagac caagcccagg    900
gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc    1020
gagaaaacca tcagcaaggc caaggccag cccagagagc ccaggtgta caccctgccc    1080
cctagcagag atgagctgac caagaaccag gtgtccctga cctgctggt gaagggcttc    1140
taccccagcg acatcgccgt ggagtgggag agcaacggcc agcccgagaa caactacaag    1200
accaccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg gcaagggatc taccgtggca    1380
gcaccatcag gatctaccgt ggcagcacca tcaggttcaa cagtagctgc tccttctgga    1440
tccgacatcc agatgaccca gagccccagc agcctgagcg ccagcgtggg cgacagggtg    1500
accattacct gcagggccag caggcccatc agcgactggc tgcactgta ccaacagaag    1560
cccggcaagg ctcccaagct gctgatcgcc tgggccagca gcctgcaggg aggcgtgccc    1620
agcaggttta gcggcagcgg cagcggcacc gacttcaccc tcaccatctc ttccctgcag    1680
cccgaggact cgccaccta ctactgccag caggagggct ggggggccccc tactttcggc    1740
cagggcacca aggtggagat caagagg                                        1767
```

<210> SEQ ID NO 100
<211> LENGTH: 597
<212> TYPE: PRT
<213> ORGANISM: Artificial Sequence
<220> FEATURE:
<223> OTHER INFORMATION: Humanised

<400> SEQUENCE: 100

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
```

```
                65                  70                  75                  80
Met Glu Leu Ser Ser Leu Arg Ser Glu Asp Thr Ala Val Tyr Tyr Cys
                        85                  90                  95

Ala Arg Ser Ile Tyr Asp Asp Tyr His Val Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly Ser Thr Val Ala Ala Pro Ser Gly
    450                 455                 460

Ser Thr Val Ala Ala Pro Ser Gly Ser Thr Val Ala Ala Pro Ser Gly
465                 470                 475                 480

Ser Thr Val Ala Ala Pro Ser Gly Ser Asp Ile Gln Met Thr Gln Ser
                485                 490                 495
```

|     |     |     |     |     |     |     |     |     |     |     |     |
| --- | --- | --- | --- | --- | --- | --- | --- | --- | --- | --- | --- |
| Pro | Ser | Ser | Leu | Ser | Ala | Ser | Val | Gly | Asp | Arg | Val | Thr | Ile | Thr | Cys |
|     |     |     | 500 |     |     |     | 505 |     |     |     | 510 |

| Arg | Ala | Ser | Arg | Pro | Ile | Ser | Asp | Trp | Leu | His | Trp | Tyr | Gln | Gln | Lys |
|     | 515 |     |     |     | 520 |     |     |     | 525 |

| Pro | Gly | Lys | Ala | Pro | Lys | Leu | Leu | Ile | Ala | Trp | Ala | Ser | Ser | Leu | Gln |
| 530 |     |     |     |     | 535 |     |     |     | 540 |

| Gly | Val | Pro | Ser | Arg | Phe | Ser | Gly | Ser | Gly | Ser | Gly | Thr | Asp | Phe |
| 545 |     |     |     | 550 |     |     |     | 555 |     |     |     |     | 560 |

| Thr | Leu | Thr | Ile | Ser | Ser | Leu | Gln | Pro | Glu | Asp | Phe | Ala | Thr | Tyr | Tyr |
|     |     |     |     | 565 |     |     |     | 570 |     |     |     |     | 575 |

| Cys | Gln | Gln | Glu | Gly | Trp | Gly | Pro | Pro | Thr | Phe | Gly | Gln | Gly | Thr | Lys |
|     |     |     | 580 |     |     |     | 585 |     |     |     |     | 590 |

Val Glu Ile Lys Arg
     595

<210> SEQ ID NO 101
<211> LENGTH: 1791
<212> TYPE: DNA
<213> ORGANISM: Artificial Sequence
<220> FEATURE:
<223> OTHER INFORMATION: Humanised

<400> SEQUENCE: 101

```
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accacgtcga cgactactac gccatggact actggggaca gggcacacta     360
gtgaccgtgt ccagcgccag caccaagggc ccagcgtgt tccccctggc cccagcagc       420
aagagcacca gcggcggcac agccgccctg ggctgcctgg tgaaggacta cttccccgaa     480
ccggtgaccg tgtcctggaa cagcggagcc ctgaccagcg gcgtgcacac cttcccgcc      540
gtgctgcaga gcagcggcct gtacagcctg agcagcgtgg tgaccgtgcc cagcagcagc     600
ctgggcaccc agacctacat ctgtaacgtg aaccacaagc ccagcaacac caaggtggac     660
aagaaggtgg agcccaagag ctgtgacaag acccacacct gcccccctg ccctgccccc      720
gagctgctgg gaggcccag cgtgttcctg ttcccccca gcctaagga caccctgatg       780
atcagcagaa ccccgaggt gacctgtgtg gtggtggatg tgagccacga ggaccctgag     840
gtgaagttca actggtacgt ggacggcgtg gaggtgcaca tgccaagac caagcccagg     900
gaggagcagt acaacagcac ctaccgggtg gtgtccgtgc tgaccgtgct gcaccaggat    960
tggctgaacg gcaaggagta caagtgtaag gtgtccaaca aggccctgcc tgccccatc    1020
gagaaaacca tcagcaaggc caagggccag ccagagagc ccaggtgta cccctgccc      1080
cctagcagag atgagctgac caagaaccag gtgtccctga cctgcctggt gaagggcttc   1140
taccccagcg acatcgccgt ggagtgggag agcaacggcc agcccgagaa caactacaag   1200
accaccccc ctgtgctgga cagcgatggc agcttcttcc tgtacagcaa gctgaccgtg    1260
gacaagagca gatggcagca gggcaacgtg ttcagctgct ccgtgatgca cgaggccctg   1320
cacaatcact acacccagaa gagcctgagc ctgtcccctg gcaagggatc taccgtggca   1380
gcaccatcag gatctaccgt ggcagcacca tcaggttcaa cagtagctgc ccttctggt    1440
tcaacagtag ctgctccttc tggatccgac atccagatga cccagagccc cagcagcctg   1500
```

```
agcgccagcg tgggcgacag ggtgaccatt acctgcaggg ccagcaggcc catcagcgac      1560
tggctgcact ggtaccaaca gaagcccggc aaggctccca agctgctgat cgcctgggcc      1620
agcagcctgc agggaggcgt gcccagcagg tttagcggca gcggcagcgg caccgacttc      1680
accctcacca tctcttccct gcagcccgag gacttcgcca cctactactg ccagcaggag      1740 ggctggggc cccctacttt cggccagggc accaaggtgg agatcaagag g                1791
```

<210> SEQ ID NO 102
<211> LENGTH: 577
<212> TYPE: PRT
<213> ORGANISM: Artificial Sequence
<220> FEATURE:
<223> OTHER INFORMATION: Humanised

<400> SEQUENCE: 102

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320
```

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys Thr Val Ala Ala Pro Ser Thr Val Ala
450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
            485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
            515                 520                 525

Ser Arg Phe Ser Gly Ser Gly Ser Gly Thr Asp Phe Thr Leu Thr Ile
            530                 535                 540

Ser Ser Leu Gln Pro Glu Asp Phe Ala Thr Tyr Tyr Cys Gln Gln Glu
545                 550                 555                 560

Gly Trp Gly Pro Pro Thr Phe Gly Gln Gly Thr Lys Val Glu Ile Lys
            565                 570                 575

Arg

<210> SEQ ID NO 103
<211> LENGTH: 1731
<212> TYPE: DNA
<213> ORGANISM: Artificial Sequence
<220> FEATURE:
<223> OTHER INFORMATION: Humanised

<400> SEQUENCE: 103
caggtgcagc tcgtgcagag cggcgccgaa gtgaaaaagc ccggcagcag cgtgaaggtg     60
agctgcaagg cctccggctt ctacatcaag gacacctaca tgcactgggt caggcaggct    120
cctggccagg gcctggagtg gatgggcact atcgaccccg ccaacggcaa caccaagtac    180
gtgcccaagt tccagggcag ggtgaccatc accgccgatg agagcaccag caccgcctac    240
atggaactga gcagcctgag gtctgaggac accgccgtgt actattgcgc caggagcatc    300
tacgacgact accacgtcga cgactactac gccatggact actggggaca gggcacacta    360
gtgaccgtgt ccagcgccag caccaagggc ccagcgtgt tccccctggc ccccagcagc    420
aagagcacca gcggcggcac agccgccctg ggctgcctgg tgaaggacta cttccccgaa    480
ccggtgaccg tgtcctggaa cagcggagcc ctgaccagcg gcgtgcacac cttccccgcc    540
gtgctgcaga gcagcggcct gtacagcctg agcagcgtgg tgaccgtgcc cagcagcagc    600

```
ctgggcaccc agacctacat ctgtaacgtg aaccacaagc ccagcaacac caaggtggac      660
aagaaggtgg agcccaagag ctgtgacaag acccacacct gcccccctg ccctgccccc       720 gagctgctgg gaggcccag cgtgttcctg ttccccccca gcctaagga caccctgatg        780 atcagcagaa ccccgaggt gacctgtgtg gtggtggatg tgagccacga ggaccctgag       840
gtgaagttca actggtacgt ggacggcgtg gaggtgcaca tgccaagac caagcccagg       900 gaggagcagt acaacagcac ctaccgggtg gtgtccgtgc tgaccgtgct gcaccaggat     960
tggctgaacg gcaaggagta caagtgtaag gtgtccaaca aggccctgcc tgcccctatc     1020
gagaaaacca tcagcaaggc caagggccag cccagagagc ccaggtgta caccctgccc    1080 cctagcagag atgagctgac caagaaccag gtgtccctga cctgcctggt gaagggcttc    1140
taccccagcg acatcgccgt ggagtgggag agcaacggcc agcccgagaa caactacaag    1200 accaccccc ctgtgctgga cagcgatggc agcttcttcc tgtacagcaa gctgaccgtg     1260
gacaagagca gatggcagca gggcaacgtg ttcagctgct ccgtgatgca cgaggccctg   1320
cacaatcact acacccagaa gagcctgagc ctgtccctg gcaagaccgt ggcagcacca    1380
tccaccgtag cagcaccatc cggatccgac atccagatga cccagagccc cagcagcctg  1440
agcgccagcg tgggcgacag ggtgaccatt acctgcaggg ccagcaggcc catcagcgac   1500
tggctgcact ggtaccaaca gaagcccggc aaggctccca gctgctgat cgcctgggcc    1560 agcagcctgc agggaggcgt gcccagcagg tttagcggca gcggcagcgg caccgacttc    1620
accctcacca tctcttccct gcagcccgag gacttcgcca cctactactg ccagcaggag   1680 ggctggggc cccctacttt cggccagggc accaaggtgg agatcaagag g              1731
```

<210> SEQ ID NO 104
<211> LENGTH: 583
<212> TYPE: PRT
<213> ORGANISM: Artificial Sequence
<220> FEATURE:
<223> OTHER INFORMATION: Humanised

<400> SEQUENCE: 104

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
```

-continued

```
                    165                 170                 175
Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Thr Val Ala
        450                 455                 460

Ala Pro Ser Thr Val Ala Ala Pro Ser Gly Ser Asp Ile Gln Met Thr
465                 470                 475                 480

Gln Ser Pro Ser Ser Leu Ser Ala Ser Val Gly Asp Arg Val Thr Ile
                485                 490                 495

Thr Cys Arg Ala Ser Arg Pro Ile Ser Asp Trp Leu His Trp Tyr Gln
            500                 505                 510

Gln Lys Pro Gly Lys Ala Pro Lys Leu Leu Ile Ala Trp Ala Ser Ser
        515                 520                 525

Leu Gln Gly Gly Val Pro Ser Arg Phe Ser Gly Ser Gly Ser Gly Thr
        530                 535                 540

Asp Phe Thr Leu Thr Ile Ser Ser Leu Gln Pro Glu Asp Phe Ala Thr
545                 550                 555                 560

Tyr Tyr Cys Gln Gln Glu Gly Trp Gly Pro Pro Thr Phe Gly Gln Gly
                565                 570                 575

Thr Lys Val Glu Ile Lys Arg
            580
```

<210> SEQ ID NO 105
<211> LENGTH: 1749
<212> TYPE: DNA
<213> ORGANISM: Artificial Sequence
<220> FEATURE:
<223> OTHER INFORMATION: Humanised

<400> SEQUENCE: 105

```
caggtgcagc tcgtgcagag cggcgccgaa gtgaaaaagc ccggcagcag cgtgaaggtg      60
agctgcaagg cctccggctt ctacatcaag gacacctaca tgcactgggt caggcaggct     120
cctggccagg gcctggagtg gatgggcact atcgaccccg ccaacggcaa caccaagtac     180
gtgcccaagt tccagggcag ggtgaccatc accgccgatg agagcaccag caccgcctac     240
atggaactga gcagcctgag gtctgaggac accgccgtgt actattgcgc caggagcatc     300
tacgacgact accacgtcga cgactactac gccatggact actggggaca gggcacacta     360
gtgaccgtgt ccagcgccag caccaagggc ccagcgtgt tccccctggc cccagcagc      420
aagagcacca gcggcggcac agccgccctg ggctgcctgg tgaaggacta cttccccgaa     480
ccggtgaccg tgtcctggaa cagcggagcc ctgaccagcg gcgtgcacac cttccccgcc     540
gtgctgcaga gcagcggcct gtacagcctg agcagcgtgg tgaccgtgcc cagcagcagc     600
ctgggcaccc agacctacat ctgtaacgtg aaccacaagc ccagcaacac caaggtggac     660
aagaaggtgg agcccaagag ctgtgacaag acccacacct gcccccctg ccctgccc      720
gagctgctgg gaggcccag cgtgttcctg ttcccccca gcctaagga caccctgatg       780
atcagcagaa ccccgaggt gacctgtgtg gtggtggatg tgagccacga ggaccctgag     840
gtgaagttca ctggtacgt ggacggcgtg gaggtgcaca tgccaagac caagcccagg     900
gaggagcagt acaacagcac ctaccgggtg gtgtccgtgc tgaccgtgct gcaccaggat     960
tggctgaacg gcaaggagta caagtgtaag gtgtccaaca aggccctgcc tgcccctatc    1020
gagaaaacca tcagcaaggc caagggccag cccagagagc ccaggtgta caccctgccc    1080
cctagcagag atgagctgac caagaaccag gtgtccctga cctgcctggt gaagggcttc    1140
tacccagcg acatcgccgt ggagtggag agcaacggcc agcccgagaa caactacaag    1200
accacccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg gcaagaccgt ggcagcacca    1380
tcaaccgtgg cagcaccatc aacagtagct gctccttctg gatccgacat ccagatgacc    1440
cagagcccca gcagcctgag cgccagcgtg ggcgacaggg tgaccattac ctgcagggcc    1500
agcaggccca tcagcgactg gctgcactgg taccaacaga gcccggcaa ggctcccaag    1560
ctgctgatcg cctgggccag cagcctgcag ggaggcgtgc ccagcaggtt tagcggcagc    1620
ggcagcggca ccgacttcac cctcaccatc tcttccctgc agcccgagga cttcgccacc    1680
tactactgcc agcaggaggg ctgggggccc cctactttcg gccagggcac caaggtggag    1740
atcaagagg                                                            1749
```

<210> SEQ ID NO 106
<211> LENGTH: 589
<212> TYPE: PRT
<213> ORGANISM: Artificial Sequence
<220> FEATURE:
<223> OTHER INFORMATION: Humanised

<400> SEQUENCE: 106

-continued

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
                 20                  25                  30

Tyr Met His Trp Val Arg Gln Ala Pro Gly Gln Gly Leu Glu Trp Met
             35                  40                  45

Gly Thr Ile Asp Pro Ala Asn Gly Asn Thr Lys Tyr Val Pro Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
                195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430
```

Cys Ser Val Met His Glu Ala Leu His Asn His Tyr Thr Gln Lys Ser
              435                 440                 445

Leu Ser Leu Ser Pro Gly Lys Thr Val Ala Ala Pro Ser Thr Val Ala
450                 455                 460

Ala Pro Ser Thr Val Ala Pro Ser Thr Val Ala Ala Pro Ser Gly
465                 470                 475                 480

Ser Asp Ile Gln Met Thr Gln Ser Pro Ser Ser Leu Ser Ala Ser Val
              485                 490                 495

Gly Asp Arg Val Thr Ile Thr Cys Arg Ala Ser Arg Pro Ile Ser Asp
          500                 505                 510

Trp Leu His Trp Tyr Gln Gln Lys Pro Gly Lys Ala Pro Lys Leu Leu
          515                 520                 525

Ile Ala Trp Ala Ser Ser Leu Gln Gly Gly Val Pro Ser Arg Phe Ser
530                 535                 540

Gly Ser Gly Ser Gly Thr Asp Phe Thr Leu Thr Ile Ser Ser Leu Gln
545                 550                 555                 560

Pro Glu Asp Phe Ala Thr Tyr Tyr Cys Gln Gln Glu Gly Trp Gly Pro
              565                 570                 575

Pro Thr Phe Gly Gln Gly Thr Lys Val Glu Ile Lys Arg
              580                 585

<210> SEQ ID NO 107
<211> LENGTH: 1767
<212> TYPE: DNA
<213> ORGANISM: Artificial Sequence
<220> FEATURE:
<223> OTHER INFORMATION: Humanised

<400> SEQUENCE: 107
caggtgcagc tcgtgcagag cggcgccgaa gtgaaaaagc ccggcagcag cgtgaaggtg     60
agctgcaagg cctccggctt ctacatcaag gacacctaca tgcactgggt caggcaggct    120
cctggccagg gcctggagtg gatgggcact atcgaccccg ccaacggcaa caccaagtac    180
gtgcccaagt tccagggcag ggtgaccatc accgccgatg agagccacag caccgcctac    240
atggaactga gcagcctgag gtctgaggac accgccgtgt actattgcgc caggagcatc    300
tacgacgact accacgtcga cgactactac gccatggact actggggaca gggcacacta    360
gtgaccgtgt ccagcgccag caccaagggc cccagcgtgt tccccctggc ccccagcagc    420
aagagcacca gcggcggcac agccgccctg ggctgcctgg tgaaggacta cttccccgaa    480
ccggtgaccg tgtcctggaa cagcggagcc ctgaccagcg gcgtgcacac cttcccgcc    540 gtgctgcaga gcagcggcct gtacagcctg agcagcgtgg tgaccgtgcc cagcagcagc    600
ctgggcaccc agacctacat ctgtaacgtg aaccacaagc ccagcaacac caaggtggac    660
aagaaggtgg agcccaagag ctgtgacaag acccacacct gccccccctg ccctgccccc    720
gagctgctgg gaggcccag cgtgttcctg ttccccccca gcctaagga caccctgatg    780 atcagcagaa cccccgaggt gacctgtgtg gtggtggatg tgagccacga ggaccctgag    840
gtgaagttca actggtacgt ggacggcgtg gaggtgcaca tgccaagac caagcccagg    900 gaggagcagt acaacagcac ctaccgggtg gtgtccgtgc tgaccgtgct gcaccaggat    960
tggctgaacg gcaaggagta caagtgtaag gtgtccaaca aggccctgcc tgcccctatc    1020
gagaaaacca tcagcaaggc caagggccag cccagagagc ccaggtgta cccctgccc    1080 cctagcagat gagctgac caagaaccag gtgtccctga cctgcctggt gaagggcttc    1140
taccccagcg acatcgccgt ggagtgggag agcaacggcc agcccgagaa caactacaag    1200

```
accacccccc ctgtgctgga cagcgatggc agcttcttcc tgtacagcaa gctgaccgtg    1260
gacaagagca gatggcagca gggcaacgtg ttcagctgct ccgtgatgca cgaggccctg    1320
cacaatcact acacccagaa gagcctgagc ctgtcccctg caagaccgt ggcagcacca    1380 tcaaccgtgg cagcaccatc aacagtagct gctccttcta cagtagctgc tccttctgga    1440
tccgacatcc agatgaccca gagccccagc agcctgagcg ccagcgtggg cgacagggtg    1500
accattacct gcagggccag caggcccatc agcgactggc tgcactggta ccaacagaag    1560
cccggcaagg ctcccaagct gctgatcgcc tgggccagca gcctgcaggg aggcgtgccc    1620
agcaggttta gcggcagcgg cagcggcacc gacttcaccc tcaccatctc ttccctgcag    1680
cccgaggact tcgccaccta ctactgccag caggagggct gggggccccc tactttcggc    1740
cagggcacca aggtggagat caagagg                                        1767
```

<210> SEQ ID NO 108
<211> LENGTH: 219
<212> TYPE: PRT
<213> ORGANISM: Artificial Sequence
<220> FEATURE:
<223> OTHER INFORMATION: Humanised

<400> SEQUENCE: 108

```
Asp Ile Gln Met Thr Gln Ser Pro Ser Ser Leu Ser Ala Ser Val Gly
  1               5                  10                  15

Asp Arg Val Thr Ile Thr Cys Arg Ser Ser Gln Asn Ile Val His Ile
             20                  25                  30

Asn Gly Asn Thr Tyr Leu Glu Trp Tyr Gln Gln Lys Pro Gly Lys Ala
         35                  40                  45

Pro Lys Leu Leu Ile Tyr Lys Ile Ser Asp Arg Phe Ser Gly Val Pro
     50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 109
<211> LENGTH: 714
<212> TYPE: DNA
<213> ORGANISM: Artificial Sequence
<220> FEATURE:
<223> OTHER INFORMATION: Humanised

<400> SEQUENCE: 109

```
atgggctggt cctgcatcat cctgtttctg gtggccaccg ccaccggcgt gcacagcgac    60
atccagatga cccagagccc cagcagcctg agcgccagcg tgggcgacag ggtgactatc   120
acctgcagga gcagccagaa catcgtgcac atcaacggca cacctacct cgagtggtac   180
cagcagaaac ccgggaaggc ccccaagctg ctgatctaca agatcagcga caggttcagc   240
ggcgtgccca gcaggtttag cggctccggc tcaggcaccg atttcaccct gaccattagc   300
agcctgcagc ccgaggactt cgccacctac tactgcttcc agggctctca cgtcccctgg   360
accttcggcc agggcaccaa gctggagatc aagcgtacgg tggccgcccc cagcgtgttc   420
atcttccccc ccagcgatga gcagctgaag agcggcaccg ccagcgtggt gtgtctgctg   480
aacaacttct accccgggga ggccaaggtg cagtggaagg tggacaatgc cctgcagagc   540
ggcaacagcc aggagagcgt gaccgagcag gacagcaagg actccaccta cagcctgagc   600
agcaccctga ccctgagcaa ggccgactac gagaagcaca aggtgtacgc ctgtgaggtg   660
acccaccagg gcctgtccag ccccgtgacc aagagcttca ccggggcga gtgc          714
```

<210> SEQ ID NO 110
<211> LENGTH: 219
<212> TYPE: PRT
<213> ORGANISM: Artificial Sequence
<220> FEATURE:
<223> OTHER INFORMATION: Humanised

<400> SEQUENCE: 110

Asp Val Leu Met Thr Gln Ser Pro Ser Ser Leu Ser Ala Ser Val Gly
1               5                   10                  15
Asp Arg Val Thr Ile Thr Cys Arg Ser Ser Gln Asn Ile Val His Ile
            20                  25                  30
Asn Gly Asn Thr Tyr Leu Glu Trp Tyr Gln Gln Lys Pro Gly Lys Ala
        35                  40                  45
Pro Lys Leu Leu Ile Tyr Lys Ile Ser Asp Arg Phe Ser Gly Val Pro
    50                  55                  60
Ser Arg Phe Ser Gly Ser Gly Ser Gly Thr Asp Phe Thr Leu Thr Ile
65                  70                  75                  80
Ser Ser Leu Gln Pro Glu Asp Phe Ala Thr Tyr Tyr Cys Phe Gln Gly
                85                  90                  95
Ser His Val Pro Trp Thr Phe Gly Gln Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 111
<211> LENGTH: 714
<212> TYPE: DNA
<213> ORGANISM: Artificial Sequence
<220> FEATURE:
<223> OTHER INFORMATION: Humanised

<400> SEQUENCE: 111
atgggctggt cctgcatcat cctgtttctg gtggccaccg ccaccggcgt gcacagcgac 60
gtgctgatga cccagagccc cagcagcctg agcgccagcg tgggcgacag ggtgactatc 120
acctgcagga gcagccagaa catcgtgcac atcaacggca acacctacct cgagtggtac 180
cagcagaaac ccgggaaggc ccccaagctg ctgatctaca agatcagcga caggttcagc 240
ggcgtgccca gcaggtttag cggctccggc tcaggcaccg atttcaccct gaccattagc 300
agcctgcagc ccgaggactt cgccacctac tactgcttcc agggctctca cgtcccctgg 360
accttcggcc agggcaccaa gctggagatc aagcgtacgg tggccgcccc cagcgtgttc 420
atcttccccc ccagcgatga gcagctgaag agcggcaccg ccagcgtggt gtgtctgctg 480
aacaacttct acccccggga ggccaaggtg cagtggaagg tggacaatgc cctgcagagc 540
ggcaacagcc aggagagcgt gaccgagcag gacagcaagg actccaccta cagcctgagc 600
agcaccctga ccctgagcaa ggccgactac gagaagcaca aggtgtacgc ctgtgaggtg 660
acccaccagg gcctgtccag ccccgtgacc aagagcttca accggggcga gtgc 714

<210> SEQ ID NO 112
<211> LENGTH: 219
<212> TYPE: PRT
<213> ORGANISM: Artificial Sequence
<220> FEATURE:
<223> OTHER INFORMATION: Humanised

<400> SEQUENCE: 112

Glu Ile Val Leu Thr Gln Ser Pro Gly Thr Leu Ser Leu Ser Pro Gly
1 5 10 15

Glu Arg Ala Thr Leu Ser Cys Arg Ser Ser Gln Asn Ile Val His Ile
20 25 30

Asn Gly Asn Thr Tyr Leu Glu Trp Tyr Gln Gln Lys Pro Gly Gln Ala
35 40 45

Pro Arg Leu Leu Ile Tyr Lys Ile Ser Asp Arg Phe Ser Gly Ile Pro
50 55 60

Asp Arg Phe Ser Gly Ser Gly Ser Gly Thr Asp Phe Thr Leu Thr Ile
65 70 75 80

Ser Arg Leu Glu Pro Glu Asp Phe Ala Val Tyr Tyr Cys Phe Gln Gly
85 90 95

Ser His Val Pro Trp Thr Phe Gly Gln Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser

```
                195                 200                 205

Pro Val Thr Lys Ser Phe Asn Arg Gly Glu Cys
    210                 215

<210> SEQ ID NO 113
<211> LENGTH: 714
<212> TYPE: DNA
<213> ORGANISM: Artificial Sequence
<220> FEATURE:
<223> OTHER INFORMATION: Humanised

<400> SEQUENCE: 113
atgggctggt cctgcatcat cctgtttctg gtggccaccg ccaccggcgt gcacagcgag    60
atcgtgctga cccagagccc tggcacactg agcctgagcc ccggagagag ggccaccctg   120
agctgcaggt ctagccagaa catcgtgcac atcaacggca cacctacct ggagtggtat   180 cagcagaagc ccggccaggc ccccaggctg ctgatctaca agatcagcga caggttcagc   240
ggcatccccg acaggtttag cggcagcggc agcggcaccg acttcaccct gaccattagc   300
aggctggagc ccgaggactt cgccgtgtac tactgcttcc aggggagcca cgtgccctgg   360
accttcggcc agggcaccaa gctcgaaatc aagcgtacgg tggccgcccc cagcgtgttc   420
atcttccccc ccagcgatga gcagctgaag agcggcaccg ccagcgtggt gtgtctgctg   480
aacaacttct accccggga ggccaaggtg cagtggaagg tggacaatgc cctgcagagc   540
ggcaacagcc aggagagcgt gaccgagcag gacagcaagg actccaccta cagcctgagc   600
agcaccctga ccctgagcaa ggccgactac gagaagcaca aggtgtacgc ctgtgaggtg   660
acccaccagg gcctgtccag ccccgtgacc aagagcttca ccggggcga gtgc         714

<210> SEQ ID NO 114
<211> LENGTH: 219
<212> TYPE: PRT
<213> ORGANISM: Artificial Sequence
<220> FEATURE:
<223> OTHER INFORMATION: Humanised

<400> SEQUENCE: 114

Asp Val Leu Met Thr Gln Ser Pro Gly Thr Leu Ser Leu Ser Pro Gly
1               5                   10                  15

Glu Arg Ala Thr Leu Ser Cys Arg Ser Ser Gln Asn Ile Val His Ile
            20                  25                  30

Asn Gly Asn Thr Tyr Leu Glu Trp Tyr Gln Gln Lys Pro Gly Gln Ala
        35                  40                  45

Pro Lys Leu Leu Ile Tyr Lys Ile Ser Asp Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Phe Gln Gly
                85                  90                  95

Ser His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                    165                 170                 175
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 115
<211> LENGTH: 657
<212> TYPE: DNA
<213> ORGANISM: Artificial Sequence
<220> FEATURE:
<223> OTHER INFORMATION: Humanised

<400> SEQUENCE: 115
gacgtgctga tgacccagag ccctggcaca ctgagcctga gccccggaga gagggccacc      60
ctgagctgca ggtctagcca gaacatcgtg cacatcaacg caacaccta cctggagtgg     120 tatcagcaga agcccggcca ggccccaag ctgctgatct acaagatcag cgacaggttc     180
agcggcgtgc ccgacaggtt tagcggcagc ggcagcggca ccgacttcac cctgaccatt     240
agcaggctgg agcccgagga cttcgccgtg tactactgct tccaggggag ccacgtgccc     300
tggaccttcg gccagggcac caagctcgaa atcaagcgta cggtggccgc ccccagcgtg     360
ttcatcttcc cccccagcga tgagcagctg aagagcggca ccgccagcgt ggtgtgtctg     420
ctgaacaact tctaccccccg ggaggccaag gtgcagtgga aggtggacaa tgccctgcag     480
agcggcaaca gccaggagag cgtgaccgag caggacagca aggactccac ctacagcctg     540
agcagcaccc tgaccctgag caaggccgac tacgagaagc acaaggtgta cgcctgtgag     600
gtgacccacc agggcctgtc cagccccgtg accaagagct caaccgggg cgagtgc       657

<210> SEQ ID NO 116
<211> LENGTH: 571
<212> TYPE: PRT
<213> ORGANISM: Artificial Sequence
<220> FEATURE:
<223> OTHER INFORMATION: Humanised

<400> SEQUENCE: 116

Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140
```

```
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Gly Ser Asp
    450                 455                 460

Ile Gln Met Thr Gln Ser Pro Ser Ser Leu Ser Ala Ser Val Gly Asp
465                 470                 475                 480

Arg Val Thr Ile Thr Cys Arg Ala Ser Arg Pro Ile Ser Asp Trp Leu
                485                 490                 495

His Trp Tyr Gln Gln Lys Pro Gly Lys Ala Pro Lys Leu Leu Ile Ala
            500                 505                 510

Trp Ala Ser Ser Leu Gln Gly Gly Val Pro Ser Arg Phe Ser Gly Ser
        515                 520                 525

Gly Ser Gly Thr Asp Phe Thr Leu Thr Ile Ser Ser Leu Gln Pro Glu
    530                 535                 540

Asp Phe Ala Thr Tyr Tyr Cys Leu Gln Glu Gly Trp Gly Pro Pro Thr
545                 550                 555                 560

Phe Gly Gln Gly Thr Lys Val Glu Ile Lys Arg
                565                 570
```

<210> SEQ ID NO 117
<211> LENGTH: 577
<212> TYPE: PRT
<213> ORGANISM: Artificial Sequence
<220> FEATURE:
<223> OTHER INFORMATION: Humanised

<400> SEQUENCE: 117

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

```
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys Thr Val Ala Ala Pro Ser Thr Val Ala
    450                 455                 460
Ala Pro Ser Gly Ser Asp Ile Gln Met Thr Gln Ser Pro Ser Ser Leu
465                 470                 475                 480
Ser Ala Ser Val Gly Asp Arg Val Thr Ile Thr Cys Arg Ala Ser Arg
                485                 490                 495
Pro Ile Ser Asp Trp Leu His Trp Tyr Gln Gln Lys Pro Gly Lys Ala
            500                 505                 510
Pro Lys Leu Leu Ile Ala Trp Ala Ser Ser Leu Gln Gly Gly Val Pro
        515                 520                 525
Ser Arg Phe Ser Gly Ser Gly Ser Gly Thr Asp Phe Thr Leu Thr Ile
    530                 535                 540
Ser Ser Leu Gln Pro Glu Asp Phe Ala Thr Tyr Tyr Cys Gly Gln Glu
545                 550                 555                 560
Gly Trp Gly Pro Pro Thr Phe Gly Gln Gly Thr Lys Val Glu Ile Lys
                565                 570                 575
Arg

<210> SEQ ID NO 118
<211> LENGTH: 577
<212> TYPE: PRT
<213> ORGANISM: Artificial Sequence
<220> FEATURE:
<223> OTHER INFORMATION: Humanised

<400> SEQUENCE: 118

Gln Val Gln Leu Val Gln Ser Gly Ala Glu Val Lys Lys Pro Gly Ser
1               5                   10                  15
Ser Val Lys Val Ser Cys Lys Ala Ser Gly Phe Tyr Ile Lys Asp Thr
            20                  25                  30
Tyr Met His Trp Val Arg Gln Ala Pro Gly Gln Gly Leu Glu Trp Met
        35                  40                  45
Gly Thr Ile Asp Pro Ala Asn Gly Asn Thr Lys Tyr Val Pro Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Ile Tyr Asp Asp Tyr His Val Asp Tyr Tyr Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Thr Val Ala
    450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Tyr Cys Ser Gln Glu
545                 550                 555                 560

Gly Trp Gly Pro Pro Thr Phe Gly Gln Gly Thr Lys Val Glu Ile Lys
                565                 570                 575

Arg
```

<210> SEQ ID NO 119
<211> LENGTH: 577
<212> TYPE: PRT
<213> ORGANISM: Artificial Sequence
<220> FEATURE:
<223> OTHER INFORMATION: Humanised

<400> SEQUENCE: 119

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

```
Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Thr Val Ala
450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
                500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
530                 535                 540

Ser Ser Leu Gln Pro Glu Asp Phe Ala Thr Tyr Tyr Cys His Gln Glu
545                 550                 555                 560

Gly Trp Gly Pro Pro Thr Phe Gly Gln Gly Thr Lys Val Glu Ile Lys
                565                 570                 575

Arg

<210> SEQ ID NO 120
<211> LENGTH: 577
<212> TYPE: PRT
<213> ORGANISM: Artificial Sequence
<220> FEATURE:
<223> OTHER INFORMATION: Humanised

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
                20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
                100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160
```

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Thr Val Ala
    450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Tyr Cys Met Gln Glu
545                 550                 555                 560

Gly Trp Gly Pro Pro Thr Phe Gly Gln Gly Thr Lys Val Glu Ile Lys
                565                 570                 575

Arg

<210> SEQ ID NO 121
<211> LENGTH: 577
<212> TYPE: PRT
<213> ORGANISM: Artificial Sequence
<220> FEATURE:
<223> OTHER INFORMATION: Humanised

<400> SEQUENCE: 121

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

-continued

```
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys Thr Val Ala Ala Pro Ser Thr Val Ala
    450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
                500                 505                 510

Pro Lys Leu Leu Ile Ala Trp Ala Ser Ser Leu Gln Gly Gly Val Pro
                515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Tyr Cys Ala Gln Glu
545                 550                 555                 560

Gly Trp Gly Pro Pro Thr Phe Gly Gln Gly Thr Lys Val Glu Ile Lys
                565                 570                 575

Arg

<210> SEQ ID NO 122
<211> LENGTH: 577
<212> TYPE: PRT
<213> ORGANISM: Artificial Sequence
<220> FEATURE:
<223> OTHER INFORMATION: Humanised

<400> SEQUENCE: 122

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
                20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
                210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
                370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys Thr Val Ala Ala Pro Ser Thr Val Ala
    450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
                500                 505                 510

Pro Lys Leu Leu Ile Ala Trp Ala Ser Ser Leu Gln Gly Gly Val Pro
                515                 520                 525

Ser Arg Phe Ser Gly Ser Gly Ser Gly Thr Asp Phe Thr Leu Thr Ile
                530                 535                 540

Ser Ser Leu Gln Pro Glu Asp Phe Ala Thr Tyr Tyr Cys Thr Gln Glu
545                 550                 555                 560

Gly Trp Gly Pro Pro Thr Phe Gly Gln Gly Thr Lys Val Glu Ile Lys
                565                 570                 575

Arg
```

<210> SEQ ID NO 123
<211> LENGTH: 577
<212> TYPE: PRT
<213> ORGANISM: Artificial Sequence
<220> FEATURE:
<223> OTHER INFORMATION: Humanised

<400> SEQUENCE: 123

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

-continued

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Thr Val Ala
450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
530                 535                 540

Ser Ser Leu Gln Pro Glu Asp Phe Ala Thr Tyr Tyr Cys Cys Gln Glu
545                 550                 555                 560

Gly Trp Gly Pro Pro Thr Phe Gly Gln Gly Thr Lys Val Glu Ile Lys
                565                 570                 575

Arg

<210> SEQ ID NO 124
<211> LENGTH: 577
<212> TYPE: PRT
<213> ORGANISM: Artificial Sequence
<220> FEATURE:
<223> OTHER INFORMATION: Humanised

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

```
Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                    245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                    325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys Thr Val Ala Ala Pro Ser Thr Val Ala
    450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
                500                 505                 510

Pro Lys Leu Leu Ile Ala Trp Ala Ser Ser Leu Gln Gly Gly Val Pro
            515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Tyr Cys Arg Gln Glu
545                 550                 555                 560

Gly Trp Gly Pro Pro Thr Phe Gly Gln Gly Thr Lys Val Glu Ile Lys
                565                 570                 575

Arg
```

<210> SEQ ID NO 125
<211> LENGTH: 577
<212> TYPE: PRT
<213> ORGANISM: Artificial Sequence
<220> FEATURE:
<223> OTHER INFORMATION: Humanised

<400> SEQUENCE: 125

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

-continued

Asn Gln Val Ser Leu Thr Cys Leu Val Lys Gly Phe Tyr Pro Ser Asp
 370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Thr Val Ala
450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
530                 535                 540

Ser Ser Leu Gln Pro Glu Asp Phe Ala Thr Tyr Tyr Cys Trp Gln Glu
545                 550                 555                 560

Gly Trp Gly Pro Pro Thr Phe Gly Gln Gly Thr Lys Val Glu Ile Lys
                565                 570                 575

Arg

<210> SEQ ID NO 126
<211> LENGTH: 577
<212> TYPE: PRT
<213> ORGANISM: Artificial Sequence
<220> FEATURE:
<223> OTHER INFORMATION: Humanised

<400> SEQUENCE: 126

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Thr Val Ala
    450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Tyr Cys Glu Gln Glu
545                 550                 555                 560

Gly Trp Gly Pro Pro Thr Phe Gly Gln Gly Thr Lys Val Glu Ile Lys
                565                 570                 575

Arg
```

<210> SEQ ID NO 127
<211> LENGTH: 577
<212> TYPE: PRT
<213> ORGANISM: Artificial Sequence
<220> FEATURE:
<223> OTHER INFORMATION: Humanised

<400> SEQUENCE: 127

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

-continued

```
Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys Thr Val Ala Ala Pro Ser Thr Val Ala
        450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                    485                 490                 495

Pro Ile Ser Asp Trp Leu His Trp Tyr Gln Gln Lys Pro Gly Lys Ala
                500                 505                 510

Pro Lys Leu Leu Ile Ala Trp Ala Ser Ser Leu Gln Gly Gly Val Pro
            515                 520                 525

Ser Arg Phe Ser Gly Ser Gly Ser Gly Thr Asp Phe Thr Leu Thr Ile
        530                 535                 540

Ser Ser Leu Gln Pro Glu Asp Phe Ala Thr Tyr Tyr Cys Lys Gln Glu
545                 550                 555                 560

Gly Trp Gly Pro Pro Thr Phe Gly Gln Gly Thr Lys Val Glu Ile Lys
                    565                 570                 575

Arg

<210> SEQ ID NO 128
<211> LENGTH: 577
<212> TYPE: PRT
<213> ORGANISM: Artificial Sequence
<220> FEATURE:
<223> OTHER INFORMATION: Humanised

<400> SEQUENCE: 128

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
                20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160
```

-continued

```
Pro Val Thr Val Ser Trp Asn Ser Gly Ala Leu Thr Ser Gly Val His
            165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
            195                 200                 205
Asn Val Asn His Lys Pro Ser Asn Thr Lys Val Asp Lys Lys Val Glu
            210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                    245                 250                 255
Asp Thr Leu Met Ile Ser Arg Thr Pro Glu Val Thr Cys Val Val Val
                260                 265                 270
Asp Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln Tyr
            290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                    325                 330                 335
Pro Ala Pro Ile Glu Lys Thr Ile Ser Lys Ala Lys Gly Gln Pro Arg
                340                 345                 350
Glu Pro Gln Val Tyr Thr Leu Pro Pro Ser Arg Asp Glu Leu Thr Lys
            355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                    405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
            435                 440                 445
Leu Ser Leu Ser Pro Gly Lys Thr Val Ala Ala Pro Ser Thr Val Ala
450                 455                 460
Ala Pro Ser Gly Ser Asp Ile Gln Met Thr Gln Ser Pro Ser Ser Leu
465                 470                 475                 480
Ser Ala Ser Val Gly Asp Arg Val Thr Ile Thr Cys Arg Ala Ser Arg
                    485                 490                 495
Pro Ile Ser Asp Trp Leu His Trp Tyr Gln Gln Lys Pro Gly Lys Ala
                500                 505                 510
Pro Lys Leu Leu Ile Ala Trp Ala Ser Ser Leu Gln Gly Gly Val Pro
            515                 520                 525
Ser Arg Phe Ser Gly Ser Gly Ser Gly Thr Asp Phe Thr Leu Thr Ile
            530                 535                 540
Ser Ser Leu Gln Pro Glu Asp Phe Ala Thr Tyr Tyr Cys Asp Gln Glu
545                 550                 555                 560
Gly Trp Gly Pro Pro Thr Phe Gly Gln Gly Thr Lys Val Glu Ile Lys
                    565                 570                 575
Arg
```

<210> SEQ ID NO 129
<211> LENGTH: 577
<212> TYPE: PRT
<213> ORGANISM: Artificial Sequence
<220> FEATURE:
<223> OTHER INFORMATION: Humanised

<400> SEQUENCE: 129

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

-continued

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Thr Val Ala
    450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Tyr Cys Asn Gln Glu
545                 550                 555                 560

Gly Trp Gly Pro Pro Thr Phe Gly Gln Gly Thr Lys Val Glu Ile Lys
                565                 570                 575

Arg

<210> SEQ ID NO 130
<211> LENGTH: 577
<212> TYPE: PRT
<213> ORGANISM: Artificial Sequence
<220> FEATURE:
<223> OTHER INFORMATION: Humanised

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

```
Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys Thr Val Ala Ala Pro Ser Thr Val Ala
450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
            515                 520                 525

Ser Arg Phe Ser Gly Ser Gly Ser Gly Thr Asp Phe Thr Leu Thr Ile
            530                 535                 540

Ser Ser Leu Gln Pro Glu Asp Phe Ala Thr Tyr Tyr Cys Tyr Gln Glu
545                 550                 555                 560

Gly Trp Gly Pro Pro Thr Phe Gly Gln Gly Thr Lys Val Glu Ile Lys
                565                 570                 575

Arg
```

<210> SEQ ID NO 131
<211> LENGTH: 577
<212> TYPE: PRT
<213> ORGANISM: Artificial Sequence
<220> FEATURE:
<223> OTHER INFORMATION: Humanised

<400> SEQUENCE: 131

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
        260                 265                 270

Asp Val Ser His Glu Asp Pro Glu Val Lys Phe Asn Trp Tyr Val Asp
    275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Asp Glu Leu Thr Lys
        355                 360                 365
```

```
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys Thr Val Ala Ala Pro Ser Thr Val Ala
    450                 455                 460
Ala Pro Ser Gly Ser Asp Ile Gln Met Thr Gln Ser Pro Ser Ser Leu
465                 470                 475                 480
Ser Ala Ser Val Gly Asp Arg Val Thr Ile Thr Cys Arg Ala Ser Arg
                485                 490                 495
Pro Ile Ser Asp Trp Leu His Trp Tyr Gln Gln Lys Pro Gly Lys Ala
            500                 505                 510
Pro Lys Leu Leu Ile Ala Trp Ala Ser Ser Leu Gln Gly Gly Val Pro
        515                 520                 525
Ser Arg Phe Ser Gly Ser Gly Ser Gly Thr Asp Phe Thr Leu Thr Ile
    530                 535                 540
Ser Ser Leu Gln Pro Glu Asp Phe Ala Thr Tyr Tyr Cys Val Gln Glu
545                 550                 555                 560
Gly Trp Gly Pro Pro Thr Phe Gly Gln Gly Thr Lys Val Glu Ile Lys
                565                 570                 575
Arg

<210> SEQ ID NO 132
<211> LENGTH: 577
<212> TYPE: PRT
<213> ORGANISM: Artificial Sequence
<220> FEATURE:
<223> OTHER INFORMATION: Humanised

<400> SEQUENCE: 132

Gln Val Gln Leu Val Gln Ser Gly Ala Glu Val Lys Lys Pro Gly Ser
1               5                   10                  15
Ser Val Lys Val Ser Cys Lys Ala Ser Gly Phe Tyr Ile Lys Asp Thr
            20                  25                  30
Tyr Met His Trp Val Arg Gln Ala Pro Gly Gln Gly Leu Glu Trp Met
        35                  40                  45
Gly Thr Ile Asp Pro Ala Asn Gly Asn Thr Lys Tyr Val Pro Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Ile Tyr Asp Asp Tyr His Val Asp Tyr Tyr Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Thr Val Ala Ala Pro Ser Thr Val Ala
    450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Tyr Cys Ile Gln Glu
545                 550                 555                 560

Gly Trp Gly Pro Pro Thr Phe Gly Gln Gly Thr Lys Val Glu Ile Lys
                565                 570                 575

Arg
```

<210> SEQ ID NO 133
<211> LENGTH: 577
<212> TYPE: PRT
<213> ORGANISM: Artificial Sequence
<220> FEATURE:
<223> OTHER INFORMATION: Humanised

<400> SEQUENCE: 133

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

```
Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys Thr Val Ala Ala Pro Ser Thr Val Ala
        450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
                500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
530                 535                 540

Ser Ser Leu Gln Pro Glu Asp Phe Ala Thr Tyr Tyr Cys Phe Gln Glu
545                 550                 555                 560

Gly Trp Gly Pro Pro Thr Phe Gly Gln Gly Thr Lys Val Glu Ile Lys
                565                 570                 575

Arg

<210> SEQ ID NO 134
<211> LENGTH: 577
<212> TYPE: PRT
<213> ORGANISM: Artificial Sequence
<220> FEATURE:
<223> OTHER INFORMATION: Humanised

<400> SEQUENCE: 134

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
                20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
        50                  55                  60

Gln Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys Thr Val Ala Ala Pro Ser Thr Val Ala
    450                 455                 460
Ala Pro Ser Gly Ser Asp Ile Gln Met Thr Gln Ser Pro Ser Ser Leu
465                 470                 475                 480
Ser Ala Ser Val Gly Asp Arg Val Thr Ile Thr Cys Arg Ala Ser Arg
                485                 490                 495
Pro Ile Ser Asp Trp Leu His Trp Tyr Gln Gln Lys Pro Gly Lys Ala
            500                 505                 510
Pro Lys Leu Leu Ile Ala Trp Ala Ser Ser Leu Gln Gly Gly Val Pro
        515                 520                 525
Ser Arg Phe Ser Gly Ser Gly Ser Gly Thr Asp Phe Thr Leu Thr Ile
    530                 535                 540
Ser Ser Leu Gln Pro Glu Asp Phe Ala Thr Tyr Tyr Cys Pro Gln Glu
545                 550                 555                 560
Gly Trp Gly Pro Pro Thr Phe Gly Gln Gly Thr Lys Val Glu Ile Lys
                565                 570                 575
Arg
```

<210> SEQ ID NO 135
<211> LENGTH: 573
<212> TYPE: PRT
<213> ORGANISM: Artificial Sequence
<220> FEATURE:
<223> OTHER INFORMATION: Humanised

<400> SEQUENCE: 135

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

-continued

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys Gly Ser Thr Val Ala Ala Pro Ser Gly
    450                 455                 460

Ser Asp Ile Gln Met Thr Gln Ser Pro Ser Ser Leu Ser Ala Ser Val
465                 470                 475                 480

Gly Asp Arg Val Thr Ile Thr Cys Arg Ala Ser Arg Pro Ile Ser Asp
            485                 490                 495

Trp Leu His Trp Tyr Gln Gln Lys Pro Gly Lys Ala Pro Lys Leu Leu
            500                 505                 510

Ile Ala Trp Ala Ser Ser Leu Gln Gly Gly Val Pro Ser Arg Phe Ser
            515                 520                 525

Gly Ser Gly Ser Gly Thr Asp Phe Thr Leu Thr Ile Ser Ser Leu Gln
    530                 535                 540

Pro Glu Asp Phe Ala Thr Tyr Tyr Cys Leu Gln Glu Gly Trp Gly Pro
545                 550                 555                 560

Pro Thr Phe Gly Gln Gly Thr Lys Val Glu Ile Lys Arg
            565                 570

<210> SEQ ID NO 136
<211> LENGTH: 581
<212> TYPE: PRT
<213> ORGANISM: Artificial Sequence
<220> FEATURE:
<223> OTHER INFORMATION: Humanised

<400> SEQUENCE: 136

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His

```
                165                 170                 175
Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys Gly Ser Thr Val Ala Ala Pro Ser Gly
            450                 455                 460

Ser Thr Val Ala Ala Pro Ser Gly Ser Asp Ile Gln Met Thr Gln Ser
465                 470                 475                 480

Pro Ser Ser Leu Ser Ala Ser Val Gly Asp Arg Val Thr Ile Thr Cys
                485                 490                 495

Arg Ala Ser Arg Pro Ile Ser Asp Trp Leu His Trp Tyr Gln Gln Lys
            500                 505                 510

Pro Gly Lys Ala Pro Lys Leu Leu Ile Ala Trp Ala Ser Ser Leu Gln
            515                 520                 525

Gly Gly Val Pro Ser Arg Phe Ser Gly Ser Gly Ser Gly Thr Asp Phe
            530                 535                 540

Thr Leu Thr Ile Ser Ser Leu Gln Pro Glu Asp Phe Ala Thr Tyr Tyr
545                 550                 555                 560

Cys Leu Gln Glu Gly Trp Gly Pro Pro Thr Phe Gly Gln Gly Thr Lys
                565                 570                 575

Val Glu Ile Lys Arg
            580
```

<210> SEQ ID NO 137
<211> LENGTH: 589
<212> TYPE: PRT
<213> ORGANISM: Artificial Sequence
<220> FEATURE:
<223> OTHER INFORMATION: Humanised

<400> SEQUENCE: 137

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Tyr Asp Asp Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
```

```
                370                 375                 380
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys Gly Ser Thr Val Ala Ala Pro Ser Gly
450                 455                 460

Ser Thr Val Ala Ala Pro Ser Gly Ser Thr Val Ala Ala Pro Ser Gly
465                 470                 475                 480

Ser Asp Ile Gln Met Thr Gln Ser Pro Ser Ser Leu Ser Ala Ser Val
                485                 490                 495

Gly Asp Arg Val Thr Ile Thr Cys Arg Ala Ser Arg Pro Ile Ser Asp
                500                 505                 510

Trp Leu His Trp Tyr Gln Gln Lys Pro Gly Lys Ala Pro Lys Leu Leu
                515                 520                 525

Ile Ala Trp Ala Ser Ser Leu Gln Gly Gly Val Pro Ser Arg Phe Ser
                530                 535                 540

Gly Ser Gly Ser Gly Thr Asp Phe Thr Leu Thr Ile Ser Ser Leu Gln
545                 550                 555                 560

Pro Glu Asp Phe Ala Thr Tyr Tyr Cys Leu Gln Glu Gly Trp Gly Pro
                565                 570                 575

Pro Thr Phe Gly Gln Gly Thr Lys Val Glu Ile Lys Arg
                580                 585

<210> SEQ ID NO 138
<211> LENGTH: 597
<212> TYPE: PRT
<213> ORGANISM: Artificial Sequence
<220> FEATURE:
<223> OTHER INFORMATION: Humanised

<400> SEQUENCE: 138

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
                20                  25                  30

Tyr Met His Trp Val Arg Gln Ala Pro Gly Gln Gly Leu Glu Trp Met
                35                  40                  45

Gly Thr Ile Asp Pro Ala Asn Gly Asn Thr Lys Tyr Val Pro Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Tyr Tyr Ala Met
                100                 105                 110

Asp Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Lys Ser Thr Ser
                130                 135                 140

Gly Gly Thr Ala Ala Leu Gly Cys Leu Val Lys Asp Tyr Phe Pro Glu
145                 150                 155                 160
```

-continued

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys Gly Ser Thr Val Ala Ala Pro Ser Gly
        450                 455                 460

Ser Thr Val Ala Ala Pro Ser Gly Ser Thr Val Ala Ala Pro Ser Gly
465                 470                 475                 480

Ser Thr Val Ala Ala Pro Ser Gly Ser Asp Ile Gln Met Thr Gln Ser
                485                 490                 495

Pro Ser Ser Leu Ser Ala Ser Val Gly Asp Arg Val Thr Ile Thr Cys
            500                 505                 510

Arg Ala Ser Arg Pro Ile Ser Asp Trp Leu His Trp Tyr Gln Gln Lys
            515                 520                 525

Pro Gly Lys Ala Pro Lys Leu Leu Ile Ala Trp Ala Ser Ser Leu Gln
            530                 535                 540

Gly Gly Val Pro Ser Arg Phe Ser Gly Ser Gly Ser Gly Thr Asp Phe
545                 550                 555                 560

Thr Leu Thr Ile Ser Ser Leu Gln Pro Glu Asp Phe Ala Thr Tyr Tyr
                565                 570                 575

Cys Leu Gln Glu Gly Trp Gly Pro Pro Thr Phe Gly Gln Gly Thr Lys

```
                    580                 585                 590

Val Glu Ile Lys Arg
        595

<210> SEQ ID NO 139
<211> LENGTH: 10
<212> TYPE: PRT
<213> ORGANISM: Artificial Sequence
<220> FEATURE:
<223> OTHER INFORMATION: Linker

<400> SEQUENCE: 139

Gly Ser Thr Val Ala Ala Pro Ser Gly Ser
1               5                  10

<210> SEQ ID NO 140
<211> LENGTH: 18
<212> TYPE: PRT
<213> ORGANISM: Artificial Sequence
<220> FEATURE:
<223> OTHER INFORMATION: Linker

<400> SEQUENCE: 140

Gly Ser Thr Val Ala Ala Pro Ser Gly Ser Thr Val Ala Ala Pro Ser
1               5                  10                  15

Gly Ser

<210> SEQ ID NO 141
<211> LENGTH: 26
<212> TYPE: PRT
<213> ORGANISM: Artificial Sequence
<220> FEATURE:
<223> OTHER INFORMATION: Linker

<400> SEQUENCE: 141

Gly Ser Thr Val Ala Ala Pro Ser Gly Ser Thr Val Ala Ala Pro Ser
1               5                  10                  15

Gly Ser Thr Val Ala Ala Pro Ser Gly Ser
            20                  25

<210> SEQ ID NO 142
<211> LENGTH: 34
<212> TYPE: PRT
<213> ORGANISM: Artificial Sequence
<220> FEATURE:
<223> OTHER INFORMATION: Linker

<400> SEQUENCE: 142

Gly Ser Thr Val Ala Ala Pro Ser Gly Ser Thr Val Ala Ala Pro Ser
1               5                  10                  15

Gly Ser Thr Val Ala Ala Pro Ser Gly Ser Thr Val Ala Ala Pro Ser
            20                  25                  30

Gly Ser

<210> SEQ ID NO 143
<211> LENGTH: 42
<212> TYPE: PRT
<213> ORGANISM: Artificial Sequence
<220> FEATURE:
<223> OTHER INFORMATION: Linker

<400> SEQUENCE: 143

Gly Ser Thr Val Ala Ala Pro Ser Gly Ser Thr Val Ala Ala Pro Ser
1               5                  10                  15
```

Gly Ser Thr Val Ala Ala Pro Ser Gly Ser Thr Val Ala Ala Pro Ser
         20                  25                  30

Gly Ser Thr Val Ala Ala Pro Ser Gly Ser
         35                  40

<210> SEQ ID NO 144
<211> LENGTH: 50
<212> TYPE: PRT
<213> ORGANISM: Artificial Sequence
<220> FEATURE:
<223> OTHER INFORMATION: Linker

<400> SEQUENCE: 144

Gly Ser Thr Val Ala Ala Pro Ser Gly Ser Thr Val Ala Ala Pro Ser
1               5                   10                  15

Gly Ser Thr Val Ala Ala Pro Ser Gly Ser Thr Val Ala Ala Pro Ser
         20                  25                  30

Gly Ser Thr Val Ala Ala Pro Ser Gly Ser Thr Val Ala Ala Pro Ser
         35                  40                  45

Gly Ser
    50

<210> SEQ ID NO 145
<211> LENGTH: 14
<212> TYPE: PRT
<213> ORGANISM: Artificial Sequence
<220> FEATURE:
<223> OTHER INFORMATION: Linker

<400> SEQUENCE: 145

Thr Val Ala Ala Pro Ser Thr Val Ala Ala Pro Ser Gly Ser
1               5                   10

<210> SEQ ID NO 146
<211> LENGTH: 20
<212> TYPE: PRT
<213> ORGANISM: Artificial Sequence
<220> FEATURE:
<223> OTHER INFORMATION: Linker

<400> SEQUENCE: 146

Thr Val Ala Ala Pro Ser Thr Val Ala Ala Pro Ser Thr Val Ala Ala
1               5                   10                  15

Pro Ser Gly Ser
         20

<210> SEQ ID NO 147
<211> LENGTH: 577
<212> TYPE: PRT
<213> ORGANISM: Artificial Sequence
<220> FEATURE:
<223> OTHER INFORMATION: Fusion protein

<400> SEQUENCE: 147

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
         20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr

```
                65                  70                  75                  80
           Met Glu Leu Ser Ser Leu Arg Ser Glu Asp Ser Ala Val Tyr Tyr Cys
                            85                  90                  95

Ala Arg Ser Ile Tyr Asp Asp Tyr His Val Asp Tyr Tyr Ala Met
                           100                 105                 110

Asp Tyr Leu Gly Gln Gly Thr Leu Val Thr Val Ser Ser Ala Ser Thr
                           115                 120                 125

Lys Gly Pro Ser Val Phe Pro Leu Ala Pro Ser Ser Lys Ser Thr Ser
                           130                 135                 140

Gly Gly Thr Ala Ala Leu Gly Cys Leu Val Lys Asp Tyr Phe Pro Glu
           145                 150                 155                 160

Pro Val Thr Val Ser Trp Asn Ser Gly Ala Leu Thr Ser Gly Val His
                           165                 170                 175

Thr Phe Pro Ala Val Leu Gln Ser Ser Gly Leu Tyr Ser Leu Ser Ser
                           180                 185                 190

Val Val Thr Val Pro Ser Ser Leu Gly Thr Gln Thr Tyr Ile Cys
                           195                 200                 205

Asn Val Asn His Lys Pro Ser Asn Thr Lys Val Asp Lys Lys Val Glu
                           210                 215                 220

Pro Lys Ser Cys Asp Lys Thr His Thr Cys Pro Pro Cys Pro Ala Pro
           225                 230                 235                 240

Glu Leu Leu Gly Gly Pro Ser Val Phe Leu Phe Pro Pro Lys Pro Lys
                           245                 250                 255

Asp Thr Leu Met Ile Ser Arg Thr Pro Glu Val Thr Cys Val Val Val
                           260                 265                 270

Asp Val Ser His Glu Asp Pro Glu Val Lys Phe Asn Trp Tyr Val Asp
                           275                 280                 285

Gly Val Glu Val His Asn Ala Lys Thr Lys Pro Arg Glu Glu Gln Tyr
                           290                 295                 300

Asn Ser Thr Tyr Arg Val Val Ser Val Leu Thr Val Leu His Gln Asp
           305                 310                 315                 320

Trp Leu Asn Gly Lys Glu Tyr Lys Cys Lys Val Ser Asn Lys Ala Leu
                           325                 330                 335

Pro Ala Pro Ile Glu Lys Thr Ile Ser Lys Ala Lys Gly Gln Pro Arg
                           340                 345                 350

Glu Pro Gln Val Tyr Thr Leu Pro Pro Ser Arg Asp Glu Leu Thr Lys
                           355                 360                 365

Asn Gln Val Ser Leu Thr Cys Leu Val Lys Gly Phe Tyr Pro Ser Asp
                           370                 375                 380

Ile Ala Val Glu Trp Glu Ser Asn Gly Gln Pro Glu Asn Asn Tyr Lys
           385                 390                 395                 400

Thr Thr Pro Pro Val Leu Asp Ser Asp Gly Ser Phe Phe Leu Tyr Ser
                           405                 410                 415

Lys Leu Thr Val Asp Lys Ser Arg Trp Gln Gln Gly Asn Val Phe Ser
                           420                 425                 430

Cys Ser Val Met His Glu Ala Leu His Asn His Tyr Thr Gln Lys Ser
                           435                 440                 445

Leu Ser Leu Ser Pro Gly Lys Thr Val Ala Ala Pro Ser Thr Val Ala
                           450                 455                 460

Ala Pro Ser Gly Ser Asp Ile Gln Met Thr Gln Ser Pro Ser Ser Leu
           465                 470                 475                 480

Ser Ala Ser Val Gly Asp Arg Val Thr Ile Thr Cys Arg Ala Ser Arg
                           485                 490                 495
```

-continued

```
Pro Ile Ser Asp Trp Leu His Trp Tyr Gln Gln Lys Pro Gly Lys Ala
                500                 505                 510
Pro Lys Leu Leu Ile Ala Trp Ala Ser Ser Leu Gln Gly Gly Val Pro
        515                 520                 525
Ser Arg Phe Ser Gly Ser Gly Ser Gly Thr Asp Phe Thr Leu Thr Ile
530                 535                 540
Ser Ser Leu Gln Pro Glu Asp Phe Ala Thr Tyr Tyr Cys Met Gln Glu
545                 550                 555                 560
Gly Trp Gly Pro Pro Thr Phe Gly Gln Gly Thr Lys Val Glu Ile Lys
                565                 570                 575
Arg

<210> SEQ ID NO 148
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 148

Pro Ala Val Pro Pro
1               5

<210> SEQ ID NO 149
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 149

Thr Val Ser Asp Val Pro
1               5

<210> SEQ ID NO 150
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 150

Thr Gly Leu Asp Ser Pro
1               5

<210> SEQ ID NO 151
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 151

Pro Ala Ser Gly Ser
1               5

<210> SEQ ID NO 152
<211> LENGTH: 8
<212> TYPE: PRT
<213> ORGANISM: Artificial Sequence
<220> FEATURE:
<223> OTHER INFORMATION: Amino acid sequence identified using molecular
```

```
<400> SEQUENCE: 152

Pro Ala Ser Pro Ala Ser Gly Ser
 1               5

<210> SEQ ID NO 153
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 153

Pro Ala Ser Pro Ala Ser Pro Ala Ser Gly Ser
 1               5                  10

<210> SEQ ID NO 154
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 154

Pro Ala Ser Pro Ala Ser Pro Ala Ser Pro Ala Ser Gly Ser
 1               5                  10

<210> SEQ ID NO 155
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 155

Pro Ala Ser Pro Ala Ser
 1               5

<210> SEQ ID NO 156
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 156

Pro Ala Ser Pro Ala Ser Pro Ala Ser
 1               5

<210> SEQ ID NO 157
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 157

Pro Ala Ser Pro Ala Ser Pro Ala Ser Pro Ala Ser
 1               5                  10

<210> SEQ ID NO 158
<211> LENGTH: 7
```

```
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 158

Gly Gly Gly Gly Ser Gly Ser
1               5

<210> SEQ ID NO 159
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 159

Gly Gly Gly Gly Ser Gly Gly Gly Gly Ser Gly Ser
1               5                   10

<210> SEQ ID NO 160
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 160

Gly Gly Gly Gly Ser Gly Gly Gly Gly Ser Gly Gly Gly Gly Ser Gly
1               5                   10                  15

Ser

<210> SEQ ID NO 161
<211> LENGTH: 22
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 161

Gly Gly Gly Gly Ser Gly Gly Gly Gly Ser Gly Gly Gly Gly Ser Gly
1               5                   10                  15

Gly Gly Gly Ser Gly Ser
            20

<210> SEQ ID NO 162
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 162

Gly Gly Gly Gly Ser Gly Gly Gly Gly Ser
1               5                   10

<210> SEQ ID NO 163
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.
```

<400> SEQUENCE: 163

Gly Gly Gly Gly Ser Gly Gly Gly Gly Ser Gly Gly Gly Gly Ser
1               5                   10                  15

<210> SEQ ID NO 164
<211> LENGTH: 20
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 164

Gly Gly Gly Gly Ser Gly Gly Gly Gly Ser Gly Gly Gly Gly Ser Gly
1               5                   10                  15

Gly Gly Gly Ser
            20

<210> SEQ ID NO 165
<211> LENGTH: 26
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 165

Thr Val Ala Ala Pro Ser Thr Val Ala Ala Pro Ser Thr Val Ala Ala
1               5                   10                  15

Pro Ser Thr Val Ala Ala Pro Ser Gly Ser
            20                  25

<210> SEQ ID NO 166
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 166

Thr Val Ala Ala Pro Ser Thr Val Ala Ala Pro Ser
1               5                   10

<210> SEQ ID NO 167
<211> LENGTH: 18
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 167

Thr Val Ala Ala Pro Ser Thr Val Ala Ala Pro Ser Thr Val Ala Ala
1               5                   10                  15

Pro Ser

<210> SEQ ID NO 168
<211> LENGTH: 24
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 168

-continued

Thr Val Ala Ala Pro Ser Thr Val Ala Ala Pro Ser Thr Val Ala Ala
1               5                   10                  15

Pro Ser Thr Val Ala Ala Pro Ser
            20

<210> SEQ ID NO 169
<211> LENGTH: 36
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 169

Gly Ser Gly Ser Gly Ser Gly Ser Gly Ser Gly Ser Gly Ser Gly Ser
1               5                   10                  15

Gly Ser Gly Ser Thr Val Ala Ala Pro Ser Gly Ser Thr Val Ala Ala
            20                  25                  30

Pro Ser Gly Ser
        35

<210> SEQ ID NO 170
<211> LENGTH: 24
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 170

Thr Val Ala Ala Pro Ser Gly Ser Thr Val Ala Ala Pro Ser Gly Ser
1               5                   10                  15

Thr Val Ala Ala Pro Ser Gly Ser
            20

<210> SEQ ID NO 171
<211> LENGTH: 8
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 171

Pro Ala Val Pro Pro Pro Gly Ser
1               5

<210> SEQ ID NO 172
<211> LENGTH: 20
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 172

Pro Ala Val Pro Pro Pro Ala Val Pro Pro Pro Ala Val Pro
1               5                   10                  15

Pro Pro Gly Ser
        20

<210> SEQ ID NO 173
<211> LENGTH: 26
<212> TYPE: PRT
<213> ORGANISM: Artificial Sequence

```
<220> FEATURE:
<223> OTHER INFORMATION: Amino acid sequence identified using molecular
      biology techniques.

<400> SEQUENCE: 173

Pro Ala Val Pro Pro Pro Ala Val Pro Pro Pro Ala Val Pro
1               5                   10                  15

Pro Pro Pro Ala Val Pro Pro Pro Gly Ser
            20                  25

<210> SEQ ID NO 174
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 174

Pro Ala Val Pro Pro Pro Ala Val Pro Pro Pro
1               5                   10

<210> SEQ ID NO 175
<211> LENGTH: 18
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 175

Pro Ala Val Pro Pro Pro Ala Val Pro Pro Pro Ala Val Pro
1               5                   10                  15

Pro Pro

<210> SEQ ID NO 176
<211> LENGTH: 24
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 176

Pro Ala Val Pro Pro Pro Ala Val Pro Pro Pro Ala Val Pro
1               5                   10                  15

Pro Pro Pro Ala Val Pro Pro Pro
            20

<210> SEQ ID NO 177
<211> LENGTH: 8
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 177

Thr Val Ser Asp Val Pro Gly Ser
1               5

<210> SEQ ID NO 178
<211> LENGTH: 14
<212> TYPE: PRT
<213> ORGANISM: Artificial Sequence
<220> FEATURE:
<223> OTHER INFORMATION: Amino acid sequence identified using molecular
``` biology techniques.

<400> SEQUENCE: 178

Thr Val Ser Asp Val Pro Thr Val Ser Asp Val Pro Gly Ser
1               5                   10

<210> SEQ ID NO 179
<211> LENGTH: 20
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 179

Thr Val Ser Asp Val Pro Thr Val Ser Asp Val Pro Thr Val Ser Asp
1               5                   10                  15

Val Pro Gly Ser
            20

<210> SEQ ID NO 180
<211> LENGTH: 26
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 180

Thr Val Ser Asp Val Pro Thr Val Ser Asp Val Pro Thr Val Ser Asp
1               5                   10                  15

Val Pro Thr Val Ser Asp Val Pro Gly Ser
            20                  25

<210> SEQ ID NO 181
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 181

Thr Val Ser Asp Val Pro Thr Val Ser Asp Val Pro
1               5                   10

<210> SEQ ID NO 182
<211> LENGTH: 18
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 182

Thr Val Ser Asp Val Pro Thr Val Ser Asp Val Pro Thr Val Ser Asp
1               5                   10                  15

Val Pro

<210> SEQ ID NO 183
<211> LENGTH: 24
<212> TYPE: PRT
<213> ORGANISM: Artificial Sequence
<220> FEATURE:
<223> OTHER INFORMATION: Amino acid sequence identified using molecular
      biology techniques.

-continued

```
<400> SEQUENCE: 183

Thr Val Ser Asp Val Pro Thr Val Ser Asp Val Pro Thr Val Ser Asp
1               5                   10                  15

Val Pro Thr Val Ser Asp Val Pro
            20

<210> SEQ ID NO 184
<211> LENGTH: 8
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 184

Thr Gly Leu Asp Ser Pro Gly Ser
1               5

<210> SEQ ID NO 185
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 185

Thr Gly Leu Asp Ser Pro Thr Gly Leu Asp Ser Pro Gly Ser
1               5                   10

<210> SEQ ID NO 186
<211> LENGTH: 20
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 186

Thr Gly Leu Asp Ser Pro Thr Gly Leu Asp Ser Pro Thr Gly Leu Asp
1               5                   10                  15

Ser Pro Gly Ser
            20

<210> SEQ ID NO 187
<211> LENGTH: 26
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 187

Thr Gly Leu Asp Ser Pro Thr Gly Leu Asp Ser Pro Thr Gly Leu Asp
1               5                   10                  15

Ser Pro Thr Gly Leu Asp Ser Pro Gly Ser
            20                  25

<210> SEQ ID NO 188
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 188
```

```
Thr Gly Leu Asp Ser Pro Thr Gly Leu Asp Ser Pro
1               5                   10

<210> SEQ ID NO 189
<211> LENGTH: 18
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 189

Thr Gly Leu Asp Ser Pro Thr Gly Leu Asp Ser Pro Thr Gly Leu Asp
1               5                   10                  15

Ser Pro

<210> SEQ ID NO 190
<211> LENGTH: 24
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 190

Thr Gly Leu Asp Ser Pro Thr Gly Leu Asp Ser Pro Thr Gly Leu Asp
1               5                   10                  15

Ser Pro Thr Gly Leu Asp Ser Pro
            20

<210> SEQ ID NO 191
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 191

Pro Ala Val Pro Pro Pro Pro Ala Val Pro Pro Pro Gly Ser
1               5                   10
```